(12) United States Patent
Brown et al.

(10) Patent No.: US 8,859,549 B2
(45) Date of Patent: Oct. 14, 2014

(54) POTASSIUM CHANNEL MODULATORS

(75) Inventors: Brian S. Brown, Evanston, IL (US);
Tongmei Li, Lake Bluff, IL (US);
Sridhar Peddi, Schaumburg, IL (US);
Arturo Perez-Medrano, Grayslake, IL (US); David DeGoey, Salem, WI (US)

(73) Assignee: AbbVie, Inc., North Chicago, IL (US)

( * ) Notice: Subject to any disclaimer, the term of this patent is extended or adjusted under 35 U.S.C. 154(b) by 52 days.

(21) Appl. No.: 13/466,490

(22) Filed: May 8, 2012

(65) Prior Publication Data
US 2012/0289500 A1 Nov. 15, 2012

Related U.S. Application Data

(60) Provisional application No. 61/485,828, filed on May 13, 2011.

(51) Int. Cl.
*A01N 43/58* (2006.01)
*A61K 31/50* (2006.01)
*C07D 403/00* (2006.01)

(52) U.S. Cl.
USPC ........... 514/248; 514/247; 544/224; 544/235; 544/237

(58) Field of Classification Search
USPC .................... 544/224, 235, 237; 514/247, 248
See application file for complete search history.

(56) References Cited

U.S. PATENT DOCUMENTS

| | | | |
|---|---|---|---|
| 6,180,629 B1 * | 1/2001 | Wang et al. | 514/248 |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0305109 A1 | 12/2010 | Scanio et al. | |
| 2011/0124642 A1 | 5/2011 | Brown et al. | |
| 2012/0122888 A1 | 5/2012 | Xu et al. | |
| 2012/0122890 A1 | 5/2012 | Perez-Medrano et al. | |
| 2012/0190665 A1 | 7/2012 | Gibbons et al. | |

FOREIGN PATENT DOCUMENTS

| | | |
|---|---|---|
| WO | 9507271 A1 | 3/1995 |
| WO | 9710223 A1 | 3/1997 |
| WO | 0140231 A1 | 6/2001 |
| WO | 2004060893 A1 | 7/2004 |
| WO | 2005090333 A1 | 9/2005 |
| WO | 2005099353 A2 | 10/2005 |
| WO | 2006008754 A1 | 1/2006 |
| WO | 2007027454 A1 | 3/2007 |
| WO | WO-2007030582 A2 | 3/2007 |
| WO | 2010112486 A1 | 10/2010 |
| WO | 2011003065 A2 | 1/2011 |
| WO | WO-20110066168 A1 | 6/2011 |

OTHER PUBLICATIONS

Wolff et al (1997).*
Burger et al (1997).*
Vippagunta et al (2001).*
International Search Report and Written Opinion for PCT/US2012/036918, dated Aug. 14, 2012.
Bergmann et al., "Synthesis and antihypertensive activity of 4-(1,2-dihydro-2-oxo-1-pyridyl)-2H-1-benzo pyrans and related compounds . . . ," J. Med. Chem. 33(2): 492-504 (1990).
Bennett, G.J. et al., "A Peripheral Mononeuropathy in Rat that Produces Disorders of Pain Sensation like those Seen in Man," Pain, 1988, vol. 33 (1 ), pp. 87-107.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blackburn-Munro, G. et al., "Retigabine: Chemical Synthesis to Clinical Application," CNS Drug Reviews, 2005, vol. 11 (1), pp. 1-20.
Blagojevic, N. et al., "Role of heavy water in Boron Neutron Capture Therapy," Topics in Dosimetry & Treatment Planning for Neutron Capture Therapy, Advanced Medical Publishing, Madison Wisconsin, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

(Continued)

*Primary Examiner* — Paul V. Ward

(57) ABSTRACT

Disclosed herein are KCNQ potassium channels modulators of formula (I)

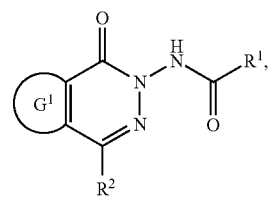

(I)

wherein ring $G^1$, $R^1$, and $R^2$ are as defined in the specification. Compositions comprising such compounds; and methods for treating conditions and disorders using such compounds and compositions are also described.

22 Claims, No Drawings

(56) References Cited

OTHER PUBLICATIONS

Chaplan, S.R. et al., "Quantitative Assessment of Tactile Allodynia in the Rat Paw," Journal of Neuroscience Methods, 1994, vol. 53, pp. 55-63.
Chiche, L. et al., "Opening of Dichlorocyclopropane in the Presence of Nucleophilic Internal. Intramolecular Absence of Participation. Rearrangement Concerted out of Allyl Chlorides." Canadian Journal of Chemistry, 1981, vol. 59 (1), pp. 164-174.
Coates, W. et al., "Reinvestigation and Extension of the Aluminum Chloride Induced Reactions of Resorcinol and Hydroquinone with 3,6-Dichloropyridazine," Journal of Organic Chemistry, 1990, vol. 55 (19), pp. 5418-5420.
Coenen, V.M. et al., "Syntheses with Trichloracetonitriles," Journal for Practical Chemistry, 1965, vol. 27 (5-6), pp. 239-250 (with English abstract).
Cross, LC. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiol., 1961, vol. 201 (2), pp. 357-362.
Dalby-Brown, W. et al., "K(V)7 Channels: Function, Pharmacology and Channel Modulators," Current Topics in Medicinal Chemistry, 2006, vol. 6 (10), pp. 999-1023.
Dixon, W.J. "Efficient Analysis of Experimental Observations," Annual Review of Pharmacology and Toxicology, 1980, vol. 20, pp. 441-462.
Eigenmann, G. W. et al., "Stereospecific Hydrogenation of α-Pinene Derivatives," Journal of American Chemical Society, 1959, vol. 81, pp. 3440-3442.
Foster, A. B. et al., "Deuterium Isotope Effects In—the Metabolism of Drugs and Xenobiotics: Implications for Drug Design," Advances in Drug Research, 1985, vol. 14, pp. 2-36.
Greene, T. et al., Editor, Protective Groups in Organic Synthesis (3rd ed.), John Wiley & Sons, NY (1999), (20 pages, Table of Contents).
Hansen, H.H. et al., "Kv7 Channels: Interaction with Dopaminergic and Serotonergic Neurotransmlsslon In the CNS." The Journal of Physiology, 2008, vol. 586 (7), pp. 1823-1832.
Hansen, H.H. et al., "The KCNQ Channel Opener Retigabine Inhibits the Activity of Mesencephalic Dopaminergic Systems of the Rat," The Journal of Pharmacology and Experimental Therapeutics, 2006, vol. 318 (3), pp. 1006-1019.
Jentsch, T.J. "Neuronal KCNQ Potassium Channels: Physiology and Role in Disease," Nature Reviews Neuroscience, 2000, vol. 1 (1), pp. 21-30.
Joshi, S. K. et al., "Comparison of Antinociceptive Actions of Standard Analgesics in Attenuating Capsaicin and Nerve-Injury-Induced Mechanical Hypersensitivity," Neuroscience, 2006, vol. 143, pp. 587-596.
Kato, S. et al., "Synthesis of Deuterated Mosapride Citrate," Journal of Labelled Compounds and Radiopharmaceuticals, 1995, vol. 36 (10), pp. 927-932.
Kim, S.H. et al., "An Experimental Model for Peripheral Neuropathy Produced by Segmental Spinal Nerve Ligation in the Rat," Pain, 1992, vol. 50(3), pp. 355-363.

Klotzer, W. et al. "Electrophilic N-Amination of Imide Sodium Salts With O-Diphenylphosphinylhydroxylamine (DPH): 7-Aminotheophylline," Organic Syntheses Coll., 1990, vol. 7, p. 8; 1986, vol. 64, pp. 96-103.
Kushner, D. J. et al., "Pharmacological uses and perspectives of heavy water and deuterated compounds," Canadian Journal of Physiology and Pharmacology, 1999, vol. 77 (2), pp. 79-88.
Lizondo, J. et al., "Linezolid: Oxazolidinone antibacterial." Drugs of the Future, 1996, vol. 21 (11), pp. 1116-1123.
Mallesham, B. et al., "Highly Efficient Cul-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
March, J., Advanced Organic Chemistry: Reactions, Mechanisms and Structure, 4th Ed, John Wiley & Sons, New York, 1992, pp. 539-542 and 1167-1171.
Miceli, F. et al., "Molecular Pharmacology and Therapeutic Potential of Neuronal Kv7-Modulating Drugs," Current Opinion in Pharmacology, 2008, vol. 8 (1), pp. 65-74.
Munro, G. et al., "Kv7 (KCNQ) Channel Modulators and Neuropathic Pain," Journal of Medicinal Chemistry, 2007, vol. 50 (11), pp. 2576-2582.
Poste, G. et al., "Lipid Vesicles as Carriers for Introducing Biologically Active Materials into Cells," Methods in Cell Biology, 1976, vol. 14, pp. 33-71.
Roeloffs, R. et al., "In Vivo Profile of ICA-27243 [N-(6-Chloropyridin-3-yl)-3,4-difluoro-benzamide], a Potent and Selective KCNQ2/Q3(Kv7.2/Kv7.3) Activator in Rodent Anticonvulsant Models," The Journal of Pharmacology and Experimental Therapeutics, 2008, vol. 326 (3), pp. 818-828.
Roza C., et al., "Retigabine, the Specific KCNQ Channel Opener, Blocks Ectopic Discharges in Axotomized Sensory Fibres," Pain, 2008, vol. 138 (3), pp. 537-545.
Settepani, J.A. et al., "Heterocyclic Amines. II. Synthesis of 3,5-Diaminopyrazole," Journal of Organic Chemistry, 1968, vol. 33, p. 2606.
Sotty, F. et al., "Antipsychotic-Like Effect of Retigabine [N-(2-Amino-4-(Fluorobenzylamino)-Phenyl)Carbamic Acid Ester], A Kcnq Potassium Channel Opener, Via Modulation of Mesolimbic Dopaminergic Neurotransmission," The Journal of Pharmacology and Experimental Therapeutics, 2009, vol. 328 (3), pp. 951-962.
Streng, T. et al., "Urodynamic Effects of the K+ Channel (KCNQ) Opener Retigabine in Freely Moving, Conscious Rats," The Journal of Urology, 2004, vol. 172 (5 pt 1), pp. 2054-2058.
Thomson, J.F., "Physiological Effects of D20 in Mammals," Annals of the New York Academv of Sciences, 1960, vol. 84, pp. 736-744.
Villemin, D. et al., "Isonitriles as Efficient Ligands in Suzuki-Miyaura Reaction," Tetrahedron Letters, 2007, vol. 48, pp. 4191-4193.
Wickenden, A.O. et al., "Retigabine, A Novel Anti-Convulsant, Enhances Activation of KCNQ2/Q3 Potassium Channels," Molecular Pharmacology, 2000, vol. 58 (3), pp. 591-600.
Wu, Y.J. et al., "(S)-N-[1-(3-Morpholin-4-Ylphenyl)Elhyl]-3-Phenylacrylamide: An Orally Bioavailable KCNQ2 Opener with Significant Activity in a Cortical Spreading Depression Model of Migraine," The Journal of Medicinal Chemistry, 2003, vol. 46 (15), pp. 3197-3200.
Wu, Y.J. et al., "Fluorine Substitution Can Block Cyp3a4 Metabolism-Dependent Inhibition: Identification of (S)-N-[1-(4-Fluoro-3-Morpholin-4-Ylphenyl)Ethyl]-3-(4-Fluorophenyl)Acrylamide as an Orally Bioavailable KCNQ2 Opener Devoid of Cyp3a4 Metabolism-Dependent Inhibition," The Journal of Medicinal Chemistry, 2003, vol. 46 (18), pp. 3778-3781.

* cited by examiner

POTASSIUM CHANNEL MODULATORS

CROSS-REFERENCE TO RELATED APPLICATIONS

This application claims the benefit of provisional application Ser. No. 61/485,828 filed May 13, 2011, which is hereby incorporated by reference as if set forth in its entirety.

TECHNICAL FIELD OF THE INVENTION

Compounds that are potassium channel modulators, compositions comprising such compounds, and methods of treating conditions and disorders using such compounds and compositions are disclosed.

BACKGROUND OF THE INVENTION

Potassium channels are membrane-bound proteins responsible for regulating the flow of potassium ions through a cell membrane. The KCNQ (or $K_v7$) family is an important class of potassium channel that plays a key role in the process of neuronal excitability. There are five recognized subtypes of KCNQ channel: KCNQ1, KCNQ2, KCNQ3, KCNQ4, and KCNQ5. The KCNQ2-KCNQ5 subtypes represent the neuronal KCNQ subtypes. Miceli, *Curr. Op. Pharmacol.*, 2008, 8, 65. Functional KCNQ channels are formed by the assemblage of four individual subunits into a homotetramer or heterotetramer. The KCNQ2/3 channel is composed of a heterotetrameric assemblage of the KCNQ2 and KCNQ3 proteins.

The neuronal KCNQ channels are voltage-gated potassium channels that control cellular excitability by hyperpolarizing membrane potential, reducing action potential firing, and decreasing neurotransmitter release. Jentsch, *Nature Reviews Neurosci.*, 2000, 1, 21; Dalby-Brown, *Curr. Top. Med. Chem.*, 2006, 6, 999; Munro, *J. Med. Chem.*, 2007, 50, 2576. Neuronal KCNQ channels become activated on cellular depolarization (i.e., a change in voltage). See, Roza et al., *Pain,* 2008, 138, 537; Wickenden et al., *Mol. Pharmacol.*, 2000, 58, 591.

Activation of KCNQ channels by KCNQ openers causes an outflow of potassium ions from the cell, reducing the membrane potential (i.e., hyperpolarization), and thereby decreasing cellular excitability and action potential generation. Miceli, *Curr. Op. Pharmacol.*, 2008, 8, 65. In view of the role that KCNQ channels play in controlling cellular excitability and their distribution throughout the nervous system, KCNQ channel openers have been reported to have therapeutic utility in the treatment of a number of disorders characterized by abnormal neuronal excitability including: epilepsy, pain, migraine, anxiety, and overactive bladder. Dalby-Brown, *Curr. Top. Med. Chem.*, 2006, 6, 999; Streng, *J. Urol.*, 2004, 172, 2054. The dampening effect on neuronal excitability of KCNQ opening has also been implicated as a mechanism to inhibit the release of neurotransmitters (e.g., dopamine and serotonin) involved in schizophrenia, anxiety, and substance abuse. Hansen, *J. Physiol.* 2008, 1823.

A number of KCNQ openers, including flupirtine and retigabine, have been reported to be efficacious in treating various pain states in humans or rodents. These pain states include neuropathic pain (including diabetic polyneuropathy), inflammatory pain, persistent pain, cancer pain, and postoperative pain. Munro, *J. Med. Chem.*, 2007, 50, 2576; Dalby-Brown, *Curr. Top. Med. Chem.*, 2006, 6, 999. Thus, KCNQ openers have utility in treating a variety of painful conditions including, but not limited to, the foregoing types of pain.

The utility of KCNQ openers in the treatment of epilepsy is shown by the anticonvulsant and antiseizure activity of flupirtine, retigabine, and ICA-27243. Roeloffs, *J. Pharmacol. Exp. Ther.,* 2008, 326, 818; Miceli, *Curr. Op. Pharmacol.,* 2008, 8, 65; Blackburn-Munro, *CNS Drug Rev.,* 2005, 11, 1.

The utility of KCNQ openers in the treatment of migraine is indicated by the activity of KCNQ openers in an animal model of migraine. Wu, *J. Med. Chem.,* 2003, 46, 3197; Wu, *J. Med. Chem.,* 2003, 46, 3778.

The utility of KCNQ openers as anxiolytics is indicated by the activity of retigabine in animal models of anxiety. Dalby-Brown, *Curr. Top. Med. Chem.,* 2006, 6, 999.

The utility of KCNQ openers in the treatment of schizophrenia is indicated by the ability of retigabine to inhibit the activity of dopaminergic systems (Hansen, *J. Pharmacol. Exp. Ther.,* 2006, 318, 1006; Hansen, *J. Physiol.* 2008, 1823; Sotty, *J. Pharmacol. Exp. Ther.,* 2009, 328, 951) and by retigabine's efficacy in animal models of schizophrenia. Sotty, *J. Pharmacol. Exp. Ther.,* 2009, 328, 951.

Flupirtine and retigabine both possess liabilities in terms of adverse effects, including: asthenia, ataxia, insomnia, headache, drowsiness, dizziness, somnolence, dry mouth, nausea, vomiting, gastric and abdominal discomfort, sedation or loss of motor coordination. Miceli, *Curr. Op. Pharmacol.,* 2008, 8, 65; Munro, *J. Med. Chem.,* 2007, 50, 2576; Blackburn-Munro, *CNS Drug Rev.,* 2005, 11, 1. These adverse effects may be related to activation of one or more KCNQ subtypes not primarily responsible for the desirable therapeutic response. Thus, there is a need for KCNQ openers with efficacy in one or more of the foregoing disorders, states, or conditions, but without the side-effects of flupirtine or retigabine. KCNQ openers that selectively activate a particular subtype or subtypes may possess such efficacy with reduced side-effects.

SUMMARY OF THE INVENTION

Provided herein are compounds of formula (I)

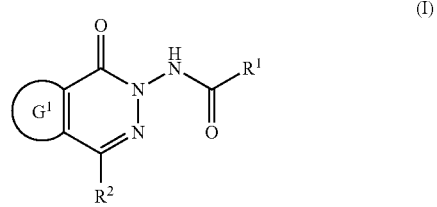

or pharmaceutically acceptable salts, prodrugs, solvates, or combinations thereof, wherein ring $G^1$ is benzo, heteroaryl, cycloalkyl, cycloalkenyl, or heterocycle, each of which is independently unsubstituted or substituted with 1, 2, 3, 4, or 5 substituents as represented by T;

$R^1$ is alkyl, alkenyl, alkynyl, haloalkyl, each of which is optionally substituted with one or two groups independently selected from the group consisting of $OR^y$, $N(R^y)_2$, $S(R^y)$, $C(O)OR^y$, $C(O)R^y$, and $C(O)N(R^y)_2$, or $R^1$ is $G^{1a}$, or $R^1$ is —$(CR^{1a}R^{1b})_n$-$G^{1a}$ wherein one of $CR^{1a}R^{1b}$ groups is optionally replaced by O, N(H), N(alkyl), S, S(O), or $S(O)_2$;

$R^{1a}$, at each occurrence, is independently hydrogen, alkyl, halogen, or haloalkyl;

$R^{1b}$, at each occurrence, is independently hydrogen, alkyl, halogen, haloalkyl, $OR^y$, $N(R^y)_2$, $S(R^y)$, $C(O)OR^y$, $C(O)R^y$, $C(O)N(R^y)_2$, —$(C_1$-$C_6$ alkylenyl)$OR^y$, —$(C_1$-$C_6$ alkylenyl)N$(R^y)_2$, —$(C_1$-$C_6$ alkylenyl)$S(R^y)$, —$(C_1$-$C_6$ alkylenyl)$C(O)$ $OR^y$, —$(C_1$-$C_6$ alkylenyl)$C(O)R^y$, or —$(C_1$-$C_6$ alkylenyl)$C(O)N(R^y)_2$;

R$^y$, at each occurrence, is independently hydrogen, alkyl, or haloalkyl;

G$^{1a}$, at each occurrence, is independently aryl, heteroaryl, heterocycle, cycloalkenyl, or cycloalkyl; each of which is independently unsubstituted or substituted with 1, 2, 3, 4, or 5 substituents as represented by R$^{101}$;

R$^2$ is —OR$^{2ac}$, —SR$^{2bc}$, —S(O)R$^{2bc}$, —S(O)$_2$R$^{2bc}$, —S(O)$_2$N(R$^{2d}$)(R$^{2e}$), —C(O)R$^{2cc}$, —C(O)OR$^{2cc}$, —C(O)N(R$^{2d}$)(R$^{2e}$), N(R$^{2d}$)(R$^{2e}$), —C(R$^{2d}$)=NOR$^{2dc}$, G$^{2a}$, —(CR$^{2a}$R$^{2b}$)$_p$-G$^{2a}$, —(CR$^{2a}$R$^{2b}$)$_p$—OR$^{2ac}$, —(CR$^{2a}$R$^{2b}$)$_p$—SR$^{2bc}$, —(CR$^{2a}$R$^{2b}$)$_p$—S(O)R$^{2bc}$, —(CR$^{2a}$R$^{2b}$)$_p$—C(O)R$^{2cc}$, —(CR$^{2a}$R$^{2b}$)$_p$—C(O)OR$^{2cc}$, —(CR$^{2a}$R$^{2b}$)$_p$—C(O)N(R$^{2d}$)(R$^{2e}$), —(CR$^{2a}$R$^{2b}$)$_p$—N(R$^{2d}$)(R$^{2e}$), or —(CR$^{2a}$R$^{2b}$)$_p$—S(O)$_2$N(R$^{2d}$)(R$^{2e}$), —(CR$^{2a}$R$^{2b}$)$_p$—S(O)$_2$R$^{2bc}$;

R$^{2a}$ and R$^{2b}$, at each occurrence, are each independently hydrogen, alkyl, haloalkyl, —C(O)OR$^{2aa}$, G$^{2b}$, or —(C$_1$-C$_6$ alkylenyl)-G$^{2b}$;

R$^{2aa}$, at each occurrence, is independently hydrogen, alkyl, haloalkyl, G$^{2b}$, or —(C$_1$-C$_6$ alkylenyl)-G$^{2b}$;

R$^{2ac}$, R$^{2bc}$, R$^{2cc}$, R$^{2dc}$, and R$^{2d}$, at each occurrence, are each independently hydrogen, alkyl, haloalkyl, G$^{2c}$, or —(C$_1$-C$_6$ alkylenyl)-G$^{2c}$;

R$^{2e}$, at each occurrence, is independently hydrogen, alkyl, haloalkyl, -alkylenyl-alkoxy, -alkylenyl-haloalkoxy, —C(O)R$^{2f}$, —C(O)OR$^{2f}$, S(O)$_2$R$^{2f}$, —C(O)NR$^{2f}$R$^{2g}$, —C(O)—(C$_1$-C$_6$ alkylenyl)NR$^{2fg}$R$^{2g}$, or -alkylenyl-CN;

R$^{2f}$, at each occurrence, is independently hydrogen, alkyl, haloalkyl, G$^{2d}$, or —(C$_1$-C$_6$ alkylenyl)-G$^{2d}$;

R$^{2fg}$, at each occurrence, is independently hydrogen, alkyl, haloalkyl, —C(O)OR$^{2h}$, G$^{2d}$, or —(C$_1$-C$_6$ alkylenyl)-G$^{2d}$;

R$^{2g}$ and R$^{2h}$, at each occurrence, are each independently hydrogen, alkyl, or haloalkyl, G$^{2a}$, at each occurrence, is independently heteroaryl or heterocycle; each of which is optionally substituted with 1, 2, 3, 4, or 5 R$^{102}$ groups;

G$^{2b}$, G$^{2c}$, and G$^{2d}$, at each occurrence, are each independently aryl, heteroaryl, heterocycle, cycloalkyl, or cycloalkenyl; each of which is optionally substituted with 1, 2, 3, 4, or 5 R$^{103}$ groups;

T, R$^{101}$, R$^{102}$, and R$^{103}$, at each occurrence, are each independently G$^a$, alkyl, alkenyl, alkynyl, halogen, haloalkyl, oxo, —CN, —NO$_2$, —OR$^a$, —OC(O)R$^a$, —OC(O)NR$^a$R$^b$, —NR$^a$R$^b$, —SR$^a$, —S(O)R$^a$, —S(O)$_2$R$^a$, —S(O)$_2$NR$^a$R$^b$, —C(O)R$^a$, —C(O)OR$^a$, —C(O)NR$^a$R$^b$, —N(R$^a$)C(O)OR$^b$, —N(R$^a$)C(O)NR$^a$R$^b$, —N(R$^a$)S(O)$_2$NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—OC(O)R$^a$, —(CR$^{za}$R$^{zb}$)$_m$—OC(O)NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—S(O)$_2$NR$^a$R$^b$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, —(CR$^{za}$R$^{zb}$)$_m$—NR$^a$R$^b$, —(CR$^{za}$R$^{zb}$)$_m$—N(R$^a$)C(O)OR$^b$, —(CR$^{za}$R$^{zb}$)$_m$—N(R$^a$)C(O)NR$^a$R$^b$, —(CR$^{za}$R$^{zb}$)$_m$—N(R$^a$)S(O)$_2$NR$^a$R$^b$, or —(CR$^{za}$R$^{zb}$)$_m$-G$^a$;

R$^a$ and R$^b$, at each occurrence, are each independently hydrogen, alkyl, haloalkyl, G$^a$, or —(C$_1$-C$_6$ alkylenyl)-G$^a$;

G$^a$, at each occurrence, is independently aryl, heteroaryl, heterocycle, cycloalkyl or cycloalkenyl, each of which is independently unsubstituted or substituted with 1, 2, 3, 4, or 5 substituents independently selected from the group consisting of alkyl, alkenyl, alkynyl, halogen, haloalkyl, oxo, —CN, —NO$_2$, —OR$^{a'}$, —OC(O)R$^{a'}$, —OC(O)NR$^{a'}$R$^{b'}$, —NR$^{a'}$R$^{b'}$, —SR$^{a'}$, —S(O)R$^{a'}$, —S(O)$_2$R$^{a'}$, —S(O)$_2$NR$^{a'}$R$^{b'}$, —C(O)R$^{a'}$, —C(O)OR$^{a'}$, —C(O)NR$^{a'}$R$^{b'}$, —N(R$^{a'}$)C(O)OR$^{b'}$, —N(R$^{a'}$)C(O)NR$^{a'}$R$^{b'}$, —N(R$^{a'}$)S(O)$_2$NR$^{a'}$R$^{b'}$, —(C$_1$-C$_6$ alkylenyl)-CN, —(C$_1$-C$_6$ alkylenyl)-NO$_2$, —(C$_1$-C$_6$ alkylenyl)-OR$^{a'}$, —(C$_1$-C$_6$ alkylenyl)-OC(O)R$^{a'}$, —(C$_1$-C$_6$ alkylenyl)-OC(O)NR$^{a'}$R$^{b'}$, —(C$_1$-C$_6$ alkylenyl)-SR$^{a'}$, —(C$_1$-C$_6$ alkylenyl)-S(O)R$^{a'}$, —(C$_1$-C$_6$ alkylenyl)-S(O)$_2$R$^{a'}$, —(C$_1$-C$_6$ alkylenyl)-S(O)$_2$NR$^{a'}$R$^{b'}$, —(C$_1$-C$_6$ alkylenyl)-C(O)R$^{a'}$, —(C$_1$-C$_6$ alkylenyl)-C(O)OR$^{a'}$, —(C$_1$-C$_6$ alkylenyl)-C(O)NR$^{a'}$R$^{b'}$, —(C$_1$-C$_6$ alkylenyl)-NR$^{a'}$R$^{b'}$, —(C$_1$-C$_6$ alkylenyl)-N(R$^{a'}$)C(O)OR$^{b'}$, —(C$_1$-C$_6$ alkylenyl)-N(R$^{a'}$)C(O)NR$^{a'}$R$^{b'}$, and —(C$_1$-C$_6$ alkylenyl)-N(R$^{a'}$)S(O)$_2$NR$^{a'}$R$^{b'}$;

R$^{za}$, R$^{zb}$, R$^{a'}$, and R$^{b'}$, at each occurrence, are each independently hydrogen, alkyl, halogen, or haloalkyl;

m, n, and p, at each occurrence, are each independently 1, 2, 3, or 4.

Compounds described herein or pharmaceutically acceptable salts or solvates thereof are modulators of KCNQ potassium channels and are thus useful in the treatment of diseases, disorders, or conditions of a subject that are responsive to the opening of the modulation of the potassium channels.

Compounds of formula (I) are openers of KCNQ potassium channels and are useful in the treatment of conditions or disorders that are responsive to the opening of the KCNQ potassium channels, including pain.

Another aspect is related to pharmaceutical compositions comprising therapeutically effective amount of a compound described herein or a pharmaceutically acceptable salt or solvate thereof, in combination with a pharmaceutically acceptable carrier. Such compositions can be administered in accordance with a method of the invention, typically as part of a therapeutic regimen for treatment or prevention of conditions and disorders related to the modulation of KCNQ channels. More particularly, the methods are useful for treating disorders or conditions related to pain such as neuropathic pain (including diabetic polyneuropathy), nociceptive pain, persistent pain, osteoarthritic pain, cancer pain, inflammatory pain, and postoperative pain, fibromyalgia, chronic widespread pain, musculoskeletal pain, myofascial pain, temporomandibular joint pain (TMJ pain), as well as epilepsy, migraine, overactive bladder, schizophrenia, anxiety, and substance abuse.

Further provided herein are the use of the present a compound described herein or a pharmaceutically acceptable salt or solvate thereof, in the manufacture of a medicament for the treatment of the disease conditions described above, alone or in combination with a pharmaceutically acceptable carrier, particularly for the treatment or alleviation of disorders or conditions related to neuropathic pain (including diabetic polyneuropathy), nociceptive pain, persistent pain, osteoarthritic pain, cancer pain, inflammatory pain, postoperative pain, fibromyalgia, chronic widespread pain, musculoskeletal pain, myofascial pain, temporomandibular joint pain (TMJ pain), epilepsy, migraine, overactive bladder, schizophrenia, anxiety, and substance abuse.

The compounds, compositions comprising the compounds or pharmaceutically acceptable salts or solvates thereof, and methods for treating or preventing conditions and disorders by administering the compounds or compositions thereof are further described herein.

These and other objectives are described in the following paragraphs. These objectives should not be deemed to narrow the scope of the invention.

DETAILED DESCRIPTION OF THE INVENTION

Provided herein are compounds of formula (I)

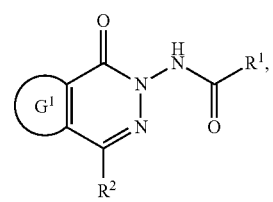

(I)

wherein $G^1$, $R^1$, and $R^2$ are as defined above in the Summary and below in the Detailed Description. Compositions comprising such compounds and methods for treating conditions and disorders using such compounds and compositions are also disclosed.

In various embodiments, there may be variables that occur more than one time in any substituent or in the compound or any other formula herein. Definition of a variable on each occurrence is independent of its definition at another occurrence. Further, combinations of variables or substituents are permissible only if such combinations result in stable compounds. Stable compounds are compounds that can be isolated from a reaction mixture.

a. Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a saturated, straight or branched hydrocarbon chain containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a saturated, straight or branched hydrocarbon chain of from 1 to 10 carbon atoms. Representative examples of alkylene include, but are not limited to, —CH$_2$—, —CH(CH$_3$)—, —CH(C$_2$H$_5$)—, —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl (including 1,2,3,4-tetrahydronaphthalen-1-yl). The phenyl and the bicyclic aryls are attached to the parent molecular moiety through any carbon atom contained within the phenyl or the bicyclic aryls respectively.

The term "cycloalkenyl" as used herein, means a monocyclic hydrocarbon ring system containing three-, four-, five-, six-, seven-, or eight carbon atoms and zero heteroatoms in the ring. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. The cycloalkenyl rings may have one or two pairs of non-adjacent carbon atoms within the ring system linked by one or two alkylene bridge(s) of 1, 2, 3, or 4 carbon atoms respectively. An example of such bridged cycloalkenyl group includes, but is not limited to, norbornene (bicyclo[2.2.1]hept-5-ene-2-yl). The cycloalkenyl groups are appended to the parent molecular moiety through any substitutable carbon atom within the groups.

The term "cycloalkyl" as used herein, means a monocyclic, or a bicyclic cycloalkyl, or a spirocyclic cycloalkyl. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl ring. An example of a spirocyclic cycloalkyl is spiro[2.5]octane. The monocyclic cycloalkyl and the bicyclic cycloalkyl rings may have one or two pairs of non-adjacent carbon atoms within the ring system linked by one or two alkylene bridge(s) of 1, 2, 3, or 4 carbon atoms respectively. Non-limiting examples of such cycloalkyls include, hexahydro-2,5-methanopentalen-3a(1H)-yl, bicyclo[2.2.1]heptyl, bicyclo[3.1.1]heptyl (including bicyclo[3.1.1]hept-2-yl), bicyclo[2.2.2]octyl, bicyclo[3.3.1]nonyl, adamantane (tricyclo[3.3.1.1$^{3,7}$]decane), and noradamantane (octahydro-2,5-methanopentalene). The monocyclic, bicyclic, and spirocyclic cycloalkyl groups are appended to the parent molecular moiety through any substitutable carbon atom of the groups.

The term "halo" or "halogen" as used herein, means —Cl, —Br, —I or —F.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "haloalkoxy" as used herein, means an alkoxy group as defined herein, in which one, two, three, four, five, six, or seven hydrogen atoms are replaced by halogen. Non-limiting examples of haloalkoxy include trifluoromethoxy, 2,2,2-trifluoroethoxy, and 2-fluoroethoxy.

The term "heteroaryl" as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, 1,2-benzoxazol-3-yl, 1,3-benzothiazolyl, benzimidazolyl, benzothienyl, furopyridine, indolyl, indazolyl, isoindolyl, isoquinolinyl, naphthyridinyl, oxazolopyridine, quinolinyl, quinazolinyl, quinoxalinyl, and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings may optionally be oxidized (e.g. 1-oxidopyridinyl) and the nitrogen atoms may optionally be quarternized, and are contemplated within the scope of the invention.

The term "heterocycle" or "heterocyclic" as used herein, means a monocyclic, bicyclic, or a spirocyclic ring system containing at least one heteroatom. The monocyclic heterocycle is a 3-, 4- 5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Representative examples of monocyclic heterocycles include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Non-limiting examples of bicyclic heterocycle include 1,3-benzodioxolyl, 1,3-benzodithiolyl, 2,3-dihydro-1,4-benzodioxinyl, 2,3-dihydrobenzofuranyl, 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl. One example of a spiroheterocycle is 5-oxaspiro[3,4]octane. One or two pairs of non-adjacent carbon atoms within the monocyclic or bicyclic ring system may be linked by one or two alkylene bridge(s) of 1, 2, 3, or 4 carbon atoms respectively, one or two carbon atoms of the alkylene bridge(s) is optionally replaced by heteroatom(s) selected from O, N or S, wherein the nitrogen and sulfur atoms are optionally oxidized, and the nitrogen atom(s) are optionally quarternized. Non-limiting examples of the heterocycloalkyls containing such bridge include, oxadamantane (oxatricyclo[3.3.1.1$^{3,7}$]decane), azaadamantane, and azabicyclo[2.2.1]heptyl. The heterocycle groups are connected to the parent molecular moiety through any substitutable carbon atom or any substitutable nitrogen atom contained within the group. The nitrogen and sulfur heteroatoms in the heterocycle rings may optionally be oxidized (e.g. 1,1-dioxidothiomorpholinyl (thiomorpholine sulfone)) and the nitrogen atoms may optionally be quarternized.

In some instances, the number of carbon atoms in a substituent (e.g., alkyl, alkenyl, alkynyl, alkoxy, haloalkoxy, or cycloalkyl) is indicated by the prefix "$C_x$-$C_y$," wherein x is the minimum and y is the maximum number of carbon atoms in the substituent. Thus, for example, "$C_1$-$C_6$ alkyl" refers to an alkyl substituent containing from 1 to 6 carbon atoms. Illustrating further, $C_3$-$C_6$ cycloalkyl means a saturated carbocyclic ring containing from 3 to 6 carbon ring atoms.

If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 5 non-hydrogen radicals, then any heteroaryl with less than 5 substitutable positions would be optionally substituted by up to only as many non-hydrogen radicals as the heteroaryl has substitutable positions. To illustrate, thienyl (which has only four substitutable positions) would be optionally substituted with up to four non-hydrogen radicals.

The term "heteroatom" means N, O, or S.

The term "oxo" means =O.

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "modulate" refers to the ability of a compound to increase or decrease the function, or activity, of KCNQ channels. "Modulation", as used herein in its various forms, is intended to encompass antagonism, agonism, partial antagonism and/or partial agonism of the activity associated with KCNQ channels. KCNQ channel activators are compounds that, e.g., bind to, stimulate, increase, open, activate, or facilitate KCNQ channels such as, but not limited to, KCNQ2, and/or KCNQ3, and/or KCNQ2/3 potassium channels. Activation of KCNQ channels encompasses either or both of: (1) increasing current through a KCNQ channel; or (2) shifting the half-activation potential of KCNQ channels to lower voltages (i.e. a hyperpolarizing shift of the $V_{1/2}$ for activation).

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. Compounds

KCNQ channel modulators have formula (I) as described above.

Particular values of variable groups in compounds of formula (I) are as follows. Such values may be used where appropriate with any of the other values, definitions, claims or embodiments defined hereinbefore or hereinafter.

In compounds of formula (I), ring $G^1$ has values as disclosed in the Summary.

In certain embodiments, ring $G^1$ is benzo, heteroaryl, or cycloalkyl.

In certain embodiments, ring $G^1$ is benzo, thus, included herein are compounds of formula (I-a)

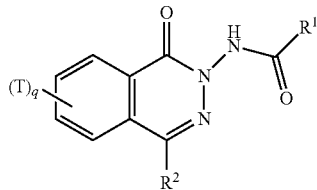
(I-a)

In certain embodiments, ring $G^1$ is heteroaryl. Examples of such heteroaryl include, but are not limited to, thienyl and pyridinyl. Examples of compounds of formula (I) containing such rings include, but are not limited to, those represented by formula (I-b), (I-c), and (I-d):

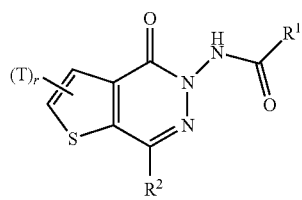
(I-b)

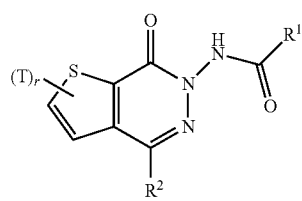
(I-c)

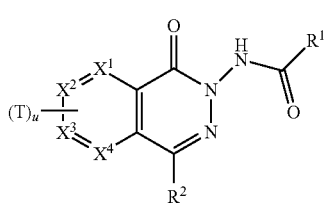
(I-d)

In certain embodiments, ring $G^1$ is cycloalkyl, for example, a monocyclic cycloalkyl which may contain one or two alkylene bridges of 1, 2, 3, or 4 carbon atoms linking one or two pairs of non-adjacent carbon atoms within the ring system respectively. Examples of compounds of formula (I) containing such rings include but are not limited to those represented by formula (I-e).

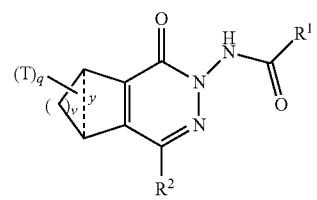
(I-e)

In compounds of formula (I-a)-(I-e) $R^1$, $R^2$, and T are as described in the Summary and in the embodiments herein; q is 0, 1, 2, 3, or 4; r is 0, 1, or 2; u is 0, 1, 2, or 3; v is 1, 2, or 3; dashed-line y is absent, a bond, —$CH_2$—, or —$CH_2CH_2$—; one or two of $X^1$, $X^2$, $X^3$, and $X^4$ are N and the others are CH.

Formula (I-e) can be described using the aforementioned values of y. For example, when y is absent, the compounds of the formula (I-e) can be represented by formula (I-e-i)

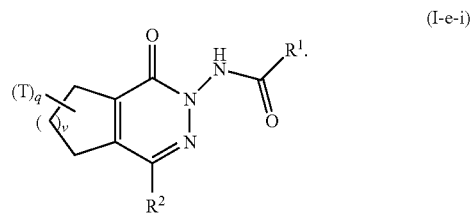
(I-e-i)

For example, when y is a bond, the compounds of the formula (I-e) can be represented by formula (I-e-ii)

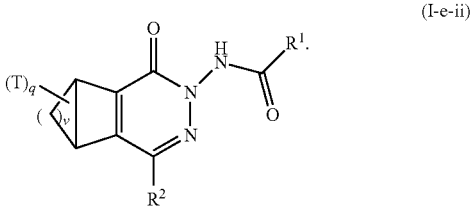
(I-e-ii)

For example, when y is a —$CH_2$—, the compounds of the formula (I-e) can be represented by formula (I-e-iii)

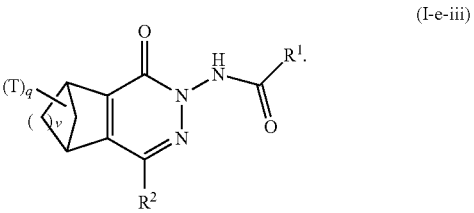
(I-e-iii)

For example, when y is a —$CH_2CH_2$—, the compounds of the formula (I-e) can be represented by formula (I-e-iv)

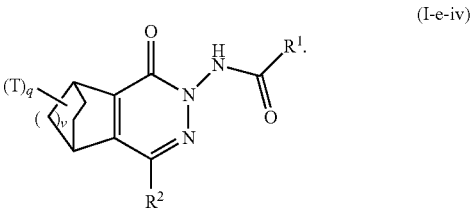
(I-e-iv)

In compounds of formula (I-e-i)-(I-e-iv), $R^1$, $R^2$, T, v, and q are as described in the embodiments herein above and below. In certain embodiments, v is 1. In yet other embodiments, v is 2.

T, when present in formula (I), (I-a)-(I-e), and (I-e-i)-(I-e-iv) is attached to any substitutable carbon atoms of ring $G^1$ and has values as described in the Summary and embodiments herein.

For example, certain compounds of formula (I), (I-a)-(I-e), and (I-e-i)-(I-e-iv) include those wherein T is absent.

Yet certain groups of compounds of formula (I), (I-a)-(I-e), and (I-e-i)-(I-e-iv) include those wherein T, at each occurrence, is independently halogen (e.g. Br, F), alkyl (e.g. $C_1$-$C_6$ alkyl such as, but not limited to, ethyl, methyl), or haloalkyl (e.g. trifluoromethyl).

$R^1$ for compounds of formula (I), (I-a)-(I-e), and (I-e-i)-(I-e-iv) have values as described in the Summary and embodiments herein.

For example, a group of compounds of formula ((I), (I-a)-(I-e), and (I-e-i)-(I-e-iv) include those wherein $R^1$ is unsubstituted alkyl (e.g. $C_1$-$C_6$ alkyl such as, but not limited to, methyl, ethyl, isopropyl, 2,2-dimethylpropyl, tert-butyl), unsubstituted haloalkyl (e.g. 2,2,2-trifluoroethyl), $G^{1a}$, or —$(CR^{1a}R^{1b})_n$-$G^{1a}$. In certain embodiments, $R^1$ is unsubstituted alkyl (e.g. $C_1$-$C_6$ alkyl such as, but not limited to, methyl, ethyl, isopropyl, 2,2-dimethylpropyl, tert-butyl) or unsubstituted haloalkyl (e.g. 2,2,2-trifluoroethyl). In certain embodiments, $R^1$ is $G^{1a}$ or —$(CR^{1a}R^{1b})_n$-$G^{1a}$. In certain embodiments, $R^1$ is —$(CR^{1a}R^{1b})_n$-$G^{1a}$. $R^{1a}$, $R^{1b}$, $G^{1a}$, and n are as described in the Summary and embodiments herein. $R^{1a}$ and $R^{1b}$ can be the same or different, and are each independently hydrogen or alkyl such as, but not limited to, $C_1$-$C_6$ alkyl (e.g. methyl). In certain embodiments, $R^{1a}$ and $R^{1b}$ are hydrogen. n, for example, is 1 or 2. In certain embodiments, n is 1. For example, $G^{1a}$ is aryl (e.g. phenyl, naphthyl), cycloalkyl such as, but not limited to $C_3$-$C_6$ alkyl (e.g. cyclopropyl, cyclobutyl, cyclopentyl, cyclohexyl), adamantyl, noradamantyl, bicyclo[2.2.1]heptyl, and bicyclo[3.1.1]heptyl; cycloalkenyl such as, but not limited to, bicyclo[2.2.1]heptenyl; hetroaryl such as, but not limited to, 1,2-benzoxazolyl; or heterocycle such as, but not limited to, benzodioxolyl, tetrahydrofuranyl. In certain embodiments, $G^{1a}$ is cycloalkyl (e.g. bicyclo[2.2.1]heptyl or bicyclo[3.1.1]heptyl). In certain embodiments, $G^{1a}$ is aryl (e.g. phenyl). Each of the aforementioned $G^{1a}$ (including exemplary rings) is optionally substituted as described in the Summary and embodiments herein. Examples of the optional substituents ($R^{101}$) of $G^{1a}$ include, but are not limited to, alkyl (e.g. $C_1$-$C_6$ alkyl such as, but not limited to, methyl, ethyl, isopropyl), halogen (e.g. Cl, F, Br), haloalkyl (e.g. trifluoromethyl), —CN, $NO_2$, —$OR^a$, —$S(O)_2R^a$, $NR^aR^b$, and $G^a$. $R^a$, $R^b$, and $G^a$ are as described in the Summary and embodiments herein. $G^a$, for example, is optionally substituted aryl such as, but not limited to, optionally substituted phenyl. $R^a$, for example, is hydrogen, $C_1$-$C_6$ alkyl such as, but not limited to, methyl, haloalkyl such as, but not limited to, trifluoromethyl, or benzyl.

$R^2$ for compounds of formula (I), (I-a)-(I-e), and (I-e-i)-(I-e-iv) have values as disclosed in the Summary and embodiments herein. In certain embodiments, $R^2$ is —$OR^{2ac}$, —$SR^{2bc}$, —$S(O)R^{2bc}$, —$S(O)_2R^{2bc}$, —$C(O)R^{2cc}$, —$C(O)OR^{2cc}$, —$C(O)N(R^{2d})(R^{2e})$, $N(R^{2d})(R^{2e})$, —$C(R^{2d})$=$NOR^{2dc}$, $G^{2a}$, —$(CR^{2a}R^{2b})_p$-$G^{2a}$, —$(CR^{2a}R^{2b})_p$—$OR^{2ac}$, —$(CR^{2a}R^{2b})_p$—$C(O)OR^{2cc}$, —$(CR^{2a}R^{2b})_p$—$C(O)N(R^{2d})(R^{2e})$, or —$(CR^{2a}R^{2b})_p$—$N(R^{2d})(R^{2e})$. $R^{2ac}$, $R^{2bc}$, $R^{2cc}$, $R^{2d}$, $R^{2e}$, $R^{2dc}$, $G^{2a}$, $R^{2a}$, $R^{2b}$, and p, are as disclosed in the Summary and embodiments herein below.

For example, included are a group of compounds of formula (I), (I-a)-(I-e), and (I-e-i)-(I-e-iv) are those wherein $R^2$ is $G^{2a}$ or —$(CR^{2a}R^{2b})_p$-$G^{2a}$. In certain embodiments, $R^2$ is $G^{2a}$. $G^{2a}$, $R^{2a}$, $R^{2b}$, and p, are as disclosed in the Summary and embodiments herein. $G^{2a}$, for example, is heteroaryl such as, but not limited to, thienyl and pyridinyl; or heterocycle such as, but not limited to, morpholinyl, dihydropyranyl (e.g. 3,6-dihydro-2H-pyran-4-yl), pyrrolidinyl, tetrahydropyranyl, thiomorpholinyl, piperidinyl, and piperazinyl. In certain embodiments, $G^{2a}$ is heterocycle such as, but not limited to, morpholinyl, dihydropyranyl (e.g. 3,6-dihydro-2H-pyran-4-yl), pyrrolidinyl, tetrahydropyranyl, thiomorpholinyl, piperidinyl, and piperazinyl. In certain embodiments, $G^{2a}$ is pyridinyl or morpholinyl. In yet other embodiments, $G^{2a}$ is morpholinyl. Each of the aforementioned $G^{2a}$ (including exemplary rings) is optionally substituted as described in the Summary and embodiments herein. Examples of the optional substituents ($R^{102}$) of $G^{2a}$ include, but are not limited to, alkyl (e.g. $C_1$-$C_6$ alkyl such as, but not limited to, methyl, ethyl), halogen (e.g. Cl, F, Br), haloalkyl (e.g. trifluoromethyl), —CN, $NO_2$, —$OR^a$, —$S(O)_2R^a$, —$C(O)NR^aR^b$, —$C(O)OR^a$, $NR^aR^b$, and benzyl wherein $R^a$ and $R^b$ are as described in the Summary and embodiments herein. For example, $R^a$ and $R^b$ can be the same or different, and are each independently hydrogen or alkyl such as, but not limited to, $C_1$-$C_6$ alkyl (e.g. methyl). While $R^2$ is —$(CR^{2a}R^{2b})_p$-$G^{2a}$, $R^{2a}$ and $R^{2b}$ are the same or different, and at each occurrence, are each independently hydrogen or alkyl (e.g. methyl). In certain embodiments where $R^2$ is —$(CR^{2a}R^{2b})_p$-$G^{2a}$, $R^{2a}$ and $R^{2b}$ are, for example, hydrogen.

In certain embodiments, $R^2$ is —$SR^{2bc}$, —$S(O)R^{2bc}$, —$S(O)_2R^{2bc}$. In certain embodiments, $R^2$ is —$S(O)_2R^{2bc}$. $R^{2bc}$ is as described in the Summary and embodiments herein. For example, in certain embodiments, $R^{2bc}$ is alkyl (e.g. $C_1$-$C_6$ alkyl such as, but not limited to, tert-butyl), $G^{2c}$, or ($C_1$-$C_6$ alkylenyl)-$G^{2c}$; wherein $G^{2a}$ is as disclosed is as disclosed in the Summary and embodiments herein. Examples of $G^{2c}$ include, but are not limited to, aryl (e.g. phenyl) and heteroaryl (e.g. pyridinyl). Each of the $G^{2a}$ rings (including exemplary rings) is optionally substituted. Examples of the optional substituents ($R^{103}$) include, but are not limited to, alkyl (e.g. $C_1$-$C_6$ alkyl such as, but not limited to, methyl, ethyl), halogen (e.g. Cl, F, Br), haloalkyl (e.g. trifluoromethyl), —CN, $NO_2$, —$OR^a$, —$S(O)_2R^a$, —$C(O)NR^aR^b$, —$C(O)OR^a$, $NR^aR^b$, and —$N(R^a)C(O)OR^b$ wherein $R^a$ and $R^b$ are as described in the Summary and embodiments herein. For example, $R^a$ and $R^b$ can be the same or different, and are each independently hydrogen or alkyl such as, but not limited to, $C_1$-$C_6$ alkyl (e.g. methyl, tert-butyl). In certain embodiments, $R^2$ is —$S(O)_2R^{2bc}$ wherein $R^{2bc}$ is optionally substituted aryl (e.g. optionally substituted phenyl) wherein the optional substituents ($R^{103}$) are as described in the Summary and embodiments herein above.

In certain embodiments, $R^2$ is —$OR^{2ac}$ or —$(CR^{2a}R^{2b})_p$—$OR^{2ac}$; wherein $R^{2ac}$ $R^{2a}$, $R^{2b}$, and p are as described in the Summary and embodiment herein. For example, in the embodiments wherein $R^2$ is —$OR^{2ac}$, $R^{2ac}$ is $G^{2c}$ wherein $G^{2c}$ is as described in the Summary and embodiments herein. In certain embodiments, $G^{2c}$ is aryl optionally substituted with 1, 2, 3, 4, or 5 $R^{103}$. In certain embodiments, $G^{2c}$ is phenyl optionally substituted with 1, 2, 3, 4, or 5 $R^{103}$. $R^{103}$ is as described in the summary and embodiments in the paragraph above. In certain embodiments, $G^{2c}$ is unsubstituted phenyl. In the embodiments wherein $R^2$ is —$(CR^{2a}R^{2b})_p$—$OR^{2ac}$, $R^{2ac}$ is hydrogen and p is 1 or 2. $R^{2a}$ and $R^{2b}$ are the same or different, and are each independently hydrogen, alkyl (e.g. methyl), or optionally substituted phenyl.

In certain embodiments, $R^2$ is —$C(O)OR^{2cc}$, —$C(O)N(R^{2d})(R^{2e})$, —$(CR^{2a}R^{2b})_p$—$C(O)OR^{2cc}$, or —$(CR^{2a}R^{2b})_p$—$C(O)N(R^{2d})(R^{2e})$ wherein $R^{2cc}$, $R^{2d}$, $R^{2e}$, $R^{2a}$, $R^{2b}$, and p are as disclosed in the Summary and embodiments herein. For example, $R^{2a}$ and $R^{2b}$ are the same or different, and are each independently hydrogen or alkyl (e.g. methyl). $R^{2cc}$ and $R^{2d}$ are the same or different, and are each independently hydrogen, $C_1$-$C_6$ alkyl (e.g. methyl, ethyl, tert-butyl, 2,2-dimethylpropyl), or $G^{2c}$ (e.g. optionally substituted phenyl). $R^{2e}$, for example, is hydrogen or $C_1$-$C_6$ alkyl (e.g. methyl, ethyl, tert-butyl, 2,2-dimethylpropyl). In certain embodiments, p is 1 or 2. In certain embodiments, p is 1.

In certain embodiments, $R^2$ is $-C(O)R^{2cc}$ or $-(CR^{2a}R^{2b})_p-C(O)R^{2cc}$. In certain embodiments, $R^2$ is $-C(O)R^{2cc}$. $R^{2cc}$, $R^{2a}$, $R^{2b}$, and p are as disclosed in the Summary and embodiments herein. For example, $R^{2cc}$ is $G^{2c}$ wherein $G^{2c}$ is as disclosed in the Summary and embodiments herein. In certain compounds wherein $R^2$ is $-C(O)R^{2cc}$ or $-(CR^{2a}R^{2b})_p-C(O)R^{2cc}$, and $R^{2cc}$ is $G^{2c}$. Examples of $G^{2c}$ include, but not limited to, optionally substituted aryl (e.g. optionally substituted phenyl) and optionally substituted heterocycle (e.g. optionally substituted morpholinyl, optionally substituted piperazinyl). $R^{2a}$ and $R^{2b}$ are the same or different, and are each independently hydrogen or alkyl. In certain embodiments, $R^{2a}$ and $R^{2b}$ are the same or different, and are each independently hydrogen or methyl. In certain embodiments, p is 1 or 2. In certain embodiments, p is 1.

In certain embodiments, $R^2$ is $N(R^{2d})(R^{2e})$ or $-(CR^{2a}R^{2b})_p-N(R^{2d})(R^{2e})$. $R^{2d}$, $R^{2e}$, $R^{2a}$, $R^{2b}$, and p are as disclosed in the Summary and embodiments herein. In certain embodiments, $R^{2d}$ for example, is hydrogen, alkyl (e.g. methyl), optionally substituted phenyl, or benzyl. $R^{2e}$, for example, is hydrogen, alkyl (e.g. methyl), $-C(O)R^{2f}$, $-C(O)OR^{2f}$, $S(O)_2R^{2f}$, $-C(O)NR^{2f}R^{2g}$, or $-C(O)-(C_1-C_6$ alkylenyl)$NR^{2fg}R^{2g}$, wherein $R^{2f}$, $R^{2g}$, and $R^{2fg}$ are as disclosed in the Summary and embodiments herein. Examples of $R^{2f}$ include, but not limited to, hydrogen, alkyl (e.g. methyl, ethyl, isopropyl, tert-butyl, isobutyl, 1,1-dimethylpropyl, 2,2-dimethylpropyl), haloalkyl (e.g. trifluoromethyl, 2,2,2-trifluoroethyl), $G^{2d}$, or $-(C_1-C_6$ alkylenyl)-$G^{2d}$; wherein $G^{2d}$ is as disclosed in the Summary and embodiments herein, for example, $G^{2d}$ is aryl (e.g. phenyl) or cycloalkyl (e.g. cyclopentyl, cyclohexyl). Each of the rings (including exemplary rings) as represent by $G^{2d}$ is optionally substituted. Examples of the optional substituents of $G^{2d}$ include, but not limited to, alkyl (e.g. methyl, isopropyl), halogen (e.g. Cl) and haloalkyl (e.g. trifluoromethyl). $R^{2g}$, for example, is hydrogen or alkyl. $R^{2fg}$, for example, is hydrogen, alkyl, haloalkyl, or $-C(O)Oalkyl$. $R^{2a}$ and $R^{2b}$ are the same or different, and are each independently hydrogen, alkyl (e.g. methyl), $G^{2b}$ (e.g. optionally substituted phenyl), or $-C(O)Oalkyl$. p, for example, is 1 or 2.

It is appreciated that compounds of formula (I), (I-a)-(I-e), and (I-e-i)-(I-e-iv) with combinations of the above embodiments, including particular, more particular and preferred embodiments are contemplated.

For example, one aspect relates to a group of compounds of formula (I) wherein ring $G^1$ is benzo, heteroaryl, or cycloalkyl; and $R^1$ is unsubstituted alkyl (e.g. $C_1-C_6$ alkyl such as, but not limited to, methyl, ethyl, isopropyl, 2,2-dimethylpropyl, tert-butyl), unsubstituted haloalkyl (e.g. 2,2,2-trifluoroethyl), $G^{1a}$, or $-(CR^{1a}R^{1b})_n-G^{1a}$.

Another aspect relates to a group of compounds of formula (I) wherein ring $G^1$ is benzo, heteroaryl, or cycloalkyl and $R^1$ is unsubstituted alkyl (e.g. $C_1-C_6$ alkyl such as, but not limited to, methyl, ethyl, isopropyl, 2,2-dimethylpropyl, tert-butyl) or unsubstituted haloalkyl (e.g. 2,2,2-trifluoroethyl).

Another aspect relates to a group of compounds of formula (I) wherein ring $G^1$ is benzo, heteroaryl, or cycloalkyl and $R^1$ is $G^{1a}$, or $-(CR^{1a}R^{1b})_n-G^{1a}$.

Another aspect relates to a group of compounds of formula (I) wherein ring $G^1$ is benzo, heteroaryl, or cycloalkyl, and $R^1$ is $-(CR^{1a}R^{1b})_n-G^{1a}$.

Another aspect relates to a group of compounds of formula (I) wherein ring $G^1$ is benzo, heteroaryl, or cycloalkyl, $R^1$ is $-(CR^{1a}R^{1b})_n-G^{1a}$, and $G^{1a}$ is aryl or cycloalkyl, each of which is optionally substituted.

Another aspect relates to a group of compounds of formula (I) wherein ring $G^1$ is benzo, heteroaryl, or cycloalkyl, $R^1$ is $-(CR^{1a}R^{1b})_n-G^{1a}$, and $G^1$ is optionally substituted aryl. In certain embodiments, $G^{1a}$ is optionally substituted phenyl or optionally substituted naphthyl. In certain embodiments, $G^{1a}$ is optionally substituted phenyl.

Another aspect relates to a group of compounds of formula (I) wherein ring $G^1$ is benzo, heteroaryl, or cycloalkyl, $R^1$ is $-(CR^{1a}R^{1b})_n-G^{1a}$, and $G^1$ is optionally substituted cycloalkyl. In certain embodiments, $G^{1a}$ is $C_3-C_6$ cycloalkyl, adamantyl, noradamantyl, bicyclo[2.2.1]heptyl, or bicyclo[3.1.1]heptyl, each of which is optionally substituted.

Another aspect relates to a group of compounds of formula (I) wherein ring $G^1$ is benzo, and $R^1$ is unsubstituted alkyl (e.g. $C_1-C_6$ alkyl such as, but not limited to, methyl, ethyl, isopropyl, 2,2-dimethylpropyl, tert-butyl), unsubstituted haloalkyl (e.g. 2,2,2-trifluoroethyl), $G^{1a}$, or $-(CR^{1a}R^{1b})_n-G^{1a}$.

Another aspect relates to a group of compounds of formula (I) wherein ring $G^1$ is benzo, and $R^1$ is unsubstituted alkyl (e.g. $C_1-C_6$ alkyl such as, but not limited to, methyl, ethyl, isopropyl, 2,2-dimethylpropyl, tert-butyl) or unsubstituted haloalkyl (e.g. 2,2,2-trifluoroethyl).

Another aspect relates to a group of compounds of formula (I) wherein ring $G^1$ is benzo, and $R^1$ is $G^{1a}$ or $-(CR^{1a}R^{1b})_n-G^{1a}$.

Another aspect relates to a group of compounds of formula (I) wherein ring $G^1$ is benzo, and $R^1$ is $-(CR^{1a}R^{1b})_n-G^{1a}$.

Another aspect relates to a group of compounds of formula (I) wherein ring $G^1$ is benzo, $R^1$ is $-(CR^{1a}R^{1b})_n-G^{1a}$, and $G^1$ is aryl or cycloalkyl, each of which is optionally substituted.

Another aspect relates to a group of compounds of formula (I) wherein ring $G^1$ is benzo, $R^1$ is $-(CR^{1a}R^{1b})_n-G^{1a}$, and $G^{1a}$ is optionally substituted aryl. In certain embodiments, $G^{1a}$ is optionally substituted phenyl or optionally substituted naphthyl. In certain embodiments, $G^{1a}$ is optionally substituted phenyl.

Another aspect relates to a group of compounds of formula (I) wherein ring $G^1$ is benzo, $R^1$ is $-(CR^{1a}R^{1b})_n-G^{1a}$, and $G^{1a}$ is optionally substituted cycloalkyl. In certain embodiments, $G^{1a}$ is $C_3-C_6$ cycloalkyl, adamantyl, noradamantyl, bicyclo[2.2.1]heptyl, or bicyclo[3.1.1]heptyl, each of which is optionally substituted.

Within each of the aforementioned groups of compounds of formula (I), (I-a)-(I-e), and (I-e-i)-(I-e-iv), $R^{1a}$, $R^{1b}$, n, and the optional substituents or $G^{1a}$ are as described in the Summary and embodiments herein above.

Within each of the aforementioned groups of compounds of formula (I), (I-a)-(I-e), and (I-e-i)-(I-e-iv), $R^2$, T, q, r, u, y, and v are as described generally in the Summary and in embodiments described above and herein.

Thus, of each of the aforementioned groups of compounds of formula (I), (I-a)-(I-e), and (I-e-i)-(I-e-iv), examples of a subgroup include those wherein $R^2$ is $-OR^{2ac}$, $-SR^{2bc}$, $-S(O)R^{2bc}$, $-S(O)_2R^{2bc}$, $-C(O)R^{2cc}$, $-C(O)OR^{2cc}$, $-C(O)N(R^{2d})(R^{2e})$, $N(R^{2d})(R^{2e})$, $-C(R^{2d})=NOR^{2dc}$, $G^{2a}$, $-(CR^{2a}R^{2b})_p-G^{2a}$, $-(CR^{2a}R^{2b})_p-OR^{2ac}$, $-(CR^{2a}R^{2b})_p-C(O)OR^{2cc}$, $-(CR^{2a}R^{2b})_p-C(O)N(R^{2d})(R^{2e})$, or $-(CR^{2a}R^{2b})_p-N(R^{2d})(R^{2e})$.

Examples of another subgroup include those wherein $R^2$ is $G^{2a}$ or $-(CR^{2a}R^{2b})_p-G^{2a}$.

Examples of another subgroup include those wherein $R^2$ is $G^{2a}$.

Examples of another subgroup include those wherein $R^2$ is $G^{2a}$ and $G^{2a}$ is optionally substituted heterocycle (e.g. morpholinyl, dihydropyranyl (e.g. 3,6-dihydro-2H-pyran-4-yl), pyrrolidinyl, tetrahydropyranyl, thiomorpholinyl, piperidinyl, and piperazinyl, each of which is optionally substituted).

Examples of another subgroup include those wherein $R^2$ is $G^{2a}$, and $G^{2a}$ is optionally substituted heteroaryl. In certain embodiments, $G^{2a}$ is thienyl or pyridinyl, each of which is optionally substituted. In certain embodiments, $G^{2a}$ is optionally substituted pyridinyl.

Examples of another subgroup include those wherein $R^2$ is $G^{2a}$, and $G^{2a}$ is optionally substituted pyridinyl or optionally substituted morpholinyl.

Examples of another subgroup include those wherein $R^2$ is $G^{2a}$, and $G^{2a}$ is optionally substituted morpholinyl.

Yet other examples of a subgroup include those wherein $R^2$ is —$SR^{2bc}$, —$S(O)R^{2bc}$, or —$S(O)_2R^{2bc}$.

Yet other examples of a subgroup include those wherein $R^2$ is —$S(O)_2R^{2bc}$.

Yet other examples of a subgroup include those wherein $R^2$ is —$S(O)_2R^{2bc}$ and $R^{2bc}$ is optionally substituted aryl.

Yet other examples of a subgroup include those wherein $R^2$ is —$OR^{2ac}$ or —$(CR^{2a}R^{2b})_p$—$OR^{2ac}$.

Yet other examples of a subgroup include those wherein $R^2$ is —$C(O)OR^{2cc}$, —$C(O)N(R^{2d})(R^{2e})$, —$(CR^{2a}R^{2b})_p$—$C(O)OR^{2cc}$, or —$(CR^{2a}R^{2b})_p$—$C(O)N(R^{2d})(R^{2e})$.

Yet other examples of a subgroup include those wherein $R^2$ is —$C(O)R^{2cc}$ or —$(CR^{2a}R^{2b})_p$—$C(O)R^{2cc}$.

Yet other examples of a subgroup include those wherein $R^2$ is $N(R^{2d})(R^{2e})$ or —$(CR^{2a}R^{2b})_p$—$N(R^{2d})(R^{2e})$.

Within each group and subgroup of compounds of formula (I), (I-a)-(I-e), and (I-e-i)-(I-e-iv) $R^{2ac}$, $R^{2bc}$, $R^{2cc}$, $R^{2d}$, $R^{2e}$, $R^{2dc}$, $G^{2a}$, $R^{2a}$, $R^{2b}$, T, p, q, u, v, and the optional substituents of $G^{2a}$ have values as described generally in the Summary and specifically in embodiments herein above.

Exemplary compounds contemplated include, but are not limited to:

2-(3,5-difluorophenyl)-N-[4-(morpholin-4-yl)-1-oxophthalazin-2(1H)-yl]acetamide;
2-(4-chlorophenyl)-N-[4-(morpholin-4-yl)-1-oxophthalazin-2(1H)-yl]acetamide;
(±)-2-[(exo)-bicyclo[2.2.1]hept-2-yl]-N-[4-(morpholin-4-yl)-1-oxophthalazin-2(1H)-yl]acetamide;
(±)-2-[(exo)-bicyclo[2.2.1]hept-2-yl]-N-[4-(6-chloropyridin-3-yl)-1-oxophthalazin-2(1H)-yl]acetamide;
2-(4-chlorophenyl)-N-[4-(6-chloropyridin-3-yl)-1-oxophthalazin-2(1H)-yl]acetamide;
(±)-2-[(exo)-bicyclo[2.2.1]hept-2-yl]-N-[4-(3,6-dihydro-2H-pyran-4-yl)-1-oxophthalazin-2(1H)-yl]acetamide;
2-(3,5-difluorophenyl)-N-[4-(3,6-dihydro-2H-pyran-4-yl)-1-oxophthalazin-2(1H)-yl]acetamide;
(±)-2-[(exo)-bicyclo[2.2.1]hept-2-yl]-N-[1-oxo-4-(pyridin-3-yl)phthalazin-2(1H)-yl]acetamide;
2-(4-chlorophenyl)-N-[1-oxo-4-(pyridin-3-yl)phthalazin-2(1H)-yl]acetamide;
2-(3,5-difluorophenyl)-N-[1-oxo-4-(thiophen-2-yl)phthalazin-2(1H)-yl]acetamide;
2-(4-chlorophenyl)-N-[1-oxo-4-(thiophen-2-yl)phthalazin-2(1H)-yl]acetamide;
(±)-2-[(exo)-bicyclo[2.2.1]hept-2-yl]-N-[1-oxo-4-(thiophen-2-yl)phthalazin-2(1H)-yl]acetamide;
2-[(1S,2S,4S)-bicyclo[2.2.1]hept-5-en-2-yl]-N-[1-oxo-4-(thiophen-2-yl)phthalazin-2(1H)-yl]acetamide;
2-(3,5-difluorophenyl)-N-[4-(3-methylthiophen-2-yl)-1-oxophthalazin-2(1H)-yl]acetamide;
2-(4-chlorophenyl)-N-[4-(3-methylthiophen-2-yl)-1-oxophthalazin-2(1H)-yl]acetamide;
(±)-2-[(exo)-bicyclo[2.2.1]hept-2-yl]-N-[4-(3-methylthiophen-2-yl)-1-oxophthalazin-2(1H)-yl]acetamide;
2-[(1S,2S,4S)-bicyclo[2.2.1]hept-5-en-2-yl]-N-[4-(3-methylthiophen-2-yl)-1-oxophthalazin-2(1H)-yl]acetamide;
2-(3,5-difluorophenyl)-N-[1-oxo-4-(pyridin-2-yl)phthalazin-2(1H)-yl]acetamide;
(±)-2-[(exo)-bicyclo[2.2.1]hept-2-yl]-N-[1-oxo-4-(pyridin-2-yl)phthalazin-2(1H)-yl]acetamide;
2-(3,5-difluorophenyl)-N-[1-oxo-4-(pyrrolidin-1-yl)phthalazin-2(1H)-yl]acetamide;
2-(4-chlorophenyl)-N-[1-oxo-4-(pyrrolidin-1-yl)phthalazin-2(1H)-yl]acetamide;
2-(3,5-difluorophenyl)-N-[1-oxo-4-(piperidin-1-yl)phthalazin-2(1H)-yl]acetamide;
(±)-2-[(exo)-bicyclo[2.2.1]hept-2-yl]-N-[1-oxo-4-(pyrrolidin-1-yl)phthalazin-2(1H)-yl]acetamide;
2-(4-chlorophenyl)-N-[1-oxo-4-(piperidin-1-yl)phthalazin-2(1H)-yl]acetamide;
(±)-2-[(exo)-bicyclo[2.2.1]hept-2-yl]-N-[1-oxo-4-(piperidin-1-yl)phthalazin-2(1H)-yl]acetamide;
(±)-2-[(exo)-bicyclo[2.2.1]hept-2-yl]-N-[4-(6-methoxypyridin-3-yl)-1-oxophthalazin-2(1H)-yl]acetamide;
N-[4-(6-chloropyridin-3-yl)-1-oxophthalazin-2(1H)-yl]-3-methyl-3-phenylbutanamide;
(±)-2-[(exo)-bicyclo[2.2.1]hept-2-yl]-N-[1-oxo-4-(tetrahydro-2H-pyran-4-yl)phthalazin-2(1H)-yl]acetamide;
(±)-2-[(exo)-bicyclo[2.2.1]hept-2-yl]-N-[4-(2-chloropyridin-4-yl)-1-oxophthalazin-2(1H)-yl]acetamide;
(±)-2-[(exo)-bicyclo[2.2.1]hept-2-yl]-N-{4-[(6-chloropyridin-3-yl)methyl]-1-oxophthalazin-2(1H)-yl}acetamide;
N-{4-[(6-chloropyridin-3-yl)methyl]-1-oxophthalazin-2(1H)-yl}-2-(3,5-difluorophenyl)acetamide;
2-(4-chlorophenyl)-N-{4-[(6-chloropyridin-3-yl)methyl]-1-oxophthalazin-2(1H)-yl}acetamide;
3-methyl-N-[4-(morpholin-4-yl)-1-oxophthalazin-2(1H)-yl]-3-phenylbutanamide;
(±)-N-[4-(benzylamino)-1-oxophthalazin-2(1H)-yl]-2-[(exo)-bicyclo[2.2.1]hept-2-yl]acetamide;
(±)-2-[(exo)-bicyclo[2.2.1]hept-2-yl]-N-{4-[(3-chlorophenyl)amino]-1-oxophthalazin-2(1H)-yl}acetamide;
N-{4-[benzyl(methyl)amino]-1-oxophthalazin-2(1H)-yl}-2-(4-chlorophenyl)acetamide;
(±)-N-{4-[benzyl(methyl)amino]-1-oxophthalazin-2(1H)-yl}-2-[(exo)-bicyclo[2.2.1]hept-2-yl]acetamide;
2-(3,5-difluorophenyl)-N-(1-oxo-4-phenoxyphthalazin-2(1H)-yl)acetamide;
(±)-2-[(exo)-bicyclo[2.2.1]hept-2-yl]-N-(1-oxo-4-phenoxyphthalazin-2(1H)-yl)acetamide;
(±)-N-(4-benzoyl-1-oxophthalazin-2(1H)-yl)-2-[(exo)-bicyclo[2.2.1]hept-2-yl]acetamide;
tert-butyl [(3-{[(4-chlorophenyl)acetyl]amino}-4-oxo-3,4-dihydrophthalazin-1-yl)methyl]carbamate;
N-[4-(aminomethyl)-1-oxophthalazin-2(1H)-yl]-2-(4-chlorophenyl)acetamide;
(±)-2-[(exo)-bicyclo[2.2.1]hept-2-yl]-N-{1-oxo-4-[6-(trifluoromethyl)pyridin-3-yl]phthalazin-2(1H)-yl}acetamide;
(±)-tert-butyl [(3-{[(exo)-bicyclo[2.2.1]hept-2-ylacetyl]amino}-4-oxo-3,4-dihydrophthalazin-1-yl)methyl]carbamate;
(±)-2-[(exo)-bicyclo[2.2.1]hept-2-yl]-N-[4-(2-cyanopyridin-4-yl)-1-oxophthalazin-2(1H)-yl]acetamide;
(±)-2-[(exo)-bicyclo[2.2.1]hept-2-yl]-N-[4-(2-hydroxypyridin-4-yl)-1-oxophthalazin-2(1H)-yl]acetamide;
(±)-2-[(exo)-bicyclo[2.2.1]hept-2-yl]-N-{4-[6-(dimethylamino)pyridin-3-yl]-1-oxophthalazin-2(1H)-yl}acetamide;
N-[4-(2-chloropyridin-4-yl)-1-oxophthalazin-2(1H)-yl]-3-methyl-3-phenylbutanamide;
2-(4-chlorophenyl)-N-[4-(2-chloropyridin-4-yl)-1-oxophthalazin-2(1H)-yl]acetamide;

(±)-2-[(exo)-bicyclo[2.2.1]hept-2-yl]-N-[4-(2-methylpyridin-4-yl)-1-oxophthalazin-2(1H)-yl]acetamide;
(±)-ethyl 3-{[(exo)-bicyclo[2.2.1]hept-2-ylacetyl]amino}-4-oxo-3,4-dihydrophthalazine-1-carboxylate;
N-{4-[benzyl(methyl)amino]-1-oxophthalazin-2(1H)-yl}-3-methyl-3-phenylbutanamide;
N-{4-[benzyl(methyl)amino]-1-oxophthalazin-2(1H)-yl}-2-(3,5-difluorophenyl)acetamide;
(±)-2-[(exo)-bicyclo[2.2.1]hept-2-yl]-N-[4-(6-fluoropyridin-3-yl)-1-oxophthalazin-2(1H)-yl]acetamide;
(±)-3-{[(exo)-bicyclo[2.2.1]hept-2-ylacetyl]amino}-4-oxo-3,4-dihydrophthalazine-1-carboxylic acid;
(±)-3-{[(exo)-bicyclo[2.2.1]hept-2-ylacetyl]amino}-N,N-dimethyl-4-oxo-3,4-dihydrophthalazine-1-carboxamide;
2-(3,5-difluorophenyl)-N-[1-oxo-4-(phenylsulfanyl)phthalazin-2(1H)-yl]acetamide;
2-(4-chlorophenyl)-N-[1-oxo-4-(phenylsulfanyl)phthalazin-2(1H)-yl]acetamide;
(±)-2-[(exo)-bicyclo[2.2.1]hept-2-yl]-N-[1-oxo-4-(phenylsulfanyl)phthalazin-2(1H)-yl]acetamide;
2-(3,5-difluorophenyl)-N-[4-(2,6-dimethylmorpholin-4-yl)-1-oxophthalazin-2(1H)-yl]acetamide;
N-[4-(2,6-dimethylmorpholin-4-yl)-1-oxophthalazin-2(1H)-yl]-3-methyl-3-phenylbutanamide;
2-(4-chlorophenyl)-N-[4-(2,6-dimethylmorpholin-4-yl)-1-oxophthalazin-2(1H)-yl]acetamide;
ethyl 3-{[(4-chlorophenyl)acetyl]amino}-4-oxo-3,4-dihydrophthalazine-1-carboxylate;
(±)-2-[(exo)-bicyclo[2.2.1]hept-2-yl]-N-[4-(2,6-dimethylmorpholin-4-yl)-1-oxophthalazin-2(1H)-yl]acetamide;
3-{[(4-chlorophenyl)acetyl]amino}-4-oxo-3,4-dihydrophthalazine-1-carboxylic acid;
N-[4-(morpholin-4-yl)-1-oxophthalazin-2(1H)-yl]-2-(tetrahydrofuran-3-yl)acetamide;
N-[4-(2-chloropyridin-4-yl)-1-oxophthalazin-2(1H)-yl]-2-(tetrahydrofuran-3-yl)acetamide;
2-(3,5-difluorophenyl)-N-[1-oxo-4-(phenylsulfonyl)phthalazin-2(1H)-yl]acetamide;
2-(4-chlorophenyl)-N-[1-oxo-4-(phenylsulfonyl)phthalazin-2(1H)-yl]acetamide;
(±)-2-[(exo)-bicyclo[2.2.1]hept-2-yl]-N-[1-oxo-4-(phenylsulfonyl)phthalazin-2(1H)-yl]acetamide;
N-[4-(2-chloropyridin-4-yl)-1-oxophthalazin-2(1H)-yl]-2-(1-hydroxycyclohexyl)acetamide;
(±)-4-(3-{[(exo)-bicyclo[2.2.1]hept-2-ylacetyl]amino}-4-oxo-3,4-dihydrophthalazin-1-yl)pyridine-2-carboxamide;
N-[4-(2-chloropyridin-4-yl)-1-oxophthalazin-2(1H)-yl]-2-(tetrahydrofuran-2-yl)acetamide;
(±)-methyl 4-(3-{[(exo)-bicyclo[2.2.1]hept-2-ylacetyl]amino}-4-oxo-3,4-dihydrophthalazin-1-yl)pyridine-2-carboxylate;
(±)-4-(3-{[(exo)-bicyclo[2.2.1]hept-2-ylacetyl]amino}-4-oxo-3,4-dihydrophthalazin-1-yl)pyridine-2-carboxylic acid;
(±)-2-[(exo)-bicyclo[2.2.1]hept-2-yl]-N-{1-oxo-4-[2-(trifluoromethyl)pyridin-4-yl]phthalazin-2(1H)-yl}acetamide;
2-(4-chlorophenyl)-N-{1-oxo-4-[2-(trifluoromethyl)pyridin-4-yl]phthalazin-2(1H)-yl}acetamide;
2-(4-chlorophenyl)-N-[4-({[(4-methylphenyl)sulfonyl]amino}methyl)-1-oxophthalazin-2(1H)-yl]acetamide;
2-(4-chlorophenyl)-N-[1-oxo-4-({[(trifluoromethyl)sulfonyl]amino}methyl)phthalazin-2(1H)-yl]acetamide;
2-(4-chlorophenyl)-N-[4-{[(methylsulfonyl)amino]methyl}-1-oxophthalazin-2(1H)-yl]acetamide;
2-(4-chlorophenyl)-N-{4-[cis-2,6-dimethylmorpholin-4-yl]-1-oxophthalazin-2(1H)-yl}acetamide;
2-(4-chlorophenyl)-N-[1-oxo-4-(phenylsulfinyl)phthalazin-2(1H)-yl]acetamide;
2-(3,5-difluorophenyl)-N-[1-oxo-4-(phenylsulfinyl)phthalazin-2(1H)-yl]acetamide;
N-[4-{[(tert-butylcarbamoyl)amino]methyl}-1-oxophthalazin-2(1H)-yl]-2-(4-chlorophenyl)acetamide;
ethyl [(3-{[(4-chlorophenyl)acetyl]amino}-4-oxo-3,4-dihydrophthalazin-1-yl)methyl]carbamate;
2-(4-chlorophenyl)-N-[1-oxo-4-{[(phenylacetyl)amino]methyl}phthalazin-2(1H)-yl]acetamide;
N-[(3-{[(4-chlorophenyl)acetyl]amino}-4-oxo-3,4-dihydrophthalazin-1-yl)methyl]-2,2-dimethylpropanamide;
2-(3,5-difluorophenyl)-N-{4-[(cis)-2,6-dimethylmorpholin-4-yl]-1-oxophthalazin-2(1H)-yl}acetamide;
N-{4-[(cis)-2,6-dimethylmorpholin-4-yl]-1-oxophthalazin-2(1H)-yl}-3-methyl-3-phenylbutanamide;
(±)-2-[(exo)-bicyclo[2.2.1]hept-2-yl]-N-{4-[(cis)-2,6-dimethylmorpholin-4-yl]-1-oxophthalazin-2(1H)-yl}acetamide;
2-(4-chlorophenyl)-N-[1-oxo-4-(thiomorpholin-4-yl)phthalazin-2(1H)-yl]acetamide;
2-(3,5-difluorophenyl)-N-[1-oxo-4-(thiomorpholin-4-yl)phthalazin-2(1H)-yl]acetamide;
(±)-2-[(exo)-bicyclo[2.2.1]hept-2-yl]-N-[1-oxo-4-(thiomorpholin-4-yl)phthalazin-2(1H)-yl]acetamide;
(±)-tert-butyl 3-{[(exo)-bicyclo[2.2.1]hept-2-ylacetyl]amino}-4-oxo-3,4-dihydrophthalazine-1-carboxylate;
(±)-2-[(exo)-bicyclo[2.2.1]hept-2-yl]-N-[4-(morpholin-4-ylcarbonyl)-1-oxophthalazin-2(1H)-yl]acetamide;
(±)-benzyl [(3-{[(exo)-bicyclo[2.2.1]hept-2-ylacetyl]amino}-4-oxo-3,4-dihydrophthalazin-1-yl)methyl]carbamate;
(±)-2-[(exo)-bicyclo[2.2.1]hept-2-yl]-N-[1-oxo-4-(pyridin-4-ylmethyl)phthalazin-2(1H)-yl]acetamide;
(±)-tert-butyl 4-[(3-{[(exo)-bicyclo[2.2.1]hept-2-ylacetyl]amino}-4-oxo-3,4-dihydrophthalazin-1-yl)carbonyl]piperazine-1-carboxylate;
(±)-3-{[(exo)-bicyclo[2.2.1]hept-2-ylacetyl]amino}-N-tert-butyl-4-oxo-3,4-dihydrophthalazine-1-carboxamide;
(±)-2-[(exo)-bicyclo[2.2.1]hept-2-yl]-N-{4-[(1-oxidopyridin-4-yl)methyl]-1-oxophthalazin-2(1H)-yl}acetamide;
N-[4-(4-benzylpiperazin-1-yl)-1-oxophthalazin-2(1H)-yl]-2-(4-chlorophenyl)acetamide;
(±)-2-[(exo)-bicyclo[2.2.1]hept-2-yl]-N-{4-[hydroxy(phenyl)methyl]-1-oxophthalazin-2(1H)-yl}acetamide;
tert-butyl {4-[(3-{[(4-chlorophenyl)acetyl]amino}-4-oxo-3,4-dihydrophthalazin-1-yl)sulfanyl]phenyl}carbamate;
N-{4-[(6-chloro-1-oxidopyridin-3-yl)methyl]-1-oxophthalazin-2(1H)-yl}-2-(4-chlorophenyl)acetamide;
N-{4-[(4-aminophenyl)sulfanyl]-1-oxophthalazin-2(1H)-yl}-2-(4-chlorophenyl)acetamide;
tert-butyl {4-[(3-{[(4-chlorophenyl)acetyl]amino}-4-oxo-3,4-dihydrophthalazin-1-yl)sulfonyl]phenyl}carbamate;
2-(4-chlorophenyl)-N-[4-(4-methylpiperazin-1-yl)-1-oxophthalazin-2(1H)-yl]acetamide;
(±)-3-{[(exo)-bicyclo[2.2.1]hept-2-ylacetyl]amino}-N-(4-chlorophenyl)-4-oxo-3,4-dihydrophthalazine-1-carboxamide;
ethyl 2-(3-{[(4-chlorophenyl)acetyl]amino}-4-oxo-3,4-dihydrophthalazin-1-yl)propanoate;
2-(3-{[(4-chlorophenyl)acetyl]amino}-4-oxo-3,4-dihydrophthalazin-1-yl)propanoic acid;
N-[4-(morpholin-4-yl)-1-oxophthalazin-2(1H)-yl]-2-phenylacetamide;
N-tert-butyl-2-(3-{[(4-chlorophenyl)acetyl]amino}-4-oxo-3,4-dihydrophthalazin-1-yl)propanamide;
2-(3-{[(4-chlorophenyl)acetyl]amino}-4-oxo-3,4-dihydrophthalazin-1-yl)-N-(2,2-dimethylpropyl)propanamide;

(3-{[(4-chlorophenyl)acetyl]amino}-4-oxo-3,4-dihydrophthalazin-1-yl)acetic acid;

N-{4-[(4-aminophenyl)sulfonyl]-1-oxophthalazin-2(1H)-yl}-2-(4-chlorophenyl)acetamide;

ethyl (3-{[(4-chlorophenyl)acetyl]amino}-4-oxo-3,4-dihydrophthalazin-1-yl)acetate;

ethyl {[(4-chlorophenyl)acetyl]amino}(3-{[(4-chlorophenyl)acetyl]amino}-4-oxo-3,4-dihydrophthalazin-1-yl)acetate;

tert-butyl {[4-oxo-3-({[4-(trifluoromethyl)phenyl]acetyl}amino)-3,4-dihydrophthalazin-1-yl]methyl}carbamate;

tert-butyl {[3-({[(1S,2S,5S)-6,6-dimethylbicyclo[3.1.1]hept-2-yl]acetyl}amino)-4-oxo-3,4-dihydrophthalazin-1-yl]methyl}carbamate;

(±)-2-[(exo)-bicyclo[2.2.1]hept-2-yl]-N-{4-[(Z)-(hydroxyimino)(phenyl)methyl]-1-oxophthalazin-2(1H)-yl}acetamide;

2-(4-chlorophenyl)-N-[4-(2-hydroxyethyl)-1-oxophthalazin-2(1H)-yl]acetamide;

N-{4-[2-(tert-butylamino)-2-oxoethyl]-1-oxophthalazin-2(1H)-yl}-2-(4-chlorophenyl)acetamide;

2-(4-chlorophenyl)-N-[4-{2-[(2,2-dimethylpropyl)amino]-2-oxoethyl}-1-oxophthalazin-2(1H)-yl]acetamide;

tert-butyl [(3-{[(4,4-difluoro cyclohexyl)acetyl]amino}-4-oxo-3,4-dihydrophthalazin-1-yl)methyl]carbamate;

tert-butyl [(3-{[(4-fluorophenyl)acetyl]amino}-4-oxo-3,4-dihydrophthalazin-1-yl)methyl]carbamate;

tert-butyl ({3-[(cyclohexylacetyl)amino]-4-oxo-3,4-dihydrophthalazin-1-yl}methyl)carbamate;

2-(4-chlorophenyl)-N-(1-oxo-4-phenoxyphthalazin-2(1H)-yl)acetamide;

cyclohexyl [(3-{[(4-chlorophenyl)acetyl]amino}-4-oxo-3,4-dihydrophthalazin-1-yl)methyl]carbamate;

2,2,2-trifluoroethyl [(3-{[(4-chlorophenyl)acetyl]amino}-4-oxo-3,4-dihydrophthalazin-1-yl)methyl]carbamate;

2-[4-(methylsulfonyl)phenyl]-N-[4-(morpholin-4-yl)-1-oxophthalazin-2(1H)-yl]acetamide;

N-[4-(morpholin-4-yl)-1-oxophthalazin-2(1H)-yl]-2-(3-phenoxyphenyl)acetamide;

N-[4-(morpholin-4-yl)-1-oxophthalazin-2(1H)-yl]-2-[4-(trifluoromethoxy)phenyl]acetamide;

(±)-2-[(exo)-bicyclo[2.2.1]hept-2-yl]-N-[4-(morpholin-4-yl)-1-oxophthalazin-2(1H)-yl]acetamide;

2-(1,2-benzoxazol-3-yl)-N-[4-(morpholin-4-yl)-1-oxophthalazin-2(1H)-yl]acetamide;

3,3-dimethyl-N-[4-(morpholin-4-yl)-1-oxophthalazin-2(1H)-yl]butanamide;

3,3,3-trifluoro-N-[4-(morpholin-4-yl)-1-oxophthalazin-2(1H)-yl]propanamide;

2-cyclopentyl-N-[4-(morpholin-4-yl)-1-oxophthalazin-2(1H)-yl]acetamide;

2-cyclohexyl-N-[4-(morpholin-4-yl)-1-oxophthalazin-2(1H)-yl]acetamide;

2-(2-methylphenyl)-N-[4-(morpholin-4-yl)-1-oxophthalazin-2(1H)-yl]acetamide;

2-(3-methylphenyl)-N-[4-(morpholin-4-yl)-1-oxophthalazin-2(1H)-yl]acetamide;

2-(4-methylphenyl)-N-[4-(morpholin-4-yl)-1-oxophthalazin-2(1H)-yl]acetamide;

N-[4-(morpholin-4-yl)-1-oxophthalazin-2(1H)-yl]-2-(2-nitrophenyl)acetamide;

2-(3-hydroxyphenyl)-N-[4-(morpholin-4-yl)-1-oxophthalazin-2(1H)-yl]acetamide;

2-(4-hydroxyphenyl)-N-[4-(morpholin-4-yl)-1-oxophthalazin-2(1H)-yl]acetamide;

2-(2-methoxyphenyl)-N-[4-(morpholin-4-yl)-1-oxophthalazin-2(1H)-yl]acetamide;

2-(3-methoxyphenyl)-N-[4-(morpholin-4-yl)-1-oxophthalazin-2(1H)-yl]acetamide;

2-(4-methoxyphenyl)-N-[4-(morpholin-4-yl)-1-oxophthalazin-2(1H)-yl]acetamide;

2-(2-fluorophenyl)-N-[4-(morpholin-4-yl)-1-oxophthalazin-2(1H)-yl]acetamide;

2-(3-fluorophenyl)-N-[4-(morpholin-4-yl)-1-oxophthalazin-2(1H)-yl]acetamide;

2-(4-fluorophenyl)-N-[4-(morpholin-4-yl)-1-oxophthalazin-2(1H)-yl]acetamide;

2-(2-chlorophenyl)-N-[4-(morpholin-4-yl)-1-oxophthalazin-2(1H)-yl]acetamide;

2-(3-chlorophenyl)-N-[4-(morpholin-4-yl)-1-oxophthalazin-2(1H)-yl]acetamide;

2-(2-bromophenyl)-N-[4-(morpholin-4-yl)-1-oxophthalazin-2(1H)-yl]acetamide;

2-(3-bromophenyl)-N-[4-(morpholin-4-yl)-1-oxophthalazin-2(1H)-yl]acetamide;

2-(4-bromophenyl)-N-[4-(morpholin-4-yl)-1-oxophthalazin-2(1H)-yl]acetamide;

N-[4-(morpholin-4-yl)-1-oxophthalazin-2(1H)-yl]-2-(3-nitrophenyl)acetamide;

N-[4-(morpholin-4-yl)-1-oxophthalazin-2(1H)-yl]-2-(4-nitrophenyl)acetamide;

2-(biphenyl-4-yl)-N-[4-(morpholin-4-yl)-1-oxophthalazin-2(1H)-yl]acetamide;

2-[4-(dimethylamino)phenyl]-N-[4-(morpholin-4-yl)-1-oxophthalazin-2(1H)-yl]acetamide;

N-[4-(morpholin-4-yl)-1-oxophthalazin-2(1H)-yl]-2-[3-(trifluoromethyl)phenyl]acetamide;

N-[4-(morpholin-4-yl)-1-oxophthalazin-2(1H)-yl]-2-[4-(trifluoromethyl)phenyl]acetamide;

N-[4-(morpholin-4-yl)-1-oxophthalazin-2(1H)-yl]-2-[3-(trifluoromethoxy)phenyl]acetamide;

N-[4-(morpholin-4-yl)-1-oxophthalazin-2(1H)-yl]-2-(4-phenoxyphenyl)acetamide;

2-[4-(benzyloxy)phenyl]-N-[4-(morpholin-4-yl)-1-oxophthalazin-2(1H)-yl]acetamide;

N-[4-(morpholin-4-yl)-1-oxophthalazin-2(1H)-yl]-2-(naphthalen-1-yl)acetamide;

N-[4-(morpholin-4-yl)-1-oxophthalazin-2(1H)-yl]-2-(naphthalen-2-yl)acetamide;

2-(2,5-dimethylphenyl)-N-[4-(morpholin-4-yl)-1-oxophthalazin-2(1H)-yl]acetamide;

N-[4-(morpholin-4-yl)-1-oxophthalazin-2(1H)-yl]-2-(2,4,6-trimethylphenyl)acetamide;

2-(2,3-dimethoxyphenyl)-N-[4-(morpholin-4-yl)-1-oxophthalazin-2(1H)-yl]acetamide;

2-(2,4-dimethoxyphenyl)-N-[4-(morpholin-4-yl)-1-oxophthalazin-2(1H)-yl]acetamide;

2-(2,5-dimethoxyphenyl)-N-[4-(morpholin-4-yl)-1-oxophthalazin-2(1H)-yl]acetamide;

2-(3,4-dimethoxyphenyl)-N-[4-(morpholin-4-yl)-1-oxophthalazin-2(1H)-yl]acetamide;

2-(3,5-dimethoxyphenyl)-N-[4-(morpholin-4-yl)-1-oxophthalazin-2(1H)-yl]acetamide;

2-(1,3-benzodioxol-5-yl)-N-[4-(morpholin-4-yl)-1-oxophthalazin-2(1H)-yl]acetamide;

2-(2,3-difluorophenyl)-N-[4-(morpholin-4-yl)-1-oxophthalazin-2(1H)-yl]acetamide;

2-(2,5-difluorophenyl)-N-[4-(morpholin-4-yl)-1-oxophthalazin-2(1H)-yl]acetamide;

2-(3,4-dichlorophenyl)-N-[4-(morpholin-4-yl)-1-oxophthalazin-2(1H)-yl]acetamide;

2-(2,6-dichlorophenyl)-N-[4-(morpholin-4-yl)-1-oxophthalazin-2(1H)-yl]acetamide;

tert-butyl [(3-{[(exo)-bicyclo[2.2.1]hept-2-ylacetyl]amino}-4-oxo-3,4-dihydrophthalazin-1-yl)(phenyl)methyl]carbamate;

(1R,2S,5R)-5-methyl-2-(propan-2-yl)cyclohexyl [(3-{[(4-chlorophenyl)acetyl]amino}-4-oxo-3,4-dihydrophthalazin-1-yl)methyl]carbamate;

2-[4-(methylsulfonyl)phenyl]-N-[1-oxo-4-(phenylsulfanyl)phthalazin-2(1H)-yl]acetamide;

2-methylbutan-2-yl [(3-{[(4-chlorophenyl)acetyl]amino}-4-oxo-3,4-dihydrophthalazin-1-yl)methyl]carbamate;

methyl [(2S)-1-{[(3-{[(4-chlorophenyl)acetyl]amino}-4-oxo-3,4-dihydrophthalazin-1-yl)methyl]amino}-3-methyl-1-oxobutan-2-yl]carbamate;

2,2-dimethylpropyl [(3-{[(4-chlorophenyl)acetyl]amino}-4-oxo-3,4-dihydrophthalazin-1-yl)methyl]carbamate;

2-methylpropyl [(3-{[(4-chlorophenyl)acetyl]amino}-4-oxo-3,4-dihydrophthalazin-1-yl)methyl]carbamate;

(1S,2R,5S)-5-methyl-2-(propan-2-yl)cyclohexyl [(3-{[(4-chlorophenyl)acetyl]amino}-4-oxo-3,4-dihydrophthalazin-1-yl)methyl]carbamate;

cyclopentyl [(3-{[(4-chlorophenyl)acetyl]amino}-4-oxo-3,4-dihydrophthalazin-1-yl)methyl]carbamate;

benzyl [(3-{[(4-chlorophenyl)acetyl]amino}-4-oxo-3,4-dihydrophthalazin-1-yl)methyl]carbamate;

2-[4-(methylsulfonyl)phenyl]-N-[1-oxo-4-(phenylsulfonyl)phthalazin-2(1H)-yl]acetamide;

(±)-2-[(exo)-bicyclo[2.2.1]hept-2-yl]-N-[4-(1,1-dioxidothiomorpholin-4-yl)-1-oxophthalazin-2(1H)-yl]acetamide;

2-(4-chlorophenyl)-N-[1-oxo-4-(pyridin-4-ylsulfanyl)phthalazin-2(1H)-yl]acetamide;

2-(4-chlorophenyl)-N-{4-[(4-methylphenyl)sulfonyl]-1-oxophthalazin-2(1H)-yl}acetamide;

2-(4-fluorophenyl)-N-[1-oxo-4-(phenylsulfonyl)phthalazin-2(1H)-yl]acetamide;

3-methyl-N-[1-oxo-4-(phenylsulfonyl)phthalazin-2(1H)-yl]-3-phenylbutanamide;

N-{4-[(4-bromophenyl)sulfanyl]-1-oxophthalazin-2(1H)-yl}-2-(4-chlorophenyl)acetamide;

2-(4-chlorophenyl)-N-{4-[(1-oxidopyridin-4-yl)sulfonyl]-1-oxophthalazin-2(1H)-yl}acetamide;

N-{4-[(4-bromophenyl)sulfanyl]-1-oxophthalazin-2(1H)-yl}-2-(3,5-difluorophenyl)acetamide;

N-[4-(tert-butylsulfanyl)-1-oxophthalazin-2(1H)-yl]-2-(4-chlorophenyl)acetamide;

N-{4-[(4-bromophenyl)sulfonyl]-1-oxophthalazin-2(1H)-yl}-2-(4-chlorophenyl)acetamide;

(±)-2-[(exo)-bicyclo[2.2.1]hept-2-yl]-N-{4-[(4-bromophenyl)sulfanyl]-1-oxophthalazin-2(1H)-yl}acetamide;

N-[4-(tert-butylsulfonyl)-1-oxophthalazin-2(1H)-yl]-2-(4-chlorophenyl)acetamide;

N-{4-[(4-bromophenyl)sulfonyl]-1-oxophthalazin-2(1H)-yl}-2-(3,5-difluorophenyl)acetamide;

2-(4-chlorophenyl)-N-[1-oxo-4-(pyridin-4-ylsulfonyl)phthalazin-2(1H)-yl]acetamide;

(±)-2-[(exo)-bicyclo[2.2.1]hept-2-yl]-N-{4-[(4-bromophenyl)sulfonyl]-1-oxophthalazin-2(1H)-yl}acetamide;

2-(3-methoxyphenyl)-N-[1-oxo-4-(phenylsulfonyl)phthalazin-2(1H)-yl]acetamide;

2-(4-bromophenyl)-N-[1-oxo-4-(phenylsulfonyl)phthalazin-2(1H)-yl]acetamide;

2-(3-methylphenyl)-N-[1-oxo-4-(phenylsulfonyl)phthalazin-2(1H)-yl]acetamide;

N-[1-oxo-4-(phenylsulfonyl)phthalazin-2(1H)-yl]-2-[3-(trifluoromethyl)phenyl]acetamide;

2-(3-chlorophenyl)-N-[1-oxo-4-(phenylsulfonyl)phthalazin-2(1H)-yl]acetamide;

2-(hexahydro-2,5-methanopentalen-3a(1H)-yl)-N-[4-(morpholin-4-yl)-1-oxophthalazin-2(1H)-yl]acetamide;

2-(hexahydro-2,5-methanopentalen-3a(1H)-yl)-N-{1-oxo-4-[6-(trifluoromethyl)pyridin-3-yl]phthalazin-2(1H)-yl}acetamide;

N-[4-(benzylsulfanyl)-1-oxophthalazin-2(1H)-yl]-2-(3,5-difluorophenyl)acetamide;

N-[4-(benzylsulfanyl)-1-oxophthalazin-2(1H)-yl]-2-(4-chlorophenyl)acetamide;

(±)-N-[4-(benzylsulfanyl)-1-oxophthalazin-2(1H)-yl]-2-[(exo)-bicyclo[2.2.1]hept-2-yl]acetamide;

N-[4-(benzylsulfonyl)-1-oxophthalazin-2(1H)-yl]-2-(3,5-difluorophenyl)acetamide;

N-[4-(benzylsulfonyl)-1-oxophthalazin-2(1H)-yl]-2-(4-chlorophenyl)acetamide;

(±)-N-[4-(benzylsulfonyl)-1-oxophthalazin-2(1H)-yl]-2-[(exo)-bicyclo[2.2.1]hept-2-yl]acetamide;

2-(hexahydro-2,5-methanopentalen-3a(1H)-yl)-N-[1-oxo-4-(phenylsulfonyl)phthalazin-2(1H)-yl]acetamide;

(±)-2-[(exo)-bicyclo[2.2.1]hept-2-yl]-N-{4-[(4-cyanophenyl)sulfonyl]-1-oxophthalazin-2(1H)-yl}acetamide;

(±)-2-[(exo)-bicyclo[2.2.1]hept-2-yl]-N-[4-(2-ethylmorpholin-4-yl)-1-oxophthalazin-2(1H)-yl]acetamide;

2-(4-chlorophenyl)-N-[4-(2-ethylmorpholin-4-yl)-1-oxophthalazin-2(1H)-yl]acetamide;

2-(4-chlorophenyl)-N-{4-[(4-cyanophenyl)sulfonyl]-1-oxophthalazin-2(1H)-yl}acetamide;

N-{4-[(4-cyanophenyl)sulfonyl]-1-oxophthalazin-2(1H)-yl}-2-(3,5-difluorophenyl)acetamide;

N-{4-[(4-cyanophenyl)sulfonyl]-1-oxophthalazin-2(1H)-yl}-2-(4-fluorophenyl)acetamide; and N-{4-[(4-cyanophenyl)sulfonyl]-1-oxophthalazin-2(1H)-yl}-3-methyl-3-phenylbutanamide.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It will be appreciated that two or more asymmetric centers may be present in the present compounds, hence several diastereomers and enantiomers of the exemplified structures will often be possible, and that pure diastereomers and enantiomers represent preferred embodiments. It is intended that pure diastereomers, pure enantiomers, and mixtures thereof, are within the scope of the invention.

Various stereoisomers (including enantiomers and diastereomers) and mixtures thereof (including racemates) are contemplated. Individual stereoisomers of present compounds may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein may exhibit the phenomenon of tautomerism and all tautomeric isomers and mixtures thereof are included in the scope of the invention.

Though structural representations within this specification may show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within drawings or the naming of the compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of KCNQ modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.,* 36(10):927-932 (1995); Kushner et al., *Can. J. Physiol. Pharmacol.,* 77, 79-88 (1999).

In addition, non-radioactive isotope-containing drugs, such as deuterated drugs called "heavy drugs," can be used for the treatment of diseases and conditions related to the activation of KCNQ channels. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physico-chemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions, potentially altering the pharmacokinetic profile or efficacy relative to the non-isotopic compound.

c. Biological Data (i) In Vitro Assay:

The following example describes the assay that can be used to identify compounds that activate KCNQ 2/3 channels.

HEK293 cells stably expressing human KCNQ2 and KCNQ3 subunits were seeded in 96-well, black-walled, clear-bottomed, poly-D-lysine coated plates (BD Biosciences, Bedford, Mass.) at a density of 1×10⁵ cells per well 24 hours before the assay. On the assay day, BTC-AM dye (Invitrogen, Carlsbad, Calif.) was loaded into the cells by replacing the cell culture medium with 55 µL/well of 3 µg/mL dye in DPBS. Dye loading was allowed to proceed for 2 hours at room temperature and then cells were washed twice with 50 µL/well of assay buffer (in mM: 10 HEPES pH 7.3, 5 glucose, 140 Na-gluconate, 2.5 K-gluconate, 3.6 Ca-gluconate, 2 MgSO4, 0.1 Ouabain) to remove unloaded dye. Cells were incubated in 50 µL of assay buffer before loading onto a FLIPR system (Molecular Devices, Sunnyvale, Calif.). Various concentrations of compounds to be assayed were added to the cells in 50 µL of assay buffer and incubated for 4 minutes. The fluorescence signal was initiated by adding 100 µL of assay buffer containing 6 mM TlNO₃ and 10 mM K₂SO₄. Fluors were excited using the 488-nm line of an argon laser and emission was filtered using a 540±30 nm bandpass filter. Fluorescent signals were recorded for 3 minutes. Sums of the responses over basal responses were plotted versus concentrations of test compounds to obtain an $EC_{50}$ value. The maximum response for each test compound was determined relative to the response produced by 10 µM retigabine. The maximum response of retigabine at 10 µM was set at 100%.

$EC_{50}$ values and the maximum response of compounds described herein assessed by the above-described assays are shown in Table 1.

TABLE 1

| Example Number | $EC_{50}$ (μM) | % MAX |
|---|---|---|
| 1 | 4.46 | 130 |
| 2 | 2.7 | 117 |
| 3 | 0.331 | 142 |
| 4 | 0.0606 | 133 |
| 5 | 0.47 | 85.2 |
| 6 | 0.515 | 140 |
| 7 | 3.13 | 140 |
| 8 | 0.455 | 129 |
| 9 | 31.6 | 19.6 |
| 10 | 0.161 | 137 |
| 11 | 0.297 | 105 |
| 12 | 0.0674 | 136 |
| 13 | 0.131 | 138 |
| 14 | 0.296 | 146 |
| 15 | 0.858 | 124 |
| 16 | 0.116 | 140 |
| 17 | 0.209 | 139 |
| 18 | 2.81 | 112 |
| 19 | 0.168 | 146 |
| 20 | 0.214 | 145 |
| 21 | 0.198 | 136 |
| 22 | 0.0875 | 134 |
| 23 | 0.0628 | 147 |
| 24 | 0.0842 | 140 |
| 25 | 0.0253 | 144 |
| 26 | 0.306 | 137 |
| 27 | 0.261 | 134 |
| 28 | 0.447 | 145 |
| 29 | 0.0671 | 137 |
| 30 | 0.0584 | 122 |
| 31 | 0.33 | 72.1 |
| 32 | 0.148 | 46.2 |
| 33 | 1.59 | 131 |
| 34 | 0.142 | 161 |
| 35 | 10 | 11.4 |
| 36 | 0.221 | 105 |
| 37 | 0.0423 | 160 |
| 38 | 0.0318 | 122 |
| 39 | 0.00905 | 150 |
| 40 | 0.0311 | 135 |
| 41 | 0.975 | 90.3 |
| 42 | 10 | 8.66 |
| 43 | 0.143 | 149 |
| 44 | 0.294 | 116 |
| 45 | 0.381 | 146 |
| 46 | 10 | 13.4 |
| 47 | 0.378 | 122 |
| 48 | 0.389 | 133 |
| 49 | 0.383 | 107 |
| 50 | 1.13 | 151 |
| 51 | 0.275 | 171 |
| 52 | 0.102 | 185 |
| 53 | 0.132 | 147 |
| 54 | 0.408 | 183 |
| 55 | 1.37 | 149 |
| 56 | 31.6 | 84.9 |
| 57 | 0.0381 | 116 |
| 58 | 0.0826 | 120 |
| 59 | 0.0146 | 192 |
| 60 | 0.474 | 105 |
| 61 | 0.228 | 123 |
| 62 | 0.369 | 85.8 |
| 63 | 0.862 | 64.8 |
| 64 | 0.0909 | 144 |
| 65 | 31.6 | 30.1 |
| 66 | 31.6 | 3.89 |
| 67 | 31.6 | 6.78 |
| 68 | 0.0699 | 79.9 |
| 69 | 0.0409 | 118 |
| 70 | 0.0131 | 179 |
| 71 | 31.6 | 34 |
| 72 | 31.6 | 13.7 |
| 73 | 8.07 | 172 |
| 74 | 31.6 | 21.8 |
| 75 | 4.12 | 183 |
| 76 | 0.126 | 127 |
| 77 | 0.458 | 74.9 |
| 78 | 9.49 | 44.1 |
| 79 | 9.08 | 33.6 |
| 80 | 31.6 | 26.5 |
| 81 | 0.663 | 85.1 |
| 82 | 0.872 | 119 |
| 83 | 1.1 | 105 |
| 84 | 31.6 | 40.8 |
| 85 | 5.35 | 87.3 |
| 86 | 31.6 | 15.7 |
| 87 | 10.1 | 89.1 |
| 88 | 0.998 | 107 |
| 89 | 0.35 | 183 |
| 90 | 0.141 | 196 |
| 91 | 0.92 | 164 |
| 92 | 0.618 | 187 |
| 93 | 0.0782 | 229 |
| 94 | 0.0767 | 201 |
| 95 | 30 | 73 |
| 96 | 0.315 | 79.4 |
| 97 | 2.7 | 173 |
| 98 | 4.97 | 140 |
| 99 | 0.206 | 177 |
| 100 | 0.916 | 53.4 |
| 101 | 3.49 | 112 |
| 102 | 0.894 | 212 |
| 103 | 31.6 | 76 |
| 104 | 31.6 | 11.7 |
| 105 | 0.889 | 120 |
| 106 | 2.01 | 46.2 |
| 107 | 31.6 | 24.3 |
| 108 | 2.04 | 155 |
| 109 | 1.42 | 53.2 |
| 110 | 31.6 | 2.26 |
| 111 | 17.3 | 70.7 |
| 112 | 31.6 | 17.1 |
| 113 | 31.6 | 21.8 |
| 114 | 31.6 | 3.72 |
| 115 | 31.6 | 42.2 |
| 116 | 7.62 | 61.4 |
| 117 | 31.6 | 26.2 |
| 118 | 2.85 | 40.7 |
| 119 | 31.6 | 33.9 |
| 120 | 3.18 | 136 |
| 121 | 31.6 | 10.5 |
| 122 | 31.6 | 14.2 |
| 123 | 31.6 | 13 |
| 124 | 8.05 | 72.5 |
| 125 | 9.9 | 93.1 |
| 126 | 31.6 | 25.6 |
| 127 | 0.18 | 87.4 |
| 128 | 31.6 | 21.6 |
| 129 | 1.28 | 33.7 |
| 130 | 31.6 | 5.33 |
| 131 | 30 | 17.1 |
| 132 | 1.69 | 105 |
| 135 | 11.8 | 75.3 |
| 136 | 6.23 | 49.1 |
| 137 | 7.68 | 135 |
| 138 | 3.89 | 153 |
| 139 | 30 | −1.4 |
| 140 | 6.89 | 103 |
| 141 | 5.24 | 72 |
| 142 | 30 | 1.59 |
| 143 | 30 | 43.8 |
| 144 | 6.87 | 39.9 |
| 145 | 30 | 1.73 |
| 146 | 30 | 17.6 |
| 147 | 30 | 18.7 |
| 148 | 30 | 18.7 |
| 149 | 5.28 | 82.7 |
| 150 | 12.9 | 71.7 |
| 151 | 30 | 7.89 |

TABLE 1-continued

| Example Number | EC$_{50}$ (μM) | % MAX |
|---|---|---|
| 152 | 5.51 | 80 |
| 153 | 30 | 1.17 |
| 154 | 2.9 | 114 |
| 155 | 2.56 | 110 |
| 156 | 30 | 32.8 |
| 158 | 30 | 6.84 |
| 160 | 9.68 | 62.1 |
| 161 | 10 | 93 |
| 162 | 1.52 | 87.4 |
| 163 | 30 | 30.8 |
| 164 | 30 | 22 |
| 165 | 30 | 7.96 |
| 166 | 30 | 15.6 |
| 167 | 30 | 3 |
| 168 | 30 | 1.91 |
| 169 | 30 | 23.6 |
| 170 | 30 | 34.2 |
| 172 | 30 | 51.7 |
| 173 | 30 | 33.9 |
| 174 | 30 | 18.7 |
| 175 | 30 | 17.3 |
| 176 | 30 | 18 |
| 177 | 0.628 | 131 |
| 178 | 31.6 | −1.83 |
| 179 | 0.267 | 185 |
| 180 | 1.61 | 57.6 |
| 181 | 5.18 | 92.6 |
| 182 | 1.32 | 63.8 |
| 183 | 31.6 | 5.96 |
| 184 | 1.32 | 62.7 |
| 185 | 1.24 | 44.6 |
| 186 | 31.6 | 11.8 |
| 187 | 31.6 | 32 |
| 188 | 31.6 | 15.3 |
| 189 | 31.6 | 37 |
| 190 | 10.6 | 74.3 |
| 191 | 1.32 | 78.5 |
| 192 | 0.116 | 103 |
| 193 | 0.0792 | 87.9 |
| 194 | 1.78 | 63.4 |
| 195 | 0.432 | 96.9 |
| 196 | 31.6 | 16.6 |
| 197 | 0.049 | 120 |
| 198 | 0.134 | 120 |
| 199 | 0.0489 | 79.2 |
| 200 | 0.0232 | 180 |
| 201 | 0.738 | 92.3 |
| 202 | 0.0647 | 106 |
| 203 | 0.621 | 85 |
| 204 | 0.024 | 164 |
| 205 | 0.938 | 71.8 |
| 206 | 0.0693 | 99.3 |
| 207 | 0.306 | 69.9 |
| 208 | 31.6 | 33.3 |
| 209 | 0.0774 | 80.9 |
| 210 | 0.164 | 154 |
| 211 | 0.201 | 137 |
| 212 | 0.152 | 109 |
| 213 | 0.0303 | 123 |
| 214 | 0.0217 | 197 |
| 215 | 0.916 | 45 |
| 216 | 1.84 | 67.1 |
| 217 | 0.0748 | 147 |
| 218 | 0.0583 | 151 |
| 219 | 0.0146 | 145 |
| 220 | 0.0579 | 139 |
| 221 | 0.32 | 101 |
| 222 | 0.0979 | 90 |
| 223 | 0.149 | 86.2 |
| 224 | 0.155 | 75.2 |
| 225 | 0.146 | 37.3 |

(ii) In Vivo Data:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under isoflurane anesthesia (4-5% to induce, 1-3% to maintain), and the incision sites were sterilized using a 10% povidone-iodine solution prior to and after surgeries.

Chronic Constriction Injury (CCI) Model of Neuropathic Pain (Bennett Model)

A model of chronic constriction injury-induced (CCI) neuropathic pain was produced by following the method of Bennett and Xie (1988, Pain, 33, 87-107). The right common sciatic nerve was isolated at mid-thigh level, and loosely ligated by 4 chromic gut (5-0) ties separated by an interval of 1 mm. The same procedure was performed on Sham rats, but without sciatic nerve constriction. All animals were left to recover for at least 2 weeks and no more than 5 weeks prior to testing of mechanical allodynia.

Tactile (mechanical) allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals as well as in the contralateral paws of nerve-injured rats. To evaluate the antinociceptive effects, animals were administered vehicle or test compound and tactile allodynia was assessed 30 minutes after i.p. administration.

Compounds were injected (i.p.) 30 minutes or more before testing. The compounds of Example 29 and Example 49 showed a statistically significant change in paw withdrawal latency versus vehicle at 30 mg/kg.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) was used to test a compound of the present application The left L5 and L6 spinal nerves of the rat were isolated adjacent to the vertebral column and tightly ligated with a 5-0 silk suture distal to the DRG, and care taken to avoid injury of the L4 spinal nerve. The same procedure was performed on Sham rats, but without nerve ligation. All animals were allowed to recover for at least one week and not more than three weeks prior to assessment of tactile allodynia.

Compounds were injected (i.p) 30 minutes or more before testing. The compounds of Examples 41, 43, 68, 69, 76, and 81 showed a statistically significant change in paw withdrawal latency versus vehicle at about 30 mg/kg.

d. Methods of Using the Compounds

In one aspect, the present invention provides methods of using one or more compounds or composition described herein to treat or prevent a disorder, disease or condition of a subject (including human), which disorder, disease, or condition is responsive to modulation of KCNQ potassium channels. In particular, compounds described herein are expected to have utility in the treatment of a disorder, disease or condition which is responsive to modulation of KCNQ potassium channels.

In one group of embodiments, diseases and conditions of humans or other animals that can be treated with activation of KCNQ channels, include, but are not limited to, diseases and conditions involving abnormal neuronal excitability such as but not limited to epilepsy, pain, migraine, anxiety, overactive bladder, schizophrenia, anxiety, and substance abuse.

One embodiment provides methods for treating pain (for example, neuropathic pain (including diabetic polyneuropathy), nociceptive pain, persistent pain, osteoarthritic pain, cancer pain, inflammatory pain, postoperative pain, fibromyalgia, chronic widespread pain, musculoskeletal pain, myofascial pain, Temporomandibular joint pain (TMJ pain), particularly, inflammatory pain, osteoarthritic pain, persistent pain, postoperative pain, cancer pain, neuropathic pain, or nociceptive pain) in mammals (including human) in need of such treatment. The methods comprise administering to the mammals therapeutically effective amounts of one or more compounds described herein, or pharmaceutically acceptable salts, solvates, or salts of solvates thereof, alone or in combination with one or more pharmaceutically acceptable carrier(s). The methods further comprise administration of compounds described herein as a single dose. The methods also comprise repeated or chronic administration of present compounds over a period of days, weeks, months, or longer. In certain embodiments, the method comprises administering to the mammal therapeutically effective amounts of one or more of the compounds described herein, or pharmaceutically acceptable salts or solvates thereof, in combination with one or more analgesics (for example, acetaminophen or opioids such as, but not limited to, morphine), or with one or more nonsteroidal anti-inflammatory drugs (NSAIDs); or administered with a combination of one or more analgesics and one or more NSAIDs. Examples of NSAIDs include, but are not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. In certain embodiments, the composition may optionally include one or more pharmaceutically acceptable carriers.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the active ingredients may be required to achieve the desired therapeutic response. "Repeated or chronic administration" refers to the administration of the compositions described herein daily (i.e., every day) or intermittently (i.e., not every day) over a period of days, weeks, months, or longer. In particular, the treatment of chronic painful conditions is anticipated to require such repeated or chronic administration of the compositions described herein. Compounds of the invention may become more effective upon repeated or chronic administration such that the therapeutically effective doses on repeated or chronic administration may be lower than the therapeutically effective dose from a single administration.

Compounds can also be administered as a pharmaceutical composition comprising the compounds of interest in combination with one or more pharmaceutically acceptable carriers. The phrase "therapeutically effective amount" of the compound of the invention means a sufficient amount of the compound to treat disorders or, or to prevent development of or alleviate to some extent one or more of the symptoms of the condition or disorder being treated, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds may be administered alone, or in combination (i.e. co-administered) with one or more additional pharmaceutical agents. For example, one or more present compounds or pharmaceutically acceptable salts or solvates thereof, may be administered in combination with one or more analgesics (e.g acetaminophen or opioids), or with one or more nonsteroidal anti-inflammatory drugs (NSAIDs), or mixtures thereof. Non limiting examples of suitable NSAIDs include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) may be administered to the patient together, in a single oral dosage composition having a fixed ratio of each active ingredient, such as a tablet or capsule; or each active ingredient may be administered in separate oral dosage formulations.

Separate dosage formulations may be administered at essentially the same time (e.g., concurrently) or at separately staggered times (e.g., sequentially).

Therapeutically effective amounts can be determined by those skilled in the art, and will be adjusted to the requirements of each particular case. Generally, a therapeutically effective amount of a KCNQ modulator will range from a total daily dose, for example in human or other animals, of about 0.01 mg/kg body weight to about 100 mg/kg body weight, preferably of about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

e. Pharmaceutical Compositions

Pharmaceutical compositions comprising compounds described herein or pharmaceutically acceptable salts, solvates, or salts of solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts, solvates, or salts of solvates thereof, and one or more pharmaceutically acceptable carriers, alone or in combination with one or more analgesics (e.g. acetaminophen or opioids), or in combination with one or more nonsteroidal anti-inflammatory drugs (NSAIDs), or a combination of one or more analgesics and one or more NSAIDs.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

Compounds described herein can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

f. General Synthesis

Compounds described herein when prepared by synthetic processes or by metabolic processes are encompassed in this application. Preparation of the compounds by metabolic processes includes those occurring in the human or animal body (in vivo) or processes occurring in vitro.

The compounds may be prepared by a variety of processes well known for the preparation of compounds of this class. For example, the compounds of formula (I) wherein the groups $G^1$, T, $R^1$, $R^2$, $G^{2a}$, $R^{2a}$, $R^{2b}$, $R^{2ac}$, $R^{2bc}$, and p have the meanings as set forth in the summary section unless otherwise noted, can be synthesized as shown in Schemes 1-6.

Abbreviations which have been used in the descriptions of the Schemes and the Examples that follow are: $(BOC)_2O$ for di-tert-butyl dicarbonate, DCM for dichloromethane, DMSO-$d_6$ for deuterated dimethyl sulfoxide, EDC for 1-(3-dimethylaminopropyl)-3-ethylcarbodiimide hydrochloride, EtOAc for ethyl acetate, $Et_2O$ for diethyl ether, EtOH for ethanol, THF for tetrahydrofuran, MeOH for methanol, DMAP for 4-(dimethylamino)pyridine, DME for dimethoxyethane, DMF for N,N-dimethylformamide, $(iPr)_2NEt$ for diisopropylethyl amine, $NEt_2$ for diethylamine, $PdCl_2(dppf)$ for [1,1'-bis(diphenylphosphino)ferrocene]dichloropalladium(II), $Pd(PPh_3)_4$ for tetrakis(triphenylphosphine)palladium(0), MeOH for methanol, and TFA for trifluoroacetic acid.

Compounds of general formula (I) can be prepared, for example, using the general method outlined in Scheme 1.

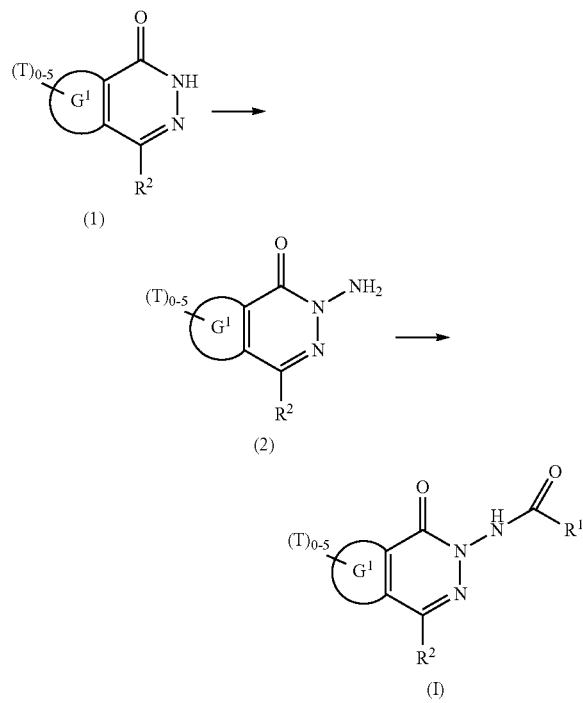

Compounds of formula (1) can be converted to compounds of formula (2) by treatment with a suitable base such as, but not limited to, potassium tert-butoxide, sodium hydride, or potassium 2-methylpropan-2-olate, followed by (diphenylphosphoryl)hydroxylamine (Klotzer, W.; Stadlwieser, J.; Raneburger, J. *Organic Syntheses* 1986, 64, 96-103), in solvents such as, but not limited to, tetrahydrofuran, dimethoxyethane, and N,N-dimethylformamide. Reactions are typically conducted at about room temperature.

Compounds of formula (2) when treated with compounds of formula $R^1COX^{101}$, wherein $X^{101}$ is chloro, bromo, or OH under coupling conditions known to one skilled in the art, can provide compounds of general formula (1). Typical conditions for the reaction of (2) with compounds of formula $R^1COX^{101}$, wherein $X^{101}$ is chloro or bromo include, but are not limited to, stirring about an equimolar mixture of the compounds in a solvent such as, but not limited to, chloroform, dichloromethane, THF, or mixture thereof, optionally in the presence of a base such as, but not limited to, diisopropylethylamine or pyridine, at about 0° C. to about 30° C. for about 8-24 hours. Acid coupling conditions for compounds of formula $R^1COX^{101}$ wherein $X^{101}$ is —OH and compounds of formula (2), include stirring about an equimolar mixture of the compounds in a solvent such as, but not limited to, THF, N,N-dimethylacetamide, N,N-dimethylformamide, pyridine, chloroform, or mixtures thereof, with a coupling reagent, optionally along with a coupling auxiliary, and in the presence or absence of a base. Typical reactions can be carried out at temperatures ranging from about 0° C. to about 65° C. or may be carried out in a microwave reactor to facilitate the coupling. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N', N'-tetramethyluronium tetrafluoroborate (TBTU), and 1-propanephosphonic acid cyclic anhydride. Non limiting examples of a coupling auxiliary include 1-hydroxy-7-azabenzotriazole (HOAT) and 1-hydroxybenzotriazole hydrate (HOBT). Suitable examples of bases include, but are not limited to, N-methylmorpholine and diisopropylethylamine.

Compounds of general formula (1) can be purchased from commercial sources or prepared using one of the methods outlined in the Schemes 2-4 below.

Compounds of general formula (1) can be prepared using the two-step method outlined in Scheme 2.

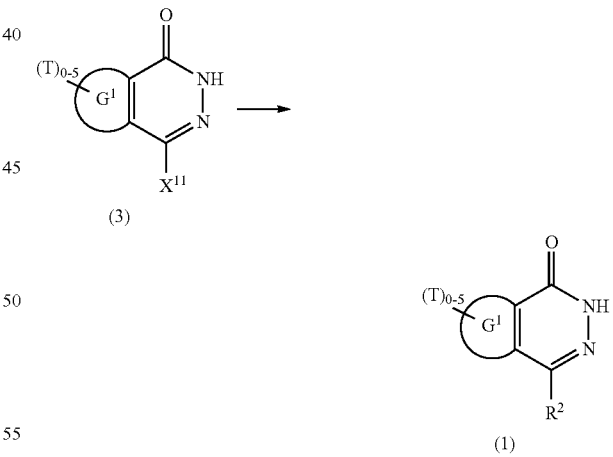

Compounds of formula (3) wherein $X^{11}$ is chloro or bromo, can be converted to compounds of formula (1) by reaction with an organozinc reagent such as, for example, a reagent $Zn(R^2)_2$, wherein $R^2$ is $G^{2a}$ or —$(CR^{2a}R^{2b})_p$-$G^{2a}$. The reaction is conducted in the presence of a palladium catalyst such as, but not limited to, $PdCl_2dpp.CH_2Cl_2$ or $Pd(PPh_3)_4$ in a solvent such as, but not limited to, dioxane, tetrahydrofuran, toluene and N,N-dimethylformamide, or mixtures thereof; at temperatures from about 50° C. to about 100° C.; however, elevated temperatures or microwave irradiation may be beneficial. Similar coupling reactions are reported using boronic acid derivatives (see Villemin, D.; Jullien, A.; Bar, N.; *Tetrahedron Letters* 2007; 48, 4191-4193) under Pd-catalyzed conditions as well. Additionally, electrophilic substitutions have been accomplished using Lewis acids such as $AlCl_3$ (see Coates, W. J.; McKillop, A.; *Journal of Organic Chemistry* 1990, 55, 5418-5420).

Alternatively, certain compounds of formula (1) can be obtained by treating (3) with $R^2X^{10}$ wherein $R^2$ is —$OR^{2ac}$ or —$SR^{2bc}$ and $X^{10}$ is hydrogen, in the presence of a base such as, but not limited to, $K_2CO_3$, and at elevated temperature and optionally under microwave irradiation.

Compounds of formula (1) can be prepared using the method outlined in Scheme 3.

Scheme 3

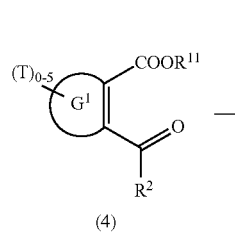

(4)

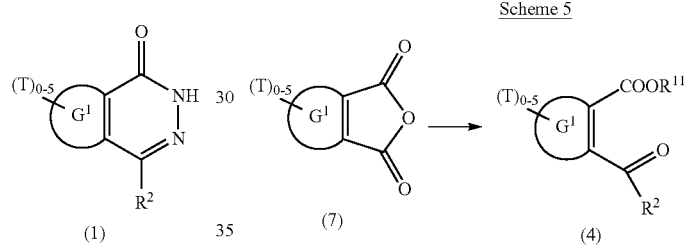

Compounds of formula (4) wherein $R^{11}$ is hydrogen or alkyl, can be converted to compounds of formula (1) by reaction with hydrazine in a solvent such as, but not limited to, methanol or ethanol; at temperatures from about room temperature to about 100° C. Typically, the reaction is conducted in ethanol at about 80° C. Compounds of formula (5) can be purchased from commercial sources, or prepared using methods set forth herein below.

Compounds of formula (1) can also be prepared using the method outlined in Scheme 4.

Scheme 4

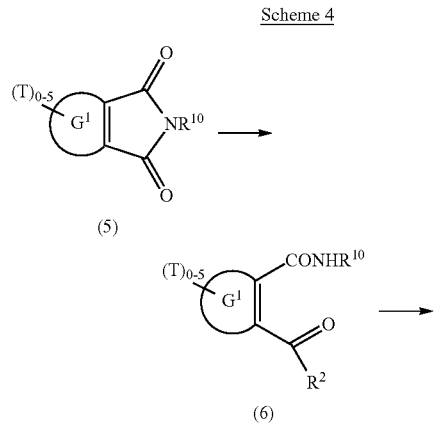

Compounds of formula (5) wherein $R^{10}$ is aryl or alkyl, can be converted to compounds of formula (6) by reaction with a Grignard reagent $R^2MgBr$, wherein $R^2$ is $G^{2a}$; in a solvent such as, but not limited to, tetrahydrofuran or diethyl ether; at temperatures ranging from about −78° C. to about room temperature. Compounds of formula (6) can be converted to compounds of formula (1) by reaction with hydrazine in a solvent such as, but not limited to, methanol or ethanol; at temperatures ranging from about room temperature to about 100° C.; and in the presence of a catalytic amount of acid such as, but not limited to, hydrochloric acid. The reaction can also be conducted at temperatures up to around 200° C. in a sealed vessel with microwave irradiation.

Compounds of formula (4) can be prepared using the method outlined in Scheme 5.

Compounds of formula (7) can be converted to compounds of formula (4) wherein $R^2$ is $G^{2a}$ and $R^{11}$ is hydrogen under Friedel-Crafts acylation reaction conditions. This reaction is well known to those skilled in the art and typically involves reaction in the presence of a Lewis acid such as, but not limited to, aluminum trichloride, and an aryl reactant (e.g., benzene, toluene). This class of chemical reaction is described more fully in Jerry March, *Advanced Organic Chemistry: Reactions, Mechanisms and Structure*, 4th Ed, pp. 539-542.

Compounds of formula (4) can also be prepared using the method outlined in Scheme 6.

Scheme 6

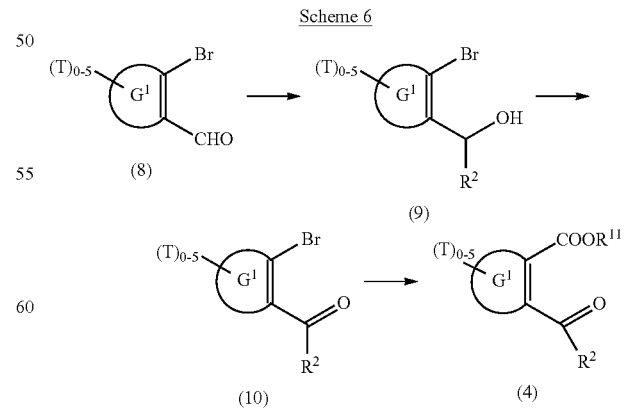

Compounds of formula (8) can be converted to compounds of formula (9) by reaction with a Grignard reagent $R^2MgBr$ or silane R²SiMe₃; in a solvent such as, but not limited to, tetrahydrofuran or diethylether; at temperatures ranging from about −78° C. to about room temperature. Compounds of formula (9) can be converted to compounds of formula (10) by an oxidation reaction. This reaction is well known to those skilled in the art and numerous reagents are known that effectuate the oxidation of an alcohol to a ketone (e.g., $MnO_2$, Dess-Martin periodinane, pyridinium chlorochromate, $KMnO_4$). This class of chemical reaction is described more fully in Jerry March, *Advanced Organic Chemistry: Reactions, Mechanisms and Structure*, 4th Ed, pp. 1167-1171. Compounds of formula (10) can be converted to compounds of formula (4) wherein $R^{11}$ is alkyl, by reaction with carbon monoxide in the presence of a palladium catalyst, an alcohol $R^{11}OH$, and a base such as, but not limited to, triethylamine. Suitable palladium catalysts include, but are not limited to $PdCl_2dppf.CH_2Cl_2$, $Pd(OAc)_2$, and $PdCl_2(PPh_3)_2$. The reaction can be performed at room temperature or at temperatures up to about 100° C. in a solvent such as N,N-dimethylformamide, methanol, ethanol, and the like.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

All experiments were conducted at room temperature unless otherwise stated.

EXAMPLES

Example 1

2-(3,5-difluorophenyl)-N-[4-(morpholin-4-yl)-1-oxophthalazin-2(1H)-yl]acetamide

Example 1A 4-morpholinophthalazin-1(2H)-one

A mixture of 4-chlorophthalazin-1-one (0.49 g, 2.7 mmol), morpholine (2.4 mL, 27 mmol), and ethylene glycol (1.5 mL) was microwaved at 190° C. for 1 hour, and 210° C. for 30 minutes, diluted with EtOAc, washed with sat $NaHCO_3$ and water, concentrated, adsorbed onto silica, and chromatographed (30% EtOAc/DCM) to give 300.0 mg of product as a white solid: $^1H$ NMR (300 MHz, DMSO-$d_6$) δ 12.13 (s, 1H), 8.27-8.20 (m, 1H), 8.00-7.79 (m, 3H), 3.86-3.77 (m, 4H), 3.07 (dd, J=10.2, 5.6, 4H).

Example 1B 2-amino-4-morpholinophthalazin-1(2H)-one

To a mixture of the product from Example 1A (0.300 g, 1.30 mmol) in THF (3.5 mL) was added a 1 M solution of potassium 2-methylpropan-2-olate in THF (1.7 mL, 1.7 mmol). The mix was stirred at room temperature for 90 minutes, and O-(diphenylphosphoryl)hydroxylamine (0.395 g, 1.70 mmol) was added and stirred overnight. The mixture was diluted with EtOAc, washed with 0.5N NaOH and water, concentrated, and chromatographed (40% EtOAc/DCM) to give 126.4 mg of product as a white solid: $^1H$ NMR (300 MHz, DMSO-$d_6$) δ 8.31-8.25 (m, 1H), 8.03-7.98 (m, 1H), 7.94-7.80 (m, 2H), 6.20 (s, 2H), 3.87-3.78 (m, 4H), 3.15-3.07 (m, 4H).

Example 1C 2-(3,5-difluorophenyl)-N-[4-(morpholin-4-yl)-1-oxophthalazin-2(1H)-yl]acetamide The product of Example 1B and 2-(3,5-difluorophenyl) acetic acid were treated using a method similar to that described in Example 10C to give the title compound. $^1H$ NMR (400 MHz, DMSO-$d_6$) δ ppm 11.55 (s, 1H), 8.31 (dd, J=7.9, 1.3 Hz, 1H), 8.02 (d, J=1.3 Hz, 1H), 7.96-8.01 (m, 1H), 7.88-7.92 (m, 1H), 7.09-7.21 (m, 3H), 3.80-3.83 (m, 4H), 3.73 (s, 2H), 3.08-3.10 (m, 4H); MS (APCI$^+$) M/Z 401 (M+H)$^+$.

Example 2

2-(4-chlorophenyl)-N-[4-(morpholin-4-yl)-1-oxophthalazin-2(1H)-yl]acetamide

The product of Example 1B and 2-(4-chlorophenyl)acetic acid were treated using a method similar to that described in Example 10C to give the title compound. $^1$H NMR (400 MHz, DMSO-d$_6$, Temp=90° C.) δ ppm 11.09-11.16 (m, 1H), 8.30 (d, J=7.1 Hz, 1H), 7.99 (d, J=1.3 Hz, 1H), 7.92-7.96 (m, 1H), 7.84-7.88 (m, 1H), 7.26-7.46 (m, 4H), 3.80-3.83 (m, 4H), 3.64-3.65 (m, 1H), 3.65 (d, J=5.0 Hz, 1H), 3.09-3.13 (m, 4H); MS (APCI$^+$) M/Z 399 (M+H)$^+$.

Example 3

(±)-2-[(exo)-bicyclo[2.2.1]hept-2-yl]-N-[4-(morpholin-4-yl)-1-oxophthalazin-2(1H)-yl]acetamide

Example 3A (±)-2-(exo-bicyclo[2.2.1]heptan-2-yl)acetyl chloride

A mixture of (±)-2-(exo-bicyclo[2.2.1]heptan-2-yl)acetic acid (0.294 g, 1.9 mmol) and oxalyl chloride (0.22 mL, 2.5 mmol) in dichloromethane (6 mL) with a catalytic amount of DMF was stirred at room temperature for 90 minutes, concentrated, and used without purification.

Example 3B (±)-2-[(exo)-bicyclo[2.2.1]hept-2-yl]-N-[4-(morpholin-4-yl)-1-oxophthalazin-2(1H)-yl]acetamide The products from Example 1B (80 mg, 0.33 mmol) and Example 3A (62 mg, 0.36 mmol), and pyridine (77 mg, 0.98 mmol) were stirred in CH$_2$Cl$_2$ (5 mL) for 1 hour, concentrated, and purified by preparative HPLC (conditions from Example 10) to give the title compound (14 mg, 11%): $^1$H NMR (400 MHz, DMSO-d$_6$, Temp=90 C) δ ppm 10.65-10.82 (m, 1H), 8.28-8.32 (m, 1H), 7.90-8.04 (m, 2H), 7.81-7.89 (m, 1H), 3.76-3.89 (m, 4H), 1.97-2.31 (m, 6H), 1.82-1.98 (m, 1H), 1.27-1.54 (m, 5H), 1.06-1.24 (m, 5H); MS (APCI$^+$) M/Z 383 (M+H)$^+$.

Example 4

(±)-2-[(exo)-bicyclo[2.2.1]hept-2-yl]-N-[4-(6-chloropyridin-3-yl)-1-oxophthalazin-2(1H)-yl]acetamide

Example 4A 4-(6-chloropyridin-3-yl)phthalazin-1(2H)-one

A mixture of ethyl 2-(6-chloronicotinoyl)benzoate (0.599 g, 2.1 mmol) and hydrazine hydrate (0.35 mL, 6.2 mmol) in ethanol (6 mL) was stirred at 75° C. for 1 hour, concentrated, and azeotroped with toluene to provide the title compound, which was used without purification: $^1$H NMR (300 MHz, DMSO-d$_6$) δ 13.01 (s, 1H), 8.65 (dd, J=2.7, 0.6, 1H), 8.44-8.25 (m, 1H), 8.13 (dd, J=8.3, 2.5, 1H), 8.08-7.82 (m, 2H), 7.82-7.59 (m, 2H).

Example 4B 2-amino-4-(6-chloropyridin-3-yl)phthalazin-1(2H)-one

A mixture of the product from Example 4A (0.527 g, 2.04 mmol) and potassium 2-methylpropan-2-olate (0.299 g, 2.66 mmol) in THF (6 mL) was stirred for 1 h, and O-(diphenylphosphoryl)hydroxylamine (0.621 g, 2.66 mmol) and DMF (2 mL) were added, stirred at room temperature for 2 hours, diluted with EtOAc, washed with 1N NaOH and brine, dried (Na$_2$SO$_4$), filtered, and chromatographed (20-60% EtOAc/DCM) to give 235 mg of title compound as a white solid: $^1$H NMR (300 MHz, DMSO-d$_6$) δ 8.67 (dd, J=2.4, 0.5, 1H), 8.38 (s, 1H), 8.14 (dd, J=8.2, 2.5, 1H), 8.02-7.82 (m, 2H), 7.81-7.65 (m, 2H), 6.54 (s, 2H).

Example 4C (±)-2-[(exo)-bicyclo[2.2.1]hept-2-yl]-N-[4-(6-chloropyridin-3-yl)-1-oxophthalazin-2(1H)-yl]acetamide A mixture of the product of Example 4B (0.10 g, 0.37 mmol), pyridine (0.040 mL, 0.49 mmol), and the product from Example 3A (0.071 g, 0.41 mmol) in DCM (1.1 mL) and DMF (0.3 mL) was stirred at room temperature for 2 hours, diluted with EtOAc, washed with sat NaHCO$_3$ and brine, dried (Na$_2$SO$_4$), filtered, and chromatographed (5-20% EtOAc/DCM) to give 101 mg of the title compound as a white solid: $^1$H NMR (300 MHz, DMSO-d$_6$) δ ppm 11.38 (s, 1H), 8.65 (d, J=2.5 Hz, 1H), 8.40-8.43 (m, 1H), 8.14 (dd, J=8.2, 2.5 Hz, 1H), 7.96-8.00 (m, 2H), 7.72-7.76 (m, 2H), 2.28 (dd, J=14.2, 8.3 Hz, 1H), 2.18-2.23 (m, 1H), 2.15 (dd, J=14.3, 7.3 Hz, 1H), 2.10-2.13 (m, 1H), 1.84-1.96 (m, 1H), 1.42-1.55 (m, 3H), 1.34-1.41 (m, 1H), 1.06-1.24 (m, 4H); MS (ESI$^+$) M/Z 409 (M+H)$^+$.

Example 5

2-(4-chlorophenyl)-N-[4-(6-chloropyridin-3-yl)-1-oxophthalazin-2(1H)-yl]acetamide The product of Example 4B was treated with 2-(4-chlorophenyl)acetyl chloride similar to the method described in Example 4C to afford the title compound. $^1$H NMR (300 MHz, DMSO-d$_6$) δ ppm 11.76 (s, 1H), 8.65 (dd, J=2.5, 0.8 Hz, 1H), 8.39-8.43 (m, 1H), 8.13 (dd, J=8.2, 2.5 Hz, 1H), 7.86-8.02 (m, 2H), 7.67-7.81 (m, 2H), 7.37-7.44 (m, 4H), 3.71 (s, 2H); MS (ESI$^+$) M/Z 425 (M+H)$^+$.

Example 6

(±)-2-[(exo)-bicyclo[2.2.1]hept-2-yl]-N-[4-(3,6-dihydro-2H-pyran-4-yl)-1-oxophthalazin-2(1H)-yl]acetamide

Example 6A 4-(3,6-dihydro-2H-pyran-4-yl)phthalazin-1(2H)-one

A mixture of 4-chlorophthalazin-1(2H)-one (150 mg, 0.831 mmol), 2-(3,6-dihydro-2H-pyran-4-yl)-4,4,5,5-tetramethyl-1,3,2-dioxaborolane (174 mg, 0.831 mmol), Na$_2$CO$_3$ (164 mg, 2.49 mmol) and Pd(PPh$_3$)$_4$ (47.8 mg, 0.042 mmol) in DMF (3 mL) and H$_2$O (1 mL) was heated at 180° C. under microwave condition for 20 minutes. The mixture was diluted with EtOAc and washed with saturated aqueous NaHCO$_3$, dried (Na$_2$SO$_4$), filtered, and concentrated to afford the title compound: MS (APCI) M/Z 229 (M+H)$^+$.

Example 6B 2-amino-4-(3,6-dihydro-2H-pyran-4-yl)phthalazin-1 (2H)-one

The product from Example 6A was processed using a method similar to that described in Example 1B to afford the title compound: MS (APCI) M/Z 244 (M+H)$^+$.

Example 6C (±)-2-[(exo)-bicyclo[2.2.1]hept-2-yl]-N-[4-(3,6-dihydro-2H-pyran-4-yl)-1-oxophthalazin-2(1H)-yl]acetamide The product from Example 6A was processed using a method similar to that described in Example 4C to afford the title compound. $^1$H NMR (400 MHz, DMSO-d$_6$) δ ppm 11.25 (s, 1H), 8.35 (ddd, J=7.8, 1.4, 0.6 Hz, 1H), 8.05 (ddd, J=8.0, 1.4, 0.7 Hz, 1H), 7.99 (ddd, J=8.0, 7.1, 1.4 Hz, 1H), 7.92 (ddd, J=7.8, 7.1, 1.4 Hz, 1H), 6.15-6.17 (m, 1H), 4.29 (q, J=2.8 Hz, 2H), 3.87 (t, J=5.3 Hz, 2H), 2.40-2.46 (m, 2H), 2.25 (dd, J=14.2, 8.4 Hz, 1H), 2.19-2.22 (m, 1H), 2.13 (dd, J=14.2, 7.4 Hz, 1H), 2.11-2.13 (m, 1H), 1.84-1.94 (m, 1H), 1.40-1.56 (m, 3H), 1.35-1.41 (m, 1H), 1.06-1.22 (m, 4H); MS (APCI) M/Z 380 (M+H)$^+$.

Example 7

2-(3,5-difluorophenyl)-N-[4-(3,6-dihydro-2H-pyran-4-yl)-1-oxophthalazin-2(1H)-yl]acetamide The product from Example 6A and 2-(3,5-difluorophenyl) acetic acid was processed using a method similar to that described in Example 10C to afford the title compound. $^1$H NMR (400 MHz, DMSO-d$_6$) δ ppm 11.68 (s, 1H), 8.36 (ddd, J=7.8, 1.5, 0.7 Hz, 1H), 8.05 (ddd, J=8.1, 1.4, 0.6 Hz, 1H), 8.00 (ddd, J=8.0, 7.2, 1.5 Hz, 1H), 7.93 (ddd, J=8.0, 7.0, 1.5 Hz, 1H), 7.08-7.22 (m, 3H), 6.15-6.17 (m, 1H), 4.29 (q, J=2.7 Hz, 2H), 3.87 (t, J=5.4 Hz, 2H), 3.75 (s, 2H), 2.41-2.47 (m, 2H); MS (APCI) M/Z 398 (M+H)$^+$.

Example 8

(±)-2-[(exo)-bicyclo[2.2.1]hept-2-yl]-N-[1-oxo-4-(pyridin-3-yl)phthalazin-2(1H)-yl]acetamide A mixture of the product of Example 4C (52 mg, 0.13 mmol) and a catalytic amount of 10% Pd/C in MeOH (0.5 mL) was stirred at room temperature under H$_2$ (1 atm) for 3 hours, filtered through celite, and concentrated to give 43 mg of the title compound as a tan solid: $^1$H NMR (300 MHz, DMSO-d$_6$) δ ppm 11.38 (s, 1H), 8.82-8.84 (m, 1H), 8.79 (dd, J=4.9, 1.4 Hz, 1H), 8.40-8.44 (m, 1H), 8.11-8.16 (m, 1H), 7.90-8.07 (m, 2H), 7.70-7.76 (m, 1H), 7.67 (ddd, J=7.9, 4.9, 0.9 Hz, 1H), 4.03 (q, J=7.1 Hz, 1H), 2.28 (dd, J=14.2, 8.4 Hz, 1H), 2.19-2.23 (m, 1H), 2.15 (dd, J=14.3, 7.4 Hz, 1H), 2.10-2.13 (m, 1H), 1.84-1.95 (m, 1H), 1.41-1.54 (m, 3H), 1.35-1.41 (m, 1H), 1.07-1.22 (m, 3H); MS (ESI$^+$) M/Z 375 (M+H)$^+$.

Example 9

2-(4-chlorophenyl)-N-[1-oxo-4-(pyridin-3-yl)phthalazin-2(1H)-yl]acetamide

A mixture of the product of Example 5 (38 mg, 0.089 mmol) and a catalytic amount of 10% Pd/C in MeOH (1 mL) and DMF (0.5 mL) was stirred at room temperature under H$_2$ (1 atm) for 3 hours, filtered through celite, and chromatographed (30-60% EtOAc/DCM) to give 17.8 mg of the title compound as a white solid: $^1$H NMR (300 MHz, DMSO-d$_6$) δ ppm 11.75 (s, 1H), 8.78 (dd, J=2.2, 0.7 Hz, 1H), 8.76 (dd, J=4.8, 1.6 Hz, 1H), 8.40-8.43 (m, 1H), 8.06 (ddd, J=7.9, 2.2, 1.7 Hz, 1H), 7.94-8.02 (m, 2H), 7.67-7.75 (m, 1H), 7.61 (ddd, J=7.9, 4.8, 0.8 Hz, 1H), 7.40 (s, 4H), 3.71 (s, 2H); MS (ESI$^+$) M/Z 391 (M+H)$^+$.

Example 10

2-(3,5-difluorophenyl)-N-[1-oxo-4-(thiophen-2-yl) phthalazin-2(1H)-yl]acetamide

Example 10A 4-(thiophen-2-yl)phthalazin-1(2H)-one

A mixture of methyl 2-(thiophene-2-carbonyl)benzoate (0.445 g, 1.81 mmol) and hydrazine hydrate (0.40 mL, 7.1 mmol) in ethanol (6 mL) was stirred at 80° C. overnight, concentrated, and azeotroped with toluene to give the title compound, which was used without purification: $^1$H NMR (300 MHz, DMSO-d$_6$) δ 12.87 (s, 1H), 8.42-8.28 (m, 1H), 8.23-8.09 (m, 1H), 7.95 (dtd, J=19.0, 7.3, 1.5, 2H), 7.82-7.69 (m, 1H), 7.68-7.55 (m, 1H), 7.33-7.19 (m, 1H), 4.12 (s, OH), 1.91 (s, OH), 1.74 (s, 1H).

Example 10B 2-amino-4-(thiophen-2-yl)phthalazin-1(2H)-one

The product from Example 10A was processed using a method similar to that described in Example 1B to afford the title compound: MS (APCI) M/Z 244 (M+H)$^+$.

Example 10C 2-(3,5-difluorophenyl)-N-[1-oxo-4-(thiophen-2-yl) phthalazin-2(1H)-yl]acetamide The product from Example 10B (60 mg, 0.25 mmol), (3,5-difluorophenyl)acetic acid (51 mg, 0.30 mmol), 1-hydroxybenzotriazole hydrate (HOBT, 76 mg, 0.49 mmol), EDC (95 mg, 0.49 mmol), and DMAP (3.0 mg, 0.025 mmol) were combined in pyridine (3 mL). The mixture was stirred at room temperature for 12 hours. The mixture was concentrated to dryness. The residue was dissolved in EtOAc and washed with NaHCO$_3$, dried (Na$_2$SO$_4$), filtered, and concentrated. The residue was purified by preparative HPLC [Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A] to afford 19 mg (19%) of the title compound. $^1$H NMR (400 MHz, DMSO-d$_6$) δ ppm 11.79 (s, 1H), 8.42 (ddd, J=7.8, 1.5, 0.6 Hz, 1H), 8.18 (ddd, J=8.1, 1.3, 0.6 Hz, 1H), 8.05 (ddd, J=8.0, 7.3, 1.5 Hz, 1H), 7.99 (ddd, J=7.9, 7.2, 1.3 Hz, 1H), 7.81 (dd, J=5.1, 1.1 Hz, 1H), 7.66 (dd, J=3.6, 1.1 Hz, 1H), 7.29 (dd, J=5.1, 3.6 Hz, 1H), 7.06-7.22 (m, 3H), 3.78 (s, 2H); MS (APCI) M/Z 398 (M+H)+.

Example 11

2-(4-chlorophenyl)-N-[1-oxo-4-(thiophen-2-yl)phthalazin-2(1H)-yl]acetamide

The product of Example 10B and 2-(4-chlorophenyl)acetic acid were treated using a method similar to that described in Example 10C to give the title compound. $^1$H NMR (400 MHz, DMSO-$d_6$) δ ppm 11.73 (s, 1H), 8.40 (ddd, J=7.7, 1.6, 0.8 Hz, 1H), 8.17 (ddd, J=8.1, 1.3, 0.6 Hz, 1H), 8.04 (ddd, J=8.0, 7.2, 1.6 Hz, 1H), 7.98 (ddd, J=7.8, 7.2, 1.3 Hz, 1H), 7.81 (dd, J=5.1, 1.1 Hz, 1H), 7.65 (dd, J=3.6, 1.1 Hz, 1H), 7.35-7.47 (m, 4H), 7.28 (dd, J=5.1, 3.6 Hz, 1H), 3.72 (s, 2H); MS (APCI) M/Z 396 (M+H)+.

Example 12

(±)-2-[(exo)-bicyclo[2.2.1]hept-2-yl]-N-[1-oxo-4-(thiophen-2-yl)phthalazin-2(1H)-yl]acetamide The product from Example 10B was processed using a method similar to that described in Example 4C to afford the title compound. $^1$H NMR (400 MHz, DMSO-$d_6$) δ ppm 11.36 (s, 1H), 8.41 (ddd, J=7.8, 1.5, 0.6 Hz, 1H), 8.18 (ddd, J=8.1, 1.3, 0.6 Hz, 1H), 8.04 (ddd, J=8.1, 7.2, 1.5 Hz, 1H), 7.98 (ddd, J=7.9, 7.3, 1.3 Hz, 1H), 7.80 (dd, J=5.1, 1.1 Hz, 1H), 7.65 (dd, J=3.6, 1.1 Hz, 1H), 7.28 (dd, J=5.1, 3.6 Hz, 1H), 2.27 (dd, J=14.2, 8.4 Hz, 1H), 2.20-2.23 (m, 1H), 2.15 (dd, J=14.3, 7.4 Hz, 1H), 2.11-2.14 (m, 1H), 1.86-1.93 (m, 1H), 1.34-1.58 (m, 4H), 1.02-1.23 (m, 4H); MS (APCI) M/Z 380 (M+H)+.

Example 13

2-[(1S,2S,4S)-bicyclo[2.2.1]hept-5-en-2-yl]-N-[1-oxo-4-(thiophen-2-yl)phthalazin-2(1H)-yl]acetamide The product from Example 10B and 2-((1S,2S,4S)-bicyclo[2.2.1]hept-5-en-2-yl)acetic acid was processed using a method similar to that described in Example 10C to afford the title compound. $^1$H NMR (400 MHz, DMSO-$d_6$) δ ppm 11.31 (s, 1H), 8.41 (dd, J=7.8, 1.4 Hz, 1H), 8.18 (d, J=8.0 Hz, 1H), 7.92-8.10 (m, 2H), 7.80 (dd, J=5.1, 1.1 Hz, 1H), 7.65 (dd, J=3.6, 1.1 Hz, 1H), 7.29 (dd, J=5.1, 3.6 Hz, 1H), 6.23 (dd, J=5.7, 3.0 Hz, 1H), 6.07 (dd, J=5.7, 2.8 Hz, 1H), 2.89-2.92 (m, 1H), 2.77-2.81 (m, 1H), 2.42-2.50 (m, 1H), 2.10 (dd, J=14.3, 7.9 Hz, 1H), 2.08 (dd, J=14.1, 8.0 Hz, 1H), 1.91 (ddd, J=11.5, 9.0, 3.8 Hz, 1H), 1.34-1.37 (m, 1H), 1.27 (d, J=8.1 Hz, 1H), 0.61 (ddd, J=11.5, 4.3, 2.5 Hz, 1H); MS (APCI) M/Z 392 (M+H)+.

Example 14

2-(3,5-difluorophenyl)-N-[4-(3-methylthiophen-2-yl)-1-oxophthalazin-2(1H)-yl]acetamide

Example 14A 4-(3-methylthiophen-2-yl)phthalazin-1(2H)-one

A mixture of 2-(3-methylthiophene-2-carbonyl)benzoic acid (0.446 g, 1.81 mmol) and hydrazine hydrate (0.41 mL, 7.3 mmol) in ethanol (6 mL) was stirred at 80° C. overnight, concentrated, and azeotroped with toluene to provide the title compound, which was used without purification: $^1$H NMR (300 MHz, DMSO-$d_6$) δ 8.41-8.23 (m, 1H), 8.01-7.80 (m, 2H), 7.68 (d, J=5.1, 1H), 7.62-7.42 (m, 1H), 7.10 (d, J=5.1, 1H), 2.08 (s, 3H).

Example 14B 2-amino-4-(3-methylthiophen-2-yl)phthalazin-1(2H)-one

The product from Example 14A was processed using a method similar to that described in Example 1B to afford the title compound: MS (APCI) M/Z 258 (M+H)+.

Example 14C 2-(3,5-difluorophenyl)-N-[4-(3-methylthiophen-2-yl)-1-oxophthalazin-2(1H)-yl]acetamide The product from Example 14B and 2-(3,5-difluorophenyl)acetic acid was processed using a method similar to that described in Example 10C to afford the title compound. $^1$H NMR (400 MHz, DMSO-$d_6$) δ ppm 11.78 (s, 1H), 8.39-8.42 (m, 1H), 7.90-8.05 (m, 2H), 7.73 (d, J=5.1 Hz, 1H), 7.62-7.65 (m, 1H), 7.08-7.22 (m, 4H), 3.77 (s, 2H), 2.10 (s, 3H); MS (APCI) M/Z 412 (M+H)+.

Example 15

2-(4-chlorophenyl)-N-[4-(3-methylthiophen-2-yl)-1-oxophthalazin-2(1H)-yl]acetamide The product from Example 14B and 2-(4-chlorophenyl)acetic acid was processed using a method similar to that described in Example 10C to afford the title compound. $^1$H NMR (400 MHz, DMSO-$d_6$) δ ppm 11.73 (s, 1H), 8.37-8.40 (m, 1H), 7.89-8.05 (m, 2H), 7.72 (d, J=5.1 Hz, 1H), 7.61-7.63 (m, 1H), 7.34-7.46 (m, 4H), 7.11 (d, J=5.1 Hz, 1H), 3.71 (s, 2H), 2.09 (s, 3H); MS (APCI) M/Z 410 (M+H)+.

Example 16

(±)-2-[(exo)-bicyclo[2.2.1]hept-2-yl]-N-[4-(3-methylthiophen-2-yl)-1-oxophthalazin-2(1H)-yl]acetamide The products from Example 14B and Example 3A were processed using a method similar to that described in Example 3B to afford the title compound. $^1$H NMR (400 MHz, DMSO-$d_6$) δ ppm 11.36 (s, 1H), 8.38-8.40 (m, 1H), 7.89-8.05 (m, 2H), 7.72 (d, J=5.0 Hz, 1H), 7.62-7.65 (m, 1H), 7.12 (d, J=5.1 Hz, 1H), 2.27 (dd, J=14.2, 8.3 Hz, 1H), 2.19-2.23 (m, 1H), 2.14 (dd, J=14.3, 7.5 Hz, 1H), 2.10-2.12 (m, 1H), 2.10 (s, 3H), 1.85-1.93 (m, 1H), 1.24-1.57 (m, 4H), 1.01-1.22 (m, 4H); MS (APCI) M/Z 394 (M+H)+.

Example 17

2-[(1S,2S,4S)-bicyclo[2.2.1]hept-5-en-2-yl]-N-[4-(3-methylthiophen-2-yl)-1-oxophthalazin-2(1H)-yl]acetamide The product from Example 14B and 2-((1S,2S,4S)-bicyclo[2.2.1]hept-5-en-2-yl)acetic acid was processed using a method similar to that described in Example 10C to afford the title compound. $^1$H NMR (400 MHz, DMSO-$d_6$) δ ppm 11.31 (s, 1H), 8.38-8.40 (m, 1H), 7.89-8.05 (m, 2H), 7.72 (d, J=5.1

Hz, 1H), 7.62-7.65 (m, 1H), 7.12 (d, J=5.1 Hz, 1H), 6.22 (dd, J=5.7, 3.0 Hz, 1H), 6.06 (dd, J=5.7, 2.8 Hz, 1H), 2.88-2.90 (m, 1H), 2.77-2.79 (m, 1H), 2.42-2.52 (m, 1H), 2.10 (s, 3H), 2.08 (m, 2H), 1.90 (ddd, J=11.5, 9.1, 3.7 Hz, 1H), 1.33-1.36 (m, 1H), 1.26 (d, J=8.0 Hz, 1H), 0.60 (ddd, J=11.5, 4.3, 2.5 Hz, 1H); MS (APCI) M/Z 392 (M+H)$^+$.

Example 18

2-(3,5-difluorophenyl)-N-[1-oxo-4-(pyridin-2-yl) phthalazin-2(1H)-yl]acetamide

Example 18A 2-amino-4-(pyridin-2-yl)phthalazin-1(2H)-one

A mixture of 4-chlorophthalazin-1(2H)-one (100 mg, 0.554 mmol), pyridin-2-ylzinc(II) bromide (0.5M in THF, 2.2 mL, 1.1 mmol) and Pd(PPh$_3$)$_4$ (32 mg, 0.028 mmol) in THF (1 mL) was heated at 150° C. under microwave condition for 30 minutes. The mixture was diluted with EtOAc and washed with saturated aqueous NaHCO$_3$, dried (Na$_2$SO$_4$), filtered, and concentrated to afford the title compound. MS (APCI$^+$) M/Z 224 (M+H)$^+$.

Example 18B 2-(3,5-difluorophenyl)-N-[1-oxo-4-(pyridin-2-yl) phthalazin-2(1H)-yl]acetamide The product from Example 18A and 2-(3,5-difluorophenyl)acetic acid were processed using a method similar to that described in Example 10C to afford the title compound. $^1$H NMR (400 MHz, DMSO-d$_6$) δ 11.83 (s, 1H), 8.78 (ddd, J=4.8, 1.7, 0.9, 1H), 8.46-8.30 (m, 2H), 7.99 (dddd, J=16.4, 15.3, 7.5, 1.6, 3H), 7.80 (dt, J=7.8, 1.0, 1H), 7.59 (ddd, J=7.6, 4.8, 1.1, 1H), 7.23-7.09 (m, 3H), 3.79 (s, 2H); MS (APCI) M/Z 393 (M+H)$^+$.

Example 19

(±)-2-[(exo)-bicyclo[2.2.1]hept-2-yl]-N-[1-oxo-4-(pyridin-2-yl)phthalazin-2(1H)-yl]acetamide The products from Example 18A and Example 3A were processed using a method similar to that described in Example 3B to afford the title compound. $^1$H NMR (400 MHz, DMSO-d$_6$) δ ppm 11.41 (s, 1H), 8.78 (ddd, J=4.8, 1.8, 0.9 Hz, 1H), 8.32-8.44 (m, 2H), 7.89-8.09 (m, 3H), 7.80 (dt, J=7.8, 1.1 Hz, 1H), 7.59 (ddd, J=7.6, 4.8, 1.2 Hz, 1H), 2.29 (dd, J=14.3, 8.3 Hz, 1H), 2.19-2.23 (m, 1H), 2.16 (dd, J=14.3, 7.5 Hz, 1H), 2.12-2.14 (m, 1H), 1.86-1.94 (m, 1H), 1.34-1.58 (m, 4H), 1.07-1.23 (m, 4H); MS (APCI) M/Z 375 (M+H)$^+$.

Example 20

2-(3,5-difluorophenyl)-N-[1-oxo-4-(pyrrolidin-1-yl) phthalazin-2(1H)-yl]acetamide

Example 20A 2-amino-4-(pyrrolidin-1-yl)phthalazin-2(1H)-one

A mixture of 4-chlorophthalazin-1(2H)-one and pyrrolidine was processed using a method similar to that described in Example 1A to give crude 4-(pyrrolidin-1-yl)phthalazin-2(1H)-one, which was processed using a method similar to that described in Example 1B to give crude 2-amino-4-(pyrrolidin-1-yl)phthalazin-2(1H)-one, which was used without purification: MS (APCI$^+$) M/Z 231 (M+H)$^+$.

Example 20B 2-(3,5-difluorophenyl)-N-[1-oxo-4-(pyrrolidin-1-yl) phthalazin-2(1H)-yl]acetamide The product from Example 20A and 2-(3,5-difluorophenyl)acetic acid were processed using a method similar to that described in Example 10C to afford the title compound. $^1$H NMR (400 MHz, DMSO-d$_6$) δ ppm 11.43 (s, 1H), 8.31 (dd, J=7.8, 1.5 Hz, 1H), 8.16 (d, J=8.0 Hz, 1H), 7.94 (ddd, J=8.0, 7.2, 1.6 Hz, 1H), 7.87 (ddd, J=7.9, 7.2, 1.2 Hz, 1H), 7.09-7.21 (m, 3H), 3.71-3.71 (bs, 2H), 3.45-3.49 (m, 4H), 1.88-1.96 (m, 4H); MS (APCI) M/Z 385 (M+H)$^+$.

Example 21

2-(4-chlorophenyl)-N-[1-oxo-4-(pyrrolidin-1-yl) phthalazin-2(1H)-yl]acetamide

The product from Example 20A and 2-(4-chlorophenyl) acetic acid were processed using a method similar to that described in Example 10C to afford the title compound. $^1$H NMR (400 MHz, DMSO-d$_6$) δ ppm 11.37 (s, 1H), 8.29 (dd, J=7.9, 1.5 Hz, 1H), 8.15 (d, J=8.3 Hz, 1H), 7.94 (ddd, J=8.1, 7.2, 1.6 Hz, 1H), 7.86 (ddd, J=7.9, 7.2, 1.2 Hz, 1H), 7.33-7.46 (m, 4H), 3.65 (s, 2H), 3.43-3.48 (m, 4H), 1.84-1.95 (m, 4H); MS (APCI) M/Z 383 (M+H)+.

Example 22

2-(3,5-difluorophenyl)-N-[1-oxo-4-(piperidin-1-yl) phthalazin-2(1H)-yl]acetamide

Example 22A 2-amino-4-(piperidin-1-yl)phthalazin-2(1H)-one

A mixture of 4-chlorophthalazin-1(2H)-one and piperidine was processed using a method similar to that described in Example 1A to give crude 4-(piperidin-1-yl)phthalazin-2(1H)-one, which was processed using a method similar to that described in Example 1B to give crude 2-amino-4-(piperidin-1-yl)phthalazin-2(1H)-one, which was used without purification: MS (APCI) M/Z 230 (M+H)+.

Example 22B 2-(3,5-difluorophenyl)-N-[1-oxo-4-(piperidin-1-yl) phthalazin-2(1H)-yl]acetamide The product from Example 22A and 2-(3,5-difluorophenyl)acetic acid were processed using a method similar to that described in Example 10C to afford the title compound. $^1$H NMR (400 MHz, DMSO-d$_6$) δ ppm 11.51 (s, 1H), 8.30 (ddd, J=7.9, 1.4, 0.7 Hz, 1H), 7.98 (ddd, J=8.1, 6.8, 1.3 Hz, 1H), 7.92-7.95 (m, 1H), 7.88 (ddd, J=8.0, 6.7, 1.4 Hz, 1H), 7.09-7.22 (m, 3H), 3.73 (s, 2H), 3.01-3.16 (m, 4H), 1.67-1.79 (m, 4H), 1.54-1.64 (m, 2H); MS (APCI) M/Z 399 (M+H)+.

Example 23

(±)-2-[(exo)-bicyclo[2.2.1]hept-2-yl]-N-[1-oxo-4-(pyrrolidin-1-yl)phthalazin-2(1H)-yl]acetamide The products from Example 20A and Example 3A were processed using a method similar to that described in Example 3B to afford the title compound. $^1$H NMR (400 MHz, DMSO-d$_6$) δ ppm 10.98 (s, 1H), 8.29 (dd, J=7.8, 1.5 Hz, 1H), 8.13-8.16 (m, 1H), 7.93 (ddd, J=8.3, 7.1, 1.4 Hz, 1H), 7.86 (ddd, J=7.7, 7.3, 1.1 Hz, 1H), 3.44-3.48 (m, 4H), 2.18-2.24 (m, 2H), 2.06-2.13 (m, 2H), 1.80-1.95 (m, 5H), 1.33-1.57 (m, 4H), 1.02-1.22 (m, 4H); MS (APCI) M/Z 367 (M+H)+.

Example 24

2-(4-chlorophenyl)-N-[1-oxo-4-(piperidin-1-yl)phthalazin-2(1H)-yl]acetamide

The product from Example 22A and 2-(4-chlorophenyl) acetic acid were processed using a method similar to that described in Example 10C to afford the title compound. $^1$H NMR (400 MHz, DMSO-d$_6$) δ ppm 11.45 (s, 1H), 8.28 (dd, J=7.9, 1.3 Hz, 1H), 7.97 (ddd, J=8.1, 6.9, 1.3 Hz, 1H), 7.94 (d, J=1.5 Hz, 1H), 7.88 (ddd, J=8.0, 6.8, 1.4 Hz, 1H), 7.40-7.41 (m, 4H), 3.66 (s, 2H), 3.03-3.06 (m, 4H), 1.69-1.74 (m, 4H), 1.57-1.62 (m, 2H); MS (APCI) M/Z 397 (M+H)$^+$.

Example 25

(±)-2-[(exo)-bicyclo[2.2.1]hept-2-yl]-N-[1-oxo-4-(piperidin-1-yl)phthalazin-2(1H)-yl]acetamide The products from Example 22A and Example 3A were processed using a method similar to that described in Example 3B to afford the title compound. $^1$H NMR (400 MHz, DMSO-d$_6$) δ ppm 11.07 (s, 1H), 8.28 (dd, J=7.9, 1.3 Hz, 1H), 7.91-8.03 (m, 2H), 7.87 (ddd, J=8.0, 6.7, 1.4 Hz, 1H), 3.03-3.06 (m, 4H), 2.19-2.25 (m, 2H), 2.12 (d, J=6.4 Hz, 2H), 1.83-1.91 (m, 1H), 1.70-1.76 (m, 4H), 1.57-1.62 (m, 2H), 1.24-1.54 (m, 4H), 1.06-1.22 (m, 4H); MS (APCI) M/Z 381 (M+H)$^+$.

Example 26

(±)-2-[(exo)-bicyclo[2.2.1]hept-2-yl]-N-[4-(6-methoxypyridin-3-yl)-1-oxophthalazin-2(1H)-yl]acetamide

Example 26A 2-amino-4-(6-methoxypyridin-3-yl)phthalazin-1(2H)-one

A mixture of ethyl 2-(6-methoxynicotinoyl)benzoate (0.496 g, 1.74 mmol) and hydrazine hydrate (0.39 mL, 6.9 mmol) in ethanol (6 mL) was stirred at 80° C. for 2 hours, concentrated, and azeotroped with PhMe to give crude 4-(6-methoxypyridin-3-yl)phthalazin-1(2H)-one, which was used without purification.
To a mix of the above material in THF (5 mL) and DMF (2 mL) was added a THF solution of potassium 2-methylpropan-2-olate (2.3 mL, 2.3 mmol). The mix was stirred at room temperature for 90 minutes, and O-(diphenylphosphoryl)hydroxylamine (0.526 g, 2.25 mmol) was added and stirred at room temperature overnight. The mixture was diluted with EtOAc, washed with 0.5N NaOH and water, and concentrated to give 424 mg of crude title compound, which was used without purification: $^1$H NMR (300 MHz, DMSO-d$_6$) δ 8.46-8.32 (m, 2H), 7.97 (d, J=8.5, 2.5, 1H), 7.93-7.85 (m, 2H), 7.73 (dd, J=6.2, 3.1, 1H), 7.02 (d, J=8.6, 1H), 6.51 (s, 2H), 3.95 (s, 3H).

Example 26B (±)-2-[(exo)-bicyclo[2.2.1]hept-2-yl]-N-[4-(6-methoxypyridin-3-yl)-1-oxophthalazin-2(1H)-yl]acetamide The products from Example 26A and Example 3A were processed using a method similar to that described in Example 3B to afford the title compound. $^1$H NMR (300 MHz, DMSO-d$_6$) δ ppm 11.34 (s, 1H), 8.34-8.46 (m, 2H), 7.89-8.05 (m, 3H), 7.73-7.76 (m, 1H), 7.02 (dd, J=8.6, 0.7 Hz, 1H), 3.95 (s, 3H), 2.23-2.32 (m, 1H), 2.19-2.23 (m, 1H), 2.10-2.19 (m, 1H), 2.09-2.13 (m, 1H), 1.84-1.94 (m, 1H), 1.32-1.55 (m, 4H), 1.08-1.22 (m, 4H); MS (ESI$^+$) M/Z 405 (M+H)$^+$.

Example 27

N-[4-(6-chloropyridin-3-yl)-1-oxophthalazin-2(1H)-yl]-3-methyl-3-phenylbutanamide The product from Example 4B and 3-methyl-3-phenylbutanoic acid were processed using a method similar to that described in Example 10C to afford the title compound. $^1$H NMR (400 MHz, DMSO-d$_6$) δ ppm 11.44 (s, 1H), 8.63-8.64 (m, 1H), 8.37-8.47 (m, 1H), 8.12 (dd, J=8.2, 2.5 Hz, 1H), 7.92-8.04 (m, 2H), 7.73-7.76 (m, 2H), 7.41-7.49 (m, 2H), 7.28-7.34 (m, 2H), 7.16-7.20 (m, 1H), 2.63 (s, 2H), 1.47 (s, 6H); MS (APCI) M/Z 433 (M+H)+.

Example 28

(±)-2-[(exo)-bicyclo[2.2.1]hept-2-yl]-N-[1-oxo-4-(tetrahydro-2H-pyran-4-yl)phthalazin-2(1H)-yl]acetamide The product from Example 6C was processed using a method similar to that described in Example 8 to afford the title compound. $^1$H NMR (400 MHz, DMSO-d$_6$) δ ppm 11.19 (s, 1H), 8.33 (dd, J=7.9, 1.4 Hz, 1H), 8.19 (d, J=8.1 Hz, 1H), 7.97-8.02 (m, 1H), 7.88-7.92 (m, 1H), 3.92-3.97 (m, 2H), 3.50-3.63 (m, 3H), 2.21-2.28 (m, 2H), 2.07-2.16 (m, 2H), 1.86-2.01 (m, 1H), 1.66-1.84 (m, 4H), 1.42-1.57 (m, 3H), 1.36-1.40 (m, 1H), 1.01-1.19 (m, 4H).

Example 29

(±)-2-[(exo)-bicyclo[2.2.1]hept-2-yl]-N-[4-(2-chloropyridin-4-yl)-1-oxophthalazin-2(1H)-yl]acetamide

Example 29A 4-(2-chloropyridin-4-yl)phthalazin-1(2H)-one

A mixture of 4-chlorophthalazin-1(2H)-one (300 mg, 1.66 mmol), 2-chloropyridin-4-ylboronic acid (314 mg, 1.99 mmol), Cs$_2$CO$_3$ (1080 mg, 3.32 mmol) and PdCl$_2$(dppf) (71.5 mg, 0.083 mmol) in dioxane (6 mL) was heated at 160° C. under microwave condition for 20 minutes. The mixture was diluted with EtOAc and washed with saturated aqueous NaHCO$_3$, dried (Na$_2$SO$_4$), filtered, and concentrated to afford the title compound: MS (APCI) M/Z 257 (M+H)$^+$.

Example 29B 2-amino-4-(2-chloropyridin-4-yl)phthalazin-1(2H)-one

The product from Example 29A was processed using a method similar to that described in Example 1B to afford the title compound, which was used without purification: MS (APCI) M/Z 273 (M+H)+.

Example 29C (±)-2-[(exo)-bicyclo[2.2.1]hept-2-yl]-N-[4-(2-chloropyridin-4-yl)-1-oxophthalazin-2(1H)-yl]acetamide The products from Example 29B and Example 3A were processed using a method similar to that described in Example 4C to afford the title compound. $^1$H NMR (500 MHz, DMSO-$d_6$) δ ppm 11.42 (s, 1H), 8.62 (d, J=5.0 Hz, 1H), 8.41-8.43 (m, 1H), 7.94-8.05 (m, 2H), 7.78 (d, J=2.2 Hz, 1H), 7.77-7.77 (m, 1H), 7.68 (dd, J=5.0, 1.5 Hz, 1H), 2.28 (dd, J=14.2, 8.3 Hz, 1H), 2.20-2.22 (m, 1H), 2.16 (dd, J=14.2, 7.4 Hz, 1H), 2.10-2.12 (m, 1H), 1.83-1.95 (m, 1H), 1.42-1.56 (m, 3H), 1.38 (d, J=9.7 Hz, 1H), 1.07-1.21 (m, 4H); MS (ESI$^+$) M/Z 411 (M+H)+.

Example 30

(±)-2-[(exo)-bicyclo[2.2.1]hept-2-yl]-N-{4-[(6-chloropyridin-3-yl)methyl]-1-oxophthalazin-2(1H)-yl}acetamide

Example 30A 2-amino-4-((6-chloropyridin-3-yl)methyl)phthalazin-1(2H)-one

A mixture of 4-chlorophthalazin-1(2H)-one (700 mg, 3.88 mmol), [(6-chloropyridin-3-yl)methyl]zinc(II) chloride (0.5M in THF, 15.5 mL, 7.75 mmol), Pd(PPh$_3$)$_4$ (224 mg, 0.194 mmol) in THF (2 mL) was heated at 180° C. under microwave condition for 20 minutes. The mixture was diluted with EtOAc and washed with saturated aqueous NaHCO$_3$, dried (Na$_2$SO$_4$), filtered, and concentrated to afford 160 mg (15%) of the title compound: MS (APCI) M/Z 272 (M+H)+.

Example 30B (±)-2-[(exo)-bicyclo[2.2.1]hept-2-yl]-N-{4-[(6-chloropyridin-3-yl)methyl]-1-oxophthalazin-2(1H)-yl}acetamide The products from Example 30A and Example 3A were processed using a method similar to that described in Example 3B to afford the title compound. $^1$H NMR (500 MHz, DMSO-$d_6$) δ ppm 11.22 (s, 1H), 8.42 (d, J=2.5 Hz, 1H), 8.32 (dd, J=7.9, 1.3 Hz, 1H), 8.06 (d, J=8.1 Hz, 1H), 7.96-7.99 (m, 1H), 7.88-7.91 (m, 1H), 7.74 (dd, J=8.2, 2.5 Hz, 1H), 7.46 (d, J=8.2 Hz, 1H), 4.39-4.39 (bs, 2H), 2.20-2.25 (m, 2H), 2.04-2.16 (m, 2H), 1.83-1.89 (m, 1H), 1.32-1.51 (m, 4H), 1.05-1.20 (m, 4H); MS (APCI) M/Z 423 (M+H)+.

Example 31

N-{4-[(6-chloropyridin-3-yl)methyl]-1-oxophthalazin-2(1H)-yl}-2-(3,5-difluorophenyl)acetamide The product from Example 30A and 2-(3,5-difluorophenyl)acetic acid were processed using a method similar to that described in Example 10C to afford the title compound. $^1$H NMR (400 MHz, DMSO-$d_6$) δ ppm 11.66 (s, 1H), 8.42 (d, J=2.5 Hz, 1H), 8.33 (dd, J=7.9, 1.4 Hz, 1H), 8.06 (d, J=8.0 Hz, 1H), 7.95-8.00 (m, 1H), 7.87-7.93 (m, 1H), 7.74 (dd, J=8.2, 2.5 Hz, 1H), 7.45 (d, J=8.2 Hz, 1H), 7.05-7.21 (m, 3H), 4.39-4.40 (bs, 2H), 3.74 (s, 2H); MS (APCI) M/Z 441 (M+H)+.

Example 32

2-(4-chlorophenyl)-N-{4-[(6-chloropyridin-3-yl)methyl]-1-oxophthalazin-2(1H)-yl}acetamide The product from Example 30A and 2-(4-chlorophenyl)acetic acid were processed using a method similar to that described in Example 10C to afford the title compound. $^1$H NMR (400 MHz, DMSO-$d_6$) δ ppm 11.60 (s, 1H), 8.42 (d, J=2.5 Hz, 1H), 8.32 (dd, J=7.9, 1.3 Hz, 1H), 8.06 (d, J=8.0 Hz, 1H), 7.97 (ddd, J=8.1, 7.2, 1.4 Hz, 1H), 7.90 (ddd, J=8.0, 7.2, 1.3 Hz, 1H), 7.73 (dd, J=8.2, 2.5 Hz, 1H), 7.46 (dd, J=8.2, 0.8 Hz, 1H), 7.39-7.43 (m, 2H), 7.35-7.38 (m, 2H), 4.39 (s, 2H), 3.68 (s, 2H); MS (APCI) M/Z 439 (M+H)+.

Example 33

3-methyl-N-[4-(morpholin-4-yl)-1-oxophthalazin-2(1H)-yl]-3-phenylbutanamide

The product from Example 1B and 3-methyl-3-phenylbutanoic acid were processed using a method similar to that described in Example 10C to afford the title compound. $^1$H NMR (400 MHz, DMSO-$d_6$) δ ppm 11.16 (s, 1H), 8.30 (dd, J=7.8, 1.3 Hz, 1H), 8.01 (ddd, J=8.0, 1.4, 0.7 Hz, 1H), 7.97 (ddd, J=8.1, 6.9, 1.3 Hz, 1H), 7.89 (ddd, J=7.9, 7.0, 1.5 Hz, 1H), 7.43-7.45 (m, 2H), 7.29-7.34 (m, 2H), 7.15-7.22 (m, 1H), 3.78-3.84 (m, 4H), 3.05-3.08 (m, 4H), 2.57 (s, 2H), 1.46 (s, 6H); MS (APCI) M/Z 407 (M+H)+.

Example 34

(±)-N-[4-(benzylamino)-1-oxophthalazin-2(1H)-yl]-2-[(exo)-bicyclo[2.2.1]hept-2-yl]acetamide

Example 34A 2-amino-4-(benzylamino)phthalazin-2(1H)-one

A mixture of 4-chlorophthalazin-1(2H)-one and benzylamine was processed using a method similar to that described in Example 1A to give crude 4-(benzylamino)phthalazin-2(1H)-one, which was processed using a method similar to that described in Example 1B to give crude 2-amino-4-(benzylamino)phthalazin-2(1H)-one, which was used without purification: MS (APCI) M/Z 252 (M+H)+.

Example 34B (±)-N-[4-(benzylamino)-1-oxophthalazin-2(1H)-yl]-2-[(exo)-bicyclo[2.2.1]hept-2-yl]acetamide The products from Example 34A and Example 3A were processed using a method similar to that described in Example 3B to afford the title compound. $^1$H NMR (400 MHz, DMSO-$d_6$) δ ppm 10.89 (s, 1H), 8.27 (d, J=7.8 Hz, 1H), 8.22 (d, J=7.9 Hz, 1H), 7.92-7.97 (m, 1H), 7.84-7.90 (m, 1H), 7.38-7.41 (m, 2H), 7.28-7.33 (m, 2H), 7.20-7.25 (m, 1H), 6.40-6.60 (m, 1H), 4.35-4.49 (m, 2H), 2.01-2.23 (m, 4H), 1.79-1.95 (m, 1H), 1.34-1.52 (m, 4H), 1.05-1.20 (m, 4H); MS (APCI) M/Z 403 (M+H)+.

Example 35

(±)-2-[(exo)-bicyclo[2.2.1]hept-2-yl]-N-{4-[(3-chlorophenyl)amino]-1-oxophthalazin-2(1H)-yl}acetamide Example 35A 2-amino-4-[(3-chlorophenyl)amino]phthalazin-2(1H)-one A mixture of 4-chlorophthalazin-1(2H)-one and 3-chloroaniline was processed using a method similar to that described in Example 1A to give crude 4-[(3-chlorophenyl)amino]phthalazin-2(1H)-one, which was processed using a method similar to that described in Example 1B to give crude 2-amino-4-[(3-chlorophenyl)amino]phthalazin-2(1H)-one, which was used without purification: MS (APCI) M/Z 287 (M+H)+.

Example 35B (±)-2-[(exo)-bicyclo[2.2.1]hept-2-yl]-N-{4-[(3-chlorophenyl)amino]-1-oxophthalazin-2(1H)-yl}acetamide The products from Example 35A and Example 3A were processed using a method similar to that described in Example 3B to afford the title compound. $^1$H NMR (400 MHz, DMSO-$d_6$) δ ppm 11.17 (s, 1H), 8.98 (s, 1H), 8.40 (d, J=8.3 Hz, 1H), 8.35 (dd, J=7.9, 1.3 Hz, 1H), 8.06 (td, J=7.7, 1.5 Hz, 1H), 7.95 (d, J=7.5 Hz, 1H), 7.83 (t, J=2.1 Hz, 1H), 7.56 (dd, J=8.1, 2.3 Hz, 1H), 7.29 (t, J=8.1 Hz, 1H), 6.98 (dd, J=7.8, 2.0 Hz, 1H), 2.20-2.27 (m, 2H), 2.08-2.14 (m, 2H), 1.87-1.93 (m, 1H), 1.43-1.52 (m, 3H), 1.36-1.42 (m, 1H), 1.06-1.22 (m, 4H); MS (APCI) M/Z 423 (M+H)+.

Example 36

N-{4-[benzyl(methyl)amino]-1-oxophthalazin-2(1H)-yl}-2-(4-chlorophenyl)acetamide Example 36A 2-amino-4-[benzyl(methyl)amino]phthalazin-2(1H)-one A mixture of 4-chlorophthalazin-1(2H)-one and N-methyl-benzylamine was processed using a method similar to that described in Example 1A to give crude 4-(benzyl(methyl)amino)phthalazin-2(1H)-one, which was processed using a method similar to that described in Example 1B to give crude 2-amino-4-(benzyl(methyl)amino)phthalazin-2(1H)-one, which was used without purification: MS (APCI) M/Z 281 (M+H)+.

Example 36B

N-{4-[benzyl(methyl)amino]-1-oxophthalazin-2(1H)-yl}-2-(4-chlorophenyl)acetamide The product from Example 36A and 2-(4-chlorophenyl)acetic acid were processed using a method similar to that described in Example 10C to afford the title compound. $^1$H NMR (400 MHz, DMSO-$d_6$) δ ppm 11.47 (s, 1H), 8.31 (d, J=7.2 Hz, 1H), 8.03-8.06 (m, 1H), 7.95-8.00 (m, 1H), 7.87-7.92 (m, 1H), 7.33-7.43 (m, 8H), 7.26-7.32 (m, 1H), 4.30-4.31 (bs, 2H), 3.66 (s, 2H), 2.69 (s, 3H); MS (APCI) M/Z 433 (M+H)+.

Example 37

(±)-N-{4-[benzyl(methyl)amino]-1-oxophthalazin-2(1H)-yl}-2-[(exo)-bicyclo[2.2.1]hept-2-yl]acetamide The products from Example 36A and Example 3A were processed using a method similar to that described in Example 3B to afford the title compound. $^1$H NMR (400 MHz, DMSO-$d_6$) δ ppm 11.09 (s, 1H), 8.32 (ddd, J=7.9, 1.4, 0.6 Hz, 1H), 8.04 (ddd, J=8.2, 1.4, 0.7 Hz, 1H), 7.97 (ddd, J=8.5, 7.1, 1.4 Hz, 1H), 7.89 (ddd, J=7.9, 7.1, 1.3 Hz, 1H), 7.34-7.44 (m, 4H), 7.27-7.33 (m, 1H), 4.30-4.31 (bs, 2H), 2.69 (s, 3H), 2.22 (dd, J=14.2, 8.3 Hz, 1H), 2.19-2.22 (m, 1H), 2.12-2.14 (m, 1H), 2.11 (dd, J=14.1, 7.3 Hz, 1H), 1.84-1.92 (m, 1H), 1.40-1.55 (m, 3H), 1.35-1.40 (m, 1H), 1.04-1.19 (m, 4H); MS (APCI) M/Z 417 (M+H)+.

Example 38

2-(3,5-difluorophenyl)-N-(1-oxo-4-phenoxyphthalazin-2(1H)-yl)acetamide

Example 38A 2-amino-4-phenoxyphthalazin-2(1H)-one

A mixture of 1,4-dichlorophthalazine (424 mg, 2.13 mmol), phenol (200 mg, 2.13 mmol) and $K_2CO_3$ (589 mg, 4.26 mmol) in DMF (10 mL) was heated at 100° C. for 40 minutes. The mixture was diluted with water and extracted with EtOAc (2×). The combined organic layer was washed with saturated aqueous $NaHCO_3$, dried ($Na_2SO_4$), filtered, and concentrated to afford the title compound. MS (APCI) M/Z 257 (M+H)+.

Example 38B 2-(3,5-difluorophenyl)-N-(1-oxo-4-phenoxyphthalazin-2(1H)-yl)acetamide The product from Example 38A and 2-(3,5-difluorophenyl)acetic acid were processed using a method similar to that described in Example 10C to afford the title compound. $^1$H NMR (500 MHz, DMSO-$d_6$) δ ppm 11.49-11.51 (bs, 1H), 8.36 (ddd, J=7.9, 1.3, 0.6 Hz, 1H), 8.18 (ddd, J=7.9, 1.3, 0.6 Hz, 1H), 8.08 (ddd, J=8.0, 7.2, 1.4 Hz, 1H), 8.02 (ddd, J=7.8, 7.3, 1.3 Hz, 1H), 7.42-7.48 (m, 2H), 7.29-7.32 (m, 2H), 7.24-7.28 (m, 1H), 7.13 (tt, J=9.5, 2.3 Hz, 1H), 7.02-7.09 (m, 2H), 3.66 (s, 2H); MS (APCI) M/Z 408 (M+H)+.

Example 39

(±)-2-[(exo)-bicyclo[2.2.1]hept-2-yl]-N-(1-oxo-4-phenoxyphthalazin-2(1H)-yl)acetamide The products from Example 38A and Example 3A were processed using a method similar to that described in Example 3B to afford the title compound. $^1$H NMR (400 MHz, DMSO-$d_6$) δ 11.10-11.02 (m, 1H), 8.40-8.30 (m, 1H), 8.20-8.13 (m, 1H), 8.10-8.04 (m, 1H), 8.03-7.96 (m, 1H), 7.51-7.40 (m, 2H), 7.33-7.22 (m, 3H), 2.20-2.10 (m, 2H), 2.08-1.99 (m, 2H), 1.88-1.76 (m, 1H), 1.51-1.27 (m, 4H), 1.18-0.99 (m, 4H); MS (APCI) M/Z 390 (M+H)+.

Example 40

(±)-N-(4-benzoyl-1-oxophthalazin-2(1H)-yl)-2-[(exo)-bicyclo[2.2.1]hept-2-yl]acetamide Example 40A 2-amino-4-benzylphthalazin-1(2H)-one 2-(2-phenylacetyl)benzoic acid was treated using methods similar to that described in Examples 4A and Example 4B to give the title compound: MS (APCI+) M/Z 253 (M+H)+.

Example 40B (±)-N-(4-benzyl-1-oxophthalazin-2(1H)-yl)-2-(exo-bicyclo[2.2.1]hept-2-yl)acetamide The product of Example 40A and the product of Example 3A were treated using a method similar to that described in Example 4C to give the title compound. $^1$H NMR (400 MHz, DMSO-$d_6$) δ ppm 11.26 (s, 1H), 8.30 (dd, J=7.8, 1.5 Hz, 1H), 7.96-7.99 (m, 1H), 7.90 (ddd, J=8.0, 7.2, 1.5 Hz, 1H), 7.85 (ddd, J=7.8, 7.1, 1.4 Hz, 1H), 7.24-7.37 (m, 4H), 7.17-7.22 (m, 1H), 4.31-4.31 (bs, 2H), 2.26 (dd, J=14.3, 8.3 Hz, 1H), 2.19-2.23 (m, 1H), 2.14 (dd, J=14.3, 7.2 Hz, 1H), 2.11-2.14 (m, 1H), 1.86-1.94 (m, 1H), 1.34-1.58 (m, 4H), 1.02-1.23 (m, 4H); MS (APCI) M/Z 388 (M+H)+.

Example 40C (±)-N-(4-benzoyl-1-oxophthalazin-2(1H)-yl)-2-[(exo)-bicyclo[2.2.1]hept-2-yl]acetamide A mixture of the product from Example 40B (80 mg, 0.21 mmol) and $Na_2Cr_2O_7$ (92 mg, 0.31 mmol) in acetic acid (1 mL) was refluxed for 12 hours, concentrated, diluted with EtOAc, washed with saturated aqueous $NaHCO_3$, dried ($Na_2SO_4$), filtered, and purified by preparative HPLC (conditions from Example 10C) to give the title compound (24 mg, 0.060 mmol): $^1$H NMR (500 MHz, DMSO-$d_6$) δ ppm 11.47-11.53 (bs, 1H), 8.41 (d, J=8.0 Hz, 1H), 8.17 (d, J=8.0 Hz, 1H), 7.94-8.07 (m, 4H), 7.71-7.76 (m, 1H), 7.54-7.59 (m, 2H), 2.25 (dd, J=14.2, 8.4 Hz, 1H), 2.17-2.20 (m, 1H), 2.14 (dd, J=14.2, 7.5 Hz, 1H), 2.05-2.09 (m, 1H), 1.84-1.91 (m, 1H), 1.38-1.51 (m, 3H), 1.33-1.38 (m, 1H), 1.07-1.18 (m, 4H); MS (APCI) M/Z 402 (M+H)+.

Example 41 tert-butyl[(3-{[(4-chlorophenyl)acetyl]amino}-4-oxo-3,4-dihydrophthalazin-1-yl)methyl]carbamate Example 41A tert-butyl(4-oxo-3,4-dihydrophthalazin-1-yl)methylcarbamate A mixture of 4-(aminomethyl)phthalazin-1(2H)-one hydrochloride hydrate (0.300 g, 1.31 mmol), $BOC_2O$ (0.314 g, 1.44 mmol), and triethylamine (0.46 mL, 3.3 mmol) in DCM (4.5 mL) was stirred for 2 hours, diluted with EtOAc, washed with saturated $NaHCO_3$ and brine, dried ($Na_2SO_4$), filtered, and chromatographed (70% EtOAc/hexanes) to give 313 mg of the title compound as a white solid: $^1$H NMR (300 MHz, DMSO-$d_6$) δ 12.62-12.50 (m, 1H), 8.30-8.22 (m, 1H), 8.01 (s, 1H), 7.92 (dd, J=11.0, 4.1, 1H), 7.89-7.80 (m, 1H), 7.41-7.26 (m, 1H), 4.44 (d, J=5.8, 2H), 1.39 (s, 9H).

Example 41B tert-butyl(3-amino-4-oxo-3,4-dihydrophthalazin-1-yl)methylcarbamate

The product of Example 41A was processed using a method similar to that described in Example 1B to give the title compound: $^1$H NMR (300 MHz, DMSO-$d_6$) δ 8.30 (dd, J=7.8, 1.4, 1H), 8.07 (dd, J=7.3, 1.5, 1H), 7.88 (pd, J=7.2, 1.4, 2H), 7.40 (s, 1H), 6.33 (s, 2H), 4.47 (d, J=5.8, 2H), 1.39 (s, 9H).

Example 41C tert-butyl[(3-{[(4-chlorophenyl)acetyl]amino}-4-oxo-3,4-dihydrophthalazin-1-yl)methyl]carbamate The product of Example 41B was treated with 2-(4-chlorophenyl)acetyl chloride using a method similar to that described in Example 4C to give the title compound. $^1$H NMR (300 MHz, DMSO-$d_6$) δ ppm 11.59 (s, 1H), 8.32 (dd, J=7.8, 1.4 Hz, 1H), 8.11 (ddd, J=8.0, 1.3, 0.7 Hz, 1H), 7.99 (ddd, J=8.0, 7.2, 1.5 Hz, 1H), 7.91 (ddd, J=7.8, 7.2, 1.3 Hz, 1H), 7.33-7.48 (m, 5H), 4.42-4.46 (m, 2H), 3.67 (s, 2H), 1.37 (s, 9H); MS (APCI+) M/Z 343 (M–$CO_2$tBu+H)+.

Example 42

N-[4-(aminomethyl)-1-oxophthalazin-2(1H)-yl]-2-(4-chlorophenyl)acetamide

A solution the product of Example 41C (28.5 mg, 0.064 mmol) in 2,2,2-trifluoroacetic acid (0.1 mL) and DCM (0.3 mL) was stirred at room temperature for 2 hours, diluted with EtOAc, washed with sat $NaHCO_3$ and brine, dried ($Na_2SO_4$), filtered, and chromatographed (10% MeOH/DCM) to give 6.7 mg of the title compound as a white solid: $^1$H NMR (300 MHz, DMSO-$d_6$) δ ppm 11.38-11.65 (m, 1H), 8.29-8.32 (m, 1H), 8.17 (dd, J=8.0, 1.1 Hz, 1H), 7.95-8.01 (m, 1H), 7.86-7.92 (m, 1H), 7.40-7.42 (m, 4H), 4.01 (s, 2H), 3.68 (s, 2H); MS (ESI+) M/Z 343 (M+H)+.

Example 43

(±)-2-[(exo)-bicyclo[2.2.1]hept-2-yl]-N-{1-oxo-4-[6-(trifluoromethyl)pyridin-3-yl]phthalazin-2(1H)-yl}acetamide Example 43A 2-amino-4-[6-(trifluoromethyl)pyridin-3-yl]phthalazin-2(1H)-one Ethyl 2-(6-(trifluoromethyl)nicotinoyl)benzoate was processed using methods similar to those described in Examples 4A and 4B to afford the title compound: MS (ESI+) M/Z 307 (M+H)+.

Example 43B (±)-2-[(exo)-bicyclo[2.2.1]hept-2-yl]-N-{1-oxo-4-[6-(trifluoromethyl)pyridin-3-yl]phthalazin-2(1H)-yl}acetamide The product of Example 43A was processed using methods similar to those described in Example 4C to give the title compound. $^1$H NMR (300 MHz, DMSO-$d_6$) δ ppm 11.41-11.43 (bs, 1H), 9.01 (d, J=2.0 Hz, 1H), 8.32-8.50 (m, 2H), 8.12 (d, J=8.1 Hz, 1H), 7.97-8.01 (m, 2H), 7.74-7.79 (m, 1H), 2.03-2.37 (m, 4H), 1.84-1.99 (m, 1H), 1.32-1.60 (m, 4H), 1.04-1.30 (m, 4H); MS (ESI$^+$) M/Z 443 (M+H)$^+$.

Example 44

(±)-tert-butyl[(3-{[(exo)-bicyclo[2.2.1]hept-2-ylacetyl]amino}-4-oxo-3,4-dihydrophthalazin-1-yl)methyl]carbamate The product of Example 41B was processed using a method similar to that described in Example 4C to give the title compound. $^1$H NMR (300 MHz, DMSO-$d_6$) δ ppm 11.21 (s, 1H), 8.32 (dd, J=7.9, 1.4 Hz, 1H), 8.10 (ddd, J=8.0, 1.4, 0.6 Hz, 1H), 7.98 (ddd, J=8.0, 7.2, 1.5 Hz, 1H), 7.90 (ddd, J=7.8, 7.2, 1.3 Hz, 1H), 7.37-7.43 (m, 1H), 4.43-4.47 (m, 2H), 2.23 (dd, J=14.2, 8.3 Hz, 1H), 2.18-2.23 (m, 1H), 2.10-2.14 (m, 1H), 2.12 (dd, J=13.9, 7.5 Hz, 1H), 1.83-1.95 (m, 1H), 1.34-1.53 (m, 4H), 1.39 (s, 9H), 1.06-1.22 (m, 4H); MS (ESI$^+$) M/Z 427 (M+H).

Example 45

(±)-2-[(exo)-bicyclo[2.2.1]hept-2-yl]-N-[4-(2-cyanopyridin-4-yl)-1-oxophthalazin-2(1H)-yl]acetamide A mixture of the product from Example 29C (60 mg, 0.15 mmol), Pd(PPh$_3$)$_4$ (17 mg, 0.015 mmol), and Zn(CN)$_2$ (34 mg, 0.29 mmol) in DMF (5 mL) was stirred at 90 C for 12 h, microwaved at 120 C for 20 min, microwaved at 150 C for 30 min, diluted with EtOAc, washed with saturated aqueous NaHCO$_3$, dried (Na$_2$SO$_4$), filtered, and purified by preparative HPLC (conditions from 10C) to give the title compound (12 mg, 0.030 mmol): $^1$H NMR (400 MHz, DMSO-$d_6$) δ ppm 11.44 (s, 1H), 8.95 (d, J=5.0 Hz, 1H), 8.40-8.48 (m, 1H), 8.32 (d, J=1.6 Hz, 1H), 7.95-8.05 (m, 3H), 7.76-7.84 (m, 1H), 2.28 (dd, J=14.3, 8.4 Hz, 1H), 2.19-2.23 (m, 1H), 2.16 (dd, J=14.2, 7.5 Hz, 1H), 2.10-2.12 (m, 1H), 1.80-1.93 (m, 1H), 1.33-1.52 (m, 4H), 1.06-1.19 (m, 4H); MS (APCI$^+$) M/Z 400 (M+H)$^+$.

Example 46

(±)-2-[(exo)-bicyclo[2.2.1]hept-2-yl]-N-[4-(2-hydroxypyridin-4-yl)-1-oxophthalazin-2(1H)-yl]acetamide A mixture of the product from Example 29C (30 mg, 0.073 mmol and sodium acetate (6 mg, 0.07 mmol) in acetic acid (0.5 mL) was microwaved at 150° C. for 20 minutes, diluted with EtOAc, washed with water, dried (Na$_2$SO$_4$), filtered, and purified by preparative HPLC (conditions from 10C) to give the title compound (24 mg, 0.063 mmol): $^1$H NMR (400 MHz, DMSO-$d_6$) δ ppm 11.89-11.93 (bs, 1H), 11.37 (s, 1H), 8.39 (dd, J=7.5, 1.7 Hz, 1H), 7.90-8.06 (m, 2H), 7.82-7.85 (m, 1H), 7.56 (d, J=6.7 Hz, 1H), 6.49 (d, J=1.6 Hz, 1H), 6.35 (dd, J=6.6, 1.8 Hz, 1H), 2.27 (dd, J=14.3, 8.3 Hz, 1H), 2.19-2.23 (m, 1H), 2.15 (dd, J=14.3, 7.5 Hz, 1H), 2.09-2.13 (m, 1H), 1.85-1.93 (m, 1H), 1.33-1.57 (m, 4H), 1.06-1.23 (m, 4H); MS (APCI$^+$) M/Z 391 (M+H)$^+$.

Example 47

(±)-2-[(exo)-bicyclo[2.2.1]hept-2-yl]-N-{4-[6-(dimethylamino)pyridin-3-yl]-1-oxophthalazin-2(1H)-yl}acetamide

Example 47A 2-amino-4-(6-(dimethylamino)pyridin-3-yl)phthalazin-1(2H)-one

A mixture of the product from Example 4A (0.296 g, 1.15 mmol) and a solution of dimethylamine in THF (2 M, 2.3 mL, 4.6 mmol) in DMF (2 mL) was microwaved at 200° C. for 30 minutes, diluted with EtOAc, washed with water and brine, dried (Na$_2$SO$_4$), filtered, and concentrated to give 0.25 g of crude 4-(6-(dimethylamino)pyridin-3-yl)phthalazin-1(2H)-one, which was used without purification.

To a suspension of the above product in THF (3.9 mL) was added a solution of potassium 2-methylpropan-2-olate (1.3 mL, 1.3 mmol) in THF. The mix was stirred at room temperature for 90 minutes, and O-(diphenylphosphoryl)hydroxylamine (0.308 g, 1.32 mmol) was added, and stirred for 2 hours, diluted with EtOAc, washed with 0.5 N NaOH and brine, and concentrated to give 238 mg of crude title compound as a white solid, which was used without purification: $^1$H NMR (300 MHz, DMSO-$d_6$) δ 8.40-8.33 (m, 1H), 8.31 (t, J=3.3, 1H), 7.94-7.85 (m, 2H), 7.83-7.71 (m, 2H), 6.83-6.77 (m, 1H), 6.47 (s, 2H), 3.11 (d, J=2.1, 6H).

Example 47B (±)-2-[(exo)-bicyclo[2.2.1]hept-2-yl]-N-{4-[6-(dimethylamino)pyridin-3-yl]-1-oxophthalazin-2(1H)-yl}acetamide The products from Example 47A and Example 3A were processed using a method similar to that described in Example 3B to give the title compound. $^1$H NMR (300 MHz, DMSO-$d_6$) δ ppm 11.29 (s, 1H), 8.37-8.40 (m, 1H), 8.30 (d, J=2.0 Hz, 1H), 7.90-8.04 (m, 2H), 7.78-7.83 (m, 1H), 7.74 (dd, J=8.8, 2.5 Hz, 1H), 6.80 (d, J=8.5 Hz, 1H), 3.12 (s, 6H), 2.26 (dd, J=14.2, 8.5 Hz, 1H), 2.18-2.23 (m, 1H), 2.14 (dd, J=14.2, 7.1 Hz, 1H), 2.11-2.13 (m, 1H), 1.84-1.94 (m, 1H), 1.32-1.55 (m, 4H), 1.08-1.22 (m, 4H); MS (ESI$^+$) M/Z 418 (M+H)$^+$.

Example 48

N-[4-(2-chloropyridin-4-yl)-1-oxophthalazin-2(1H)-yl]-3-methyl-3-phenylbutanamide The product from Example 29B and 3-methyl-3-phenylbutanoic acid were processed using a method similar to that described in Example 10C to give the title compound. $^1$H NMR (400 MHz, DMSO-$d_6$) δ ppm 11.46 (s, 1H), 8.63 (dd, J=5.0, 0.7 Hz, 1H), 8.40-8.43 (m, 1H), 7.93-8.04 (m, 2H), 7.77-7.79 (m, 1H), 7.74 (dd, J=1.4, 0.7 Hz, 1H), 7.66 (dd, J=5.0, 1.5 Hz, 1H), 7.43-7.46 (m, 2H), 7.29-7.33 (m, 2H), 7.16-7.21 (m, 1H), 2.63 (s, 2H), 1.47 (s, 6H); MS (APCI$^+$) M/Z 433 (M+H)$^+$.

Example 49

2-(4-chlorophenyl)-N-[4-(2-chloropyridin-4-yl)-1-oxophthalazin-2(1H)-yl]acetamide The product from Example 29B and 2-(4-chlorophenyl)acetyl chloride were processed using a method similar to that described in Example 4C to give the title compound. $^1$H NMR (500 MHz, DMSO-d$_6$) δ ppm 11.79 (s, 1H), 8.62 (d, J=5.0 Hz, 1H), 8.40-8.44 (m, 1H), 7.94-8.05 (m, 2H), 7.73-7.81 (m, 2H), 7.68 (dd, J=5.0, 1.5 Hz, 1H), 7.36-7.45 (m, 4H), 3.72 (s, 2H); MS (APCI$^+$) M/Z 425 (M+H)$^+$.

Example 50

(±)-2-[(exo)-bicyclo[2.2.1]hept-2-yl]-N-[4-(2-methylpyridin-4-yl)-1-oxophthalazin-2(1H)-yl]acetamide A mixture of the product from Example 29C (14 mg, 0.034 mmol), Pd(PPh$_3$)$_4$ (4 mg, 0.003 mmol), and a solution of trimethylaluminum solution (2M in toluene, 0.043 mL, 0.086 mmol) in DMF (0.5 mL) was stirred at 80° C. for 12 hours, diluted with EtOAc, washed with saturated aqueous NaHCO$_3$, dried (Na$_2$SO$_4$), filtered, and purified by preparative HPLC (conditions from 10C) to give the title compound (7.9 mg, 0.020 mmol): $^1$H NMR (400 MHz, DMSO-d$_6$) δ 11.45-11.39 (m, 1H), 8.79-8.70 (m, 1H), 8.47-8.39 (m, 1H), 8.04-7.96 (m, 2H), 7.83-7.76 (m, 1H), 7.75-7.69 (m, 1H), 7.68-7.61 (m, 1H), 2.67-2.63 (m, 3H), 2.32-2.24 (m, 1H), 2.24-2.09 (m, 3H), 1.94-1.84 (m, 1H), 1.55-1.32 (m, 4H), 1.21-1.06 (m, 4H); MS (APCI$^+$) M/Z 389 (M+H)$^+$.

Example 51

(±)-ethyl 3-{[(exo)-bicyclo[2.2.1]hept-2-ylacetyl]amino}-4-oxo-3,4-dihydrophthalazine-1-carboxylate

Example 51A ethyl 4-oxo-3,4-dihydrophthalazine-1-carboxylate

Ethyl 2-(2-ethoxy-2-oxoacetyl)benzoate (0.501 g, 2.00 mmol) was processed using a method similar to that described in Example 4A to give the title compound: $^1$H NMR (300 MHz, DMSO-d$_6$) δ 13.15 (s, 1H), 8.51 (d, J=7.8, 1H), 8.34-8.25 (m, 1H), 7.99 (dd, J=11.2, 4.3, 1H), 7.90 (t, J=7.5, 1H), 4.40 (q, J=7.1, 2H), 1.35 (s, 3H).

Example 51B ethyl 3-amino-4-oxo-3,4-dihydrophthalazine-1-carboxylate

The product from Example 51A was processed using a method similar to that described in Example 4B to give the title compound: MS (APCI) M/Z 234 (M+H)$^+$.

Example 51C (±)-ethyl 3-{[(exo)-bicyclo[2.2.1]hept-2-ylacetyl]amino}-4-oxo-3,4-dihydrophthalazine-1-carboxylate The product from Example 51B was processed using a method similar to that described in Example 4C to give the title compound. $^1$H NMR (300 MHz, DMSO-d$_6$) δ ppm 11.47 (s, 1H), 8.49 (d, J=8.1 Hz, 1H), 8.36 (dd, J=7.9, 1.4 Hz, 1H), 8.03-8.09 (m, 1H), 7.93-7.99 (m, 1H), 4.42 (q, J=7.1 Hz, 2H), 2.08-2.33 (m, 4H), 1.84-1.94 (m, 1H), 1.43-1.57 (m, 3H), 1.35-1.42 (m, 1H), 1.36 (t, J=7.1 Hz, 3H), 1.07-1.20 (m, 4H); MS (ESI$^-$) M/Z 368 (M–H)$^-$.

Example 52

N-{4-[benzyl(methyl)amino]-1-oxophthalazin-2(1H)-yl}-3-methyl-3-phenylbutanamide The product from Example 36A and 3-methyl-3-phenylbutanoic acid were processed using a method similar to that described in Example 10C to afford the title compound. $^1$H NMR (400 MHz, DMSO-d$_6$) δ ppm 11.14 (s, 1H), 8.32 (dd, J=7.9, 1.4 Hz, 1H), 8.02-8.05 (m, 1H), 7.95-8.00 (m, 1H), 7.89 (ddd, J=7.9, 7.1, 1.3 Hz, 1H), 7.34-7.47 (m, 6H), 7.27-7.34 (m, 3H), 7.15-7.20 (m, 1H), 4.29-4.30 (bs, 2H), 2.68 (s, 3H), 2.57 (s, 2H), 1.47 (s, 6H); MS (APCI$^+$) M/Z 441 (M+H)$^+$.

Example 53

N-{4-[benzyl(methyl)amino]-1-oxophthalazin-2(1H)-yl}-2-(3,5-difluorophenyl)acetamide The product from Example 36A and 2-(3,5-difluorophenyl)acetic acid were processed using a method similar to that described in Example 10C to afford the title compound: $^1$H NMR (400 MHz, DMSO-d$_6$) δ ppm 11.53-11.55 (bs, 1H), 8.33 (dd, J=7.9, 1.3 Hz, 1H), 8.05 (ddd, J=8.1, 1.4, 0.7 Hz, 1H), 7.99 (ddd, J=8.0, 7.2, 1.4 Hz, 1H), 7.90 (ddd, J=7.9, 7.2, 1.3 Hz, 1H), 7.33-7.44 (m, 4H), 7.27-7.33 (m, 1H), 7.09-7.21 (m, 3H), 4.31-4.32 (bs, 2H), 3.73 (s, 2H), 2.70 (s, 3H); MS (APCI$^+$) M/Z 435 (M+H)$^+$.

Example 54

(±)-2-[(exo)-bicyclo[2.2.1]hept-2-yl]-N-[4-(6-fluoropyridin-3-yl)-1-oxophthalazin-2(1H)-yl]acetamide

Example 54A 2-amino-4-(6-fluoropyridin-3-yl)-1-oxophthalazin-2(1H)-one

A mixture of 4-chlorophthalazin-1(2H)-one (0.105 g, 0.583 mmol), Pd(PPh$_3$)$_4$ (0.0642 g, 0.056 mmol), Cs$_2$CO$_3$ (0.567 g, 1.74 mmol), and 2-fluoro-5-(4,4,5,5-tetramethyl-1,3,2-dioxaborolan-2-yl)pyridine (0.134 g, 0.60 mmol) in DME (2.25 mL) and water (0.75 mL) was microwaved at 170° C. for 10 minutes and 175° C. for 5 minutes, diluted with EtOAc, washed with water and brine, dried (Na$_2$SO$_4$), filtered, and chromatographed (4% MeOH/DCM and 15% acetone/DCM) to provide 112.0 mg of impure 4-(6-fluoropyridin-3-yl)-1-oxophthalazin-2(1H)-one.

The above material was processed using a method similar to that described in Example 1B to afford the title compound: MS (APCI) M/Z 257 (M+H)$^+$.

Example 54B (±)-2-[(exo)-bicyclo[2.2.1]hept-2-yl]-N-[4-(6-fluoropyridin-3-yl)-1-oxophthalazin-2(1H)-yl]acetamide The product from Example 54A was processed using a method similar to that described in Example 4C to give the title compound: $^1$H NMR (300 MHz, CDCl$_3$) δ ppm 8.53-8.61 (m, 1H), 8.48-8.52 (m, 1H), 8.22-8.25 (bs, 1H), 8.07 (td, J=7.9, 2.4 Hz, 1H), 7.79-7.91 (m, 2H), 7.60-7.73 (m, 1H), 7.11 (dd, J=8.4, 2.9 Hz, 1H), 2.37-2.50 (m, 1H), 2.23-2.35 (m, 2H), 2.14-2.20 (m, 1H), 2.00-2.12 (m, 1H), 1.45-1.68 (m, 2H), 1.23-1.41 (m, 3H), 1.10-1.24 (m, 3H); MS (ESI$^-$) M/Z 391 (M−H)$^-$.

Example 55

(±)-3-{[(exo)-bicyclo[2.2.1]hept-2-ylacetyl]amino}-4-oxo-3,4-dihydrophthalazine-1-carboxylic acid A solution of aq 1N sodium hydroxide (0.24 mL, 0.24 mmol) was added to a solution of the product from Example 51C (0.0411 g, 0.111 mmol) in THF (0.2 mL) and MeOH (0.1 mL), and stirred at room temperature for 1 hour, concentrated, acidified with 1N HCl (0.3 mL), diluted with EtOAc, washed with water and brine, dried (Na$_2$SO$_4$), filtered, and concentrated to give 36.0 mg of the title compound as a white solid: $^1$H NMR (300 MHz, DMSO-d$_6$) δ 14.83-13.06 (m, 1H), 11.44 (s, 1H), 8.54 (d, J=8.0, 1H), 8.39-8.31 (m, 1H), 8.04 (s, 1H), 7.94 (s, 1H), 2.35-2.08 (m, 4H), 1.96-1.82 (m, 1H), 1.48 (d, J=3.2, 4H), 1.21-1.09 (m, 4H); MS (ESI$^-$) M/Z 340 (M−H)$^-$.

Example 56

(±)-3-{[(exo)-bicyclo[2.2.1]hept-2-ylacetyl]amino}-N,N-dimethyl-4-oxo-3,4-dihydrophthalazine-1-carboxamide A mixture of the product from Example 55 (34 mg, 0.10 mmol), O-(7-azabenzotriazol-1-yl)-N,N,N',N'-tetramethyluronium hexafluorophosphate (HATU, 42 mg, 0.11 mmol), triethylamine (0.021 mL, 0.15 mmol), and dimethylamine (2M in THF, 0.065 mL, 0.13 mmol) in DMF (0.3 mL) was stirred at room temperature overnight, diluted with EtOAc, washed with water, concentrated, and chromatographed (25% EtOAc/DCM) to give 2.6 mg of the title compound as a white solid: $^1$H NMR (300 MHz, CDCl$_3$) δ ppm 8.46 (d, J=7.4 Hz, 1H), 8.30-8.33 (bs, 1H), 7.75-7.89 (m, 3H), 3.20 (s, 3H), 3.08 (s, 3H), 1.97-2.50 (m, 5H), 0.80-1.40 (m, 8H); MS (ESI$^-$) M/Z 367 (M−H)$^-$.

Example 57

2-(3,5-difluorophenyl)-N-[1-oxo-4-(phenylsulfanyl)phthalazin-2(1H)-yl]acetamide

Example 57A 4-(phenylthio)phthalazin-1(2H)-one

A mixture of 4-chlorophthalazin-1(2H)-one (2.1 g, 12 mmol), thiophenol (2.6 g, 23 mmol), and K$_2$CO$_3$ (2.4 g, 17 mmol) in DMF (40 mL) was microwaved at 125° C. for 30 minutes, diluted with EtOAc, washed with water and brine, dried (Na$_2$SO$_4$), filtered, concentrated, and triturated with Et$_2$O to give the title compound (2.5 g, 10 mmol): $^1$H NMR (400 MHz, DMSO-d$_6$) δ 12.88 (s, 1H), 8.28 (dd, J=7.8, 1.1, 1H), 8.06-7.99 (m, 1H), 7.98-7.92 (m, 1H), 7.92-7.85 (m, 1H), 7.44 (d, J=1.2, 2H), 7.38 (s, 3H).

Example 57B 2-amino-4-(phenylthio)phthalazin-1(2H)-one

The product from Example 57A was processed using a method similar to that in Example 1B to provide the title compound: MS (APCI) M/Z 270 (M+H)$^+$.

Example 57C 2-(3,5-difluorophenyl)-N-[1-oxo-4-(phenylsulfanyl)phthalazin-2(1H)-yl]acetamide The product from Example 57B and 2-(3,5-difluorophenyl)acetic acid were processed using a method similar to that described in Example 10C to afford the title compound: $^1$H NMR (500 MHz, DMSO-d$_6$) δ 11.74 (s, 1H), 8.35 (dd, J=7.9, 1.0, 1H), 8.09 (d, J=7.8, 1H), 8.04-7.98 (m, 1H), 7.94 (td, J=7.7, 1.1, 1H), 7.47-7.40 (m, 2H), 7.39-7.28 (m, 3H), 7.16 (tt, J=9.5, 2.3, 1H), 7.12-7.04 (m, 2H), 3.73 (s, 2H); MS (APCI$^+$) M/Z 424 (M+H)$^+$.

Example 58

2-(4-chlorophenyl)-N-[1-oxo-4-(phenylsulfanyl)phthalazin-2(1H)-yl]acetamide

The product from Example 57B and 2-(4-chlorophenyl)acetyl chloride were processed using a method similar to that described in Example 4C to afford the title compound. $^1$H NMR (400 MHz, DMSO-d$_6$) δ 11.69 (s, 1H), 8.34 (dd, J=7.9, 1.1, 1H), 8.08 (d, J=7.4, 1H), 8.00 (td, J=7.7, 1.5, 1H), 7.94 (td, J=7.6, 1.3, 1H), 7.40 (d, J=8.8, 9H), 3.66 (s, 2H); MS (APCI$^+$) M/Z 422 (M+H)$^+$.

Example 59

(±)-2-[(exo)-bicyclo[2.2.1]hept-2-yl]-N-[1-oxo-4-(phenylsulfanyl)phthalazin-2(1H)-yl]acetamide The product from Example 57B was processed using a method similar to that described in Example 4C to afford the title compound: $^1$H NMR (400 MHz, DMSO-d$_6$) δ 11.32 (s, 1H), 8.34 (dd, J=7.8, 1.4, 1H), 8.08 (ddd, J=8.0, 1.4, 0.6, 1H), 8.00 (td, J=7.6, 1.4, 1H), 7.94 (td, J=7.6, 1.3, 1H), 7.48-7.41 (m, 2H), 7.42-7.29 (m, 3H), 2.27-2.17 (m, 2H), 2.15-2.03 (m, 2H), 1.90-1.79 (m, 1H), 1.57-1.28 (m, 4H), 1.22-1.02 (m, 4H); MS (APCI$^+$) M/Z 406 (M+H)$^+$.

Example 60

2-(3,5-difluorophenyl)-N-[4-(2,6-dimethylmorpholin-4-yl)-1-oxophthalazin-2(1H)-yl]acetamide

Example 60A 2-amino-4-(2,6-dimethylmorpholin-4-yl)phthalazin-1(2H)-one

A mixture of 4-chlorophthalazin-1(2H)-one and a mixture of cis- and trans-2,6-dimethylmorpholine was processed using a method similar to that described in Example 1A to give crude 4-(2,6-dimethylmorpholin-4-yl)phthalazin-1(2H)-one, which was processed using a method similar to that described in Example 1B to give crude 2-amino-4-(2,6-dimethylmorpholin-4-yl)phthalazin-1(2H)-one, which was used without purification: MS (APCI) M/Z 275 (M+H)$^+$.

Example 60B 2-(3,5-difluorophenyl)-N-[4-(2,6-dimethylmorpholin-4-yl)-1-oxophthalazin-2(1H)-yl]acetamide The product from Example 60A and 2-(3,5-difluorophenyl)acetic acid were processed using a method similar to that described in Example 10C to afford the title compound. $^1$H NMR (400 MHz, DMSO-$d_6$) δ ppm 11.54-11.55 (m, 1H), 8.30-8.34 (m, 1H), 8.01-8.04 (m, 1H), 7.96-8.01 (m, 1H), 7.87-7.92 (m, 1H), 7.11-7.19 (m, 3H), 3.84-3.93 (m, 2H), 3.73 (s, 2H), 3.32-3.36 (buried m, 2H), 2.40-2.47 (m, 2H), 1.12 (d, J=6.2 Hz, 6H); MS (APCI$^+$) M/Z 429 (M+H)$^+$.

Example 61

N-[4-(2,6-dimethylmorpholin-4-yl)-1-oxophthalazin-2(1H)-yl]-3-methyl-3-phenylbutanamide The product from Example 60A and 3-methyl-3-phenylbutanoic acid were processed using a method similar to that described in Example 10C to afford the title compound. $^1$H NMR (400 MHz, DMSO-$d_6$) δ 11.13 (s, 1H), 8.30 (d, J=7.5, 1H), 8.03-7.92 (m, 2H), 7.92-7.84 (m, 1H), 7.44 (dd, J=8.4, 1.1, 2H), 7.32 (dd, J=10.5, 5.0, 2H), 7.19 (dd, J=10.4, 4.2, 1H), 3.91-3.83 (m, 2H), 3.30 (m, 2H, buried), 2.57 (s, 2H), 2.45-2.36 (m, 2H), 1.46 (s, 6H), 1.13 (d, J=6.3, 6H); MS (DCI$^+$) M/Z 452 (M+HN$_4$)$^+$.

Example 62

2-(4-chlorophenyl)-N-[4-(2,6-dimethylmorpholin-4-yl)-1-oxophthalazin-2(1H)-yl]acetamide The product from Example 60A and 2-(4-chlorophenyl) acetyl chloride were processed using a method similar to that described in Example 4C to afford the title compound. $^1$H NMR (400 MHz, DMSO-$d_6$) δ ppm 11.48-11.49 (bs, 1H), 8.29 (ddd, J=7.9, 1.4, 0.6 Hz, 1H), 8.01 (ddd, J=8.1, 1.5, 0.7 Hz, 1H), 7.98 (ddd, J=8.2, 6.9, 1.3 Hz, 1H), 7.89 (ddd, J=7.9, 6.9, 1.5 Hz, 1H), 7.40-7.41 (m, 4H), 3.81-3.94 (m, 2H), 3.67 (s, 2H), 3.29-3.36 (m, 2H), 2.43 (dd, J=12.3, 10.3 Hz, 2H), 1.12 (d, J=6.2 Hz, 6H); MS (APCI$^+$) M/Z 427 (M+H)$^+$.

Example 63 ethyl 3-{[(4-chlorophenyl)acetyl]amino}-4-oxo-3,4-dihydrophthalazine-1-carboxylate The product from Example 51B and 2-(4-chlorophenyl) acetyl chloride were processed using a method similar to that described in Example 4C to afford the title compound. $^1$H NMR (300 MHz, DMSO-$d_6$) δ 11.83 (s, 1H), 8.49 (d, J=8.0, 1H), 8.35 (d, J=7.9, 1H), 8.10-8.01 (m, 1H), 7.97 (dd, J=11.8, 4.3, 1H), 7.47-7.35 (m, 4H), 4.42 (q, J=7.1, 2H), 3.73 (s, 2H), 1.35 (t, J=7.1, 3H); MS (ESI–) M/Z 384 (M–H)$^-$.

Example 64

(±)-2-[(exo)-bicyclo[2.2.1]hept-2-yl]-N-[4-(2,6-dimethylmorpholin-4-yl)-1-oxophthalazin-2(1H)-yl] acetamide The product from Example 60B was processed using a method similar to that described in Example 4C to afford the title compound. $^1$H NMR (400 MHz, DMSO-$d_6$) δ ppm 11.09 (s, 1H), 8.30 (d, J=7.8 Hz, 1H), 7.94-8.06 (m, 2H), 7.84-7.92 (m, 1H), 3.83-3.94 (m, 2H), 3.30 (buried m, 2H), 2.39-2.47 (m, 2H), 2.20-2.26 (m, 2H), 2.08-2.14 (m, 2H), 1.81-1.91 (m, 1H), 1.33-1.56 (m, 4H), 1.05-1.23 (m, 10H); MS (APCI$^+$) M/Z 411 (M+H)$^+$.

Example 65

3-{[(4-chlorophenyl)acetyl]amino}-4-oxo-3,4-dihydrophthalazine-1-carboxylic acid The product from Example 63 was processed using a method similar to that described in Example 55 to afford the title compound. $^1$H NMR (300 MHz, DMSO-$d_6$) δ ppm 13.83-14.14 (m, 1H), 11.80 (s, 1H), 8.54 (d, J=8.7 Hz, 1H), 8.34 (dd, J=7.9, 1.4 Hz, 1H), 8.01-8.07 (m, 1H), 7.95 (td, J=7.6, 1.2 Hz, 1H), 7.33-7.49 (m, 4H), 3.72 (s, 2H); MS (ESI$^-$) M/Z 356 (M–H)$^-$.

Example 66

N-[4-(morpholin-4-yl)-1-oxophthalazin-2(1H)-yl]-2-(tetrahydrofuran-3-yl)acetamide The product from Example 1B and 2-(tetrahydrofuran-3-yl)acetic acid were processed using a method similar to that described in Example 10C to afford the title compound. $^1$H NMR (500 MHz, CDCl$_3$) δ ppm 8.44-8.46 (m, 1H), 8.27-8.29 (bs, 1H), 7.89-7.94 (m, 1H), 7.80-7.86 (m, 1H), 7.74-7.79 (m, 1H), 3.91-3.98 (m, 6H), 3.70-3.82 (m, 1H), 3.57-3.61 (m, 1H), 3.21-3.23 (m, 4H), 2.77-2.81 (m, 1H), 2.51-2.54 (m, 2H), 2.15-2.30 (m, 1H), 1.68-1.78 (m, 1H); MS (APCI$^+$) M/Z 359 (M+H)$^+$.

Example 67

N-[4-(2-chloropyridin-4-yl)-1-oxophthalazin-2(1H)-yl]-2-(tetrahydrofuran-3-yl)acetamide The product from Example 29B and 2-(tetrahydrofuran-3-yl)acetic acid were processed using a method similar to that described in Example 10C to afford the title compound. $^1$H NMR (400 MHz, CDCl$_3$) δ ppm 8.60-8.60 (bs, 1H), 8.55-8.59 (m, 1H), 8.54-8.57 (m, 1H), 7.84-7.93 (m, 2H), 7.69-7.73 (m, 1H), 7.62 (s, 1H), 7.50-7.53 (m, 1H), 3.92-4.04 (m, 2H), 3.78-3.85 (m, 1H), 3.64-3.68 (m, 1H), 2.77-2.87 (m, 1H), 2.50-2.67 (m, 2H), 2.21-2.30 (m, 1H), 1.69-1.81 (m, 1H); MS (APCI$^+$) M/Z 385 (M+H)$^+$.

Example 68

2-(3,5-difluorophenyl)-N-[1-oxo-4-(phenylsulfonyl) phthalazin-2(1H)-yl]acetamide Example 68A 4-(phenylsulfonyl)phthalazin-1(2H)-one The product from 57A (710 mg, 2.79 mmol) was treated with 3-chlorobenzoperoxoic acid (1.56 g, 6.98 mmol) in CH$_2$Cl$_2$ (40 mL). The mixture was stirred at room temperature for 12 hours. The reaction was quenched with saturated NaHCO$_3$, and extracted with CH$_2$Cl$_2$. The combined organic layers were dried (Na$_2$SO$_4$), filtered, and concentrated to afford the title compound. MS (APCI) M/Z 287 (M+H)$^+$.

Example 68B 2-amino-4-(phenylsulfonyl)phthalazin-1(2H)-one

The product from Example 68A was processed using a method similar to that described in Example 1B to afford the title compound. MS (APCI) M/Z 302 (M+H)$^+$.

Example 68C 2-(3,5-difluorophenyl)-N-[1-oxo-4-(phenylsulfonyl)
phthalazin-2(1H)-yl]acetamide The product from Example 68B and 2-(3,5-difluorophenyl)acetic acid were processed using a method similar to that described in Example 10C to afford the title compound. $^1$H NMR (500 MHz, CDCl$_3$) δ ppm 8.69-8.72 (m, 1H), 8.44-8.47 (m, 1H), 8.31-8.35 (bs, 1H), 8.00-8.06 (m, 2H), 7.93-7.98 (m, 1H), 7.85-7.90 (m, 1H), 7.66-7.70 (m, 1H), 7.55-7.61 (m, 2H), 6.82-6.91 (m, 2H), 6.74-6.81 (m, 1H), 3.69-3.74 (bs, 2H); MS (APCI$^+$) M/Z 456 (M+H)$^+$.

Example 69

2-(4-chlorophenyl)-N-[1-oxo-4-(phenylsulfonyl)
phthalazin-2(1H)-yl]acetamide

The product from Example 68B and (4-chlorophenyl)acetyl chloride were processed using a method similar to that described in Example 4C to afford the title compound. $^1$H NMR (500 MHz, CDCl$_3$) δ ppm 8.67-8.69 (m, 1H), 8.43 (d, J=8.0 Hz, 1H), 8.22-8.24 (bs, 1H), 8.00-8.04 (m, 2H), 7.90-7.97 (m, 1H), 7.82-7.87 (m, 1H), 7.66-7.70 (m, 1H), 7.54-7.58 (m, 2H), 7.33-7.36 (m, 2H), 7.24-7.30 (m, 2H), 3.71-3.74 (bs, 2H); MS (APCI$^+$) M/Z 454 (M+H)$^+$.

Example 70

(±)-2-[(exo)-bicyclo[2.2.1]hept-2-yl]-N-[1-oxo-4-
(phenylsulfonyl)phthalazin-2(1H)-yl]acetamide The product from Example 68B was processed using a method similar to that described in Example 4C to afford the title compound. $^1$H NMR (500 MHz, CDCl$_3$) δ ppm 8.67-8.74 (m, 1H), 8.46-8.52 (m, 1H), 8.10-8.14 (bs, 1H), 8.02-8.07 (m, 2H), 7.91-7.97 (m, 1H), 7.82-7.88 (m, 1H), 7.64-7.70 (m, 1H), 7.65-7.69 (m, 1H), 7.55-7.61 (m, 2H), 2.28-2.38 (m, 1H), 2.22-2.27 (m, 1H), 2.15-2.23 (m, 1H), 2.01-2.07 (m, 1H), 1.91-1.99 (m, 1H), 1.45-1.54 (m, 2H), 1.28-1.34 (m, 1H), 1.20-1.27 (m, 1H), 1.13-1.18 (m, 2H), 1.06-1.13 (m, 1H); MS (APCI$^+$) M/Z 438 (M+H)$^+$.

Example 71

N-[4-(2-chloropyridin-4-yl)-1-oxophthalazin-2(1H)-
yl]-2-(1-hydroxycyclohexyl)acetamide The product from Example 29B and 2-(1-hydroxycyclohexyl)acetic acid were processed using a method similar to that described in Example 10C to afford the title compound. $^1$H NMR (500 MHz, CDCl$_3$) δ ppm 9.29 (s, 1H), 8.58 (d, J=4.9 Hz, 1H), 8.52-8.57 (m, 1H), 7.82-7.93 (m, 2H), 7.70-7.72 (m, 1H), 7.62 (s, 1H), 7.50 (dd, J=5.0, 1.4 Hz, 1H), 2.62 (s, 2H), 1.79-1.90 (m, 3H), 1.65-1.74 (m, 2H), 1.52-1.65 (m, 5H), 1.28-1.38 (m, 1H)); MS (APCI$^+$) M/Z 413 (M+H)$^+$.

Example 72

(±)-4-(3-{[(exo)-bicyclo[2.2.1]hept-2-ylacetyl]
amino}-4-oxo-3,4-dihydrophthalazin-1-yl)pyridine-
2-carboxamide The product from Example 45 (15 mg, 0.038 mmol) in dioxane (1 mL) was treated with 20% NaOH (0.1 mL). The mixture was heated at 100° C. for 1.5 hours. The mixture was diluted with EtOAc, washed with water, concentrated, and chromatographed (40% EtOAc/DCM) to give 10 mg (64%) of the title compound. $^1$H NMR (400 MHz, CDCl$_3$) δ 8.80-8.73 (m, 1H), 8.60-8.52 (m, 1H), 8.50-8.44 (m, 1H), 8.39-8.31 (m, 1H), 7.94-7.88 (m, 1H), 7.88-7.81 (m, 2H), 7.78-7.73 (m, 1H), 7.73-7.68 (m, 1H), 5.71-5.63 (m, 1H), 2.49-2.37 (m, 1H), 2.34-2.23 (m, 2H), 2.21-2.13 (m, 1H), 2.11-1.99 (m, 1H), 1.56 (s, 8H+water); MS (APCI$^+$) M/Z 418 (M+H)$^+$.

Example 73

N-[4-(2-chloropyridin-4-yl)-1-oxophthalazin-2(1H)-
yl]-2-(tetrahydrofuran-2-yl)acetamide The product from Example 29B and 2-(tetrahydrofuran-2-yl)acetic acid were processed using a method similar to that described in Example 10C to afford the title compound. $^1$H NMR (400 MHz, DMSO-d$_6$) δ ppm 11.46-11.62 (m, 1H), 8.63 (d, J=5.0 Hz, 1H), 8.40-8.43 (m, 1H), 7.93-8.06 (m, 2H), 7.75-7.79 (m, 2H), 7.69 (dd, J=5.0, 1.5 Hz, 1H), 4.16 (p, J=6.7 Hz, 1H), 3.79 (td, J=7.7, 6.1 Hz, 1H), 3.63 (td, J=7.8, 6.4 Hz, 1H), 2.57 (dd, J=14.2, 6.9 Hz, 1H), 2.44-2.52 (m, 1H), 1.99-2.07 (m, 1H), 1.78-1.95 (m, 2H), 1.57-1.66 (m, 1H); MS (APCI$^+$) M/Z 385 (M+H)$^+$.

Example 74

(±)-methyl 4-(3-{[(exo)-bicyclo[2.2.1]hept-2-
ylacetyl]amino}-4-oxo-3,4-dihydrophthalazin-1-yl)
pyridine-2-carboxylate The product from Example 29C (50 mg, 0.12 mmol) in MeOH (10 mL) was added to PdCl$_2$dppf (Heraeus) (0.895 mg, 1.22 μmol) and NEt$_3$ (0.034 mL, 0.245 mmol) in a 50 mL pressure bottle. The mixture was pressurized with CO (60 psi), and stirred for 4 hours at 80° C. The mixture was filtered, concentrated, and purified by HPLC (conditions from Example 10C) to afford 31 mg (59%) of the title compound. $^1$H NMR (400 MHz, CDCl$_3$) δ ppm 8.85-9.00 (m, 1H), 8.56-8.58 (m, 1H), 8.39-8.42 (m, 2H), 7.80-7.93 (m, 2H), 7.64-7.83 (m, 2H), 4.06 (s, 3H), 2.43 (dd, J=14.4, 7.6 Hz, 1H), 2.26-2.34 (m, 1H), 2.25-2.28 (m, 1H), 2.13-2.20 (m, 1H), 2.04-2.08 (m, 1H), 1.42-1.58 (m, 2H), 1.33-1.39 (m, 1H), 1.11-1.32 (m, 5H); MS (APCI$^+$) M/Z 433 (M+H)$^+$.

Example 75

(±)-4-(3-{[(exo)-bicyclo[2.2.1]hept-2-ylacetyl]
amino}-4-oxo-3,4-dihydrophthalazin-1-yl)pyridine-
2-carboxylic acid The product from Example 74 (20 mg, 0.046 mmol) in THF (2 mL) and water (1 mL) was treated with lithium hydroxide monohydrate (8.4 mg, 0.2 mmol). The mixture was stirred at room temperature for 4 hours, filtered, concentrated, and purified by HPLC (conditions from Example 10C) to afford 4.5 mg (23%) of the title compound. $^1$H NMR (400 MHz, DMSO-d$_6$) δ ppm 11.43 (s, 1H), 8.92 (dd, J=4.9, 0.8 Hz, 1H), 8.41-8.45 (m, 1H), 8.22 (dd, J=1.7, 0.9 Hz, 1H), 7.96-8.02 (m, 2H), 7.90-7.96 (m, 1H), 7.76-7.82 (m, 1H), 2.10-2.32 (m, 4H), 1.88-1.93 (m, 1H), 1.41-1.54 (m, 3H), 1.35-1.42 (m, 1H), 1.08-1.20 (m, 4H); MS (APCI$^+$) M/Z 419 (M+H)$^+$.

Example 76

(±)-2-[(exo)-bicyclo[2.2.1]hept-2-yl]-N-{1-oxo-4-[2-(trifluoromethyl)pyridin-4-yl]phthalazin-2(1H)-yl}acetamide

Example 76A 4-(2-(trifluoromethyl)pyridin-4-yl)phthalazin-1(2H)-one

A solution of 4-bromo-2-(trifluoromethyl)pyridine (860 mg, 3.81 mmol) in Et$_2$O (30 mL) was treated dropwise with butyllithium (2.5 M in hexane, 1.52 mL, 3.81 mmol) at −78 C for 30 min. To the mixture was added isobenzofuran-1,3-dione (512 mg, 3.46 mmol) in THF (15 mL) in one portion at −78° C. The mixture was stirred at −78° C. for 30 minutes and allowed to warm to room temperature, and quenched with water (30 mL). The pH was adjusted with HCl (6N) to 4-5, and extracted with isopropanol/CH$_2$Cl$_2$. The organic layer was dried (Na$_2$SO$_4$), filtered, and concentrated. The residue was dissolved in EtOH (20 mL), treated with hydrazine hydrate (5 mL), refluxed for 2 hours, concentrated and the precipitate was collected and washed with water and Et$_2$O to afford 340 mg (34%) of the title compound. MS (APCI) M/Z 332 (M+H+CH$_3$CN)$^+$.

Example 76B 2-amino-4-(2-(trifluoromethyl)pyridin-4-yl)phthalazin-1(2H)-one

The product from Example 76A was processed using a method similar to that described in Example 1B to afford the title compound. MS (APCI) M/Z 306 (M+H)$^+$.

Example 76C (±)-2-[(exo)-bicyclo[2.2.1]hept-2-yl]-N-{1-oxo-4-[2-(trifluoromethyl)pyridin-4-yl]phthalazin-2(1H)-yl}acetamide The product from Example 76B was processed using a method similar to that described in Example 4C to afford the title compound. $^1$H NMR (400 MHz, DMSO-d$_6$) δ ppm 11.44 (s, 1H), 8.99 (d, J=5.0 Hz, 1H), 8.42-8.45 (m, 1H), 8.11-8.13 (m, 1H), 7.97-8.03 (m, 3H), 7.76-7.80 (m, 1H), 2.28 (dd, J=14.3, 8.3 Hz, 1H), 2.19-2.22 (m, 1H), 2.17 (dd, J=14.3, 7.4 Hz, 1H), 2.10-2.13 (m, 1H), 1.85-1.95 (m, 1H), 1.41-1.55 (m, 3H), 1.35-1.41 (m, 1H), 1.08-1.20 (m, 4H); MS (APCI) M/Z 443 (M+H)$^+$.

Example 77

2-(4-chlorophenyl)-N-{1-oxo-4-[2-(trifluoromethyl)pyridin-4-yl]phthalazin-2(1H)-yl}acetamide The product from Example 76B and 2-(4-chlorophenyl)acetyl chloride were processed using a method similar to that described in Example 4C to afford the title compound. $^1$H NMR (400 MHz, DMSO-d$_6$) δ ppm 11.80-11.82 (bs, 1H), 8.96-8.99 (m, 1H), 8.40-8.46 (m, 1H), 8.12 (s, 1H), 7.96-8.04 (m, 3H), 7.71-7.79 (m, 1H), 7.36-7.44 (m, 4H), 3.72 (s, 2H); MS (APCI) M/Z 459 (M+H)$^+$.

Example 78

2-(4-chlorophenyl)-N-[4-({[(4-methylphenyl)sulfonyl]amino}methyl)-1-oxophthalazin-2(1H)-yl]acetamide The product from Example 42 and 4-methylbenzene-1-sulfonyl chloride were processed using a method similar to that described in Example 4C to afford the title compound. $^1$H NMR (300 MHz, DMSO-d$_6$) δ ppm 11.53-11.64 (bs, 1H), 8.19-8.33 (bs, 1H), 8.23 (ddd, J=7.8, 1.5, 0.6 Hz, 1H), 8.06 (ddd, J=8.1, 1.4, 0.7 Hz, 1H), 7.95 (ddd, J=8.0, 7.2, 1.5 Hz, 1H), 7.87 (ddd, J=7.9, 7.2, 1.3 Hz, 1H), 7.57-7.61 (m, 2H), 7.33-7.49 (m, 4H), 7.21-7.25 (m, 2H), 4.22-4.24 (m, 2H), 3.69 (s, 2H), 2.31 (s, 3H); MS (ESI$^+$) M/Z 497 (M+H)$^+$.

Example 79

2-(4-chlorophenyl)-N-[1-oxo-4-({[(trifluoromethyl)sulfonyl]amino}methyl)phthalazin-2(1H)-yl]acetamide The product from Example 42 and trifluoromethanesulfonic anhydride were processed using a method similar to that described in Example 4C to afford the title compound. $^1$H NMR (300 MHz, DMSO-d$_6$) δ ppm 11.68 (s, 1H), 10.15-10.18 (bs, 1H), 8.35 (d, J=7.9 Hz, 1H), 8.01-8.12 (m, 2H), 7.91-7.98 (m, 1H), 7.41 (s, 4H), 4.71-4.73 (bs, 2H), 3.69 (s, 2H); MS (ESI$^+$) M/Z 475 (M+H)$^+$.

Example 80

2-(4-chlorophenyl)-N-[4-{[(methylsulfonyl)amino]methyl}-1-oxophthalazin-2(1H)-yl]acetamide The product from Example 42 and methanesulfonyl chloride were processed using a method similar to that described in Example 4C to afford the title compound. $^1$H NMR (300 MHz, DMSO-d$_6$) δ ppm 11.66-11.72 (m, 1H), 8.31-8.43 (m, 1H), 8.15 (d, J=8.0 Hz, 1H), 7.99-8.06 (m, 1H), 7.89-7.96 (m, 1H), 7.66-7.74 (bs, 1H), 7.36-7.45 (m, 4H), 4.46-4.49 (m, 2H), 3.68 (s, 2H), 2.94 (s, 3H); MS (ESI$^+$) M/Z 421 (M+H)$^+$.

Example 81

2-(4-chlorophenyl)-N-{4-[cis-2,6-dimethylmorpholin-4-yl]-1-oxophthalazin-2(1H)-yl}acetamide

Example 81A

4-[cis-2,6-dimethylmorpholin-4-yl]-1-oxophthalazin-2(1H)-one

A mixture of 4-chlorophthalazin-1(2H)-one and cis-2,6-dimethylmorpholine was processed using a method similar to that described in Example 1A to give the title compound: MS (APCI) M/Z 260 (M+H)$^+$.

Example 81B 2-amino-4-[cis-2,6-dimethylmorpholin-4-yl]-1-oxophthalazin-2(1H)-one The product from Example 81A was processed using a method similar to that described in Example 1B to afford the title compound: MS (APCI) M/Z 275 (M+H)$^+$.

Example 81C 2-(4-chlorophenyl)-N-{4-[cis-2,6-dimethylmorpholin-4-yl]-1-oxophthalazin-2(1H)-yl}acetamide The product from Example 81B and 2-(4-chlorophenyl)acetyl chloride were processed using a method similar to that described in Example 4C to afford the title compound. $^1$H NMR (300 MHz, CDCl$_3$) δ ppm 8.43 (d, J=7.8 Hz, 1H), 8.01-8.21 (m, 1H), 7.68-7.94 (m, 3H), 7.28-7.49 (m, 4H), 3.88-4.02 (m, 2H), 3.78-3.80 (m, 2H), 3.30-3.36 (m, 2H), 2.56-2.65 (m, 2H), 1.23 (d, J=6.3 Hz, 6H); MS (ESI$^+$) M/Z 427 (M+H)$^+$.

Example 82

2-(4-chlorophenyl)-N-[1-oxo-4-(phenylsulfinyl)phthalazin-2(1H)-yl]acetamide

A mixture of the product from Example 58 (0.0200 g, 0.047 mmol) and 3-chlorobenzoperoxoic acid (0.0125 g, 0.051 mmol) in DCM (0.5 mL) was stirred at room temperature for 1 hour, diluted with EtOAc, washed with sat NaHCO$_3$ and brine, dried (Na$_2$SO$_4$), filtered, and chromatographed (8-10% EtOAc/DCM) to give 4.5 mg of the title compound. $^1$H NMR (300 MHz, DMSO-d$_6$) δ ppm 11.90 (s, 1H), 8.44-8.48 (m, 1H), 8.30-8.34 (m, 1H), 7.86-7.96 (m, 2H), 7.70-7.76 (m, 2H), 7.50-7.61 (m, 3H), 7.38-7.46 (m, 4H), 3.76 (s, 2H); MS (ESI$^-$) M/Z 436 (M–H)$^-$.

Example 83

2-(3,5-difluorophenyl)-N-[1-oxo-4-(phenylsulfinyl)phthalazin-2(1H)-yl]acetamide

The product from Example 57 was processed using a method similar to that described in Example 82 to afford the title compound. $^1$H NMR (400 MHz, DMSO-d$_6$) δ ppm 11.90-12.04 (bs, 1H), 8.44-8.47 (m, 1H), 8.32-8.35 (m, 1H), 7.86-7.98 (m, 2H), 7.72-7.76 (m, 2H), 7.48-7.64 (m, 3H), 7.09-7.24 (m, 3H), 3.82 (s, 2H); MS (APCI) M/Z 440 (M+H)$^+$.

Example 84

N-[4-{[(tert-butylcarbamoyl)amino]methyl}-1-oxophthalazin-2(1H)-yl]-2-(4-chlorophenyl)acetamide A mixture of the product from Example 42 (13.8 mg, 0.040 mmol) and 2-isocyanato-2-methylpropane (5.2 μL, 0.044 mmol) in DCM (0.4 mL) was stirred at room temperature for 2 hours, concentrated, and chromatographed (5% MeOH/DCM) to give 12.1 mg of the title compound as a white solid: $^1$H NMR (300 MHz, DMSO-d$_6$) δ ppm 11.58-11.61 (bs, 1H), 8.32 (dd, J=7.8, 1.4 Hz, 1H), 8.14 (d, J=8.0 Hz, 1H), 7.98 (ddd, J=8.0, 7.2, 1.5 Hz, 1H), 7.90 (ddd, J=7.9, 7.2, 1.3 Hz, 1H), 7.41 (s, 4H), 6.19 (t, J=5.8 Hz, 1H), 5.81 (s, 1H), 4.50 (d, J=5.8 Hz, 2H), 3.68 (s, 2H), 1.22 (s, 9H); MS (ESI$^-$) M/Z 440 (M–H)$^-$, 486 (M+COOH)$^-$.

Example 85 ethyl[(3-{[(4-chlorophenyl)acetyl]amino}-4-oxo-3,4-dihydrophthalazin-1-yl)methyl]carbamate The product from Example 42 and ethyl carbonochloridate were processed using a method similar to that described in Example 4C to afford the title compound. $^1$H NMR (300 MHz, CDCl$_3$) δ ppm 8.45 (d, J=7.8 Hz, 1H), 8.14-8.16 (bs, 1H), 7.73-7.97 (m, 3H), 7.30-7.50 (m, 4H), 5.38-5.49 (bs, 1H), 4.69 (d, J=5.4 Hz, 2H), 4.18 (q, J=7.1 Hz, 2H), 3.80-3.82 (m, 2H), 1.27 (t, J=6.2 Hz, 3H); MS (ESI$^-$) M/Z 413 (M–H)$^-$.

Example 86

2-(4-chlorophenyl)-N-[1-oxo-4-{[(phenylacetyl)amino]methyl}phthalazin-2(1H)-yl]acetamide The product from Example 42 and 2-phenylacetyl chloride were processed using a method similar to that described in Example 4C to afford the title compound. $^1$H NMR (500 MHz, CDCl$_3$) δ ppm 8.42 (d, J=7.8 Hz, 1H), 8.11-8.13 (bs, 1H), 7.83-7.91 (m, 2H), 7.76-7.82 (m, 1H), 7.39 (s, 3H), 7.23-7.35 (buried m, 6H), 6.24-6.30 (bs, 1H), 4.72-4.74 (m, 2H), 3.79-3.80 (bs, 2H), 3.63-3.63 (bs, 2H); MS (ESI$^-$) M/Z 459 (M–H)$^-$.

Example 87

N-[(3-{[(4-chlorophenyl)acetyl]amino}-4-oxo-3,4-dihydrophthalazin-1-yl)methyl]-2,2-dimethylpropanamide The product from Example 42 and pivaloyl chloride were processed using a method similar to that described in Example 4C to afford the title compound. $^1$H NMR (300 MHz, CDCl$_3$) δ ppm 8.45 (d, J=7.8 Hz, 1H), 8.23-8.26 (bs, 1H), 7.73-7.96 (m, 3H), 7.29-7.51 (m, 4H), 6.45-6.47 (m, 1H), 4.74-4.77 (m, 2H), 3.80-3.82 (m, 2H), 1.21 (s, 9H); MS (ESI$^-$) M/Z 425 (M–H)$^-$.

Example 88

2-(3,5-difluorophenyl)-N-{4-[(cis)-2,6-dimethylmorpholin-4-yl]-1-oxophthalazin-2(1H)-yl}acetamide The product from Example 81B and 2-(3,5-difluorophenyl)acetic acid were processed using a method similar to that described in Example 10C to afford the title compound. $^1$H NMR (500 MHz, DMSO-d$_6$) δ ppm 11.54 (s, 1H), 8.31 (dd, J=7.9, 1.3 Hz, 1H), 8.02 (ddd, J=8.1, 1.4, 0.7 Hz, 1H), 7.98 (ddd, J=8.1, 7.0, 1.3 Hz, 1H), 7.90 (ddd, J=7.9, 7.1, 1.4 Hz, 1H), 7.08-7.20 (m, 3H), 3.83-3.94 (m, 2H), 3.73 (s, 2H), 3.31-3.36 (buried m, 2H), 2.24-2.44 (m, 2H), 1.12 (d, J=6.2 Hz, 6H); MS (APCI$^+$) M/Z 429 (M+H)$^+$.

Example 89

N-{4-[(cis)-2,6-dimethylmorpholin-4-yl]-1-oxophthalazin-2(1H)-yl}-3-methyl-3-phenylbutanamide The product from Example 81B and 3-methyl-3-phenylbutanoic acid were processed using a method similar to that described in Example 10C to afford the title compound. $^1$H NMR (500 MHz, DMSO-d$_6$) δ 11.14 (s, 1H), 8.30 (dd, J=7.9, 0.7, 1H), 8.02-7.94 (m, 2H), 7.88 (ddd, J=8.3, 7.0, 1.5, 1H), 7.44 (dd, J=8.4, 1.1, 2H), 7.34-7.28 (m, 2H), 7.22-7.15 (m, 1H), 3.92-3.82 (m, 2H), 3.35-3.27 (buried, m, 2H), 2.57 (s, 2H), 2.42 (dd, J=12.4, 10.4, 2H), 1.46 (s, 6H), 1.13 (d, J=6.2, 6H); MS (APCI$^+$) M/Z 435 (M+H)$^+$.

Example 90

(±)-2-[(exo)-bicyclo[2.2.1]hept-2-yl]-N-{4-[(cis)-2,6-dimethylmorpholin-4-yl]-1-oxophthalazin-2(1H)-yl}acetamide The product from Example 81B was processed using a method similar to that described in Example 4C to afford the title compound. $^1$H NMR (400 MHz, DMSO-$d_6$) δ 11.09 (s, 1H), 8.29 (d, J=7.9, 1H), 8.03-7.9 (m, 2H), 7.89 (dd, J=11.4, 4.7, 1H), 3.93-3.83 (m, 2H), 3.36-3.29 (buried m, 2H), 2.47-2.39 (m, 2H), 2.27-2.17 (m, 2H), 2.15-2.06 (m, 2H), 1.93-1.82 (m, 1H), 1.52-1.33 (m, 4H), 1.20-1.06 (m, 10H); MS (APCI$^+$) M/Z 411 (M+H)$^+$.

Example 91

2-(4-chlorophenyl)-N-[1-oxo-4-(thiomorpholin-4-yl)phthalazin-2(1H)-yl]acetamide

Example 91A 4-thiomorpholinophthalazin-1(2H)-one 4-chlorophthalazin-1(2H)-one and thiomorpholine were processed using a method similar to that described in Example 1A to afford the title compound. MS (APCI$^+$) M/Z 248 (M+H)$^+$.

Example 91B 2-amino-4-thiomorpholinophthalazin-1(2H)-one

The product from Example 91A was processed using a method similar to that described in Example 1B to afford the title compound. MS (APCI$^+$) M/Z 263 (M+H)$^+$.

Example 91C 2-(4-chlorophenyl)-N-[1-oxo-4-(thiomorpholin-4-yl)phthalazin-2(1H)-yl]acetamide The product from Example 91B and 2-(4-chlorophenyl)acetic acid were processed using a method similar to that described in Example 10C to afford the title compound. $^1$H NMR (400 MHz, DMSO-$d_6$) δ ppm 11.49 (s, 1H), 8.29 (d, J=7.8 Hz, 1H), 7.93-8.03 (m, 2H), 7.89 (ddd, J=8.0, 6.2, 1.9 Hz, 1H), 7.34-7.47 (m, 4H), 3.67 (s, 2H), 2.83-2.86 (m, 4H); MS (APCI$^+$) M/Z 415 (M+H)$^+$.

Example 92

2-(3,5-difluorophenyl)-N-[1-oxo-4-(thiomorpholin-4-yl)phthalazin-2(1H)-yl]acetamide The product from Example 91B and 2-(3,5-difluorophenyl)acetic acid were processed using a method similar to that described in Example 10C to afford the title compound. $^1$H NMR (400 MHz, DMSO-$d_6$) δ ppm 11.55 (s, 1H), 8.30 (d, J=7.9 Hz, 1H), 7.84-8.02 (m, 3H), 7.05-7.19 (m, 3H), 3.73 (s, 2H), 2.83-2.87 (m, 4H); MS (APCI$^+$) M/Z 417 (M+H)$^+$.

Example 93

(±)-2-[(exo)-bicyclo[2.2.1]hept-2-yl]-N-[1-oxo-4-(thiomorpholin-4-yl)phthalazin-2(1H)-yl]acetamide The product from Example 91B was processed using a method similar to that described in Example 4C to afford the title compound. $^1$H NMR (400 MHz, DMSO-$d_6$) δ 11.11 (s, 1H), 8.32-8.26 (m, 1H), 8.00-7.93 (m, 2H), 7.92-7.85 (m, 1H), 3.28 (buried m, 4H), 2.89-2.80 (m, 4H), 2.27-2.18 (m, 2H), 2.16-2.06 (m, 2H), 1.92-1.80 (m, 1H), 1.55-1.34 (m, 4H), 1.19-1.08 (m, 4H); MS (APCI$^+$) M/Z 399 (M+H)$^+$.

Example 94

(±)-tert-butyl 3-{[[(exo)-bicyclo[2.2.1]hept-2-ylacetyl]amino}-4-oxo-3,4-dihydrophthalazine-1-carboxylate A solution of BOC$_2$O (0.027 mL, 0.115 mmol), DMAP (2.0 mg, 0.016 mmol), and the product from Example 55 (0.0195 g, 0.057 mmol) in tBuOH (0.5 mL) was stirred at room temperature for 2 hours, heated at 60° C. for 2 hours, diluted with EtOAc, washed with water and brine, dried (Na$_2$SO$_4$), filtered, and chromatographed (5% EtOAc/DCM) to give 9.6 mg of the title compound as a white solid: $^1$H NMR (300 MHz, DMSO-$d_6$) δ ppm 11.43 (s, 1H), 8.26-8.41 (m, 2H), 8.06 (dd, J=7.4, 1.3 Hz, 1H), 7.93-7.99 (m, 1H), 2.06-2.33 (m, 4H), 1.81-1.94 (m, 1H), 1.61 (s, 9H), 1.31-1.55 (m, 4H), 1.05-1.24 (m, 4H); MS (DCI$^+$) M/Z 415 (M+NH$_4$)$^+$.

Example 95

(±)-2-[(exo)-bicyclo[2.2.1]hept-2-yl]-N-[4-(morpholin-4-ylcarbonyl)-1-oxophthalazin-2(1H)-yl]acetamide A solution of the product from Example 55 (0.0263 g, 0.077 mmol), EDC (0.0238 g, 0.124 mmol), pyridine (25 µL, 0.309 mmol), and morpholine (20 µL, 0.230 mmol) in DMF (0.25 mL) was stirred at room temperature for 2 hours, heated at 60° C. for 2 hours, diluted with EtOAc, washed with water and brine, dried (Na$_2$SO$_4$), filtered, and chromatographed (10-15% acetone/DCM and 67% EtOAc/hexanes) to give 6.7 mg of the title compound as a white solid: $^1$H NMR (300 MHz, DMSO-$d_6$) δ 11.37 (s, 1H), 8.35 (dd, J=7.7, 1.0, 1H), 8.06-7.90 (m, 2H), 7.87-7.80 (m, 1H), 3.72 (s, 4H), 3.53-3.47 (m, 2H), 3.43-3.37 (m, 2H), 2.31-2.07 (m, 4H), 1.92-1.81 (m, 1H), 1.53-1.33 (m, 4H), 1.24-1.07 (m, 4H); MS (ESI$^-$) M/Z 409 (M–H)$^-$.

Example 96

(±)-benzyl[(3-{[(exo)-bicyclo[2.2.1]hept-2-ylacetyl]amino}-4-oxo-3,4-dihydrophthalazin-1-yl)methyl]carbamate The product from Example 44 was processed using a method similar to that described in Example 42 to afford the corresponding free amine, which was processed with benzyl carbonochloridate using a method similar to that described in Example 4C to afford the title compound. $^1$H NMR (300 MHz, DMSO-$d_6$) δ ppm 11.22 (s, 1H), 8.31-8.38 (m, 1H), 8.06-8.11 (m, 1H), 7.86-8.01 (m, 3H), 7.25-7.40 (m, 5H), 5.07 (s, 2H), 4.54 (d, J=5.9 Hz, 2H), 2.24 (dd, J=14.3, 8.4 Hz, 1H), 2.18-2.23 (m, 1H), 2.12 (dd, J=14.2, 7.5 Hz, 1H), 2.11-2.13 (m, 1H), 1.83-1.93 (m, 1H), 1.40-1.54 (m, 3H), 1.34-1.41 (m, 1H), 1.05-1.20 (m, 4H); MS (ESI$^-$) M/Z 459 (M–H)$^-$, 505 (M+COOH)$^-$.

Example 97

(±)-2-[(exo)-bicyclo[2.2.1]hept-2-yl]-N-[1-oxo-4-(pyridin-4-ylmethyl)phthalazin-2(1H)-yl]acetamide 4-(Pyridin-4-ylmethyl)phthalazin-1(2H)-one (Waterstone) was processed using a method similar to that described in Example 1B to afford 2-amino-4-(pyridin-4-ylmethyl)phthalazin-1(2H)-one, which was processed using a method similar to that described in Example 4C to afford the title compound. ¹H NMR (300 MHz, DMSO-d₆) δ ppm 11.27 (s, 1H), 8.46-8.49 (m, 2H), 8.29-8.35 (m, 1H), 7.92-8.00 (m, 2H), 7.84-7.92 (m, 1H), 7.30-7.32 (m, 2H), 4.36-4.37 (bs, 2H), 2.25 (dd, J=14.3, 8.3 Hz, 1H), 2.18-2.22 (m, 1H), 2.13 (dd, J=14.3, 7.1 Hz, 1H), 2.09-2.13 (m, 1H), 1.86-1.94 (m, 1H), 1.34-1.60 (m, 4H), 1.07-1.18 (m, 4H); MS (ESI⁺) M/Z 389 (M+H)⁺.

Example 98

(±)-tert-butyl 4-[(3-{[(exo)-bicyclo[2.2.1]hept-2-ylacetyl]amino}-4-oxo-3,4-dihydrophthalazin-1-yl)carbonyl]piperazine-1-carboxylate The product from Example 55 and tert-butyl piperazine-1-carboxylate were processed using a method similar to that described in Example 95 to afford the title compound. ¹H NMR (400 MHz, DMSO) δ 11.42 (s, 1H), 8.36 (d, J=7.3, 1H), 8.05-7.92 (m, 2H), 7.84 (d, J=7.7, 1H), 3.74-3.68 (m, 2H), 3.50-3.23 (buried m, 6H), 2.32-2.06 (m, 4H), 1.92-1.83 (m, 1H), 1.50-1.35 (m, 4H), 1.40 (s, 9H), 1.28-1.21 (m, 2H), 1.20-1.06 (m, 4H); MS (ESI⁻) M/Z 508 (M–H)⁻.

Example 99

(±)-3-{[(exo)-bicyclo[2.2.1]hept-2-ylacetyl]amino}-N-tert-butyl-4-oxo-3,4-dihydrophthalazine-1-carboxamide The product from Example 55 and 2-methylpropan-2-amine were processed using a method similar to that described in Example 95 to afford the title compound. ¹H NMR (300 MHz, DMSO-d₆) δ 11.29 (s, 1H), 8.33 (dd, J=7.9, 0.9, 1H), 8.23 (s, 1H), 8.15-8.08 (m, 1H), 8.06-7.97 (m, 1H), 7.97-7.88 (m, 1H), 2.33-2.11 (m, 4H), 1.95-1.83 (m, 1H), 1.52-1.35 (m, 13H), 1.23-1.07 (m, 4H); MS (ESI⁻) M/Z 395 (M–H)⁻.

Example 100

(±)-2-[(exo)-bicyclo[2.2.1]hept-2-yl]-N-{4-[(1-oxidopyridin-4-yl)methyl]-1-oxophthalazin-2(1H)-yl}acetamide A mixture of the product of Example 97 (0.0352 g, 0.091 mmol) and m-chloroperbenzoic acid (0.0340 g, 0.138 mmol) in DCM (2 mL) was stirred at room temperature for 90 minutes, concentrated, and chromatographed (6% MeOH/DCM) to give 32.2 mg of the title compound as a white solid: ¹H NMR (300 MHz, DMSO-d₆) δ 11.24 (s, 1H), 8.36-8.29 (m, 1H), 8.14 (dd, J=7.5, 2.2, 2H), 8.04-7.84 (m, 3H), 7.30 (d, J=7.0, 2H), 4.34 (s, 2H), 2.31-2.06 (m, 4H), 1.91-1.81 (m, 1H), 1.53-1.33 (m, 4H), 1.20-1.05 (m, 4H); MS (ESI⁺) M/Z 405 (M+H)⁺.

Example 101

N-[4-(4-benzylpiperazin-1-yl)-1-oxophthalazin-2(1H)-yl]-2-(4-chlorophenyl)acetamide Example 101A 4-(4-benzylpiperazin-1-yl)phthalazin-1(2H)-one 4-Chlorophthalazin-1-one and 1-benzylpiperazine were processed using a method similar to that described in Example 1A to afford the title compound. MS (APCI⁺) M/Z 321 (M+H)⁺.

Example 101B

The product from Example 101A was processed using a method similar to that described in Example 1B to afford the title compound. MS (APCI⁺) M/Z 336 (M+H)⁺.

Example 101C

N-[4-(4-benzylpiperazin-1-yl)-1-oxophthalazin-2(1H)-yl]-2-(4-chlorophenyl)acetamide The product from Example 101B and (4-chlorophenyl)acetyl chloride were processed using a method similar to that described in Example 4C to afford the title compound. ¹H NMR (400 MHz, DMSO-d₆) δ 11.52 (s, 1H), 8.31 (d, J=7.9, 1H), 8.02-7.96 (m, 2H), 7.95-7.89 (m, 1H), 7.58-7.45 (m, 5H), 7.43-7.36 (m, 4H), 4.46 (s, 2H), 3.67 (s, 2H), 3.66-3.57 (m, 2H), 3.51-3.42 (m, 2H), 3.11-3.00 (m, 4H); MS (APCI⁺) M/Z 488 (M+H)⁺.

Example 102

(±)-2-[(exo)-bicyclo[2.2.1]hept-2-yl]-N-{4-[hydroxy(phenyl)methyl]-1-oxophthalazin-2(1H)-yl}acetamide A mixture of the product from Example 40 (0.0438 g, 0.109 mmol), and NaBH₄ (8.6 mg, 0.227 mmol) in MeOH (0.4 mL) was stirred at room temperature for 3 hours, diluted with EtOAc, washed with sat NaHCO₃ and brine, dried (Na₂SO₄), filtered, and chromatographed (20% EtOAc/DCM) to give 24.6 mg of the title compound as a white solid: ¹H NMR (300 MHz, DMSO-d₆) δ 11.27 (s, 1H), 8.31-8.25 (m, 1H), 8.17-8.09 (m, 1H), 7.85-7.76 (m, 2H), 7.44 (d, J=7.8, 2H), 7.33 (t, J=7.5, 2H), 7.27-7.19 (m, 1H), 6.69 (s, 1H), 5.91 (s, 1H), 2.32-2.10 (m, 4H), 1.97-1.84 (m, 1H), 1.55-1.35 (m, 4H), 1.28-1.05 (m, 4H); MS (ESI⁺) M/Z 404 (M+H)⁺.

Example 103 tert-butyl{4-[(3-{[(4-chlorophenyl)acetyl]amino}-4-oxo-3,4-dihydrophthalazin-1-yl)sulfanyl]phenyl}carbamate Example 103A tert-butyl 4-(4-oxo-3,4-dihydrophthalazin-1-ylthio)phenylcarbamate 4-chlorophthalazin-1(2H)-one and tert-butyl 4-mercaptophenylcarbamate were processed using a method similar to that described in Example 57A to afford the title compound. MS (APCI⁺) M/Z 370 (M+H)⁺.

Example 103B tert-butyl 4-(3-amino-4-oxo-3,4-dihydrophthalazin-1-ylthio)phenylcarbamate The product from Example 103A was processed using a method similar to that described in Example 1B to afford the title compound. MS (APCI⁺) M/Z 385 (M+H)⁺.

Example 103C tert-butyl{4-[(3-{[(4-chlorophenyl)acetyl]amino}-4-oxo-3,4-dihydrophthalazin-1-yl)sulfanyl]phenyl}carbamate The product from Example 103B and 2-(4-chlorophenyl)acetyl chloride were processed using a method similar to that described in Example 4C to afford the title compound. $^1$H NMR (400 MHz, DMSO-d$_6$) δ 10.83-10.76 (m, 1H), 8.30-8.25 (m, 1H), 8.06-7.99 (m, 1H), 7.99-7.93 (m, 1H), 7.93-7.86 (m, 1H), 7.44 (d, J=8.8, 2H), 7.41-7.37 (m, 2H), 7.35-7.31 (m, 4H), 3.53 (s, 2H), 1.32 (s, 9H); MS (APCI$^+$) M/Z 537 (M+H)$^+$.

Example 104

N-{4-[(6-chloro-1-oxidopyridin-3-yl)methyl]-1-oxophthalazin-2(1H)-yl}-2-(4-chlorophenyl)acetamide The product from Example 32 was processed using a method similar to that described in Example 100 to afford the title compound. $^1$H NMR (300 MHz, DMSO-d$_6$) δ 11.59 (s, 1H), 8.51 (d, J=1.7, 1H), 8.33 (d, J=6.9, 1H), 8.08 (d, J=7.6, 1H), 7.99 (t, J=6.9, 1H), 7.94-7.87 (m, 1H), 7.72 (d, J=8.4, 1H), 7.44-7.32 (m, 4H), 7.22 (dd, J=8.5, 1.9, 1H), 4.35 (s, 2H), 3.68 (s, 2H); MS (ESI$^+$) M/Z 455 (M+H)$^+$.

Example 105

N-{4-[(4-aminophenyl)sulfanyl]-1-oxophthalazin-2(1H)-yl}-2-(4-chlorophenyl)acetamide The product from Example 103C (23 mg, 0.043 mmol) in CH$_2$Cl$_2$ (4 mL) was treated with TFA (1 mL). The reaction mixture was stirred at room temperature for 20 minutes, concentrated, and the resulting residue was purified by HPLC (conditions from Example 10C) to afford 9.3 mg (50%) of the title compound. $^1$H NMR (400 MHz, DMSO-d$_6$) δ 11.56 (s, 1H), 8.31 (dd, J=7.9, 0.9, 1H), 8.12 (d, J=7.8, 1H), 8.06-7.98 (m, 1H), 7.97-7.89 (m, 1H), 7.46-7.36 (m, 2H), 7.34-7.28 (m, 2H), 7.24-7.15 (m, 2H), 6.64-6.56 (m, 2H), 3.63 (s, 2H); MS (APCI$^+$) M/Z 437 (M+H)$^+$.

Example 106 tert-butyl{4-[(3-{[(4-chlorophenyl)acetyl]amino}-4-oxo-3,4-dihydrophthalazin-1-yl)sulfonyl]phenyl}carbamate The product from Example 103C was processed using a method similar to that described in Example 68A to afford the title compound. $^1$H NMR (400 MHz, DMSO-d$_6$) δ 11.82 (s, 1H), 10.05 (s, 1H), 8.56 (d, J=8.1, 1H), 8.37 (dd, J=8.0, 0.9, 1H), 8.15-8.07 (m, 1H), 8.04-7.96 (m, 1H), 7.94-7.85 (m, 2H), 7.77-7.69 (m, 2H), 7.44-7.36 (m, 2H), 7.33-7.24 (m, 2H), 3.68 (s, 2H), 1.49 (s, 9H); MS (APCI$^+$) M/Z 569 (M+H)$^+$.

Example 107

2-(4-chlorophenyl)-N-[4-(4-methylpiperazin-1-yl)-1-oxophthalazin-2(1H)-yl]acetamide

Example 107A 4-(4-methylpiperazin-1-yl)phthalazin-1(2H)-one 4-chlorophthalazin-1-one and 1-methylpiperazine were treated using methods similar to that described in Examples 1A to give the title compound. MS (APCI$^+$) M/Z 245 (M+H)$^+$.

Example 107B 2-amino-4-(4-methylpiperazin-1-yl)phthalazin-1(2H)-one

The product from Example 107A was processed using a method similar to that described in Example 1B to afford the title compound. MS (APCI$^+$) M/Z 259 (M+H)$^+$.

Example 107C 2-(4-chlorophenyl)-N-[4-(4-methylpiperazin-1-yl)-1-oxophthalazin-2(1H)-yl]acetamide The product from Example 107B and (4-chlorophenyl)acetyl chloride were processed using a method similar to that described in Example 4C to afford the title compound. $^1$H NMR (400 MHz, DMSO-d$_6$) δ 11.55 (s, 1H), 9.77 (s, 1H), 8.32 (d, J=7.9, 1H), 8.03-7.97 (m, 2H), 7.96-7.89 (m, 1H), 7.45-7.36 (m, 4H), 3.68 (s, 2H), 3.65-3.50 (m, 4H), 3.08-2.98 (m, 2H), 2.91 (s, 3H), 2.49-2.44 (buried m, 2H); MS (APCI$^+$) M/Z 412 (M+H)$^+$.

Example 108

(±)-3-{[(exo)-bicyclo[2.2.1]hept-2-ylacetyl]amino}-N-(4-chlorophenyl)-4-oxo-3,4-dihydrophthalazine-1-carboxamide The product of Example 55 and 4-chloroaniline were processed using a method similar to that described in Example 10C to give the title compound. $^1$H NMR (300 MHz, DMSO-d$_6$) δ 11.42 (bs, 1H), 10.89 (bs, 1H), 8.42-8.30 (m, 2H), 8.08-7.92 (m, 2H), 7.85-7.78 (m, 2H), 7.49-7.42 (m, 2H), 2.36-2.25 (m, 1H), 2.24-2.11 (m, 3H), 1.97-1.84 (m, 1H), 1.53-1.35 (m, 4H), 1.26-1.07 (m, 4H); MS (ESI$^+$) M/Z 451 (M+H)$^+$.

Example 109 ethyl 2-(3-{[(4-chlorophenyl)acetyl]amino}-4-oxo-3,4-dihydrophthalazin-1-yl)propanoate

Example 109A ethyl 2-(4-oxo-3,4-dihydrophthalazin-1-yl)propanoate

To a solution of 4-(1-carboxyethyl)-1(2H)-phthalazinone (1.5 g, 6.9 mmol) in EtOH (50 mL) was added thionyl chloride (1.10 mL, 15.1 mmol). The mixture was stirred at 80° C. for 4 hours, cooled to 0° C., and quenched with 1M NaHCO$_3$ (40 mL). The aq layer was extracted with EtOAc (2×50 mL), dried (Na$_2$SO$_4$), filtered, and concentrated to give the title compound: MS (ESI$^+$) M/Z 247 (M+H)$^+$.

Example 109B ethyl 2-(3-amino-4-oxo-3,4-dihydrophthalazin-1-yl)propanoate

The product of Example 109A was processed using a method similar to that described in Example 1B to give the title compound: MS (ESI$^+$) M/Z 262 (M+H)$^+$.

Example 109C ethyl 2-(3-{[(4-chlorophenyl)acetyl]amino}-4-oxo-3,4-dihydrophthalazin-1-yl)propanoate The product of Example 109B and 2-(4-chlorophenyl)acetyl chloride were processed using a method similar to that described in Example 4C to give the title compound. $^1$H NMR (300 MHz, DMSO-$d_6$) δ 11.60 (s, 1H), 8.34 (d, J=7.8, 1H), 8.05-7.96 (m, 2H), 7.92 (ddd, J=8.1, 6.1, 2.3, 1H), 7.45-7.35 (m, 4H), 4.52 (q, J=7.1, 1H), 4.12-3.99 (m, 2H), 3.68 (s, 2H), 1.46 (d, 3H), 1.06 (t, 3H); MS (ESI$^+$) M/Z 414 (M+H)$^+$.

Example 110

2-(3-{[(4-chlorophenyl)acetyl]amino}-4-oxo-3,4-dihydrophthalazin-1-yl)propanoic acid To a solution of the product from Example 109C (1.4 g, 3.4 mmol) in THF (8 mL), water (4 mL), and MeOH (8 mL) was added 5M NaOH (3.4 mL, 17 mmol). After stirring at room temperature for 16 hours, the reaction mixture was concentrated to half the volume, diluted to 10 mL (water), washed with DCM, acidified to pH~2 with aq 3N HCl, and filtered to obtain the precipitated product: $^1$H NMR (300 MHz, DMSO-$d_6$) δ 12.72 (s, 1H), 11.60 (s, 1H), 8.33 (d, J=7.7, 1H), 8.03-7.97 (m, 2H), 7.91 (ddd, J=8.2, 6.7, 4.0, 1H), 7.41 (s, 4H), 4.40 (q, J=7.1, 1H), 3.69 (s, 2H), 1.45 (d, J=7.1, 3H); MS (ESI$^+$) M/Z 386 (M+H)$^+$.

Example 111

N-[4-(morpholin-4-yl)-1-oxophthalazin-2(1H)-yl]-2-phenylacetamide

To a 4 mL vial was added the product from Example 1B (20 mg in dimethyl acetamide), phenylacetic acid [1.5 equivalents in dimethyl acetamide], O-(7-azabenzotriazol-1-yl)-N,N,N',N'-tetramethyluronium hexafluorophosphate (HATU, 2 equivalents in dimethyl acetamide) and triethylamine (3 equivalents, neat). The vial was capped and microwaved at 150° C. for 30 minutes. The reaction was checked by LC/MS and concentrated to dryness upon completion. The residue was dissolved in 1:1 MeOH:DMSO and purified by reverse phase HPLC (conditions from Example 10C): $^1$H NMR (500 MHz, DMSO-$d_6$/D$_2$O) δ 8.33-8.28 (m, 1H), 8.03 (d, J=7.5, 1H), 8.01-7.96 (m, 1H), 7.94-7.87 (m, 1H), 7.40-7.33 (m, 4H), 7.33-7.25 (m, 1H), 3.86-3.78 (m, 4H), 3.67 (s, 2H), 3.11-3.06 (m, 4H); MS (ESI$^+$) M/Z 365 (M+H)$^+$.

Example 112

N-tert-butyl-2-(3-{[(4-chlorophenyl)acetyl]amino}-4-oxo-3,4-dihydrophthalazin-1-yl)propanamide To a solution of 2-methylpropan-2-amine (34.1 mg, 0.467 mmol) in THF (5 mL), were added the product from Example 110 (150 mg, 0.389 mmol), triethylamine (0.163 mL, 1.17 mmol), and 1-propanephosphonic acid cyclic anhydride (50% in EtOAc, 0.463 mL, 0.778 mmol). The mixture was stirred at 70° C. for 16 hours, cooled, quenched with 1M NaHCO$_3$ (10 mL), extracted with EtOAc (2×20 mL), dried (Na$_2$SO$_4$-$d_6$), filtered, and concentrated. The residue was purified by chromatography (SiO$_2$, 0-100% of 1/10 MeOH/EtOAc in hexanes) to afford the title compound. $^1$H NMR (300 MHz, DMSO-$d_6$) δ 11.59 (s, 1H), 8.31 (d, J=7.8, 1H), 8.01-7.97 (m, 2H), 7.93 (s, 1H), 7.87 (ddd, J=8.2, 5.4, 3.0, 1H), 7.41 (s, 4H), 4.24 (q, J=6.8, 1H), 3.68 (s, 2H), 1.39 (d, J=6.9, 3H), 1.23 (s, 9H); MS (ESI$^+$) M/Z 441 (M+H)$^+$.

Example 113

2-(3-{[(4-chlorophenyl)acetyl]amino}-4-oxo-3,4-dihydrophthalazin-1-yl)-N-(2,2-dimethylpropyl)propanamide A mixture of the product from Example 110 and 2,2-dimethylpropan-1-amine was processed using a method similar to that described in Example 112 to afford the title compound. $^1$H NMR (300 MHz, DMSO-$d_6$) δ ppm 11.59-11.62 (bs, 1H), 8.31 (dd, J=7.8, 1.4 Hz, 1H), 8.16-8.21 (m, 1H), 8.04 (d, J=8.1 Hz, 1H), 7.93-8.00 (m, 1H), 7.85-7.91 (m, 1H), 7.41 (s, 4H), 4.38 (q, J=6.9 Hz, 1H), 3.68 (s, 2H), 2.94 (dd, J=13.1, 6.4 Hz, 1H), 2.85 (dd, J=13.1, 6.0 Hz, 1H), 1.44 (d, J=6.9 Hz, 3H), 0.81 (s, 9H); MS (ESI$^+$) M/Z 455 (M+H)$^+$.

Example 114

(3-{[(4-chlorophenyl)acetyl]amino}-4-oxo-3,4-dihydrophthalazin-1-yl)acetic acid

The product of Example 116 was processed using a method similar to that described in Example 110 to afford the title compound. $^1$H NMR (300 MHz, DMSO-$d_6$) δ 12.78 (s, 1H), 11.60 (s, 1H), 8.32 (d, J=8.1, 1H), 8.04-7.97 (m, 1H), 7.96-7.86 (m, 2H), 7.45-7.36 (m, 4H), 3.98 (s, 2H), 3.68 (s, 2H); MS (ESI$^+$) M/Z 372 (M+H)$^+$.

Example 115

N-{4-[(4-aminophenyl)sulfonyl]-1-oxophthalazin-2(1H)-yl}-2-(4-chlorophenyl)acetamide The product from Example 106 was processed using a method similar to that described in Example 105 to afford the title compound. $^1$H NMR (400 MHz, DMSO-$d_6$) δ 11.80 (s, 1H), 8.58 (d, J=8.2, 1H), 8.41-8.30 (m, 1H), 8.14-8.04 (m, 1H), 8.03-7.94 (m, 1H), 7.59 (d, J=8.8, 2H), 7.48-7.37 (m, 2H), 7.33 (d, J=8.5, 2H), 6.66 (d, J=8.8, 2H), 6.39 (s, 2H), 3.70 (s, 2H); MS (APCI$^+$) M/Z 469 (M+H)$^+$.

Example 116 ethyl(3-{[(4-chlorophenyl)acetyl]amino}-4-oxo-3,4-dihydrophthalazin-1-yl)acetate Ethyl 2-(4-oxo-3,4-dihydrophthalazin-1-yl)acetate (Alinda Chemical, Ltd.) was processed using a method similar to that described in Example 1B to give ethyl 2-(3-amino-4-oxo-3,4-dihydrophthalazin-1-yl)acetate. This material was treated with 2-(4-chlorophenyl)acetyl chloride using a method similar to that described in Example 4C to provide the title compound. $^1$H NMR (300 MHz, DMSO-$d_6$) δ 11.62 (s, 1H), 8.36-8.29 (m, 1H), 8.05-7.96 (m, 1H), 7.95-7.87 (m, 2H), 7.45-7.36 (m, 4H), 4.17-4.04 (m, 4H), 3.67 (s, 2H), 1.16 (t, J=7.1, 3H); MS (ESI$^+$) M/Z 400 (M+H)$^+$.

Example 117 ethyl{[(4-chlorophenyl)acetyl]amino}(3-{[(4-chlorophenyl)acetyl]amino}-4-oxo-3,4-dihydrophthalazin-1-yl)acetate The procedure from Example 116 also resulted in the formation of this title compound. $^1$H NMR (300 MHz, DMSO-d$_6$) δ 11.67 (s, 1H), 9.29 (d, J=8.2, 1H), 8.37-8.32 (m, 1H), 7.94 (p, J=6.9, 2H), 7.83-7.76 (m, 1H), 7.44-7.35 (m, 4H), 7.35-7.29 (m, 2H), 7.25 (d, J=8.5, 2H), 6.06 (d, J=8.2, 1H), 4.20-3.97 (m, 2H), 3.66 (s, 2H), 3.53 (s, 2H), 1.03 (t, J=7.1, 3H); MS (ESI⁻) M/Z 565 (M−H)⁻.

Example 118 tert-butyl{[4-oxo-3-({[4-(trifluoromethyl)phenyl]acetyl}amino)-3,4-dihydrophthalazin-1-yl]methyl}carbamate The product of Example 41B and 2-[4-(trifluoromethyl)phenyl]acetic acid were treated using a method similar to that described in Example 56 to give the title compound. ¹H NMR (300 MHz, DMSO-d$_6$) δ 11.67 (s, 1H), 8.32 (dd, J=7.8, 1.4, 1H), 8.11 (d, J=8.0, 1H), 8.04-7.95 (m, 1H), 7.95-7.86 (m, 1H), 7.76-7.69 (m, 2H), 7.63-7.57 (m, 2H), 7.44-7.37 (m, 1H), 4.48-4.41 (m, 2H), 3.79 (bs, 2H), 1.37 (s, 9H); MS (ESI⁻) M/Z 475 (M−H)⁻.

Example 119 tert-butyl{[3-({[(1S,2S,5S)-6,6-dimethylbicyclo[3.1.1]hept-2-yl]acetyl}amino)-4-oxo-3,4-dihydrophthalazin-1-yl]methyl}carbamate The product of Example 41B and 2-[(1S,2S,5S)-6,6-dimethylbicyclo[3.1.1]hept-2-yl]acetic acid (Eigenmann, G. W.; Arnold, R. T. JACS 1959, 81, 3440-2) were treated using a method similar to that described in Example 56 to give the title compound. ¹H NMR (300 MHz, DMSO-d$_6$) δ 11.24 (s, 1H), 8.36-8.28 (m, 1H), 8.10 (d, J=7.8, 1H), 7.98 (dd, J=11.1, 4.1, 1H), 7.90 (t, J=7.1, 1H), 7.40 (s, 1H), 4.45 (d, J=5.7, 2H), 2.41-2.29 (m, 3H), 2.07-1.80 (m, 5H), 1.64-1.47 (m, 1H), 1.43-1.29 (m, 10H), 1.21 (s, 3H), 1.07 (s, 3H), 0.91 (d, J=9.5, 1H). MS (ESI⁺) M/Z 472 (M+NH$_4$)⁺.

Example 120

(±)-2-[(exo)-bicyclo[2.2.1]hept-2-yl]-N-{4-[(Z)-(hydroxyimino)(phenyl)methyl]-1-oxophthalazin-2(1H)-yl}acetamide A mixture of the product from Example 40C (120 mg, 0.299 mmol) and hydroxylamine hydrochloride (31.2 mg, 0.448 mmol) in MeOH (5 mL) was stirred at room temperature overnight, concentrated, diluted with EtOAc, washed with sat NaHCO$_3$ and brine, dried (Na$_2$SO$_4$), filtered, concentrated, and purified by column chromatography (0-50% of 1/10 MeOH/EtOAc in hexanes) to afford the title compound. ¹H NMR (501 MHz, DMSO-d$_6$/Deuterium Oxide) δ 8.39-8.34 (m, 1H), 7.93-7.86 (m, 2H), 7.59-7.55 (m, 2H), 7.51-7.46 (m, 1H), 7.41-7.34 (m, 3H), 2.30-2.07 (m, 4H), 1.94-1.85 (m, 1H), 1.51-1.33 (m, 4H), 1.20-1.05 (m, 4H); MS (APCI⁺) M/Z 417 (M+H)⁺.

Example 121

2-(4-chlorophenyl)-N-[4-(2-hydroxyethyl)-1-oxophthalazin-2(1H)-yl]acetamide

To a 0° C. solution of the product from Example 116 (365 mg, 0.938 mmol) in THF (10 mL) was added LiBH$_4$ in THF (2M, 0.69 mL, 1.4 mmol). The mixture was stirred for 6 hours, quenched with water (10 mL), extracted with EtOAc (4×20 mL), dried (Na$_2$SO$_4$), filtered, and concentrated. The residue was purified by column chromatography (0-100% of 1/10 MeOH/EtOAc in hexanes) to afford the title compound. ¹H NMR (300 MHz, DMSO-d$_6$) δ 11.56 (s, 1H), 8.31 (dd, J=7.9, 1.4, 1H), 8.08 (d, J=8.1, 1H), 8.04-7.94 (m, 1H), 7.94-7.85 (m, 1H), 7.43-7.35 (m, 4H), 4.74 (t, J=5.4, 1H), 3.81-3.71 (m, 2H), 3.68 (s, 2H), 3.08 (t, J=6.7, 2H); MS (ESI⁺) M/Z 358 (M+H)⁺.

Example 122

N-{4-[2-(tert-butylamino)-2-oxoethyl]-1-oxophthalazin-2(1H)-yl}-2-(4-chlorophenyl)acetamide The product of Example 114 and tert-butylamine were treated using a method similar to that described in Example 112 to give the title compound. ¹H NMR (300 MHz, DMSO-d$_6$) δ 11.60 (s, 1H), 8.30 (d, J=7.9, 1H), 8.02-7.85 (m, 4H), 7.45-7.37 (m, 4H), 3.78 (s, 2H), 3.67 (s, 2H), 1.25 (s, 9H); MS (ESI⁻) M/Z 425 (M−H)⁻.

Example 123

2-(4-chlorophenyl)-N-[4-{2-[(2,2-dimethylpropyl)amino]-2-oxoethyl}-1-oxophthalazin-2(1H)-yl]acetamide The product of Example 114 and 2,2-dimethylpropan-1-amine were treated using a method similar to that described in Example 112 to give the title compound. ¹H NMR (300 MHz, CDCl$_3$) δ 8.48-8.41 (m, 1H), 8.30 (bs, 1H), 7.97 (d, J=8.0, 1H), 7.92-7.76 (m, 2H), 7.38 (bs, 4H), 6.11-5.98 (m, 1H), 3.89 (s, 2H), 3.80 (bs, 2H), 3.02 (d, J=6.3, 2H), 0.80 (s, 9H); MS (ESI⁻) M/Z 439 (M−H)⁻.

Example 124 tert-butyl[(3-{[(4,4-difluorocyclohexyl)acetyl]amino}-4-oxo-3,4-dihydrophthalazin-1-yl)methyl]carbamate The product of Example 41B and 2-(4,4-difluorocyclohexyl)acetic acid were treated using a method similar to that described in Example 56 to give the title compound. ¹H NMR (300 MHz, DMSO-d$_6$) δ 11.31 (s, 1H), 8.32 (dd, J=7.8, 1.4, 1H), 8.11 (d, J=8.0, 1H), 8.04-7.95 (m, 1H), 7.95-7.86 (m, 1H), 7.48-7.37 (m, 1H), 4.48-4.42 (m, 2H), 2.32-2.22 (m, 3H), 2.05-1.70 (m, 6H), 1.39 (s, 9H), 1.35-1.20 (m, 2H); MS (ESI⁻) M/Z 449 (M−H)⁻.

Example 125 tert-butyl[(3-{[(4-fluorophenyl)acetyl]amino}-4-oxo-3,4-dihydrophthalazin-1-yl)methyl]carbamate The product of Example 41B and 2-(4-fluorophenyl)acetyl chloride were treated using a method similar to that described in Example 4C to give the title compound. ¹H NMR (300 MHz, DMSO-d$_6$) δ 11.59 (s, 1H), 8.32 (dd, J=7.8, 1.4, 1H), 8.11 (d, J=8.0, 1H), 8.04-7.94 (m, 1H), 7.95-7.86 (m, 1H), 7.45-7.36 (m, 3H), 7.23-7.13 (m, 2H), 4.47-4.41 (m, 2H), 3.66 (s, 2H), 1.37 (s, 9H); MS (ESI⁻) M/Z 425 (M−H)⁻.

Example 126 tert-butyl({3-[(cyclohexylacetyl)amino]-4-oxo-3,4-dihydrophthalazin-1-yl}methyl)carbamate The product of Example 41B and 2-cyclohexylacetyl chloride were treated using a method similar to that described in Example 4C to give the title compound. ¹H NMR (300 MHz, DMSO-d₆) δ 11.24 (s, 1H), 8.32 (dd, J=7.8, 1.4, 1H), 8.11 (d, J=8.0, 1H), 8.03-7.94 (m, 1H), 7.90 (td, J=7.5, 1.2, 1H), 7.45-7.36 (m, 1H), 4.48-4.41 (m, 2H), 2.16 (d, J=6.7, 2H), 1.85-1.58 (m, 6H), 1.39 (s, 9H), 1.28-0.95 (m, 5H); MS (ESI⁻) M/Z 413 (M–H)⁻.

Example 127

2-(4-chlorophenyl)-N-(1-oxo-4-phenoxyphthalazin-2(1H)-yl)acetamide

The product from Example 38A and (4-chlorophenyl)acetic acid were processed using a method similar to that described in Example 10C to afford the title compound. ¹H NMR (400 MHz, DMSO-d₆) δ 11.44 (s, 1H), 8.34 (dd, J=7.9, 1.1, 1H), 8.17 (d, J=7.6, 1H), 8.07 (td, J=7.6, 1.4, 1H), 8.01 (td, J=7.6, 1.3, 1H), 7.51-7.40 (m, 2H), 7.39-7.34 (m, 2H), 7.33-7.24 (m, 5H), 3.60 (s, 2H); MS (APCI⁺) M/Z 406 (M+H)⁺.

Example 128 cyclohexyl[(3-{[(4-chlorophenyl)acetyl]amino}-4-oxo-3,4-dihydrophthalazin-1-yl)methyl]carbamate A mixture of the product of Example 42 (90 mg, 0.26 mmol), iPr₂NEt (0.078 mL, 0.45 mmol), and cyclohexyl carbonochloridate (51.2 mg, 0.315 mmol) in DCM (4 mL) was stirred at room temperature for 8 hours, diluted with Et₂O, washed with sat NaHCO₃ and brine, dried (MgSO₄), filtered, concentrated, and chromatographed (17-25% EtOAc/DCM) to give the title compound. ¹H NMR (300 MHz, DMSO-d₆) δ ppm 11.60 (s, 1H), 8.32 (dd, J=7.8, 1.4 Hz, 1H), 8.10 (d, J=8.0 Hz, 1H), 7.97-8.03 (m, 1H), 7.91 (td, J=7.5, 1.2 Hz, 1H), 7.60-7.65 (m, 1H), 7.41 (s, 4H), 4.47-4.51 (m, 3H), 3.67 (s, 2H), 1.58-1.84 (m, 4H), 1.41-1.54 (m, 1H), 1.10-1.35 (m, 4H); MS (ESI⁻) M/Z 467 (M–H)⁻.

Example 129

2,2,2-trifluoroethyl[(3-{[(4-chlorophenyl)acetyl]amino}-4-oxo-3,4-dihydrophthalazin-1-yl)methyl]carbamate The product of Example 42 and 2,2,2-trifluoroethyl carbonochloridate were treated using a method similar to that described in Example 128 to give the title compound. ¹H NMR (300 MHz, DMSO-d₆) δ 11.61 (s, 1H), 8.36-8.27 (m, 2H), 8.07 (d, J=7.5, 1H), 8.03-7.96 (m, 1H), 7.95-7.87 (m, 1H), 7.45-7.36 (m, 4H), 4.67 (q, J=9.1, 2H), 4.56 (d, J=5.9, 2H), 3.68 (s, 2H); MS (ESI⁻) M/Z 467 (M–H)⁻.

Example 130

2-[4-(methylsulfonyl)phenyl]-N-[4-(morpholin-4-yl)-1-oxophthalazin-2(1H)-yl]acetamide The product of Example 1B and 2-(4-(methylsulfonyl) phenyl)acetic acid were treated using a method similar to that described in Example 111 to give the title compound. ¹H NMR (500 MHz, DMSO-d₆/Deuterium Oxide) δ ppm 8.25-8.35 (m, 1H), 7.97-8.05 (m, 2H), 7.91-7.93 (m, 3H), 7.65-7.67 (m, 2H), 3.83 (s, 3H), 3.82 (d, J=8.4 Hz, 2H), 3.35-3.63 (m, 1H), 3.21 (s, 3H), 3.08-3.11 (m, 4H); MS (ESI⁺) M/Z 443 (M+H)⁺.

Example 131

N-[4-(morpholin-4-yl)-1-oxophthalazin-2(1H)-yl]-2-(3-phenoxyphenyl)acetamide The product of Example 1B and 2-(3-phenoxyphenyl)acetic acid were treated using a method similar to that described in Example 111 to give the title compound. ¹H NMR (500 MHz, DMSO-d₆/Deuterium Oxide) δ ppm 8.30 (dd, J=7.9, 1.3 Hz, 1H), 8.03 (d, J=8.0 Hz, 1H), 7.97-8.01 (m, 1H), 7.89-7.93 (m, 1H), 7.36-7.43 (m, 3H), 7.14-7.18 (m, 2H), 7.00-7.08 (m, 3H), 6.91 (dd, J=8.2, 2.5 Hz, 1H), 3.80-3.85 (m, 4H), 3.67 (s, 2H) 3.06-3.12 (m, 4H); MS (ESI⁺) M/Z 457 (M+H)⁺.

Example 132

N-[4-(morpholin-4-yl)-1-oxophthalazin-2(1H)-yl]-2-[4-(trifluoromethoxy)phenyl]acetamide The product of Example 1B and 2-[4-(trifluoromethoxy) phenyl]acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=8.0 Hz, 1H), 7.97-8.01 (m, 1H), 7.89-7.93 (m, 1H), 7.50-7.52 (m, 2H), 7.34-7.37 (m, 2H), 3.80-3.84 (m, 4H), 3.75 (s, 2H), 3.07-3.11 (m, 2H); MS (ESI⁺) M/Z 449 (M+H)⁺.

Example 133

(±)-2-[(exo)-bicyclo[2.2.1]hept-2-yl]-N-[4-(morpholin-4-yl)-1-oxophthalazin-2(1H)-yl]acetamide The product of Example 1B and (±)-2-[(exo)-bicyclo [2.2.1]hept-2-yl]acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=8.0 Hz, 1H), 7.96-8.01 (m, 1H), 7.89-7.93 (m, 1H), 3.79-3.83 (m, 4H), 3.08-3.10 (m, 4H), 2.20-2.27 (m, 2H), 2.10-2.17 (m, 2H), 1.82-1.91 (m, 1H), 1.37-1.54 (m, 4H), 1.07-1.19 (m, 4H); MS (ESI⁺) M/Z 383 (M+H)⁺.

Example 134

2-(1,2-benzoxazol-3-yl)-N-[4-(morpholin-4-yl)-1-oxophthalazin-2(1H)-yl]acetamide The product of Example 1B and 2-(1,2-benzoxazol-3-yl) acetic acid were treated using a method similar to that described in Example 111 to give the title compound. ¹H NMR (500 MHz, DMSO-d₆/D₂O) δ 8.32 (d, J=7.9, 1H), 8.07-7.97 (m, 3H), 7.95-7.89 (m, 1H), 7.76 (d, J=8.4, 1H), 7.69 (ddd, J=8.3, 7.0, 1.1, 1H), 7.48-7.41 (m, 1H), 4.19 (s, 2H), 3.86-3.80 (m, 4H), 3.16-3.07 (m, 4H); MS (ESI⁺) M/Z 406 (M+H)⁺.

Example 135

3,3-dimethyl-N-[4-(morpholin-4-yl)-1-oxophthalazin-2(1H)-yl]butanamide

The product of Example 1B and 3,3-dimethylbutanoic acid were treated using a method similar to that described in Example 111 to give the title compound. ¹H NMR (500 MHz, DMSO-d₆/Deuterium Oxide) δ ppm 8.31 (dd, J=7.9, 1.2 Hz, 1H), 8.03 (d, J=8.0 Hz, 1H), 7.97-8.00 (m, 1H), 7.89-7.93 (m, 1H), 3.79-3.84 (m, 4H), 3.08-3.13 (m, 4H), 2.16 (s, 2H), 1.07 (s, 9H); MS (ESI⁻) M/Z 343 (M−H)⁻.

Example 136

3,3,3-trifluoro-N-[4-(morpholin-4-yl)-1-oxophthalazin-2(1H)-yl]propanamide

The product of Example 1B and 3,3,3-trifluoropropanoic acid were treated using a method similar to that described in Example 111 to give the title compound. ¹H NMR (500 MHz, DMSO-d₆/Deuterium Oxide) δ ppm 8.32 (dd, J=7.9, 1.3 Hz, 1H), 8.04 (dd, J=8.1, 1.3 Hz, 1H), 7.98-8.02 (m, 1H), 7.93 (td, J=7.5, 1.3 Hz, 1H), 3.82-3.84 (m, 4H), 3.53-3.60 (m, 2H), 3.09-3.11 (m, 4H); MS (ESI⁺) M/Z 357 (M+H)⁺.

Example 137

2-cyclopentyl-N-[4-(morpholin-4-yl)-1-oxophthalazin-2(1H)-yl]acetamide

The product of Example 1B and 2-cyclopentylacetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=8.0 Hz, 1H), 7.97-8.00 (m, 1H), 7.91 (td, J=7.5, 1.3 Hz, 1H), 3.81-3.84 (m, 4H), 3.05-3.14 (m, 4H), 2.29 (d, J=7.5 Hz, 2H), 2.13-2.23 (m, 1H), 1.75-1.84 (m, 2H), 1.49-1.66 (m, 4H), 1.21-1.29 (m, 2H); MS (ESI⁻) M/Z 355 (M−H)⁻.

Example 138

2-cyclohexyl-N-[4-(morpholin-4-yl)-1-oxophthalazin-2(1H)-yl]acetamide

The product of Example 1B and 2-cyclohexylacetic acid were treated using a method similar to that described in Example 111 to give the title compound. ¹H NMR (500 MHz, DMSO-d₆/Deuterium Oxide) δ ppm 8.31 (dd, J=7.8, 1.4 Hz, 1H), 8.03 (dd, J=8.1, 1.3 Hz, 1H), 7.97-8.00 (m, 1H), 7.91 (td, J=7.5, 1.3 Hz, 1H), 3.75-3.83 (m, 4H), 3.08-3.10 (m, 4H), 2.16 (d, J=7.0 Hz, 2H), 1.61-1.83 (m, 6H), 0.96-1.28 (m, 5H); MS (ESI⁻) M/Z 369 (M−H)⁻.

Example 139

2-(2-methylphenyl)-N-[4-(morpholin-4-yl)-1-oxophthalazin-2(1H)-yl]acetamide

The product of Example 1B and 2-(2-methylphenyl)acetic acid were treated using a method similar to that described in Example 111 to give the title compound. ¹H NMR (500 MHz, DMSO-d₆/D₂O) δ 8.31 (d, J=7.8, 1H), 8.03 (d, J=7.7, 1H), 8.01-7.96 (m, 1H), 7.94-7.87 (m, 1H), 7.33-7.30 (m, 1H), 7.24-7.14 (m, 3H), 3.84-3.81 (m, 4H), 3.68 (s, 2H), 3.15-3.06 (m, 4H), 2.35 (s, 3H); MS (ESI⁺) M/Z 379 (M+H)⁺.

Example 140

2-(3-methylphenyl)-N-[4-(morpholin-4-yl)-1-oxophthalazin-2(1H)-yl]acetamide

The product of Example 1B and 2-(3-methylphenyl)acetic acid were treated using a method similar to that described in Example 111 to give the title compound. ¹H NMR (500 MHz, DMSO-d₆/D₂O) δ 8.31 (d, J=7.9, 1H), 8.04-8.01 (m, 1H), 8.01-7.96 (m, 1H), 7.94-7.88 (m, 1H), 7.26-7.22 (m, 1H), 7.19-7.16 (s, 2H), 7.11-7.08 (t, J=9.0, 1H), 3.86-3.78 (m, 4H), 3.62 (s, 2H), 3.13-3.06 (m, 4H), 2.31 (s, 3H); MS (ESI⁺) M/Z 379 (M+H)⁺.

Example 141

2-(4-methylphenyl)-N-[4-(morpholin-4-yl)-1-oxophthalazin-2(1H)-yl]acetamide

The product of Example 1B and 2-(4-methylphenyl)acetic acid were treated using a method similar to that described in Example 111 to give the title compound. ¹H NMR (500 MHz, DMSO-d₆/D₂O) δ 8.30 (dd, J=7.9, 0.8, 1H), 8.04-8.02 (m, 1H), 8.01-7.96 (m, 1H), 7.94-7.88 (m, 1H), 7.26 (d, J=8.0, 2H), 7.16 (d, J=7.9, 2H), 3.87-3.78 (m, 4H), 3.61 (s, 2H), 3.13-3.05 (m, 4H), 2.30 (s, 3H); MS (ESI⁺) M/Z 379 (M+H)⁺.

Example 142

N-[4-(morpholin-4-yl)-1-oxophthalazin-2(1H)-yl]-2-(2-nitrophenyl)acetamide

The product of Example 1B and 2-(2-nitrophenyl)acetic acid were treated using a method similar to that described in Example 111 to give the title compound. ¹H NMR (500 MHz, DMSO-d₆/D₂O) δ 8.30 (d, J=7.7, 1H), 8.09-7.95 (m, 4H), 7.94-7.87 (m, 1H), 7.73 (dt, J=7.6, 3.8, 1H), 7.63 (d, J=6.7, 1H), 7.59 (dd, J=11.2, 4.4, 1H), 4.13 (s, 2H), 3.86-3.79 (m, 4H), 3.14-3.04 (m, 4H); MS (ESI⁺) M/Z 410 (M+H)⁺.

Example 143

2-(3-hydroxyphenyl)-N-[4-(morpholin-4-yl)-1-oxophthalazin-2(1H)-yl]acetamide

The product of Example 1B and 2-(3-hydroxyphenyl)acetic acid were treated using a method similar to that described in Example 111 to give the title compound. ¹H NMR (500 MHz, DMSO-d₆/D₂O) δ 8.31-8.30 (s, 1H), 8.05-8.01 (m, 1H), 8.01-7.96 (m, 1H), 7.93-7.89 (s, 1H), 7.17-7.13 (m, 1H), 6.86-6.77 (m, 2H), 6.68 (dd, J=7.8, 2.0, 1H), 3.87-3.78 (m, 4H), 3.57 (s, 2H), 3.14-3.03 (m, 4H); MS (ESI⁺) M/Z 381 (M+H)⁺.

Example 144

2-(4-hydroxyphenyl)-N-[4-(morpholin-4-yl)-1-oxophthalazin-2(1H)-yl]acetamide

The product of Example 1B and 2-(4-hydroxyphenyl)acetic acid were treated using a method similar to that described in Example 111 to give the title compound. ¹H NMR (500 MHz, DMSO-d₆/Deuterium Oxide) δ ppm 8.30 (dd, J=7.9, 1.2 Hz, 1H), 8.03 (d, J=8.0 Hz, 1H), 7.97-8.00 (m, 1H), 7.89-7.92 (m, 1H), 7.18 (s, 2H), 6.75 (d, 2H), 3.81-3.83 (m, 4H), 3.53 (s, 2H), 3.07-3.11 (m, 4H); MS (ESI⁻) M/Z 379 (M−H)⁻.

Example 145

2-(2-methoxyphenyl)-N-[4-(morpholin-4-yl)-1-oxophthalazin-2(1H)-yl]acetamide

The product of Example 1B and 2-(2-methoxyphenyl)acetic acid were treated using a method similar to that described in Example 111 to give the title compound. ¹H NMR (500 MHz, DMSO-d₆/Deuterium Oxide) δ ppm 8.32 (dd, J=7.9, 1.3 Hz, 1H), 8.03 (d, J=8.0 Hz, 1H), 7.97-8.01 (m, 1H), 7.91 (td, J=7.5, 1.3 Hz, 1H), 7.33 (dd, J=7.4, 1.7 Hz, 1H), 7.27 (td, J=7.8, 1.7 Hz, 1H), 7.00 (d, J=8.7 Hz, 1H), 6.93 (td, J=7.4, 1.1 Hz, 1H), 3.85-3.82 (m, 4H), 3.82 (s, 3H), 3.62 (s, 2H), 3.09-3.11 (m, 4H); MS (ESI⁺) M/Z 395 (M+H)⁺.

Example 146

2-(3-methoxyphenyl)-N-[4-(morpholin-4-yl)-1-oxophthalazin-2(1H)-yl]acetamide

The product of Example 1B and 2-(3-methoxyphenyl)acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 7.97-8.05 (m, 2H), 7.91 (td, J=7.5, 1.3 Hz, 1H), 7.27 (t, J=7.8 Hz, 1H), 6.98-6.99 (m, 1H), 6.96 (d, J=7.6 Hz, 1H), 6.86 (dd, J=8.2, 2.6 Hz, 1H), 3.81-3.83 (m, 4H), 3.77 (s, 3H), 3.63 (s, 2H), 3.03-3.13 (m, 4H); MS (ESI⁻) M/Z 393 (M−H)⁻.

Example 147

2-(4-methoxyphenyl)-N-[4-(morpholin-4-yl)-1-oxophthalazin-2(1H)-yl]acetamide

The product of Example 1B and 2-(4-methoxyphenyl)acetic acid were treated using a method similar to that described in Example 111 to give the title compound. ¹H NMR (500 MHz, DMSO-d₆/Deuterium Oxide) δ ppm 8.30 (dd, J=7.9, 1.3 Hz, 1H), 8.03 (d, J=1.3 Hz, 1H), 7.97-8.01 (m, 1H), 7.91 (td, J=7.5, 1.3 Hz, 1H), 7.28-7.31 (m, 2H), 6.91-6.93 (m, 2H), 3.81-3.83 (m, 4H), 3.75 (s, 3H), 3.59 (s, 3H), 3.07-3.10 (m, 4H); MS (ESI⁺) M/Z 395 (M+H)⁺.

Example 148

2-(2-fluorophenyl)-N-[4-(morpholin-4-yl)-1-oxophthalazin-2(1H)-yl]acetamide

The product of Example 1B and 2-(2-fluorophenyl)acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=8.0 Hz, 1H), 7.97-8.01 (m, 1H), 7.89-7.93 (m, 1H), 7.46-7.49 (m, 1H), 7.35 (tdd, J=7.7, 5.7, 1.9 Hz, 1H), 7.18-7.23 (m, 2H), 3.81-3.84 (m, 5H), 3.44-3.59 (m, 1H), 3.05-3.14 (m, 4H); MS (ESI⁺) M/Z 383 (M+H)⁺.

Example 149

2-(3-fluorophenyl)-N-[4-(morpholin-4-yl)-1-oxophthalazin-2(1H)-yl]acetamide

The product of Example 1B and 2-(3-fluorophenyl)acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.04 (d, J=8.0 Hz, 1H), 7.97-8.01 (m, 1H), 7.89-7.93 (m, 1H), 7.41 (td, J=8.0, 6.2 Hz, 1H), 7.21-7.26 (m, 2H), 7.10-7.14 (m, 1H), 3.81-3.83 (m, 4H), 3.71 (s, 2H), 3.08-3.11 (m, 4H); MS (ESI⁻) M/Z 381 (M−H)⁻.

Example 150

2-(4-fluorophenyl)-N-[4-(morpholin-4-yl)-1-oxophthalazin-2(1H)-yl]acetamide

The product of Example 1B and 2-(4-fluorophenyl)acetic acid were treated using a method similar to that described in Example 111 to give the title compound. ¹H NMR (500 MHz, DMSO-d₆/Deuterium Oxide) δ ppm 8.30 (dd, J=7.9, 1.3 Hz, 1H), 8.02-8.05 (m, 1H), 7.97-8.01 (m, 1H), 7.91 (td, J=7.5, 1.3 Hz, 1H), 7.40-7.43 (m, 2H), 7.16-7.20 (m, 2H), 3.78-3.83 (m, 4H), 3.70 (s, 2H), 3.04-3.13 (m, 4H); MS (ESI⁻) M/Z 381 (M−H)⁻.

Example 151

2-(2-chlorophenyl)-N-[4-(morpholin-4-yl)-1-oxophthalazin-2(1H)-yl]acetamide

The product of Example 1B and 2-(2-chlorophenyl)acetic acid were treated using a method similar to that described in Example 111 to give the title compound. ¹H NMR (500 MHz, DMSO-d₆/Deuterium Oxide) δ ppm 8.32 (d, J=8.4 Hz, 1H), 8.02-8.05 (m, 1H), 7.97-8.01 (m, 1H), 7.89-7.93 (m, 1H), 7.46-7.54 (m, 2H), 7.31-7.36 (m, 2H), 3.82-3.83 (m, 6H), 3.09-3.12 (m, 4H); MS (ESI⁻) M/Z 397 (M−H)⁻.

Example 152

2-(3-chlorophenyl)-N-[4-(morpholin-4-yl)-1-oxophthalazin-2(1H)-yl]acetamide

The product of Example 1B and 2-(3-chlorophenyl)acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.04 (d, J=8.0 Hz, 1H), 7.97-8.01 (m, 1H), 7.89-7.93 (m, 1H), 7.47-7.45 (m, 1H), 7.39-7.42 (m, 1H), 7.33-7.37 (m, 2H), 3.78-3.87 (m, 4H), 3.70 (s, 2H), 3.08-3.14 (m, 4H); MS (ESI⁻) M/Z 397 (M−H)⁻.

Example 153

2-(2-bromophenyl)-N-[4-(morpholin-4-yl)-1-oxophthalazin-2(1H)-yl]acetamide

The product of Example 1B and 2-(2-bromophenyl)acetic acid were treated using a method similar to that described in Example 111 to give the title compound. ¹H NMR (500 MHz, DMSO-d₆/Deuterium Oxide) δ ppm 8.32 (dd, J=7.9, 1.3 Hz, 1H), 8.04 (d, J=8.0 Hz, 1H), 7.97-8.01 (m, 1H), 7.90-7.93 (m, 1H), 7.64 (dd, J=7.9, 1.2 Hz, 1H), 7.53 (dd, J=7.6, 1.7 Hz, 1H), 7.39 (td, J=7.5, 1.3 Hz, 1H), 7.23-7.28 (m, 1H), 3.82-3.87 (m, 5H), 3.49-3.62 (m, 1H), 3.09-3.14 (m, 4H); MS (ESI⁺) M/Z 443 (M+H)⁺.

Example 154

2-(3-bromophenyl)-N-[4-(morpholin-4-yl)-1-oxophthalazin-2(1H)-yl]acetamide

The product of Example 1B and 2-(3-bromophenyl)acetic acid were treated using a method similar to that described in Example 111 to give the title compound. ¹H NMR (500 MHz, DMSO-d$_6$/Deuterium Oxide) δ ppm 8.31 (dd, J=7.9, 1.3 Hz, 1H), 8.04 (d, J=8.0 Hz, 1H), 7.97-8.01 (m, 1H), 7.89-7.93 (m, 1H), 7.60 (t, J=1.8 Hz, 1H), 7.49 (dt, J=7.8, 1.5 Hz, 1H), 7.39 (d, J=7.6 Hz, 1H), 7.34 (t, J=7.7 Hz, 1H), 3.83 (d, J=4.2 Hz, 4H), 3.69 (s, 2H), 3.09-3.11 (m, 4H); MS (ESI$^-$) M/Z 441 (M−H)$^-$.

Example 155

2-(4-bromophenyl)-N-[4-(morpholin-4-yl)-1-oxophthalazin-2(1H)-yl]acetamide

The product of Example 1B and 2-(4-bromophenyl)acetic acid were treated using a method similar to that described in Example 111 to give the title compound. $^1$H NMR (500 MHz, DMSO-d$_6$/Deuterium Oxide) δ ppm 8.30 (dd, J=7.9, 1.3 Hz, 1H), 8.03 (dd, J=8.1, 1.3 Hz, 1H), 7.97-8.01 (m, 1H), 7.91 (td, J=7.5, 1.3 Hz, 1H), 7.54-7.56 (m, 2H), 7.33-7.36 (m, 2H), 3.78-3.83 (m, 4H), 3.65 (s, 2H), 3.08-3.13 (m, 4H); MS (ESI$^-$) M/Z 441 (M−H)$^-$.

Example 156

N-[4-(morpholin-4-yl)-1-oxophthalazin-2(1H)-yl]-2-(3-nitrophenyl)acetamide

The product of Example 1B and 2-(3-nitrophenyl)acetic acid were treated using a method similar to that described in Example 111 to give the title compound. $^1$H NMR (500 MHz, DMSO-d$_6$/Deuterium Oxide) δ ppm 8.31 (dd, J=7.9, 1.3 Hz, 1H), 8.28 (t, J=1.9 Hz, 1H), 8.17 (ddd, J=8.2, 2.3, 1.2 Hz, 1H), 8.03-8.05 (m, 1H), 7.97-8.01 (m, 1H), 7.91 (td, J=7.5, 1.3 Hz, 1H), 7.84 (d, J=7.7 Hz, 1H), 7.68 (t, J=7.9 Hz, 1H), 3.88 (s, 2H), 3.81-3.83 (m, 4H), 3.09-3.11 (m, 4H); MS (ESI$^-$) M/Z 408 (M−H)$^-$.

Example 157

N-[4-(morpholin-4-yl)-1-oxophthalazin-2(1H)-yl]-2-(4-nitrophenyl)acetamide

The product of Example 1B and 2-(4-nitrophenyl)acetic acid were treated using a method similar to that described in Example 111 to give the title compound. $^1$H NMR (500 MHz, DMSO-d$_6$/D$_2$O) δ 8.30 (d, J=7.4, 1H), 8.27-8.21 (m, 2H), 8.04 (d, J=7.8, 1H), 8.02-7.96 (m, 1H), 7.94-7.88 (m, 1H), 7.67 (d, J=8.6, 2H), 3.84-3.81 (m, 4H), 3.70 (s, 2H), 3.11-3.07 (m, 4H); MS (ESI$^-$) M/Z 408 (M−H)$^-$.

Example 158

2-(biphenyl-4-yl)-N-[4-(morpholin-4-yl)-1-oxophthalazin-2(1H)-yl]acetamide

The product of Example 1B and 2-(biphenyl-4-yl)acetic acid were treated using a method similar to that described in Example 111 to give the title compound. $^1$H NMR (500 MHz, DMSO-d$_6$/Deuterium Oxide) δ ppm 8.32 (d, J=7.9 Hz, 1H), 8.04 (d, J=8.0 Hz, 1H), 7.97-8.01 (m, 1H), 7.89-7.93 (m, 1H), 7.56-7.69 (m, 4H), 7.47-7.50 (m, 4H), 7.38 (t, J=7.4 Hz, 1H), 3.78-3.84 (m, 4H), 3.72 (s, 2H), 3.09-3.11 (m, 4H); MS (ESI$^+$) M/Z 441 (M+H)$^+$.

Example 159

2-[4-(dimethylamino)phenyl]-N-[4-(morpholin-4-yl)-1-oxophthalazin-2(1H)-yl]acetamide The product of Example 1B and 2-[4-(dimethylamino)phenyl]acetic acid were treated using a method similar to that described in Example 111 to give the title compound. $^1$H NMR (500 MHz, DMSO-d$_6$/D$_2$O) δ 8.30 (dd, J=7.9, 1.0, 1H), 8.04 (d, J=7.5, 1H), 8.02-7.96 (m, 1H), 7.94-7.88 (m, 1H), 7.47 (d, J=8.7, 2H), 7.37 (d, J=8.6, 2H), 3.85-3.80 (m, 4H), 3.69 (s, 2H), 3.11 (s, 6H), 3.11-3.06 (m, 4H); MS (ESI$^-$) M/Z 406 (M−H)$^-$.

Example 160

N-[4-(morpholin-4-yl)-1-oxophthalazin-2(1H)-yl]-2-[3-(trifluoromethyl)phenyl]acetamide The product of Example 1B and 2-[3-(trifluoromethyl)phenyl]acetic acid were treated using a method similar to that described in Example 111 to give the title compound. $^1$H NMR (500 MHz, DMSO-d$_6$/Deuterium Oxide) δ ppm 8.31 (dd, J=7.9, 1.3 Hz, 1H), 7.97-8.05 (m, 2H), 12.84-3.14 (m, 4H), 7.91 (td, J=7.5, 1.3 Hz, 1H), 7.75-7.76 (bs, 1H), 7.60-7.70 (m, 3H), 3.80-3.86 (m, 6H); MS (ESI$^+$) M/Z 433 (M+H)$^+$.

Example 161

N-[4-(morpholin-4-yl)-1-oxophthalazin-2(1H)-yl]-2-[4-(trifluoromethyl)phenyl]acetamide The product of Example 1B and 2-[4-(trifluoromethyl)phenyl]acetic acid were treated using a method similar to that described in Example 111 to give the title compound. $^1$H NMR (500 MHz, DMSO-d$_6$/Deuterium Oxide) δ ppm 8.31 (d, J=7.3 Hz, 1H), 8.04 (d, J=8.0 Hz, 1H), 7.97-8.01 (m, 1H), 7.89-7.93 (m, 1H), 7.72-7.75 (m, 2H), 7.60-7.62 (m, 2H), 3.80-3.83 (m, 6H), 3.03-3.14 (m, 4H); MS (ESI$^-$) M/Z 431 (M−H)$^-$.

Example 162

N-[4-(morpholin-4-yl)-1-oxophthalazin-2(1H)-yl]-2-[3-(trifluoromethoxy)phenyl]acetamide The product of Example 1B and 2-[3-(trifluoromethoxy)phenyl]acetic acid were treated using a method similar to that described in Example 111 to give the title compound. $^1$H NMR (500 MHz, DMSO-d$_6$/D$_2$O) δ 8.31 (d, J=7.7, 1H), 8.04 (d, J=7.8, 1H), 8.02-7.96 (m, 1H), 7.94-7.88 (m, 1H), 7.51 (t, J=7.9, 1H), 7.45-7.37 (m, 2H), 7.29 (d, J=8.2, 1H), 3.85-3.79 (m, 4H), 3.76 (s, 2H), 3.14-3.05 (m, 4H); MS (ESI$^-$) M/Z 447 (M−H)$^-$.

Example 163

N-[4-(morpholin-4-yl)-1-oxophthalazin-2(1H)-yl]-2-(4-phenoxyphenyl)acetamide

The product of Example 1B and 2-(4-phenoxyphenyl)acetic acid were treated using a method similar to that described in Example 111 to give the title compound. $^1$H NMR (500 MHz, DMSO-d$_6$/D$_2$O) δ 8.31 (dd, J=7.9, 0.7, 1H), 8.03 (d, J=7.7, 1H), 8.02-7.96 (m, 1H), 7.95-7.87 (m, 1H), 7.46-7.36 (m, 4H), 7.20-7.12 (m, 1H), 7.05-6.97 (m, 4H), 3.88-3.78 (m, 4H), 3.67 (s, 2H), 3.13-3.05 (m, 4H); MS (ESI$^-$) M/Z 455 (M−H)$^-$.

Example 164

2-[4-(benzyloxy)phenyl]-N-[4-(morpholin-4-yl)-1-oxophthalazin-2(1H)-yl]acetamide The product of Example 1B and 2-[4-(benzyloxy)phenyl]acetic acid were treated using a method similar to that described in Example 111 to give the title compound. ¹H NMR (500 MHz, DMSO-d₆/Deuterium Oxide) δ ppm 8.30 (dd, J=7.9, 1.2 Hz, 1H), 8.02 (d, J=1.2 Hz, 1H), 7.97-8.00 (m, 1H), 7.89-7.92 (m, 1H), 7.28-7.47 (m, 7H), 6.98-7.00 (m, 2H), 5.10 (s, 2H), 3.75-3.83 (m, 4H), 3.58-3.60 (m, 2H), 3.07-3.13 (m, 4H); MS (ESI⁻) M/Z 469 (M–H)⁻.

Example 165

N-[4-(morpholin-4-yl)-1-oxophthalazin-2(1H)-yl]-2-(naphthalen-1-yl)acetamide

The product of Example 1B and 2-(naphthalen-1-yl)acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.18 (d, J=8.2 Hz, 1H), 7.87-8.04 (m, 5H), 7.49-7.62 (m, 4H), 4.15 (s, 2H), 3.78-3.85 (m, 4H), 3.07-3.12 (m, 4H); MS (ESI⁻) M/Z 413 (M–H)⁻.

Example 166

N-[4-(morpholin-4-yl)-1-oxophthalazin-2(1H)-yl]-2-(naphthalen-2-yl)acetamide

The product of Example 1B and 2-(naphthalen-2-yl)acetic acid were treated using a method similar to that described in Example 111 to give the title compound. ¹H NMR (500 MHz, DMSO-d₆/D₂O) δ 8.33-8.29 (m, 1H), 8.03-8.01 (m, 1H), 8.01-7.96 (m, 1H), 7.95-7.88 (m, 5H), 7.58-7.49 (m, 3H), 3.85 (s, 2H), 3.84-3.79 (m, 4H), 3.13-3.06 (m, 4H); MS (ESI⁻) M/Z 413 (M–H)⁻.

Example 167

2-(2,5-dimethylphenyl)-N-[4-(morpholin-4-yl)-1-oxophthalazin-2(1H)-yl]acetamide

The product of Example 1B and 2-(2,5-dimethylphenyl) acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.02-8.04 (m, 1H), 7.97-8.00 (m, 1H), 7.91 (td, J=7.5, 1.3 Hz, 1H), 7.13 (s, 1H), 7.07 (d, J=7.6 Hz, 1H), 6.99 (d, J=7.7 Hz, 1H), 3.81-3.84 (m, 4H), 3.62 (s, 2H), 3.05-3.11 (m, 4H), 2.29 (s, 3H), 2.26 (s, 3H); MS (ESI⁺) M/Z 393 (M+H)⁺.

Example 168

N-[4-(morpholin-4-yl)-1-oxophthalazin-2(1H)-yl]-2-(2,4,6-trimethylphenyl)acetamide The product of Example 1B and 2-(2,4,6-trimethylphenyl) acetic acid were treated using a method similar to that described in Example 111 to give the title compound. ¹H NMR (500 MHz, DMSO-d₆/Deuterium Oxide) δ ppm 8.30 (d, J=7.3 Hz, 1H), 8.02 (d, J=8.0 Hz, 1H), 7.96-8.00 (m, 1H), 7.88-7.92 (m, 1H), 6.84-6.85 (bs, 2H), 3.77-3.85 (m, 4H), 3.66 (s, 2H), 3.08-3.13 (m, 4H), 2.31 (s, 6H), 2.21 (s, 3H); MS (ESI⁺) M/Z 407 (M+H)⁺.

Example 169

2-(2,3-dimethoxyphenyl)-N-[4-(morpholin-4-yl)-1-oxophthalazin-2(1H)-yl]acetamide The product of Example 1B and 2-(2,3-dimethoxyphenyl) acetic acid were treated using a method similar to that described in Example 111 to give the title compound. ¹H NMR (500 MHz, DMSO-d₆/Deuterium Oxide) δ ppm 8.31 (d, J=7.9 Hz, 1H), 7.97-8.04 (m, 2H), 7.89-7.92 (m, 1H), 7.04 (t, J=7.8 Hz, 1H), 6.93-6.99 (m, 2H), 3.84-3.81 (d, J=4.2 Hz, 4H), 3.81 (s, 3H), 3.77 (s, 3H), 3.64 (s, 2H), 3.06-3.10 (m, 4H); MS (ESI⁺) M/Z 425 (M+H)⁺.

Example 170

2-(2,4-dimethoxyphenyl)-N-[4-(morpholin-4-yl)-1-oxophthalazin-2(1H)-yl]acetamide The product of Example 1B and 2-(2,4-dimethoxyphenyl) acetic acid were treated using a method similar to that described in Example 111 to give the title compound. ¹H NMR (500 MHz, DMSO-d₆/Deuterium Oxide) δ ppm 8.31 (d, J=7.8 Hz, 1H), 8.03 (d, J=8.0 Hz, 1H), 7.97-8.00 (m, 1H), 7.89-7.92 (m, 1H), 7.22 (d, J=8.2 Hz, 1H), 6.56 (d, J=2.4 Hz, 1H), 6.51 (dd, J=8.2, 2.4 Hz, 1H), 3.82-3.84 (m, 4H), 3.80 (s, 3H), 3.76 (s, 3H), 3.53 (s, 2H), 3.06-3.14 (m, 4H); MS (ESI⁺) M/Z 425 (M+H)⁺.

Example 171

2-(2,5-dimethoxyphenyl)-N-[4-(morpholin-4-yl)-1-oxophthalazin-2(1H)-yl]acetamide The product of Example 1B and 2-(2,5-dimethoxyphenyl) acetic acid were treated using a method similar to that described in Example 111 to give the title compound. ¹H NMR (500 MHz, DMSO-d₆/D₂O) δ 8.32 (d, J=7.8, 1H), 8.03 (d, J=7.8, 1H), 8.01-7.95 (m, 1H), 7.94-7.88 (m, 1H), 6.99 (d, J=3.1, 1H), 6.93 (d, J=8.9, 1H), 6.82 (dd, J=8.9, 3.1, 1H), 3.85-3.81 (m, 4H), 3.76 (s, 3H), 3.72 (s, 3H), 3.59 (s, 2H), 3.14-3.07 (m, 4H); MS (ESI⁺) M/Z 425 (M+H)⁺.

Example 172

2-(3,4-dimethoxyphenyl)-N-[4-(morpholin-4-yl)-1-oxophthalazin-2(1H)-yl]acetamide The product of Example 1B and 2-(3,4-dimethoxyphenyl) acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=8.0 Hz, 1H), 7.97-8.01 (m, 1H), 7.89-7.93 (m, 1H), 7.02 (d, J=1.9 Hz, 1H), 6.92 (q, J=8.3 Hz, 1H), 3.80-3.83 (m, 5H), 3.78 (s, 3H), 3.75 (s, 3H), 3.59 (s, 2H), 3.17 (s, 1H), 3.08-3.10 (m, 3H); MS (ESI⁻) M/Z 423 (M–H)⁻.

Example 173

2-(3,5-dimethoxyphenyl)-N-[4-(morpholin-4-yl)-1-oxophthalazin-2(1H)-yl]acetamide The product of Example 1B and 2-(3,5-dimethoxyphenyl) acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=1.3 Hz, 1H), 7.97-8.01 (m, 1H), 7.91 (td, J=7.5, 1.3 Hz, 1H), 6.58 (d, J=2.3 Hz, 2H), 6.41

(t, J=2.3 Hz, 1H), 3.80-3.84 (m, 4H), 3.76 (s, 6H), 3.59 (s, 2H), 3.08-3.11 (m, 4H); MS (ESI⁻) M/Z 423 (M−H)⁻.

Example 174

2-(1,3-benzodioxol-5-yl)-N-[4-(morpholin-4-yl)-1-oxophthalazin-2(1H)-yl]acetamide The product of Example 1B and 2-(1,3-benzodioxol-5-yl) acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=8.0 Hz, 1H), 7.97-8.01 (m, 1H), 7.89-7.93 (m, 1H), 6.96 (d, J=1.7 Hz, 1H), 6.89 (d, J=7.9 Hz, 1H), 6.84 (dd, J=7.9, 1.7 Hz, 1H), 6.00 (s, 2H), 3.81-3.83 (m, 4H), 3.58 (s, 2H), 3.08-3.10 (m, 4H); MS (ESI⁺) M/Z 409 (M+H)⁺.

Example 175

2-(2,3-difluorophenyl)-N-[4-(morpholin-4-yl)-1-oxophthalazin-2(1H)-yl]acetamide

The product of Example 1B and 2-(2,3-difluorophenyl) acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=8.0 Hz, 1H), 7.97-8.01 (m, 1H), 7.91 (td, J=7.5, 1.3 Hz, 1H), 7.35 (dtd, J=10.2, 8.1, 1.9 Hz, 1H), 7.27-7.31 (m, 1H), 7.19-7.25 (m, 1H), 3.81-3.84 (m, 4H), 3.80 (s, 2H), 3.07-3.12 (m, 4H); MS (ESI⁺) M/Z 401 (M+H)⁺.

Example 176

2-(2,5-difluorophenyl)-N-[4-(morpholin-4-yl)-1-oxophthalazin-2(1H)-yl]acetamide

The product of Example 1B and 2-(2,5-difluorophenyl) acetic acid were treated using a method similar to that described in Example 111 to give the title compound. ¹H NMR (500 MHz, DMSO-d₆/Deuterium Oxide) δ ppm 8.32 (dd, J=7.9, 1.3 Hz, 1H), 8.03 (d, J=8.0 Hz, 1H), 7.97-8.01 (m, 1H), 7.90-7.93 (m, 1H), 7.36 (ddd, J=9.0, 5.8, 3.2 Hz, 1H), 7.12-7.29 (m, 2H), 3.82-3.84 (m, 4H), 3.75 (s, 2H), 3.09-3.11 (m, 4H); MS (ESI⁺) M/Z 401 (M+H)⁺.

Example 177

2-(3,4-dichlorophenyl)-N-[4-(morpholin-4-yl)-1-oxophthalazin-2(1H)-yl]acetamide

The product of Example 1B and 2-(3,4-dichlorophenyl) acetic acid were treated using a method similar to that described in Example 111 to give the title compound. ¹H NMR (500 MHz, DMSO-d₆/Deuterium Oxide) δ ppm 8.31 (dd, J=7.9, 1.3 Hz, 1H), 8.03 (d, J=8.0 Hz, 1H), 7.97-8.01 (m, 1H), 7.89-7.93 (m, 1H), 7.66 (d, J=2.0 Hz, 1H), 7.63 (d, J=8.2 Hz, 1H), 7.37 (dd, J=8.2, 2.1 Hz, 1H), 3.80-3.84 (m, 4H), 3.72 (s, 2H), 3.08-3.11 (m, 4H); MS (ESI⁻) M/Z 431 (M−H)⁻.

Example 178

2-(2,6-dichlorophenyl)-N-[4-(morpholin-4-yl)-1-oxophthalazin-2(1H)-yl]acetamide

The product of Example 1B and 2-(2,6-dichlorophenyl) acetic acid were treated using a method similar to that described in Example 111 to give the title compound. ¹H NMR (500 MHz, DMSO-d₆/Deuterium Oxide) δ ppm 8.31 (d, J=7.9 Hz, 1H), 8.02-8.08 (m, 1H), 7.96-8.00 (m, 1H), 7.89-7.95 (m, 1H), 7.49-7.51 (m, 2H), 7.30-7.45 (m, 1H), 4.04 (s, 2H), 3.81-3.84 (m, 4H), 3.08-3.12 (m, 4H); MS (ESI⁺) M/Z 433 (M+H)⁺.

Example 179 tert-butyl(±)-[(3-{[(exo)-bicyclo[2.2.1]hept-2-ylacetyl]amino}-4-oxo-3,4-dihydrophthalazin-1-yl)(phenyl)methyl]carbamate A mixture of the product from Example 120 (35 mg, 0.084 mmol) and Ra—Ni 2800, water slurry (50 mg, 0.85 mmol) in EtOH (5 ml) in a 50 mL pressure bottle was stirred at room temperature for 29 hours under H₂ (30 psi). The mixture was filtered through a nylon membrane and concentrated to provide crude (±)-N-(4-(amino(phenyl)methyl)-1-oxophthalazin-2(1H)-yl)-2-((exo)-bicyclo[2.2.1]heptan-2-yl)acetamide.

A mixture of the above material (30 mg, 0.075 mmol), di-tert-butyl dicarbonate (19.5 mg, 0.089 mmol), and triethylamine (0.031 mL, 0.22 mmol) in DCM (5.0 mL) was stirred at room temperature for 4 hours, diluted with EtOAc, washed with sat NaHCO₃ and water, and concentrated. The residue was purified by column chromatography (0-50% of EtOAc in hexanes) to give the title compound. ¹H NMR (400 MHz, DMSO-d₆) δ 11.25 (s, 1H), 8.31 (dd, J=7.8, 1.4, 1H), 8.01 (d, J=8.0, 1H), 7.88 (dt, J=18.9, 6.7, 2H), 7.80-7.72 (m, 1H), 7.45-7.39 (m, 2H), 7.33-7.22 (m, 3H), 6.35 (d, J=8.4, 1H), 2.28-2.06 (m, 4H), 1.91-1.84 (m, 1H), 1.50-1.32 (m, 13H), 1.19-1.05 (m, 4H); MS (ESI⁺) M/Z 520 (M+NH₄)⁺.

Example 180

(1R,2S,5R)-5-methyl-2-(propan-2-yl)cyclohexyl[(3-{[(4-chlorophenyl)acetyl]amino}-4-oxo-3,4-dihydrophthalazin-1-yl)methyl]carbamate The product of Example 42 and (1R,2S,5R)-5-methyl-2-(propan-2-yl)cyclohexyl carbonochloridate were treated using a method similar to that described in Example 128 to give the title compound. ¹H NMR (300 MHz, DMSO-d₆) δ 11.60 (s, 1H), 8.32 (dd, J=7.7, 1.4, 1H), 8.09 (d, J=7.8, 1H), 7.93 (ddt, J=14.9, 7.4, 3.5, 2H), 7.66 (s, 1H), 7.40 (s, 4H), 4.60-4.40 (m, 3H), 3.67 (s, 2H), 1.93-1.77 (m, 2H), 1.67-1.53 (m, 2H), 1.50-1.35 (s, 1H), 1.30-1.19 (m, 1H), 1.10-0.87 (m, 3H), 0.87 (d, J=6.5, 3H), 0.81 (d, J=7.0, 3H), 0.72 (d, J=6.9, 3H); MS (ESI⁻) M/Z 532 (M−H)⁻.

Example 181

2-[4-(methylsulfonyl)phenyl]-N-[1-oxo-4-(phenylsulfanyl)phthalazin-2(1H)-yl]acetamide The product from Example 57B and 2-(4-(methylsulfonyl)phenyl)acetic acid were processed using a method similar to that described in Example 10C to afford the title compound. ¹H NMR (500 MHz, DMSO-d₆) δ 11.78 (s, 1H), 8.34 (dd, J=7.9, 1.1, 1H), 8.08 (d, J=7.7, 1H), 8.03-7.97 (m, 1H), 7.97-7.92 (m, 1H), 7.92-7.87 (m, 2H), 7.60 (d, J=8.3, 2H), 7.45-7.40 (m, 2H), 7.40-7.30 (m, 3H), 3.81 (s, 2H), 3.22 (s, 3H); MS (APCI⁺) M/Z 466 (M+H)⁺.

Example 182

2-methylbutan-2-yl[(3-{[(4-chlorophenyl)acetyl]amino}-4-oxo-3,4-dihydrophthalazin-1-yl)methyl]carbamate The product of Example 42 and di-tert-pentyl dicarbonate were treated using a method similar to that described in Example 128 to give the title compound. $^1$H NMR (300 MHz, DMSO-$d_6$) δ ppm 11.59 (s, 1H), 8.32 (dd, J=8.0, 1.3 Hz, 1H), 8.10 (d, J=8.0 Hz, 1H), 7.95-8.02 (m, 1H), 7.91 (td, J=7.5, 1.2 Hz, 1H), 7.37-7.44 (m, 5H), 4.42-4.46 (m, 2H), 3.67 (s, 2H), 1.59-1.76 (m, 2H), 1.33 (s, 6H), 0.77-0.84 (m, 3H); MS (ESI$^+$) M/Z 474 (M+NH$_4$)$^+$.

Example 183 methyl[(2S)-1-{[(3-{[(4-chlorophenyl)acetyl]amino}-4-oxo-3,4-dihydrophthalazin-1-yl)methyl]amino}-3-methyl-1-oxobutan-2-yl]carbamate The product of Example 42 and (S)-2-(methoxycarbonylamino)-3-methylbutanoic acid were treated using a method similar to that described in Example 56 to give the title compound. $^1$H NMR (300 MHz, DMSO-$d_6$) δ ppm 11.59-11.62 (bs, 1H), 8.53 (d, J=5.5 Hz, 1H), 8.32 (dd, J=7.5, 1.7 Hz, 1H), 8.03 (d, J=7.1 Hz, 1H), 7.88-7.99 (m, 2H), 7.37-7.45 (m, 4H), 7.09-7.13 (m, 1H), 4.52-4.67 (m, 2H), 3.78-3.86 (m, 1H), 3.67 (s, 2H), 3.51 (s, 3H), 1.85-1.96 (m, 1H), 0.71-0.83 (d, 6H); MS (ESI$^+$) M/Z 500 (M+H)$^+$.

Example 184

2,2-dimethylpropyl[(3-{[(4-chlorophenyl)acetyl]amino}-4-oxo-3,4-dihydrophthalazin-1-yl)methyl]carbamate The product of Example 42 and 2,2-dimethylpropyl carbonochloridate were treated using a method similar to that described in Example 128 to give the title compound. $^1$H NMR (300 MHz, DMSO-$d_6$) δ ppm 11.59-11.61 (bs, 1H), 8.32 (dd, J=7.8, 1.4 Hz, 1H), 8.10 (d, J=8.0 Hz, 1H), 7.88-8.02 (m, 2H), 7.70-7.75 (m, 1H), 7.41 (s, 4H), 4.51 (d, J=5.9 Hz, 2H), 3.67-3.71 (m, 4H), 0.86-0.87 (m, 8H), 0.78 (d, J=2.8 Hz, 1H); MS (ESI$^-$) M/Z 455 (M−H)$^-$.

Example 185

2-methylpropyl[(3-{[(4-chlorophenyl)acetyl]amino}-4-oxo-3,4-dihydrophthalazin-1-yl)methyl]carbamate The product of Example 42 and 2-methylpropyl carbonochloridate were treated using a method similar to that described in Example 128 to give the title compound. $^1$H NMR (300 MHz, DMSO-$d_6$) δ ppm 11.59-11.61 (bs, 1H), 8.32 (dd, J=7.8, 1.4 Hz, 1H), 8.10 (d, J=8.0 Hz, 1H), 7.96-8.02 (m, 1H), 7.88-7.94 (m, 1H), 7.65-7.75 (m, 1H), 7.36-7.45 (m, 4H), 4.50 (d, J=5.9 Hz, 2H), 3.77 (d, J=6.6 Hz, 2H), 3.67 (s, 2H), 1.73-1.89 (m, 1H), 0.67-0.68 (m, 6H); MS (ESI$^-$) M/Z 441 (M−H)$^-$.

Example 186

(1S,2R,5S)-5-methyl-2-(propan-2-yl)cyclohexyl[(3-{[(4-chlorophenyl)acetyl]amino}-4-oxo-3,4-dihydrophthalazin-1-yl)methyl]carbamate The product of Example 42 and (1S,2R,5S)-5-methyl-2-(propan-2-yl)cyclohexyl carbonochloridate were treated using a method similar to that described in Example 128 to give the title compound. $^1$H NMR (300 MHz, DMSO-$d_6$) δ 11.66-11.55 (br s, 1H), 8.32 (dd, J=7.7, 1.1, 1H), 8.11-8.06 (m, 1H), 8.02-7.86 (m, 2H), 7.71-7.61 (m, 1H), 7.40 (s, 4H), 4.60-4.40 (m, 3H), 3.67 (s, 2H), 1.96-1.74 (m, 2H), 1.61 (s, 2H), 1.51-1.33 (m, 1H), 1.32-1.17 (m, 1H), 1.10-0.89 (m, 3H), 0.87 (d, J=6.4, 3H), 0.81 (d, J=7.0, 3H), 0.72 (d, J=6.8, 3H); MS (ESI$^-$) M/Z 523 (M−H)$^-$.

Example 187 cyclopentyl[(3-{[(4-chlorophenyl)acetyl]amino}-4-oxo-3,4-dihydrophthalazin-1-yl)methyl]carbamate The product of Example 42 and cyclopentyl carbonochloridate were treated using a method similar to that described in Example 128 to give the title compound. $^1$H NMR (300 MHz, DMSO-$d_6$) δ ppm 11.60-11.62 (bs, 1H), 8.32 (d, J=7.8 Hz, 1H), 8.10 (d, J=8.0 Hz, 1H), 7.88-8.03 (m, 2H), 7.58-7.64 (m, 1H), 7.23-7.45 (m, 4H), 4.95-5.01 (bs, 1H), 4.47-4.50 (m, 2H), 3.67-3.68 (bs, 2H), 1.76-1.81 (m, 2H), 1.50-1.69 (m, 6H); MS (ESI$^+$) M/Z 455 (M+H)$^+$.

Example 188 benzyl[(3-{[(4-chlorophenyl)acetyl]amino}-4-oxo-3,4-dihydrophthalazin-1-yl)methyl]carbamate The product of Example 42 and benzyl carbonochloridate were treated using a method similar to that described in Example 128 to give the title compound. $^1$H NMR (300 MHz, DMSO-$d_6$) δ ppm 11.50-11.71 (m, 1H), 8.32 (dd, J=7.6, 1.5 Hz, 1H), 8.08-8.11 (m, 1H), 7.88-8.01 (m, 3H), 7.28-7.48 (m, 9H), 5.06-5.07 (bs, 2H), 4.54 (d, J=5.9 Hz, 2H), 3.68 (s, 2H); MS (ESI$^+$) M/Z 494 (M+NH$_4$)$^+$.

Example 189

2-[4-(methylsulfonyl)phenyl]-N-[1-oxo-4-(phenylsulfonyl)phthalazin-2(1H)-yl]acetamide The product from Example 68B and 2-(4-(methylsulfonyl)phenyl)acetic acid were processed using a method similar to that described in Example 10C to afford the title compound. $^1$H NMR (500 MHz, DMSO-$d_6$) δ 11.97 (s, 1H), 8.56 (d, J=8.2, 1H), 8.42-8.35 (m, 1H), 8.15-8.08 (m, 1H), 8.04-7.99 (m, 3H), 7.91 (d, J=8.3, 2H), 7.82-7.77 (m, 1H), 7.71-7.65 (m, 2H), 7.57 (d, J=8.3, 2H), 3.83 (s, 2H), 3.24 (s, 3H); MS (DCI$^+$) M/Z 515 (M+NH$_4$)$^+$.

Example 190

(±)-2-[(exo)-bicyclo[2.2.1]hept-2-yl]-N-[4-(1,1-dioxidothiomorpholin-4-yl)-1-oxophthalazin-2(1H)-yl]acetamide The product from Example 93 was processed using a method similar to that described in Example 68A to afford the title compound. $^1$H NMR (400 MHz, DMSO-$d_6$) δ 11.17 (s, 1H), 8.31 (dd, J=7.9, 1.0, 1H), 8.06 (d, J=7.5, 1H), 8.02-7.95 (m, 1H), 7.92 (dd, J=10.9, 4.2, 1H), 3.56 (br s, 4H), 3.43-3.35 (buried m, 4H), 2.26-2.18 (m, 2H), 2.15-2.08 (m, 2H), 1.92-1.81 (m, 1H), 1.53-1.35 (m, 4H), 1.20-1.06 (m, 4H); MS (DCI$^+$) M/Z 448 (M+NH$_4$)$^+$.

Example 191

2-(4-chlorophenyl)-N-[1-oxo-4-(pyridin-4-ylsulfanyl)phthalazin-2(1H)-yl]acetamide

Example 191A 4-(pyridin-4-ylthio)phthalazin-1(2H)-one 4-chlorophthalazin-1(2H)-one and pyridine-4-thiol were processed using a method similar to that described in Example 57A to afford the title compound. MS (APCI) M/Z 256 (M+H)$^+$.

Example 191B 2-amino-4-(pyridin-4-ylthio)phthalazin-1(2H)-one

The product from Example 191A was processed using a method similar to that described in Example 1B to afford the title compound. MS (APCI) M/Z 271 (M+H)$^+$.

Example 191C 2-(4-chlorophenyl)-N-[1-oxo-4-(pyridin-4-ylsulfanyl)phthalazin-2(1H)-yl]acetamide The product from Example 191B and (4-chlorophenyl)acetyl chloride were processed using a method similar to that described in Example 4C to afford the title compound. $^1$H NMR (400 MHz, DMSO-d$_6$) δ 11.84 (s, 1H), 8.44-8.35 (m, 3H), 8.05-7.92 (m, 3H), 7.44-7.35 (m, 4H), 7.29-7.22 (m, 2H), 3.71 (s, 2H); MS (DCI$^+$) M/Z 423 (M+H)$^+$.

Example 192

2-(4-chlorophenyl)-N-{4-[(4-methylphenyl)sulfonyl]-1-oxophthalazin-2(1H)-yl}acetamide

Example 192A 4-(4-methylphenylthio)phthalazin-1(2H)-one

A mixture of 4-chlorophthalazin-1(2H)-one (0.233 g, 1.29 mmol) and sodium 4-methylbenzenesulfinate (0.460 g, 2.58 mmol) in ethane-1,2-diol (0.29 mL, 5.19 mmol) and methyl-2-pyrrolidinone (2.6 mL) was microwaved at 230° C. for 30 minutes, diluted with EtOAc, washed with water and brine, dried (Na$_2$SO$_4$), filtered, and chromatographed (15% EtOAc/DCM) to give 0.260 g of impure title compound as a white solid: MS (APCI$^+$) M/Z 269 (M+H)$^+$.

Example 192B 2-amino-4-(4-methylphenylthio)phthalazin-1(2H)-one

The product from Example 192A was processed using a method similar to that described in Example 1B to afford the title compound. MS (APCI$^+$) M/Z 284 (M+H)$^+$.

Example 192C 2-(4-chlorophenyl)-N-{4-[(4-methylphenyl)sulfonyl]-1-oxophthalazin-2(1H)-yl}acetamide The product from Example 192B and 2-(4-chlorophenyl)acetyl chloride were processed using a method similar to that described in Example 4C to afford the title compound. $^1$H NMR (300 MHz, DMSO-d$_6$) δ 11.89-11.80 (br s, 1H), 8.59-8.52 (m, 1H), 8.41-8.34 (m, 1H), 8.15-8.05 (m, 1H), 8.05-7.96 (m, 1H), 7.87 (d, 2H), 7.52-7.45 (m, 2H), 7.42 (d, 2H), 7.32 (d, 2H), 3.69 (s, 2H), 2.41 (s, 3H); MS (ESI$^+$) M/Z 485 (M+NH$_4$)$^+$.

Example 193

2-(4-fluorophenyl)-N-[1-oxo-4-(phenylsulfonyl)phthalazin-2(1H)-yl]acetamide

The product from Example 68B and 2-(4-fluorophenyl)acetic acid were processed using a method similar to that described in Example 10C to afford the title compound. $^1$H NMR (400 MHz, DMSO-d$_6$) δ 11.85 (s, 1H), 8.60-8.53 (m, 1H), 8.42-8.35 (m, 1H), 8.15-8.07 (m, 1H), 8.05-7.95 (m, 3H), 7.84-7.76 (m, 1H), 7.72-7.66 (m, 2H), 7.35-7.29 (m, 2H), 7.17 (t, J=8.9, 2H), 3.67 (s, 2H); MS (APCI$^+$) M/Z 438 (M+H)$^+$.

Example 194

3-methyl-N-[1-oxo-4-(phenylsulfonyl)phthalazin-2(1H)-yl]-3-phenylbutanamide

The product from Example 68B and 3-methyl-3-phenylbutanoic acid were processed using a method similar to that described in Example 10C to afford the title compound. $^1$H NMR (500 MHz, DMSO-d$_6$) δ 11.45 (s, 1H), 8.56 (d, J=8.2, 1H), 8.41-8.34 (m, 1H), 8.14-8.08 (m, 1H), 8.04-7.96 (m, 3H), 7.84-7.77 (m, 1H), 7.68 (dd, J=10.8, 5.0, 2H), 7.38 (dd, J=8.4, 1.1, 2H), 7.33-7.27 (m, 2H), 7.20-7.14 (m, 1H), 2.54 (s, 2H), 1.32 (s, 6H); MS (DCI$^+$) M/Z 479 (M+NH$_4$)$^+$.

Example 195

N-{4-[(4-bromophenyl)sulfanyl]-1-oxophthalazin-2(1H)-yl}-2-(4-chlorophenyl)acetamide

Example 195A 4-(4-bromophenylthio)phthalazin-1(2H)-one 4-chlorophthalazin-1(2H)-one and 4-bromobenzenethiol were processed using a method similar to that described in Example 57A to afford the title compound. MS (APCI) M/Z 374 (M+CH$_3$CN)$^+$.

Example 195B 2-amino-4-(4-bromophenylthio)phthalazin-1(2H)-one

The product from Example 195A was processed using a method similar to that described in Example 1B to afford the title compound. MS (APCI) M/Z 350 (M+H)$^+$.

Example 195C

N-{4-[(4-bromophenyl)sulfanyl]-1-oxophthalazin-2(1H)-yl}-2-(4-chlorophenyl)acetamide The product from Example 195B and 2-(4-chlorophenyl)acetyl chloride were processed using a method similar to that described in Example 4C to afford the title compound. $^1$H NMR (500 MHz, DMSO-d$_6$) δ 11.70 (s, 1H), 8.34 (d, J=7.1, 1H), 8.08-8.03 (m, 1H), 8.03-7.98 (m, 1H), 7.97-7.92 (m, 1H), 7.56 (d, J=8.6, 2H), 7.44-7.36 (m, 4H), 7.35-7.31 (m, 2H), 3.67 (s, 2H); MS (DCI⁺) M/Z 519 (M+NH₄)⁺.

Example 196

2-(4-chlorophenyl)-N-{4-[(1-oxidopyridin-4-yl)sulfonyl]-1-oxophthalazin-2(1H)-yl}acetamide The product from 191C was processed using a method similar to that described in Example 68A to afford the title compound. ¹H NMR (500 MHz, DMSO-d₆) δ 11.90 (s, 1H), 8.54 (d, J=8.2, 1H), 8.48-8.43 (m, 2H), 8.43-8.38 (m, 1H), 8.18-8.11 (m, 1H), 8.05 (t, J=7.7, 1H), 7.99-7.93 (m, 2H), 7.46-7.38 (m, 2H), 7.29 (d, J=8.4, 2H), 3.68 (s, 2H); MS (DCI⁺) M/Z 488 (M+NH₄)⁺.

Example 197

N-{4-[(4-bromophenyl)sulfanyl]-1-oxophthalazin-2(1H)-yl}-2-(3,5-difluorophenyl)acetamide The product from Example 195B and 2-(3,5-difluorophenyl)acetic acid were processed using a method similar to that described in Example 10C to afford the title compound. ¹H NMR (500 MHz, DMSO-d₆) δ 11.76 (s, 1H), 8.39-8.32 (m, 1H), 8.08-8.04 (m, 1H), 8.02 (ddd, J=8.1, 7.6, 1.3, 1H), 7.95 (td, J=8.2, 1.3, 1H), 7.59-7.52 (m, 2H), 7.38 (ddd, J=6.6, 2.4, 1.4, 2H), 7.19-7.13 (m, 1H), 7.12-7.05 (m, 2H), 3.73 (s, 2H); MS (DCI⁺) M/Z 502 (M+H)⁺.

Example 198

N-[4-(tert-butylsulfanyl)-1-oxophthalazin-2(1H)-yl]-2-(4-chlorophenyl)acetamide

Example 198A 4-(tert-butylthio)phthalazin-1(2H)-one

A mixture of 4-chlorophthalazin-1(2H)-one (200 mg, 1.11 mmol), sodium 2-methylpropane-2-thiolate (248 mg, 2.22 mmol), tris(trifluoromethylsulfonyloxy)scandium (54.5 mg, 0.11 mmol) and K₂CO₃ (308 mg, 2.22 mmol) was heated at 160° C. under microwave condition for 30 minutes. The mixture was diluted with EtOAc and washed with saturated aqueous NaHCO₃, dried (Na₂SO₄), filtered, and chromatographed (0-30% EtOAc/DCM) to give 52 mg (20%) of the title compound as a white solid: MS (DCI) 235 (M+H).

Example 198B 2-amino-4-(tert-butylthio)phthalazin-1(2H)-one

The product from Example 198A was processed using a method similar to that described in Example 1B to afford the title compound. MS (APCI) M/Z 250 (M+H)⁺.

Example 198C

N-[4-(tert-butylsulfanyl)-1-oxophthalazin-2(1H)-yl]-2-(4-chlorophenyl)acetamide

The product from Example 198B and 2-(4-chlorophenyl)acetyl chloride were processed using a method similar to that described in Example 4C to afford the title compound. ¹H NMR (500 MHz, DMSO-d₆) δ 11.74 (s, 1H), 8.32 (d, J=7.9, 1H), 8.12 (d, J=8.0, 1H), 8.01 (t, J=7.6, 1H), 7.93 (t, J=7.5, 1H), 7.44-7.37 (m, 4H), 3.70 (s, 2H), 1.43 (s, 9H); MS (DCI⁺) M/Z 419 (M+NH₄)⁺.

Example 199

N-{4-[(4-bromophenyl)sulfonyl]-1-oxophthalazin-2(1H)-yl}-2-(4-chlorophenyl)acetamide The product from 195C was processed using a method similar to that described in Example 68A to afford the title compound. ¹H NMR (400 MHz, DMSO-d₆) δ 11.86 (s, 1H), 8.54 (d, J=8.1, 1H), 8.39 (d, J=7.1, 1H), 8.16-8.09 (m, 1H), 8.03 (dd, J=11.2, 4.1, 1H), 7.96-7.88 (m, 4H), 7.45-7.38 (m, 2H), 7.30 (d, J=8.5, 2H), 3.68 (s, 2H); MS (ESI⁻) M/Z 532 (M−H)⁻.

Example 200

(±)-2-[(exo)-bicyclo[2.2.1]hept-2-yl]-N-{4-[(4-bromophenyl)sulfanyl]-1-oxophthalazin-2(1H)-yl}acetamide The product from Example 195B was processed using a method similar to that described in Example 4C to afford the title compound. ¹H NMR (400 MHz, DMSO-d₆) δ 11.31 (s, 1H), 8.38-8.32 (m, 1H), 8.07-7.98 (m, 2H), 7.98-7.92 (m, 1H), 7.58 (d, 2H), 7.40 (d, 2H), 2.25-2.17 (m, 2H), 2.14-2.05 (m, 1H), 2.02 (s, 1H), 1.89-1.78 (m, 1H), 1.52-1.31 (m, 4H), 1.18-1.05 (m, 4H); MS (DCI⁺) M/Z 501 (M+NH₄)⁺.

Example 201

N-[4-(tert-butylsulfonyl)-1-oxophthalazin-2(1H)-yl]-2-(4-chlorophenyl)acetamide

The product from 198C was processed using a method similar to that described in Example 68A to afford the title compound. ¹H NMR (400 MHz, DMSO-d₆) δ ppm 11.98-12.02 (bs, 1H), 8.70 (d, J=8.2 Hz, 1H), 8.40 (dd, J=7.9, 1.4 Hz, 1H), 8.08-8.12 (m, 1H), 7.98-8.03 (m, 1H), 7.37-7.44 (m, 4H), 3.75 (s, 2H), 1.34 (s, 9H); MS (DCI⁺) M/Z 451 (M+NH₄)⁺.

Example 202

N-{4-[(4-bromophenyl)sulfonyl]-1-oxophthalazin-2(1H)-yl}-2-(3,5-difluorophenyl)acetamide The product from Example 197 was processed using a method similar to that described in Example 68A to afford the title compound. ¹H NMR (400 MHz, DMSO-d₆) δ 11.91 (s, 1H), 8.55 (d, J=8.1, 1H), 8.40 (d, J=6.9, 1H), 8.17-8.08 (m, 1H), 8.07-7.99 (m, 1H), 7.97-7.87 (m, 4H), 7.17 (ddd, J=9.5, 5.9, 2.4, 1H), 7.05 (d, J=6.4, 2H), 3.75 (s, 2H); MS (ESI⁻) M/Z 532 (M−H)⁻.

Example 203

2-(4-chlorophenyl)-N-[1-oxo-4-(pyridin-4-ylsulfonyl)phthalazin-2(1H)-yl]acetamide The product from Example 196 (10 mg, 0.021 mmol) was treated with 10% Pd/C (5 mg) in MeOH (5 mL) under H₂ (1 atm) for 12 hrs. The mixture was filtered, and washed with MeOH, concentrated, and the resulting residue was purified by HPLC (conditions from Example 10C) to afford 1.8 mg of the title compound. ¹H NMR (400 MHz, DMSO-d$_6$) δ 11.97-11.79 (br s, 1H), 8.96 (dd, J=4.5, 1.6, 2H), 8.52 (d, J=8.1, 1H), 8.39 (d, J=7.1, 1H), 8.12 (dd, J=12.0, 4.9, 1H), 8.03 (t, J=7.2, 1H), 7.96 (dd, J=4.5, 1.6, 2H), 7.41 (d, J=8.5, 2H), 7.29 (d, J=8.4, 2H), 3.68 (s, 2H); MS (ESI⁺) M/Z 455 (M+H)⁺.

Example 204

(±)-2-[(exo)-bicyclo[2.2.1]hept-2-yl]-N-{4-[(4-bromophenyl)sulfonyl]-1-oxophthalazin-2(1H)-yl}acetamide The product from Example 200 was processed using a method similar to that described in Example 68A to afford the title compound. ¹H NMR (400 MHz, DMSO-d$_6$) δ 11.48 (s, 1H), 8.55 (d, J=8.1, 1H), 8.40 (dd, J=8.0, 0.9, 1H), 8.17-8.10 (m, 1H), 8.07-8.00 (m, 1H), 7.92 (s, 4H), 2.25-2.16 (m, 2H), 2.08 (dd, J=14.0, 7.8, 1H), 1.95 (s, 1H), 1.83-1.74 (m, 1H), 1.55-1.40 (m, 2H), 1.39-1.27 (m, 2H), 1.17-0.98 (m, 4H); MS (ESI⁻) M/Z 514 (M−H)⁻.

Example 205

2-(3-methoxyphenyl)-N-[1-oxo-4-(phenylsulfonyl) phthalazin-2(1H)-yl]acetamide

The product from Example 68B and 2-(3-methoxyphenyl) acetic acid were processed using a method similar to that described in Example 10C to afford the title compound. ¹H NMR (400 MHz, DMSO-d$_6$) δ 11.85 (s, 1H), 8.56 (d, J=8.1, 1H), 8.38 (dd, J=8.0, 0.9, 1H), 8.15-8.06 (m, 1H), 8.05-7.96 (m, 3H), 7.84-7.76 (m, 1H), 7.72-7.62 (m, 2H), 7.26 (t, J=7.9, 1H), 6.95-6.88 (m, 1H), 6.85 (dd, J=8.2, 2.6, 2H), 3.77 (s, 3H), 3.64 (s, 2H); MS (ESI⁺) M/Z 467 (M+NH$_4$)⁺.

Example 206

2-(4-bromophenyl)-N-[1-oxo-4-(phenylsulfonyl) phthalazin-2(1H)-yl]acetamide

The product from Example 68B and 2-(4-bromophenyl) acetic acid were processed using a method similar to that described in Example 10C to afford the title compound. ¹H NMR (400 MHz, DMSO-d$_6$) δ 11.86 (s, 1H), 8.56 (d, J=8.1, 1H), 8.38 (dd, J=8.0, 0.9, 1H), 8.14-8.08 (m, 1H), 8.01 (ddd, J=7.3, 4.4, 1.2, 3H), 7.80 (ddd, J=7.0, 4.0, 1.2, 1H), 7.68 (dd, J=10.6, 5.0, 2H), 7.58-7.51 (m, 2H), 7.25 (d, J=8.4, 2H), 3.66 (s, 2H); MS (ESI⁺) M/Z 498 (M+H)⁺, 515 (M+NH$_4$)⁺, 556 (M+CH3CN+NH$_4$)⁺.

Example 207

2-(3-methylphenyl)-N-[1-oxo-4-(phenylsulfonyl) phthalazin-2(1H)-yl]acetamide

The product from Example 68B and 2-(3-methylphenyl) acetic acid were processed using a method similar to that described in Example 10C to afford the title compound. ¹H NMR (400 MHz, DMSO-d$_6$) δ ppm 11.83 (s, 1H), 8.54-8.57 (m, 1H), 8.37-8.40 (m, 1H), 8.08-8.13 (m, 1H), 7.98-8.03 (m, 3H), 7.78-7.83 (m, 1H), 7.66-7.70 (m, 2H), 7.23 (t, J=7.5 Hz, 1H), 7.12-7.14 (bs, 1H), 7.07-7.10 (m, 2H), 3.63 (s, 2H), 2.31 (s, 3H); MS (ESI⁺) M/Z 434 (M+H)⁺, 451 (M+NH$_4$)⁺.

Example 208

N-[1-oxo-4-(phenylsulfonyl)phthalazin-2(1H)-yl]-2-[3-(trifluoromethyl)phenyl]acetamide The product from Example 68B and 2-(3-(trifluoromethyl) phenyl)acetic acid were processed using a method similar to that described in Example 10C to afford the title compound. ¹H NMR (400 MHz, DMSO-d$_6$) δ ppm 11.93-11.95 (bs, 1H), 8.55-8.57 (m, 1H), 8.37-8.40 (m, 1H), 8.09-8.13 (m, 1H), 7.98-8.03 (m, 3H), 7.77-7.82 (m, 1H), 7.59-7.71 (m, 6H), 3.83 (s, 2H); MS (ESI⁻) M/Z 486 (M−H)⁻.

Example 209

2-(3-chlorophenyl)-N-[1-oxo-4-(phenylsulfonyl) phthalazin-2(1H)-yl]acetamide

The product from Example 68B and 2-(3-chlorophenyl) acetic acid were processed using a method similar to that described in Example 10C to afford the title compound. ¹H NMR (400 MHz, DMSO-d$_6$) δ ppm 11.87-11.90 (m, 1H), 8.56 (d, J=8.1 Hz, 1H), 8.38 (dd, J=7.9, 1.3 Hz, 1H), 8.09-8.14 (m, 1H), 7.99-8.03 (m, 3H), 7.78-7.83 (m, 1H), 7.66-7.70 (m, 2H), 7.34-7.41 (m, 3H), 7.24-7.27 (m, 1H), 3.71 (s, 2H); MS (APCI⁺) M/Z 454 (M+H)⁺.

Example 210

2-(hexahydro-2,5-methanopentalen-3a(1H)-yl)-N-[4-(morpholin-4-yl)-1-oxophthalazin-2(1H)-yl]acetamide Example 210A 3-noradamantyl diazomethyl ketone A solution of (diazomethyl)trimethylsilane (2.70 mL, 5.40 mmol) in Et$_2$O was added to a solution of 3-noradamantanecarbonyl chloride (0.495 g, 2.68 mmol) in acetonitrile (4 mL) and THF (4 mL), stirred at room temperature overnight, diluted with EtOAc, washed with water and brine, dried (Na$_2$SO$_4$), filtered, and concentrated to give 551 mg of crude title compound as a yellow solid: MS (APCI⁺) M/Z 191 (M+H)⁺.

Example 210B 2-(hexahydro-2,5-methanopentalen-3a(1H)-yl)-N-[4-(morpholin-4-yl)-1-oxophthalazin-2(1H)-yl]acetamide A solution of the product from Example 1B (48.5 mg, 0.197 mmol) and the product from Example 210A (0.0384 g, 0.202 mmol) in 1,2-dichloroethane (0.6 mL) and 1-methyl-2-pyrrolidinone (0.20 mL) was microwaved at 180° C. for 20 minutes, diluted with EtOAc, washed with sat NaHCO3 and brine, dried (Na$_2$SO$_4$), filtered, and chromatographed (12% EtOAc/DCM) to give 31.2 mg of the title compound as a tan solid: ¹H NMR (300 MHz, DMSO-d$_6$) δ 11.11 (s, 1H), 8.34-8.27 (m, 1H), 8.06-7.93 (m, 2H), 7.93-7.84 (m, 1H), 3.85-

3.78 (m, 4H), 3.12-3.04 (m, 4H), 2.44 (s, 2H), 2.33 (t, J=6.6, 1H), 2.17 (s, 2H), 1.83-1.46 (m, 10H); MS (ESI$^+$) M/Z 409 (M+H)$^+$.

Example 211

2-(hexahydro-2,5-methanopentalen-3a(1H)-yl)-N-{1-oxo-4-[6-(trifluoromethyl)pyridin-3-yl]phthalazin-2(1H)-yl}acetamide The products from Example 210A and Example 43A were processed using a method similar to that described in Example 210B to afford the title compound. $^1$H NMR (300 MHz, DMSO-d$_6$) δ ppm 11.42 (s, 1H), 9.00 (d, J=2.4 Hz, 1H), 8.35-8.51 (m, 2H), 8.13 (dd, J=8.1, 0.9 Hz, 1H), 7.96-8.01 (m, 2H), 7.75-7.80 (m, 1H), 2.26-2.35 (m, 1H), 2.16-2.18 (m, 2H), 1.47-1.79 (m, 10H); MS (ESI$^-$) M/Z 467 (M−H)$^-$.

Example 212

N-[4-(benzylsulfanyl)-1-oxophthalazin-2(1H)-yl]-2-(3,5-difluorophenyl)acetamide

Example 212A 4-(benzylthio)phthalazin-1(2H)-one

A mixture of 4-chlorophthalazin-1(2H)-one (500 mg, 2.77 mmol), phenylmethanethiol (412 mg, 3.32 mmol) and sodium hydride (144 mg, 3.6 mmol) in DMF (30 mL) was stirred at 125 C for 2 hours. The reaction mixture was quenched with water, and extracted with EtOAc (2×). The combined organic layer was washed with water, and concentrated to give 456 mg (61%) of title compound. MS (APCI$^+$) M/Z 269 (M+H)$^+$.

Example 212B 2-amino-4-(benzylthio)phthalazin-1(2H)-one

The product from Example 212A was processed using a method similar to that described in Example 1B to afford the title compound. MS (APCI$^+$) M/Z 284 (M+H)$^+$.

Example 212C

N-[4-(benzylsulfanyl)-1-oxophthalazin-2(1H)-yl]-2-(3,5-difluorophenyl)acetamide

The product from Example 212B and (3,5-difluorophenyl)acetic acid were processed using a method similar to that described in Example 10C to afford the title compound. $^1$H NMR (400 MHz, DMSO-d$_6$) δ ppm 11.75 (s, 1H), 8.32-8.35 (m, 1H), 7.91-8.02 (m, 3H), 7.39-7.41 (m, 2H), 7.24-7.27 (m, 3H), 7.14-7.18 (m, 3H), 4.34 (s, 2H), 3.79 (s, 2H); MS (DCI$^+$) M/Z 455 (M+NH$_4$)$^+$.

Example 213

N-[4-(benzylsulfanyl)-1-oxophthalazin-2(1H)-yl]-2-(4-chlorophenyl)acetamide

The product from Example 212B and (4-chlorophenyl)acetyl chloride were processed using a method similar to that described in Example 4C to afford the title compound. $^1$H NMR (400 MHz, DMSO-d$_6$) δ ppm 11.69 (s, 1H), 8.32 (dd, J=8.1, 1.3 Hz, 1H), 7.90-8.01 (m, 3H), 7.37-7.43 (m, 6H), 7.23-7.26 (m, 3H), 4.32 (s, 2H), 3.72 (s, 2H); MS (DCI$^+$) M/Z 453 (M+NH$_4$)$^+$.

Example 214

(±)-N-[4-(benzylsulfanyl)-1-oxophthalazin-2(1H)-yl]-2-[(exo)-bicyclo[2.2.1]hept-2-yl]acetamide The product from Example 212B was processed using a method similar to that described in Example 4C to afford the title compound. $^1$H NMR (400 MHz, DMSO-d$_6$) δ 11.33 (s, 1H), 8.36-8.29 (m, 1H), 8.03-7.88 (m, 3H), 7.45 (dd, J=7.9, 1.5, 2H), 7.34-7.22 (m, 3H), 4.35 (s, 2H), 2.35-2.12 (m, 4H), 1.98-1.84 (m, 1H), 1.53-1.37 (m, 4H), 1.22-1.08 (m, 4H); MS (DCI$^+$) M/Z 437 (M+NH$_4$)$^+$.

Example 215

N-[4-(benzylsulfonyl)-1-oxophthalazin-2(1H)-yl]-2-(3,5-difluorophenyl)acetamide

The product from 212C was processed using a method similar to that described in Example 68A to afford the title compound. $^1$H NMR (500 MHz, DMSO-d$_6$) δ ppm 11.99-12.09 (brs, 1H), 8.37-8.40 (m, 2H), 7.97-8.04 (m, 2H), 7.24-7.36 (m, 5H), 7.15-7.19 (m, 3H), 4.95 (s, 2H), 3.83 (s, 2H); MS (DCI$^+$) M/Z 487 (M+NH$_4$)$^+$.

Example 216

N-[4-(benzylsulfonyl)-1-oxophthalazin-2(1H)-yl]-2-(4-chlorophenyl)acetamide

The product from Example 213 was processed using a method similar to that described in Example 68A to afford the title compound. $^1$H NMR (500 MHz, DMSO-d$_6$) δ ppm 11.98 (s, 1H), 8.37-8.39 (m, 2H), 7.97-8.04 (m, 2H), 7.43 (s, 4H), 7.32-7.35 (m, 2H), 7.24-7.30 (m, 3H), 4.94 (s, 2H), 3.77 (s, 2H); MS (DCI$^+$) M/Z 485 (M+NH$_4$)$^+$.

Example 217

(±)-N-[4-(benzylsulfonyl)-1-oxophthalazin-2(1H)-yl]-2-[(exo)-bicyclo[2.2.1]hept-2-yl]acetamide The product from Example 214 was processed using a method similar to that described in Example 68A to afford the title compound. $^1$H NMR (500 MHz, DMSO-d$_6$) δ ppm 11.64 (s, 1H), 8.37-8.40 (m, 2H), 7.97-8.04 (m, 2H), 7.29-7.38 (m, 5H), 4.95-4.96 (bs, 2H), 2.33 (dd, J=14.3, 8.3 Hz, 1H), 2.19-2.24 (m, 2H), 2.13-2.15 (m, 1H), 1.89-1.96 (m, 1H), 1.39-1.54 (m, 4H), 1.11-1.21 (m, 4H); MS (DCI$^+$) M/Z 469 (M+NH$_4$)$^+$.

Example 218

2-(hexahydro-2,5-methanopentalen-3a(1H)-yl)-N-[1-oxo-4-(phenylsulfonyl)phthalazin-2(1H)-yl]acetamide The products from Example 210A and Example 68B were processed using a method similar to that described in Example 210B to afford the title compound. $^1$H NMR (300 MHz, DMSO-d$_6$) δ ppm 11.48 (s, 1H), 8.57-8.61 (m, 1H), 8.40 (ddd, J=7.9, 1.5, 0.6 Hz, 1H), 7.98-8.16 (m, 4H), 7.78-

7.84 (m, 1H), 7.66-7.72 (m, 2H), 2.42 (s, 2H), 2.18-2.25 (m, 1H), 2.12-2.17 (brs, 2H), 1.45-1.70 (m, 10H); MS (ESI⁻) M/Z 462 (M−H)⁻.

Example 219

(±)-2-[(exo)-bicyclo[2.2.1]hept-2-yl]-N-{4-[(4-cyanophenyl)sulfonyl]-1-oxophthalazin-2(1H)-yl}acetamide A mixture of the product of Example 204 (0.0111 g, 0.021 mmol), dicyanozinc (1.9 mg, 0.016 mmol), and Pd(PPh$_3$)$_4$ (1.2 mg, 1.0 μmol) in DMF (0.10 mL) was stirred at 90° C. overnight, diluted with EtOAc, washed with sat NaHCO$_3$ and brine, dried (Na$_2$SO), and concentrated to give a mix of product and starting material. This crude material was re-subjected with similar amounts of the above reagents in DMF (0.5 mL), microwaved at 180° C. for 20 minutes, re-worked up, and chromatographed (5% EtOAc/DCM) and triturated (hexanes/Et$_2$O) to give 6.1 mg of the title compound. $^1$H NMR (300 MHz, DMSO-d$_6$) δ 11.49 (s, 1H), 8.54 (d, J=8.0, 1H), 8.40 (d, J=8.0, 1H), 8.19 (s, 4H), 8.14 (t, J=7.1, 1H), 8.03 (t, J=7.1, 1H), 2.24-2.03 (m, 3H), 1.91-1.95 (m, 1H), 1.72-1.85 (m, 1H), 1.43-1.50 (m, 2H), 1.25-1.35 (m, 2H), 0.95-1.15 (m, 4H); MS (ESI⁻) M/Z 461 (M−H)⁻.

Example 220

(±)-2-[(exo)-bicyclo[2.2.1]hept-2-yl]-N-[4-(2-ethylmorpholin-4-yl)-1-oxophthalazin-2(1H)-yl]acetamide Example 220A 4-(2-ethylmorpholino)phthalazin-1(2H)-one 4-chlorophthalazin-1(2H)-one and 2-ethylmorpholine were processed using a method similar to that described in Example 1A to afford the title compound. MS (APCI⁺) M/Z 260 (M+H)⁺.

Example 220B 2-amino-4-(2-ethylmorpholino)phthalazin-1(2H)-one

The product from 220A was processed using a method similar to that described in Example 1B to afford the title compound. MS (APCI⁺) M/Z 275 (M+H)⁺.

Example 220C (±)-2-[(exo)-bicyclo[2.2.1]hept-2-yl]-N-[4-(2-ethylmorpholin-4-yl)-1-oxophthalazin-2(1H)-yl]acetamide The product from Example 220B was processed using a method similar to that described in Example 4C to afford the title compound. $^1$H NMR (400 MHz, DMSO-d$_6$) δ 11.10 (s, 1H), 8.30 (dd, J=7.9, 0.6, 1H), 8.05-7.93 (m, 2H), 7.93-7.85 (m, 1H), 3.92 (d, J=10.0, 1H), 3.79 (dd, J=11.4, 9.2, 1H), 3.61 (dt, J=6.3, 5.3, 1H), 3.25-3.35 (buried m, 2H), 2.81 (td, J=12.4, 3.1, 1H), 2.54 (dd, J=11.7, 9.5, 1H), 2.27-2.17 (m, 2H), 2.108-2.15 (m, 2H), 1.82-1.91 (m, 1H), 1.54-1.34 (m, 6H), 1.06-1.20 (m, 4H), 0.92 (t, J=7.5, 3H); MS (DCI⁺) M/Z 411 (M+H)⁺.

Example 221

2-(4-chlorophenyl)-N-[4-(2-ethylmorpholin-4-yl)-1-oxophthalazin-2(1H)-yl]acetamide The product from Example 220B and (4-chlorophenyl)acetyl chloride were processed using a method similar to that described in Example 4C to afford the title compound. $^1$H NMR (400 MHz, DMSO-d$_6$) δ ppm 11.48 (s, 1H), 8.29 (dd, J=7.8, 1.2 Hz, 1H), 7.96-8.03 (m, 2H), 7.90 (ddd, J=7.9, 6.7, 1.4 Hz, 1H), 7.40-7.41 (m, 4H), 3.91 (dd, J=11.1, 2.6 Hz, 1H), 3.79 (td, J=11.4, 2.3 Hz, 1H), 3.67 (s, 2H), 3.56-3.65 (m, 1H), 3.26-3.32 (m, 2H), 2.76-2.84 (m, 1H), 2.51-2.57 (m, 1H), 1.48 (p, J=7.1 Hz, 2H), 0.92 (t, J=7.4 Hz, 3H); MS (DCI⁺) M/Z 427 (M+H)⁺, 444 (M+NH$_4$)⁺.

Example 222

2-(4-chlorophenyl)-N-{4-[(4-cyanophenyl)sulfonyl]-1-oxophthalazin-2(1H)-yl}acetamide The product from Example 199 was processed using a method similar to that described in Example 219 to afford the title compound. $^1$H NMR (400 MHz, DMSO-d$_6$) δ ppm 11.89 (s, 1H), 8.52-8.55 (m, 1H), 8.39 (d, J=7.2 Hz, 1H), 8.14-8.22 (m, 4H), 8.09-8.16 (m, 1H), 8.03 (t, J=7.6 Hz, 1H), 7.40-7.43 (m, 2H), 7.29-7.32 (m, 2H), 3.67-3.68 (bs, 2H); MS (DCI⁺) M/Z 496 (M+NH$_4$)⁺.

Example 223

N-{4-[(4-cyanophenyl)sulfonyl]-1-oxophthalazin-2(1H)-yl}-2-(3,5-difluorophenyl)acetamide The product from Example 202 was processed using a method similar to that described in Example 219 to afford the title compound. $^1$H NMR (400 MHz, DMSO-d$_6$) δ ppm 11.94 (s, 1H), 8.54 (d, J=8.1 Hz, 1H), 8.39-8.42 (m, 1H), 8.18-8.21 (m, 2H), 8.14-8.18 (m, 2H), 8.10-8.16 (m, 1H), 8.01-8.06 (m, 1H), 7.16 (tt, J=9.5, 2.4 Hz, 1H), 7.02-7.05 (m, 2H), 3.74 (s, 2H); MS (DCI⁺) M/Z 498 (M+NH$_4$)⁺.

Example 224

N-{4-[(4-cyanophenyl)sulfonyl]-1-oxophthalazin-2(1H)-yl}-2-(4-fluorophenyl)acetamide Example 224A 2-amino-4-[(4-cyanophenyl)sulfonyl]phthalazin-1(2H)-one The product from Example 195A was processed using methods similar to those described in Examples 68A, 219, and Example 1B to afford the title compound. MS (APCI⁺) M/Z 327 (M+H)⁺.

Example 224B

N-{4-[(4-cyanophenyl)sulfonyl]-1-oxophthalazin-2(1H)-yl}-2-(4-fluorophenyl)acetamide The product from Example 224A and 2-(4-fluorophenyl)acetyl chloride were processed using a method similar to that described in Example 4C to afford the title compound. $^1$H NMR (300 MHz, DMSO-d$_6$) δ ppm 11.86-11.86 (m, 1H), 8.53 (d, J=8.1 Hz, 1H), 8.31-8.47 (m, 1H), 8.14-8.20 (m, 4H), 8.09-8.16 (m, 1H), 7.99-8.07 (m, 1H), 7.28-7.34 (m, 2H), 7.14-7.20 (m, 2H), 3.66 (s, 2H); MS (ESI⁻) M/Z 461 (M–H)⁻.

Example 225

N-{4-[(4-cyanophenyl)sulfonyl]-1-oxophthalazin-2(1H)-yl}-3-methyl-3-phenylbutanamide A solution of 3-methyl-3-phenyl butanoic acid (37.7 mg, 0.212 mmol) and oxalyl chloride (0.024 mL, 0.275 mmol) in dichloromethane (0.80 mL) with a drop of DMF was stirred at room temperature for 90 minutes, concentrated to dryness, and re-dissolved in DCM (0.80 mL). To this solution was added the product from Example 224A (60.6 mg, 0.186 mmol) and pyridine (0.020 mL, 0.248 mmol), and the mixture was stirred at room temperature for 2 hours, concentrated, and chromatographed (2% acetone/DCM) to afford 46.4 mg of the title compound. ¹H NMR (300 MHz, DMSO-d₆) δ ppm 11.55 (s, 1H), 8.55 (d, J=8.1 Hz, 1H), 8.41 (d, J=7.4 Hz, 1H), 8.16-8.23 (m, 4H), 8.11-8.17 (m, 1H), 8.04 (t, J=7.6 Hz, 1H), 7.40 (d, J=1.7 Hz, 1H), 7.37-7.38 (m, 1H), 7.28-7.34 (m, 2H), 7.19 (t, J=7.2 Hz, 1H), 2.50-2.56 (m, 2H), 1.29 (s, 6H); MS (ESI⁺) M/Z 487 (M+H)⁺, 504 (M+NH₄)⁺.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:

1. A compound of formula (I-a)

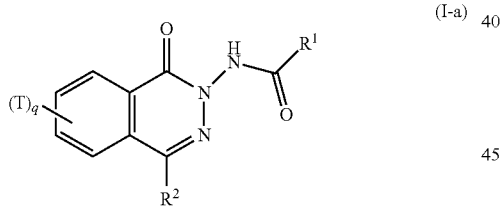

(I-a)

or a pharmaceutically acceptable salt thereof, wherein $R^1$ is —$(CR^{1a}R^{1b})_n$-$G^{1a}$ $R^{1a}$, at each occurrence, is independently hydrogen, alkyl, halogen, or haloalkyl;

$R^{1b}$, at each occurrence, is independently hydrogen, alkyl, halogen, haloalkyl, $OR^y$, $N(R^y)_2$, $S(R^y)$, $C(O)OR^y$, $C(O)R^y$, $C(O)N(R^y)_2$, —$(C_1$-$C_6$ alkylenyl)$OR^y$, —$(C_1$-$C_6$ alkylenyl)$N(R^y)_2$, —$(C_1$-$C_6$ alkylenyl)$S(R^y)$, —$(C_1$-$C_6$ alkylenyl)$C(O)OR^y$, —$(C_1$-$C_6$ alkylenyl)$C(O)R^y$, or —$(C_1$-$C_6$ alkylenyl)$C(O)N(R^y)_2$;

$R^y$, at each occurrence, is independently hydrogen, alkyl, or haloalkyl;

$G^{1a}$, at each occurrence, is independently aryl, heteroaryl, heterocycle, cycloalkenyl, or cycloalkyl; each of which is independently unsubstituted or substituted with 1, 2, 3, 4, or 5 substituents as represented by $R^{101}$;

$R^2$ is —$OR^{2ac}$, —$SR^{2bc}$, —$S(O)R^{2bc}$, —$S(O)_2R^{2bc}$, —$S(O)_2N(R^{2d})(R^{2e})$, —$C(O)R^{2cc}$, —$C(O)OR^{2cc}$, —$C(O)N(R^{2d})(R^{2e})$, $N(R^{2d})(R^{2e})$, —$C(R^{2d})$=$NOR^{2dc}$, $G^{2a}$, —$(CR^{2a}R^{2b})_p$-$G^{2a}$, —$(CR^{2a}R^{2b})_p$—$OR^{2ac}$, —$(CR^{2a}R^{2b})_p$—$SR^{2bc}$, —$(CR^{2a}R^{2b})_p$—$S(O)R^{2bc}$, —$(CR^{2a}R^{2b})_p$—$C(O)R^{2cc}$, —$(CR^{2a}R^{2b})_p$—$C(O)OR^{2cc}$, —$(CR^{2a}R^{2b})_p$—$C(O)N(R^{2d})(R^{2e})$, —$(CR^{2a}R^{2b})_p$—$N(R^{2d})(R^{2e})$, or —$(CR^{2a}R^{2b})_p$—$S(O)_2N(R^{2d})(R^{2e})$, —$(CR^{2a}R^{2b})_p$—$S(O)_2R^{2bc}$;

$R^{2a}$ and $R^{2b}$, at each occurrence, are each independently hydrogen, alkyl, haloalkyl, —$C(O)OR^{2aa}$, $G^{2b}$, or —$(C_1$-$C_6$ alkylenyl)-$G^{2b}$;

$R^{2aa}$, at each occurrence, is independently hydrogen, alkyl, haloalkyl, $G^{2b}$, or —$(C_1$-$C_6$ alkylenyl)-$G^{2b}$;

$R^{2ac}$, $R^{2bc}$, $R^{2cc}$, $R^{2dc}$, and $R^{2d}$, at each occurrence, are each independently hydrogen, alkyl, haloalkyl, $G^{2c}$, or —$(C_1$-$C_6$ alkylenyl)-$G^{2c}$;

$R^{2e}$, at each occurrence, is independently hydrogen, alkyl, haloalkyl, -alkylenyl-alkoxy, -alkylenyl-haloalkoxy, —$C(O)R^{2f}$, —$C(O)OR^{2f}$, $S(O)_2R^{2f}$, —$C(O)NR^{2f}R^{2g}$, —$C(O)$—$(C_1$-$C_6$ alkylenyl)$NR^{2fg}R^{2g}$, or -alkylenyl-CN;

$R^{2f}$, at each occurrence, is independently hydrogen, alkyl, haloalkyl, $G^{2d}$, or —$(C_1$-$C_6$ alkylenyl)-$G^{2d}$;

$R^{2fg}$, at each occurrence, is independently hydrogen, alkyl, haloalkyl, —$C(O)OR^{2h}$, $G^{2d}$, or —$(C_1$-$C_6$ alkylenyl)-$G^{2d}$;

$R^{2g}$ and $R^{2h}$, at each occurrence, are each independently hydrogen, alkyl, or haloalkyl, $G^{2a}$, at each occurrence, is independently heteroaryl or heterocycle; each of which is optionally substituted with 1, 2, 3, 4, or 5 $R^{102}$ groups;

$G^{2b}$, $G^{2c}$, and $G^{2d}$, at each occurrence, are each independently aryl, heteroaryl, heterocycle, cycloalkyl, or cycloalkenyl; each of which is optionally substituted with 1, 2, 3, 4, or 5 $R^{103}$ groups;

T, $R^{101}$, $R^{102}$, and $R^{103}$, at each occurrence, are each independently $G^a$, alkyl, alkenyl, alkynyl, halogen, haloalkyl, oxo, —CN, —NO₂, —$OR^a$, —$OC(O)R^a$, —$OC(O)NR^aR^b$, —$NR^aR^b$, —$SR^a$, —$S(O)R^a$, —$S(O)_2R^a$, —$S(O)_2NR^aR^b$, —$C(O)R^a$, —$C(O)OR^a$, —$C(O)NR^aR^b$, —$N(R^a)C(O)OR^b$, —$N(R^a)C(O)NR^aR^b$, —$N(R^a)S(O)_2NR^aR^b$, —$(CR^{za}R^{zb})_m$—CN, —$(CR^{za}R^{zb})_m$—NO₂, —$(CR^{za}R^{zb})_m$—$OR^a$, —$(CR^{za}R^{zb})_m$—$OC(O)R^a$, —$(CR^{za}R^{zb})_m$—$OC(O)NR^aR^b$, —$(CR^{za}R^{zb})_m$—$SR^a$, —$(CR^{za}R^{zb})_m$—$S(O)R^a$, —$(CR^{za}R^{zb})_m$—$S(O)_2R^a$, —$(CR^{za}R^{zb})_m$—$S(O)_2NR^aR^b$, —$(CR^{za}R^{zb})_m$—$C(O)R^a$, —$(CR^{za}R^{zb})_m$—$C(O)OR^a$, —$(CR^{za}R^{zb})_m$—$C(O)NR^aR^b$, —$(CR^{za}R^{zb})_m$—$NR^aR^b$, —$(CR^{za}R^{zb})_m$—$N(R^a)C(O)OR^b$, —$(CR^{za}R^{zb})_m$—$N(R^a)C(O)NR^aR^b$, —$(CR^{za}R^{zb})_m$—$N(R^a)S(O)_2NR^aR^b$, or —$(CR^{za}R^{zb})_m$-$G^a$;

$R^a$ and $R^b$, at each occurrence, are each independently hydrogen, alkyl, haloalkyl, $G^a$, or —$(C_1$-$C_6$ alkylenyl)-$G^a$;

$G^a$, at each occurrence, is independently aryl, heteroaryl, heterocycle, cycloalkyl or cycloalkenyl, each of which is independently unsubstituted or substituted with 1, 2, 3, 4, or 5 substituents independently selected from the group consisting of alkyl, alkenyl, alkynyl, halogen, haloalkyl, oxo, —CN, —NO₂, —$OR^{a'}$, —$OC(O)R^{a'}$, —$OC(O)NR^{a'}R^{b'}$, —$NR^{a'}R^{b'}$, —$SR^{a'}$, —$S(O)R^{a'}$, —$S(O)_2R^{a'}$, —$S(O)_2NR^{a'}R^{b'}$, —$C(O)R^{a'}$, —$C(O)OR^{a'}$, —$C(O)NR^{a'}R^{b'}$, —$N(R^{a'})C(O)OR^{b'}$, —$N(R^{a'})C(O)NR^{a'}R^{b'}$, —$N(R^{a'})S(O)_2NR^{a'}R^{b'}$, —$(C_1$-$C_6$ alkylenyl)-CN, —$(C_1$-$C_6$ alkylenyl)-NO₂, —$(C_1$-$C_6$ alkylenyl)-$OR^{a'}$, —$(C_1$-$C_6$ alkylenyl)-$OC(O)R^{a'}$, —$(C_1$-$C_6$ alkylenyl)-$OC(O)NR^{a'}R^{b'}$, —$(C_1$-$C_6$ alkylenyl)-$SR^{a'}$, —$(C_1$-$C_6$ alkylenyl)-$S(O)R^{a'}$, —$(C_1$-$C_6$ alkylenyl)-$S(O)_2R^{a'}$, —$(C_1$-$C_6$ alkylenyl)-$S(O)_2NR^{a'}R^{b'}$, —$(C_1$-$C_6$ alkylenyl)-C(O)R$^{a'}$, —(C$_1$-C$_6$ alkylenyl)-C(O)OR$^{a'}$, —(C$_1$-C$_6$ alkylenyl)-C(O)NR$^{a'}$R$^{b'}$, —(C$_1$-C$_6$ alkylenyl)-NR$^{a'}$R$^{b'}$, —(C$_1$-C$_6$ alkylenyl)-N(R$^{a'}$)C(O)OR$^{b'}$, —(C$_1$-C$_6$ alkylenyl)-N(R$^{a'}$)C(O)NR$^{a'}$R$^{b'}$, and —(C$_1$-C$_6$ alkylenyl)-N(R$^{a'}$)S(O)$_2$NR$^{a'}$R$^{b'}$;

R$^{za}$, R$^{zb}$, R$^{a'}$, and R$^{b'}$, at each occurrence, are each independently hydrogen, alkyl, halogen, or haloalkyl;

m, n, and p, at each occurrence, are each independently 1, 2, 3, or 4; and q is 0, 1, 2, 3, or 4;

wherein heteroaryl at each occurrence is independently monocyclic heteroaryl or bicyclic heteroaryl; and wherein heterocycle at each occurrence is independently monocyclic heterocycle, bicyclic heterocycle, or spirocyclic heterocycle.

2. The compound according to claim 1 or a pharmaceutically acceptable salt thereof, wherein R$^2$ is —OR$^{2ac}$, —SR$^{2bc}$, —S(O)R$^{2bc}$, —S(O)$_2$R$^{2bc}$, —C(O)R$^{2cc}$, —C(O)OR$^{2cc}$, —C(O)N(R$^{2d}$)(R$^{2e}$), N(R$^{2d}$)(R$^{2e}$), —C(R$^{2d}$)=NOR$^{2dc}$, G$^{2a}$, —(CR$^{2a}$R$^{2b}$)$_p$-G$^{2a}$, —(CR$^{2a}$R$^{2b}$)$_p$—OR$^{2ac}$, —(CR$^{2a}$R$^{2b}$)$_p$—C(O)OR$^{2cc}$, —(CR$^{2a}$R$^{2b}$)$_p$—C(O)N(R$^{2d}$)(R$^{2e}$), or —(CR$^{2a}$R$^{2b}$)$_p$—N(R$^{2d}$)(R$^{2e}$).

3. The compound according to claim 1 or a pharmaceutically acceptable salt thereof, wherein R$^2$ is —S(O)$_2$R$^{2bc}$.

4. The compound according to claim 1 or a pharmaceutically acceptable salt thereof, wherein R$^2$ is G$^{2a}$ or —(CR$^{2a}$R$^{2b}$)$_p$-G$^{2a}$.

5. The compound according to claim 1 or a pharmaceutically acceptable salt thereof, wherein G$^{1a}$ is aryl, cycloalkyl, cycloalkenyl, or heterocycle, each of which is optionally substituted as set forth in claim 1.

6. The compound according to claim 1 or a pharmaceutically acceptable salt thereof, wherein G$^{1a}$ is aryl or cycloalkyl, each of which is optionally substituted as set forth in claim 1.

7. The compound according to claim 1 or a pharmaceutically acceptable salt, solvate, or salt of a solvate thereof, wherein G$^{1a}$ is optionally substituted aryl.

8. The compound according to claim 6 or a pharmaceutically acceptable salt thereof, wherein R$^2$ is —OR$^{2ac}$, —SR$^{2bc}$, —S(O)R$^{2bc}$, —S(O)$_2$R$^{2bc}$, —C(O)R$^{2cc}$, —C(O)OR$^{2cc}$, —C(O)N(R$^{2d}$)(R$^{2e}$), N(R$^{2d}$)(R$^{2e}$), —C(R$^{2d}$)=NOR$^{2dc}$, G$^{2a}$, —(CR$^{2a}$R$^{2b}$)$_p$-G$^{2a}$, —(CR$^{2a}$R$^{2b}$)$_p$—OR$^{2ac}$, —(CR$^{2a}$R$^{2b}$)$_p$—C(O)OR$^{2cc}$, —(CR$^{2a}$R$^{2b}$)$_p$—C(O)N(R$^{2d}$)(R$^{2e}$), or —(CR$^{2a}$R$^{2b}$)$_p$—N(R$^{2d}$)(R$^{2e}$).

9. The compound according to claim 6 or a pharmaceutically acceptable salt thereof, wherein R$^2$ is —SR$^{2bc}$, —S(O)R$^{2bc}$, or S(O)$_2$R$^{2bc}$.

10. The compound according to claim 6 or a pharmaceutically acceptable salt thereof, wherein R$^2$ is —S(O)$_2$R$^{2bc}$.

11. The compound according to claim 10 or a pharmaceutically acceptable salt thereof, wherein G$^{1a}$ is optionally substituted phenyl or optionally substituted naphthyl.

12. The compound according to claim 6 or a pharmaceutically acceptable salt thereof, wherein R$^2$ is G$^{2a}$ or —(CR$^{2a}$R$^{2b}$)$_p$-G$^{2a}$.

13. The compound according to claim 6 or a pharmaceutically acceptable salt thereof, wherein R$^2$ is G$^{2a}$.

14. The compound according to claim 6 or a pharmaceutically acceptable salt thereof, wherein R$^2$ is G$^{2a}$ and G$^{2a}$ is optionally substituted heterocycle.

15. The compound according to claim 14 or a pharmaceutically acceptable salt thereof, wherein G$^{1a}$ is optionally substituted phenyl or optionally substituted naphthyl.

16. The compound according to claim 6 or a pharmaceutically acceptable salt thereof, wherein R$^2$ is G$^{2a}$ and G$^{2a}$ is optionally substituted heteroaryl.

17. The compound according to claim 16 or a pharmaceutically acceptable salt thereof, wherein G$^{1a}$ is optionally substituted phenyl or optionally substituted naphthyl.

18. The compound according to claim 6 or a pharmaceutically acceptable salt thereof, wherein R$^2$ is —C(O)R$^{2cc}$ or —(CR$^{2a}$R$^{2b}$)$_p$—C(O)R$^{2cc}$.

19. The compound according to claim 6 or a pharmaceutically acceptable salt thereof, wherein R$^2$ is N(R$^{2d}$)(R$^{2e}$) or —(CR$^{2a}$R$^{2b}$)$_p$—N(R$^{2d}$)(R$^{2e}$).

20. The compound of formula (I) according to claim 1 or a pharmaceutically acceptable salt thereof, wherein the compound is selected from the group consisting of 2-(3,5-difluorophenyl)-N-[4-(morpholin-4-yl)-1-oxophthalazin-2(1H)-yl]acetamide;

2-(4-chlorophenyl)-N-[4-(morpholin-4-yl)-1-oxophthalazin-2(1H)-yl]acetamide;

(±)-2-[(exo)-bicyclo[2.2.1]hept-2-yl]-N-[4-(morpholin-4-yl)-1-oxophthalazin-2(1H)-yl]acetamide;

(±)-2-[(exo)-bicyclo[2.2.1]hept-2-yl]-N-[4-(6-chloropyridin-3-yl)-1-oxophthalazin-2(1H)-yl]acetamide;

2-(4-chlorophenyl)-N-[4-(6-chloropyridin-3-yl)-1-oxophthalazin-2(1H)-yl]acetamide;

(±)-2-[(exo)-bicyclo[2.2.1]hept-2-yl]-N-[4-(3,6-dihydro-2H-pyran-4-yl)-1-oxophthalazin-2(1H)-yl]acetamide;

2-(3,5-difluorophenyl)-N-[4-(3,6-dihydro-2H-pyran-4-yl)-1-oxophthalazin-2(1H)-yl]acetamide;

(±)-2-[(exo)-bicyclo[2.2.1]hept-2-yl]-N-[1-oxo-4-(pyridin-3-yl)phthalazin-2(1H)-yl]acetamide;

2-(4-chlorophenyl)-N-[1-oxo-4-(pyridin-3-yl)phthalazin-2(1H)-yl]acetamide;

2-(3,5-difluorophenyl)-N-[1-oxo-4-(thiophen-2-yl)phthalazin-2(1H)-yl]acetamide;

2-(4-chlorophenyl)-N-[1-oxo-4-(thiophen-2-yl)phthalazin-2(1H)-yl]acetamide;

(±)-2-[(exo)-bicyclo[2.2.1]hept-2-yl]-N-[1-oxo-4-(thiophen-2-yl)phthalazin-2(1H)-yl]acetamide;

2-[(1S,2S,4S)-bicyclo[2.2.1]hept-5-en-2-yl]-N-[1-oxo-4-(thiophen-2-yl)phthalazin-2(1H)-yl]acetamide;

2-(3,5-difluorophenyl)-N-[4-(3-methylthiophen-2-yl)-1-oxophthalazin-2(1H)-yl]acetamide;

2-(4-chlorophenyl)-N-[4-(3-methylthiophen-2-yl)-1-oxophthalazin-2(1H)-yl]acetamide;

(±)-2-[(exo)-bicyclo[2.2.1]hept-2-yl]-N-[4-(3-methylthiophen-2-yl)-1-oxophthalazin-2(1H)-yl]acetamide;

2-[(1S,2S,4S)-bicyclo[2.2.1]hept-5-en-2-yl]-N-[4-(3-methylthiophen-2-yl)-1-oxophthalazin-2(1H)-yl]acetamide;

2-(3,5-difluorophenyl)-N-[1-oxo-4-(pyridin-2-yl)phthalazin-2(1H)-yl]acetamide;

(±)-2-[(exo)-bicyclo[2.2.1]hept-2-yl]-N-[1-oxo-4-(pyridin-2-yl)phthalazin-2(1H)-yl]acetamide;

2-(3,5-difluorophenyl)-N-[1-oxo-4-(pyrrolidin-1-yl)phthalazin-2(1H)-yl]acetamide;

2-(4-chlorophenyl)-N-[1-oxo-4-(pyrrolidin-1-yl)phthalazin-2(1H)-yl]acetamide;

2-(3,5-difluorophenyl)-N-[1-oxo-4-(piperidin-1-yl)phthalazin-2(1H)-yl]acetamide;

(±)-2-[(exo)-bicyclo[2.2.1]hept-2-yl]-N-[1-oxo-4-(pyrrolidin-1-yl)phthalazin-2(1H)-yl]acetamide;

2-(4-chlorophenyl)-N-[1-oxo-4-(piperidin-1-yl)phthalazin-2(1H)-yl]acetamide;

(±)-2-[(exo)-bicyclo[2.2.1]hept-2-yl]-N-[1-oxo-4-(piperidin-1-yl)phthalazin-2(1H)-yl]acetamide;

(±)-2-[(exo)-bicyclo[2.2.1]hept-2-yl]-N-[4-(6-methoxypyridin-3-yl)-1-oxophthalazin-2(1H)-yl]acetamide;
N-[4-(6-chloropyridin-3-yl)-1-oxophthalazin-2(1H)-yl]-3-methyl-3-phenylbutanamide;
(±)-2-[(exo)-bicyclo[2.2.1]hept-2-yl]-N-[1-oxo-4-(tetrahydro-2H-pyran-4-yl)phthalazin-2(1H)-yl]acetamide;
(±)-2-[(exo)-bicyclo[2.2.1]hept-2-yl]-N-[4-(2-chloropyridin-4-yl)-1-oxophthalazin-2(1H)-yl]acetamide;
(±)-2-[(exo)-bicyclo[2.2.1]hept-2-yl]-N-{4-[(6-chloropyridin-3-yl)methyl]-1-oxophthalazin-2(1H)-yl}acetamide;
N-{4-[(6-chloropyridin-3-yl)methyl]-1-oxophthalazin-2(1H)-yl}-2-(3,5-difluorophenyl)acetamide;
2-(4-chlorophenyl)-N-{4-[(6-chloropyridin-3-yl)methyl]-1-oxophthalazin-2(1H)-yl}acetamide;
3-methyl-N-[4-(morpholin-4-yl)-1-oxophthalazin-2(1H)-yl]-3-phenylbutanamide;
(±)-N-[4-(benzylamino)-1-oxophthalazin-2(1H)-yl]-2-[(exo)-bicyclo[2.2.1]hept-2-yl]acetamide;
(±)-2-[(exo)-bicyclo[2.2.1]hept-2-yl]-N-{4-[(3-chlorophenyl)amino]-1-oxophthalazin-2(1H)-yl}acetamide;
N-{4-[benzyl(methyl)amino]-1-oxophthalazin-2(1H)-yl}-2-(4-chlorophenyl)acetamide;
(±)-N-{4-[benzyl(methyl)amino]-1-oxophthalazin-2(1H)-yl}-2-[(exo)-bicyclo[2.2.1]hept-2-yl]acetamide;
2-(3,5-difluorophenyl)-N-(1-oxo-4-phenoxyphthalazin-2(1H)-yl)acetamide;
(±)-2-[(exo)-bicyclo[2.2.1]hept-2-yl]-N-(1-oxo-4-phenoxyphthalazin-2(1H)-yl)acetamide;
(±)-N-(4-benzoyl-1-oxophthalazin-2(1H)-yl)-2-[(exo)-bicyclo[2.2.1]hept-2-yl]acetamide;
tert-butyl [(3-{[(4-chlorophenyl)acetyl]amino}-4-oxo-3,4-dihydrophthalazin-1-yl)methyl]carbamate;
N-[4-(aminomethyl)-1-oxophthalazin-2(1H)-yl]-2-(4-chlorophenyl)acetamide;
(±)-2-[(exo)-bicyclo[2.2.1]hept-2-yl]-N-{1-oxo-4-[6-(trifluoromethyl)pyridin-3-yl]phthalazin-2(1H)-yl}acetamide;
(±)-tert-butyl [(3-{[(exo)-bicyclo[2.2.1]hept-2-ylacetyl]amino}-4-oxo-3,4-dihydrophthalazin-1-yl)methyl]carbamate;
(±)-2-[(exo)-bicyclo[2.2.1]hept-2-yl]-N-[4-(2-cyanopyridin-4-yl)-1-oxophthalazin-2(1H)-yl]acetamide;
(±)-2-[(exo)-bicyclo[2.2.1]hept-2-yl]-N-[4-(2-hydroxypyridin-4-yl)-1-oxophthalazin-2(1H)-yl]acetamide;
(±)-2-[(exo)-bicyclo[2.2.1]hept-2-yl]-N-{4-[6-(dimethylamino)pyridin-3-yl]-1-oxophthalazin-2(1H)-yl}acetamide;
N-[4-(2-chloropyridin-4-yl)-1-oxophthalazin-2(1H)-yl]-3-methyl-3-phenylbutanamide;
2-(4-chlorophenyl)-N-[4-(2-chloropyridin-4-yl)-1-oxophthalazin-2(1H)-yl]acetamide;
(±)-2-[(exo)-bicyclo[2.2.1]hept-2-yl]-N-[4-(2-methylpyridin-4-yl)-1-oxophthalazin-2(1H)-yl]acetamide;
(±)-ethyl 3-{[(exo)-bicyclo[2.2.1]hept-2-ylacetyl]amino}-4-oxo-3,4-dihydrophthalazine-1-carboxylate;
N-{4-[benzyl(methyl)amino]-1-oxophthalazin-2(1H)-yl}-3-methyl-3-phenylbutanamide;
N-{4-[benzyl(methyl)amino]-1-oxophthalazin-2(1H)-yl}-2-(3,5-difluorophenyl)acetamide;
(±)-2-[(exo)-bicyclo[2.2.1]hept-2-yl]-N-[4-(6-fluoropyridin-3-yl)-1-oxophthalazin-2(1H)-yl]acetamide;
(±)-3-{[(exo)-bicyclo[2.2.1]hept-2-ylacetyl]amino}-4-oxo-3,4-dihydrophthalazine-1-carboxylic acid;
(±)-3-{[(exo)-bicyclo[2.2.1]hept-2-ylacetyl]amino}-N,N-dimethyl-4-oxo-3,4-dihydrophthalazine-1-carboxamide;
2-(3,5-difluorophenyl)-N-[1-oxo-4-(phenylsulfanyl)phthalazin-2(1H)-yl]acetamide;
2-(4-chlorophenyl)-N-[1-oxo-4-(phenylsulfanyl)phthalazin-2(1H)-yl]acetamide;
(±)-2-[(exo)-bicyclo[2.2.1]hept-2-yl]-N-[1-oxo-4-(phenylsulfanyl)phthalazin-2(1H)-yl]acetamide;
2-(3,5-difluorophenyl)-N-[4-(2,6-dimethylmorpholin-4-yl)-1-oxophthalazin-2(1H)-yl]acetamide;
N-[4-(2,6-dimethylmorpholin-4-yl)-1-oxophthalazin-2(1H)-yl]-3-methyl-3-phenylbutanamide;
2-(4-chlorophenyl)-N-[4-(2,6-dimethylmorpholin-4-yl)-1-oxophthalazin-2(1H)-yl]acetamide;
ethyl 3-{[(4-chlorophenyl)acetyl]amino}-4-oxo-3,4-dihydrophthalazine-1-carboxylate;
(±)-2-[(exo)-bicyclo[2.2.1]hept-2-yl]-N-[4-(2,6-dimethylmorpholin-4-yl)-1-oxophthalazin-2(1H)-yl]acetamide;
3-{[(4-chlorophenyl)acetyl]amino}-4-oxo-3,4-dihydrophthalazine-1-carboxylic acid;
N-[4-(morpholin-4-yl)-1-oxophthalazin-2(1H)-yl]-2-(tetrahydrofuran-3-yl)acetamide;
N-[4-(2-chloropyridin-4-yl)-1-oxophthalazin-2(1H)-yl]-2-(tetrahydrofuran-3-yl)acetamide;
2-(3,5-difluorophenyl)-N-[1-oxo-4-(phenylsulfonyl)phthalazin-2(1H)-yl]acetamide;
2-(4-chlorophenyl)-N-[1-oxo-4-(phenylsulfonyl)phthalazin-2(1H)-yl]acetamide;
(±)-2-[(exo)-bicyclo[2.2.1]hept-2-yl]-N-[1-oxo-4-(phenylsulfonyl)phthalazin-2(1H)-yl]acetamide;
N-[4-(2-chloropyridin-4-yl)-1-oxophthalazin-2(1H)-yl]-2-(1-hydroxycyclohexyl)acetamide;
(±)-4-(3-{[(exo)-bicyclo[2.2.1]hept-2-ylacetyl]amino}-4-oxo-3,4-dihydrophthalazin-1-yl)pyridine-2-carboxamide;
N-[4-(2-chloropyridin-4-yl)-1-oxophthalazin-2(1H)-yl]-2-(tetrahydrofuran-2-yl)acetamide;
(±)-methyl 4-(3-{[(exo)-bicyclo[2.2.1]hept-2-ylacetyl]amino}-4-oxo-3,4-dihydrophthalazin-1-yl)pyridine-2-carboxylate;
(±)-4-(3-{[(exo)-bicyclo[2.2.1]hept-2-ylacetyl]amino}-4-oxo-3,4-dihydrophthalazin-1-yl)pyridine-2-carboxylic acid;
(±)-2-[(exo)-bicyclo[2.2.1]hept-2-yl]-N-{1-oxo-4-[2-(trifluoromethyl)pyridin-4-yl]phthalazin-2(1H)-yl}acetamide;
2-(4-chlorophenyl)-N-{1-oxo-4-[2-(trifluoromethyl)pyridin-4-yl]phthalazin-2(1H)-yl}acetamide;
2-(4-chlorophenyl)-N-[4-({[(4-methylphenyl)sulfonyl]amino}methyl)-1-oxophthalazin-2(1H)-yl]acetamide;
2-(4-chlorophenyl)-N-[1-oxo-4-({[(trifluoromethyl)sulfonyl]amino}methyl)phthalazin-2(1H)-yl]acetamide;
2-(4-chlorophenyl)-N-[4-{[(methylsulfonyl)amino]methyl}-1-oxophthalazin-2(1H)-yl]acetamide;
2-(4-chlorophenyl)-N-{4-[cis-2,6-dimethylmorpholin-4-yl]-1-oxophthalazin-2(1H)-yl}acetamide;
2-(4-chlorophenyl)-N-[1-oxo-4-(phenylsulfinyl)phthalazin-2(1H)-yl]acetamide;
2-(3,5-difluorophenyl)-N-[1-oxo-4-(phenylsulfinyl)phthalazin-2(1H)-yl]acetamide;
N-[4-{[(tert-butylcarbamoyl)amino]methyl}-1-oxophthalazin-2(1H)-yl]-2-(4-chlorophenyl)acetamide;
ethyl [(3-{[(4-chlorophenyl)acetyl]amino}-4-oxo-3,4-dihydrophthalazin-1-yl)methyl]carbamate;

2-(4-chlorophenyl)-N-[1-oxo-4-{[(phenylacetyl)amino]methyl}phthalazin-2(1H)-yl]acetamide;

N-[(3-{[(4-chlorophenyl)acetyl]amino}-4-oxo-3,4-dihydrophthalazin-1-yl)methyl]-2,2-dimethylpropanamide;

2-(3,5-difluorophenyl)-N-{4-[(cis)-2,6-dimethylmorpholin-4-yl]-1-oxophthalazin-2(1H)-yl}acetamide;

N-{4-[(cis)-2,6-dimethylmorpholin-4-yl]-1-oxophthalazin-2(1H)-yl}-3-methyl-3-phenylbutanamide;

(±)-2-[(exo)-bicyclo[2.2.1]hept-2-yl]-N-{4-[(cis)-2,6-dimethylmorpholin-4-yl]-1-oxophthalazin-2(1H)-yl}acetamide;

2-(4-chlorophenyl)-N-[1-oxo-4-(thiomorpholin-4-yl)phthalazin-2(1H)-yl]acetamide;

2-(3,5-difluorophenyl)-N-[1-oxo-4-(thiomorpholin-4-yl)phthalazin-2(1H)-yl]acetamide;

(±)-2-[(exo)-bicyclo[2.2.1]hept-2-yl]-N-[1-oxo-4-(thiomorpholin-4-yl)phthalazin-2(1H)-yl]acetamide;

(±)-tert-butyl 3-{[(exo)-bicyclo[2.2.1]hept-2-ylacetyl]amino}-4-oxo-3,4-dihydrophthalazine-1-carboxylate;

(±)-2-[(exo)-bicyclo[2.2.1]hept-2-yl]-N-[4-(morpholin-4-ylcarbonyl)-1-oxophthalazin-2(1H)-yl]acetamide;

(±)-benzyl [(3-{[(exo)-bicyclo[2.2.1]hept-2-ylacetyl]amino}-4-oxo-3,4-dihydrophthalazin-1-yl)methyl]carbamate;

(±)-2-[(exo)-bicyclo[2.2.1]hept-2-yl]-N-[1-oxo-4-(pyridin-4-ylmethyl)phthalazin-2(1H)-yl]acetamide;

(±)-tert-butyl 4-[(3-{[(exo)-bicyclo[2.2.1]hept-2-ylacetyl]amino}-4-oxo-3,4-dihydrophthalazin-1-yl)carbonyl]piperazine-1-carboxylate;

(±)-3-{[(exo)-bicyclo[2.2.1]hept-2-ylacetyl]amino}-N-tert-butyl-4-oxo-3,4-dihydrophthalazine-1-carboxamide;

(±)-2-[(exo)-bicyclo[2.2.1]hept-2-yl]-N-{4-[(1-oxidopyridin-4-yl)methyl]-1-oxophthalazin-2(1H)-yl}acetamide;

N-[4-(4-benzylpiperazin-1-yl)-1-oxophthalazin-2(1H)-yl]-2-(4-chlorophenyl)acetamide;

(±)-2-[(exo)-bicyclo[2.2.1]hept-2-yl]-N-{4-[hydroxy(phenyl)methyl]-1-oxophthalazin-2(1H)-yl}acetamide;

tert-butyl {4-[(3-{[(4-chlorophenyl)acetyl]amino}-4-oxo-3,4-dihydrophthalazin-1-yl)sulfanyl]phenyl}carbamate;

N-{4-[(6-chloro-1-oxidopyridin-3-yl)methyl]-1-oxophthalazin-2(1H)-yl}-2-(4-chlorophenyl)acetamide;

N-{4-[(4-aminophenyl)sulfanyl]-1-oxophthalazin-2(1H)-yl}-2-(4-chlorophenyl)acetamide;

tert-butyl {4-[(3-{[(4-chlorophenyl)acetyl]amino}-4-oxo-3,4-dihydrophthalazin-1-yl)sulfonyl]phenyl}carbamate;

2-(4-chlorophenyl)-N-[4-(4-methylpiperazin-1-yl)-1-oxophthalazin-2(1H)-yl]acetamide;

(±)-3-{[(exo)-bicyclo[2.2.1]hept-2-ylacetyl]amino}-N-(4-chlorophenyl)-4-oxo-3,4-dihydrophthalazine-1-carboxamide;

ethyl 2-(3-{[(4-chlorophenyl)acetyl]amino}-4-oxo-3,4-dihydrophthalazin-1-yl)propanoate;

2-(3-{[(4-chlorophenyl)acetyl]amino}-4-oxo-3,4-dihydrophthalazin-1-yl)propanoic acid;

N-[4-(morpholin-4-yl)-1-oxophthalazin-2(1H)-yl]-2-phenylacetamide;

N-tert-butyl-2-(3-{[(4-chlorophenyl)acetyl]amino}-4-oxo-3,4-dihydrophthalazin-1-yl)propanamide;

2-(3-{[(4-chlorophenyl)acetyl]amino}-4-oxo-3,4-dihydrophthalazin-1-yl)-N-(2,2-dimethylpropyl)propanamide;

(3-{[(4-chlorophenyl)acetyl]amino}-4-oxo-3,4-dihydrophthalazin-1-yl)acetic acid;

N-{4-[(4-aminophenyl)sulfonyl]-1-oxophthalazin-2(1H)-yl}-2-(4-chlorophenyl)acetamide;

ethyl (3-{[(4-chlorophenyl)acetyl]amino}-4-oxo-3,4-dihydrophthalazin-1-yl)acetate;

ethyl {[(4-chlorophenyl)acetyl]amino}(3-{[(4-chlorophenyl)acetyl]amino}-4-oxo-3,4-dihydrophthalazin-1-yl)acetate;

tert-butyl {[4-oxo-3-({[4-(trifluoromethyl)phenyl]acetyl}amino)-3,4-dihydrophthalazin-1-yl]methyl}carbamate;

tert-butyl {[3-({[(1S,2S,5S)-6,6-dimethylbicyclo[3.1.1]hept-2-yl]acetyl}amino)-4-oxo-3,4-dihydrophthalazin-1-yl]methyl}carbamate;

(±)-2-[(exo)-bicyclo[2.2.1]hept-2-yl]-N-{4-[(Z)-(hydroxyimino)(phenyl)methyl]-1-oxophthalazin-2(1H)-yl}acetamide;

2-(4-chlorophenyl)-N-[4-(2-hydroxyethyl)-1-oxophthalazin-2(1H)-yl]acetamide;

N-{4-[2-(tert-butylamino)-2-oxoethyl]-1-oxophthalazin-2(1H)-yl}-2-(4-chlorophenyl)acetamide;

2-(4-chlorophenyl)-N-[4-{2-[(2,2-dimethylpropyl)amino]-2-oxoethyl}-1-oxophthalazin-2(1H)-yl]acetamide;

tert-butyl [(3-{[(4,4-difluorocyclohexyl)acetyl]amino}-4-oxo-3,4-dihydrophthalazin-1-yl)methyl]carbamate;

tert-butyl [(3-{[(4-fluorophenyl)acetyl]amino}-4-oxo-3,4-dihydrophthalazin-1-yl)methyl]carbamate;

tert-butyl ({3-[(cyclohexylacetyl)amino]-4-oxo-3,4-dihydrophthalazin-1-yl}methyl)carbamate;

2-(4-chlorophenyl)-N-(1-oxo-4-phenoxyphthalazin-2(1H)-yl)acetamide;

cyclohexyl [(3-{[(4-chlorophenyl)acetyl]amino}-4-oxo-3,4-dihydrophthalazin-1-yl)methyl]carbamate;

2,2,2-trifluoroethyl [(3-{[(4-chlorophenyl)acetyl]amino}-4-oxo-3,4-dihydrophthalazin-1-yl)methyl]carbamate;

2-[4-(methylsulfonyl)phenyl]-N-[4-(morpholin-4-yl)-1-oxophthalazin-2(1H)-yl]acetamide;

N-[4-(morpholin-4-yl)-1-oxophthalazin-2(1H)-yl]-2-(3-phenoxyphenyl)acetamide;

N-[4-(morpholin-4-yl)-1-oxophthalazin-2(1H)-yl]-2-[4-(trifluoromethoxy)phenyl]acetamide;

(±)-2-[(exo)-bicyclo[2.2.1]hept-2-yl]-N-[4-(morpholin-4-yl)-1-oxophthalazin-2(1H)-yl]acetamide;

2-(1,2-benzoxazol-3-yl)-N-[4-(morpholin-4-yl)-1-oxophthalazin-2(1H)-yl]acetamide;

2-cyclopentyl-N-[4-(morpholin-4-yl)-1-oxophthalazin-2(1H)-yl]acetamide;

2-cyclohexyl-N-[4-(morpholin-4-yl)-1-oxophthalazin-2(1H)-yl]acetamide;

2-(2-methylphenyl)-N-[4-(morpholin-4-yl)-1-oxophthalazin-2(1H)-yl]acetamide;

2-(3-methylphenyl)-N-[4-(morpholin-4-yl)-1-oxophthalazin-2(1H)-yl]acetamide;

2-(4-methylphenyl)-N-[4-(morpholin-4-yl)-1-oxophthalazin-2(1H)-yl]acetamide;

N-[4-(morpholin-4-yl)-1-oxophthalazin-2(1H)-yl]-2-(2-nitrophenyl)acetamide;

2-(3-hydroxyphenyl)-N-[4-(morpholin-4-yl)-1-oxophthalazin-2(1H)-yl]acetamide;

2-(4-hydroxyphenyl)-N-[4-(morpholin-4-yl)-1-oxophthalazin-2(1H)-yl]acetamide;

2-(2-methoxyphenyl)-N-[4-(morpholin-4-yl)-1-oxophthalazin-2(1H)-yl]acetamide;

2-(3-methoxyphenyl)-N-[4-(morpholin-4-yl)-1-oxophthalazin-2(1H)-yl]acetamide;

2-(4-methoxyphenyl)-N-[4-(morpholin-4-yl)-1-oxophthalazin-2(1H)-yl]acetamide;

2-(2-fluorophenyl)-N-[4-(morpholin-4-yl)-1-oxophthalazin-2(1H)-yl]acetamide;
2-(3-fluorophenyl)-N-[4-(morpholin-4-yl)-1-oxophthalazin-2(1H)-yl]acetamide;
2-(4-fluorophenyl)-N-[4-(morpholin-4-yl)-1-oxophthalazin-2(1H)-yl]acetamide;
2-(2-chlorophenyl)-N-[4-(morpholin-4-yl)-1-oxophthalazin-2(1H)-yl]acetamide;
2-(3-chlorophenyl)-N-[4-(morpholin-4-yl)-1-oxophthalazin-2(1H)-yl]acetamide;
2-(2-bromophenyl)-N-[4-(morpholin-4-yl)-1-oxophthalazin-2(1H)-yl]acetamide;
2-(3-bromophenyl)-N-[4-(morpholin-4-yl)-1-oxophthalazin-2(1H)-yl]acetamide;
2-(4-bromophenyl)-N-[4-(morpholin-4-yl)-1-oxophthalazin-2(1H)-yl]acetamide;
N-[4-(morpholin-4-yl)-1-oxophthalazin-2(1H)-yl]-2-(3-nitrophenyl)acetamide;
N-[4-(morpholin-4-yl)-1-oxophthalazin-2(1H)-yl]-2-(4-nitrophenyl)acetamide;
2-(biphenyl-4-yl)-N-[4-(morpholin-4-yl)-1-oxophthalazin-2(1H)-yl]acetamide;
2-[4-(dimethylamino)phenyl]-N-[4-(morpholin-4-yl)-1-oxophthalazin-2(1H)-yl]acetamide;
N-[4-(morpholin-4-yl)-1-oxophthalazin-2(1H)-yl]-2-[3-(trifluoromethyl)phenyl]acetamide;
N-[4-(morpholin-4-yl)-1-oxophthalazin-2(1H)-yl]-2-[4-(trifluoromethyl)phenyl]acetamide;
N-[4-(morpholin-4-yl)-1-oxophthalazin-2(1H)-yl]-2-[3-(trifluoromethoxy)phenyl]acetamide;
N-[4-(morpholin-4-yl)-1-oxophthalazin-2(1H)-yl]-2-(4-phenoxyphenyl)acetamide;
2-[4-(benzyloxy)phenyl]-N-[4-(morpholin-4-yl)-1-oxophthalazin-2(1H)-yl]acetamide;
N-[4-(morpholin-4-yl)-1-oxophthalazin-2(1H)-yl]-2-(naphthalen-1-yl)acetamide;
N-[4-(morpholin-4-yl)-1-oxophthalazin-2(1H)-yl]-2-(naphthalen-2-yl)acetamide;
2-(2,5-dimethylphenyl)-N-[4-(morpholin-4-yl)-1-oxophthalazin-2(1H)-yl]acetamide;
N-[4-(morpholin-4-yl)-1-oxophthalazin-2(1H)-yl]-2-(2,4,6-trimethylphenyl)acetamide;
2-(2,3-dimethoxyphenyl)-N-[4-(morpholin-4-yl)-1-oxophthalazin-2(1H)-yl]acetamide;
2-(2,4-dimethoxyphenyl)-N-[4-(morpholin-4-yl)-1-oxophthalazin-2(1H)-yl]acetamide;
2-(2,5-dimethoxyphenyl)-N-[4-(morpholin-4-yl)-1-oxophthalazin-2(1H)-yl]acetamide;
2-(3,4-dimethoxyphenyl)-N-[4-(morpholin-4-yl)-1-oxophthalazin-2(1H)-yl]acetamide;
2-(3,5-dimethoxyphenyl)-N-[4-(morpholin-4-yl)-1-oxophthalazin-2(1H)-yl]acetamide;
2-(1,3-benzodioxol-5-yl)-N-[4-(morpholin-4-yl)-1-oxophthalazin-2(1H)-yl]acetamide;
2-(2,3-difluorophenyl)-N-[4-(morpholin-4-yl)-1-oxophthalazin-2(1H)-yl]acetamide;
2-(2,5-difluorophenyl)-N-[4-(morpholin-4-yl)-1-oxophthalazin-2(1H)-yl]acetamide;
2-(3,4-dichlorophenyl)-N-[4-(morpholin-4-yl)-1-oxophthalazin-2(1H)-yl]acetamide;
2-(2,6-dichlorophenyl)-N-[4-(morpholin-4-yl)-1-oxophthalazin-2(1H)-yl]acetamide;
tert-butyl [(3-{[(exo)-bicyclo[2.2.1]hept-2-ylacetyl]amino}-4-oxo-3,4-dihydrophthalazin-1-yl)(phenyl)methyl]carbamate;
(1R,2S,5R)-5-methyl-2-(propan-2-yl)cyclohexyl [(3-{[(4-chlorophenyl)acetyl]amino}-4-oxo-3,4-dihydrophthalazin-1-yl)methyl]carbamate;
2-[4-(methylsulfonyl)phenyl]-N-[1-oxo-4-(phenylsulfanyl)phthalazin-2(1H)-yl]acetamide;
2-methylbutan-2-yl [(3-{[(4-chlorophenyl)acetyl]amino}-4-oxo-3,4-dihydrophthalazin-1-yl)methyl]carbamate;
methyl [(2S)-1-{[(3-{[(4-chlorophenyl)acetyl]amino}-4-oxo-3,4-dihydrophthalazin-1-yl)methyl]amino}-3-methyl-1-oxobutan-2-yl]carbamate;
2,2-dimethylpropyl [(3-{[(4-chlorophenyl)acetyl]amino}-4-oxo-3,4-dihydrophthalazin-1-yl)methyl]carbamate;
2-methylpropyl [(3-{[(4-chlorophenyl)acetyl]amino}-4-oxo-3,4-dihydrophthalazin-1-yl)methyl]carbamate;
(1S,2R,5S)-5-methyl-2-(propan-2-yl)cyclohexyl [(3-{[(4-chlorophenyl)acetyl]amino}-4-oxo-3,4-dihydrophthalazin-1-yl)methyl]carbamate;
cyclopentyl [(3-{[(4-chlorophenyl)acetyl]amino}-4-oxo-3,4-dihydrophthalazin-1-yl)methyl]carbamate;
benzyl [(3-{[(4-chlorophenyl)acetyl]amino}-4-oxo-3,4-dihydrophthalazin-1-yl)methyl]carbamate;
2-[4-(methylsulfonyl)phenyl]-N-[1-oxo-4-(phenylsulfonyl)phthalazin-2(1H)-yl]acetamide;
(±)-2-[(exo)-bicyclo[2.2.1]hept-2-yl]-N-[4-(1,1-dioxidothiomorpholin-4-yl)-1-oxophthalazin-2(1H)-yl]acetamide;
2-(4-chlorophenyl)-N-[1-oxo-4-(pyridin-4-ylsulfanyl)phthalazin-2(1H)-yl]acetamide;
2-(4-chlorophenyl)-N-{4-[(4-methylphenyl)sulfonyl]-1-oxophthalazin-2(1H)-yl}acetamide;
2-(4-fluorophenyl)-N-[1-oxo-4-(phenylsulfonyl)phthalazin-2(1H)-yl]acetamide;
3-methyl-N-[1-oxo-4-(phenylsulfonyl)phthalazin-2(1H)-yl]-3-phenylbutanamide;
N-{4-[(4-bromophenyl)sulfanyl]-1-oxophthalazin-2(1H)-yl}-2-(4-chlorophenyl)acetamide;
2-(4-chlorophenyl)-N-{4-[(1-oxidopyridin-4-yl)sulfonyl]-1-oxophthalazin-2(1H)-yl}acetamide;
N-{4-[(4-bromophenyl)sulfanyl]-1-oxophthalazin-2(1H)-yl}-2-(3,5-difluorophenyl)acetamide;
N-[4-(tert-butylsulfanyl)-1-oxophthalazin-2(1H)-yl]-2-(4-chlorophenyl)acetamide;
N-{4-[(4-bromophenyl)sulfonyl]-1-oxophthalazin-2(1H)-yl}-2-(4-chlorophenyl)acetamide;
(±)-2-[(exo)-bicyclo[2.2.1]hept-2-yl]-N-{4-[(4-bromophenyl)sulfanyl]-1-oxophthalazin-2(1H)-yl}acetamide;
N-[4-(tert-butylsulfonyl)-1-oxophthalazin-2(1H)-yl]-2-(4-chlorophenyl)acetamide;
N-{4-[(4-bromophenyl)sulfonyl]-1-oxophthalazin-2(1H)-yl}-2-(3,5-difluorophenyl)acetamide;
2-(4-chlorophenyl)-N-[1-oxo-4-(pyridin-4-ylsulfonyl)phthalazin-2(1H)-yl]acetamide;
(±)-2-[(exo)-bicyclo[2.2.1]hept-2-yl]-N-{4-[(4-bromophenyl)sulfonyl]-1-oxophthalazin-2(1H)-yl}acetamide;
2-(3-methoxyphenyl)-N-[1-oxo-4-(phenylsulfonyl)phthalazin-2(1H)-yl]acetamide;
2-(4-bromophenyl)-N-[1-oxo-4-(phenylsulfonyl)phthalazin-2(1H)-yl]acetamide;
2-(3-methylphenyl)-N-[1-oxo-4-(phenylsulfonyl)phthalazin-2(1H)-yl]acetamide;
N-[1-oxo-4-(phenylsulfonyl)phthalazin-2(1H)-yl]-2-[3-(trifluoromethyl)phenyl]acetamide;
2-(3-chlorophenyl)-N-[1-oxo-4-(phenylsulfonyl)phthalazin-2(1H)-yl]acetamide;

2-(hexahydro-2,5-methanopentalen-3a(1H)-yl)-N-[4-(morpholin-4-yl)-1-oxophthalazin-2(1H)-yl]acetamide;

2-(hexahydro-2,5-methanopentalen-3a(1H)-yl)-N-{1-oxo-4-[6-(trifluoromethyl)pyridin-3-yl]phthalazin-2(1H)-yl}acetamide;

N-[4-(benzylsulfanyl)-1-oxophthalazin-2(1H)-yl]-2-(3,5-difluorophenyl)acetamide;

N-[4-(benzylsulfanyl)-1-oxophthalazin-2(1H)-yl]-2-(4-chlorophenyl)acetamide;

(±)-N-[4-(benzylsulfanyl)-1-oxophthalazin-2(1H)-yl]-2-[(exo)-bicyclo[2.2.1]hept-2-yl]acetamide;

N-[4-(benzylsulfonyl)-1-oxophthalazin-2(1H)-yl]-2-(3,5-difluorophenyl)acetamide;

N-[4-(benzylsulfonyl)-1-oxophthalazin-2(1H)-yl]-2-(4-chlorophenyl)acetamide;

(±)-N-[4-(benzylsulfonyl)-1-oxophthalazin-2(1H)-yl]-2-[(exo)-bicyclo[2.2.1]hept-2-yl]acetamide;

2-(hexahydro-2,5-methanopentalen-3a(1H)-yl)-N-[1-oxo-4-(phenylsulfonyl)phthalazin-2(1H)-yl]acetamide;

(±)-2-[(exo)-bicyclo[2.2.1]hept-2-yl]-N-{4-[(4-cyanophenyl)sulfonyl]-1-oxophthalazin-2(1H)-yl}acetamide;

(±)-2-[(exo)-bicyclo[2.2.1]hept-2-yl]-N-[4-(2-ethylmorpholin-4-yl)-1-oxophthalazin-2(1H)-yl]acetamide;

2-(4-chlorophenyl)-N-[4-(2-ethylmorpholin-4-yl)-1-oxophthalazin-2(1H)-yl]acetamide;

2-(4-chlorophenyl)-N-{4-[(4-cyanophenyl)sulfonyl]-1-oxophthalazin-2(1H)-yl}acetamide;

N-{4-[(4-cyanophenyl)sulfonyl]-1-oxophthalazin-2(1H)-yl}-2-(3,5-difluorophenyl)acetamide;

N-{4-[(4-cyanophenyl)sulfonyl]-1-oxophthalazin-2(1H)-yl}-2-(4-fluorophenyl)acetamide; and N-{4-[(4-cyanophenyl)sulfonyl]-1-oxophthalazin-2(1H)-yl}-3-methyl-3-phenylbutanamide.

21. A pharmaceutical composition comprising a therapeutically effective amount of a compound of formula (I) according to claim 1 or a pharmaceutically acceptable salt thereof, in combination with a pharmaceutically acceptable carrier.

22. A method for treating pain in a subject in need of such treatment comprising administering to the subject a therapeutically effective amount of a compound of formula (I) according to claim 1, or a pharmaceutically acceptable salt thereof, alone or in combination with a pharmaceutically acceptable carrier.

* * * * *